(12) United States Patent
Kufer et al.

(10) Patent No.: US 8,784,821 B1
(45) Date of Patent: Jul. 22, 2014

(54) HUMAN-ANTI-HUMAN CD3 BINDING MOLECULES

(75) Inventors: Peter Kufer, Moosburg (DE); Tobias Raum, Munich (DE); Meera Berry, Ulm (DE); Roman Kischel, Karlsfeld (DE); Susanne Mangold, Munich (DE); Eva Krinner, Munich (DE); Birgit Kohleisen, Munich (DE); Steven Zeman, Pullad (DE); Christian Itin, Feldajiug (DE); Patrick Bäuerle, Gauting (DE)

(73) Assignee: Amgen Research (Munich) GmbH, Munich (DE)

( * ) Notice: Subject to any disclaimer, the term of this patent is extended or adjusted under 35 U.S.C. 154(b) by 1449 days.

(21) Appl. No.: 10/554,731

(22) PCT Filed: May 26, 2004

(86) PCT No.: PCT/EP2004/005684
§ 371 (c)(1),
(2), (4) Date: Nov. 9, 2006

(87) PCT Pub. No.: WO2004/106380
PCT Pub. Date: Dec. 9, 2004

(30) Foreign Application Priority Data

May 31, 2003 (EP) ..................................... 03012132

(51) Int. Cl.
*A61K 38/00* (2006.01)
(52) U.S. Cl.
USPC .................. 424/154.1; 424/136.1; 424/134.1; 424/138.1; 424/135.1; 530/387.3; 530/387.7; 530/388.15
(58) Field of Classification Search
None
See application file for complete search history.

(56) References Cited

U.S. PATENT DOCUMENTS

2004/0038339 A1*   2/2004   Kufer et al.   .................. 435/69.1

FOREIGN PATENT DOCUMENTS

WO    WO 93/11236    6/1993
WO    WO 99/54440    10/1999

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin-binding and mitogenic activities of heparin-binding (acidic fibroblast) growth factor-1 from its receptor-binding activities by site-directed mutagenesis of a single lysine residue. Journal of Cell Biology, 1990. vol. 111, pp. 2129-2138.*
Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*
Rudikoff, Giusti, Cook, and Scharff. Single amino acid substitution altering antigen binding specificity. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanzied monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen binding site of an Anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Rudikoff et al (PNAS, 1982, 79:1979).*
MacCallum et al (J of Mol Biol, 1996, 262:732-745).*
De Pascalis et al (J of Immunol, 2002, 169:3076-3084).*
Casset et al (Biochem and Biophys Res Commun, 2003, 307:198-205).*
Vajdos et al (J Mol Biol, 2002, 320:415-428).*
Holm et al (Mol Immunol, 2007:1075-1084).*
Chen et al (J Mol Biol, 1999, 293:865-881).*
Wu et al (J Mol Biol, 1999, 294:151-162).*
Alegre et al., "Effect of a single amino accid (AA) mutation in the Fc portion of a 'humanized' OKT3 on T cell responses in vitro," *J. Am. Soc. Nephol.*, 2(3): 1991 (abstract).
Barbas III and Burton, "Selection and Evolution of high-affinity human anti-viral antibodies," *TIBTECH*, 14:230, 1996.
Database EMBL EBI, Database accession No. Q9UL77, 2003.
De Kruif et al., "Rapid selection of cell subpopulation-specific human monoclonal antibodies from a synthetic phage antibody library," *Proc. Natl. Acad. Sci., USA*, 92:3938-3942, 1995.

(Continued)

*Primary Examiner* — Misook Yu
*Assistant Examiner* — Julie Wu
(74) *Attorney, Agent, or Firm* — Marshall, Gerstein & Borun LLP

(57) ABSTRACT

The present invention provides a method for the preparation of a human binding molecule, fragment or derivative thereof which specifically binds to the human CD3 complex. Furthermore, the invention provides a human binding molecules specifically binding to the human CD3 complex and means comprising said human binding molecules.

23 Claims, 64 Drawing Sheets

(56) References Cited

OTHER PUBLICATIONS

Figure 2:
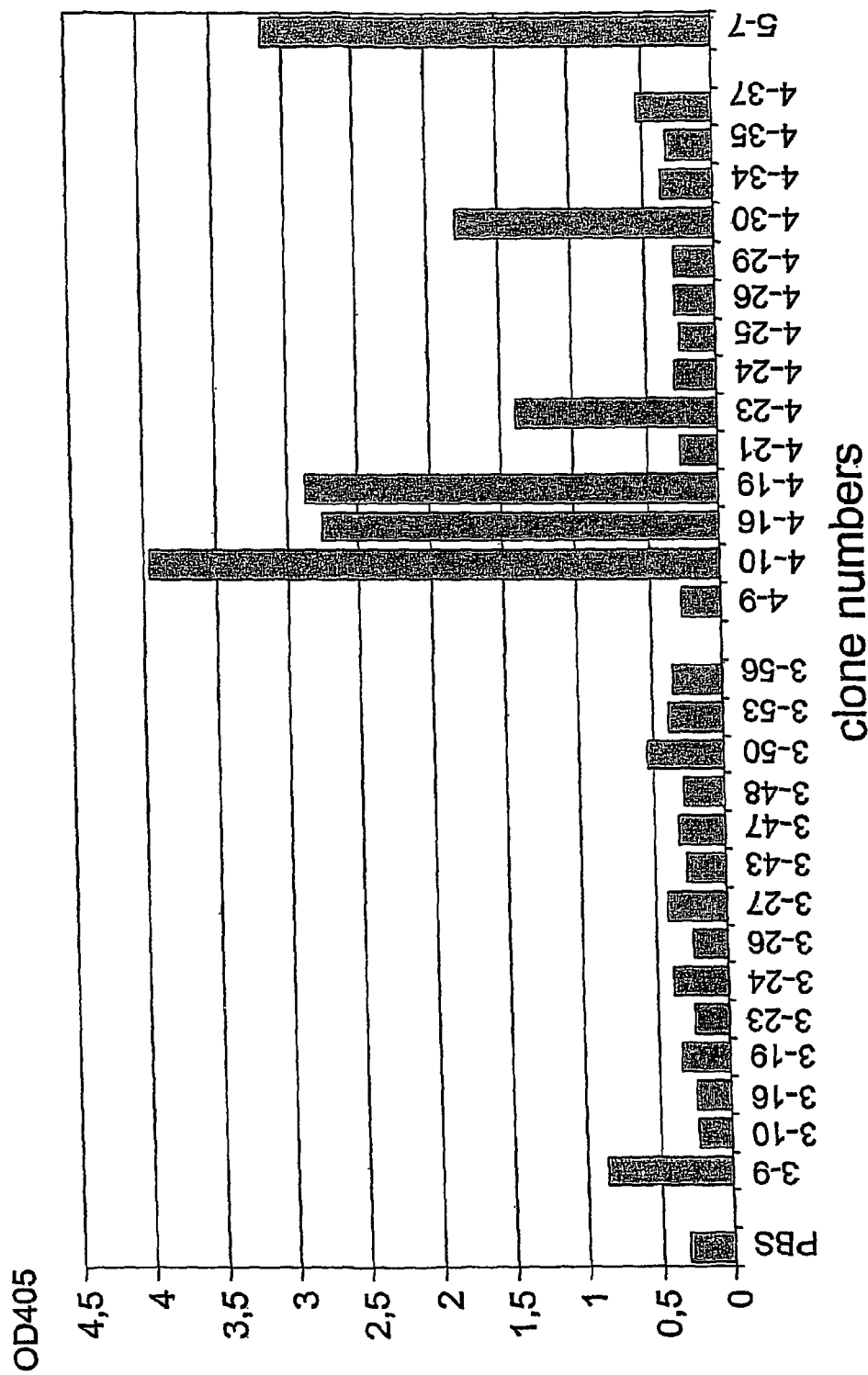

Gil et al., "Recruitment of Nck by CDε reveals a ligand-induced conformational change essential for T cell receptor signaling and synapse formation," *Cell*, 109:901-912, 2002.

Hoogenboom and Chames, "Natural and designer building sites made by phage display technology," *Immun Today*, 21:371-378, 2000.

Hoogenboom, "Overview of Antibody Phage-Display Technology and Its Applications," *Methods Mol Biol*, 178:1-37, 2002.

Kastrup et al., "In Vitro Production and Characterization of Partly Assembled Human CD3 Complexes," *Scand J Immunol*, 56:436442, 2002.

Krebs et al., "Recombinant human single chain Fv antibodies recognizing human interleukin-6,"*J. Biol. Chem.*, 273(5)2858-2865, 1998.

Kufer et al., "Construction and biological activity of a recombinant bispecific single-chain antibody designed for therapy of minimal residual colorectal cancer," *Cancer Immunol. Immunother.*, 45:193-197, 1997.

Kufer et al., "Minimal costimulatory requirements for T cell priming and TH1 differentiation: Activation of naïve human T lymphocytes by tumor cells armed with bifunctional antibody constructs," *Cancer Immunity*, 1:10, 2001.

Lanzavecchia and Scheldegger, "The use of hybrid hybridomas to target human cytotoxic T lymphocytes," *Eur. J. Immunol.*, 17:105-111, 1987.

Loffler et al, "A recombinant bispecific single-chain antibody, CD19xCD3, induces rapid and high lymphoma-directed cytotoxicity by unstimulated T lymphocytes," *Blood*, 95(6):2098-2103, 2000.

Mack et al, "A small bispecfic antibody construct expressed as a functional single-chain molecule with high tumor cell cytotoxicity," *Proc. Natl. Acad. Sci. USA*, 92:7021-7025, 1995.

Mack et al., "Biological Properties of a Bispecific Single-Chain Antibody Directed Against 17-1A (EpCAM) and CD3,"*J. Immunol.*, 158:3965-3970, 1997.

Maletz et al., "Bispecific single-chain antibodies as effective tools for eliminating epithelial cancer cells from human stem cell preparations by redirected cell cytotoxivity," *Int. J. Cancer*, 93:409-416, 2001.

Mason et al., "Detection of T cells in paraffin wax embedded tissue using antibodies against a peptide sequence from the CD3 antigen,"*J. Clin Pathol*, 42:1194-1200, 1989.

Naundorf et al., "In Vitro and In Vivo Activity of MT201, a Fully Human Monoclonal Antibody for Pancarcinoma Treatment," *Int. J. Cancer*, 100:101-110, 2002.

Popov et al., "A novel and efficient route for the isolation of antibodies that recognise T cell receptor V$\alpha$s," *Molecular Immunology*, 33(6):493-502, 1996.

Raum et al., "Anti-self antibodies selected from a human IgD heavy chain repertoire: a novel approach to generate therapeutic human antibodies against tumor-associated differentiation antigens," *Cancer Immuno. Imunnother.*, 50:141-150, 2001.

Traunecker et al., "Bispecfic single chain molecules (Janusins) target cytotoxic lymphocytes on HIV infected cells," *EMBO J.*, 10:3655-3659, 1991.

Weidanz et al., "Display of functional $\alpha\beta$ single-chain T-cell receptor molecules on the surface of bacteriophage," *Journal of Immunological Methods*, 221:59-76, 1998.

\* cited by examiner

BsiWI

```
     R   T   D   A   A   P   T       V   S   I       F   P   P   S       E   Q       L   T   S
  1  CGTACGGATG CTGCACCAAC TGTATCCATC TTCCCACCAT CCAGTGAGCA GTTAACATCT
     GCATGCCTAC GACGTGGTTG ACATAGGTAG AAGGGTGGTA GGTCACTCGT CAATTGTAGA

G   G   A   S       V   V   C       F   L   N       N   F   Y   P       K   D   I       N   V   K
 61  GGAGGTGCCT CAGTCGTGTG CTTCTTGAAC AACTTCTACC CCAAAGACAT CAATGTCAAG
     CCTCCACGGA GTCAGCACAC GAAGAACTTG TTGAAGATGG GGTTTCTGTA GTTACAGTTC

W   K   I   D       G   S   E       R   Q   N       G   V   L   N       S   W   T       D   Q   D
121  TGGAAGATTG ATGGCAGTGA ACGACAAAAT GGCGTCCTGA ACAGTTGGAC TGATCAGGAC
     ACCTTCTAAC TACCGTCACT TGCTGTTTTA CCGCAGGACT TGTCAACCTG ACTAGTCCTG

S   K   D   S       T   Y   S       M   S   S       T   L   T   L       T   K   D       E   Y   E
181  AGCAAAGACA GCACCTACAG CATGAGCAGC ACCCTCACGT TGACCAAGGA CGAGTATGAA
     TCGTTTCTGT CGTGGATGTC GTACTCGTCG TGGGAGTGCA ACTGGTTCCT GCTCATACTT
```

Fig. 1

```
              R   H   N   S       Y   T   C       E   A   T       H   K   T   S       T   S   P       I   V   K
241         CGACATAACA GCTATACCTG TGAGGCCACT CACAAGACAT CAACTTCACC CATTGTCAAG
            GCTGTATTGT CGATATGGAC ACTCCGGTGA GTGTTCTGTA GTTGAAGTGG GTAACAGTTC

S   F   N   R       N   E   C       E   E   Q       K   L   I   S       E   E   D       L   H   H
301         AGCTTCAACA GGAATGAGTG TGAGGAACAG AAGCTGATCT CAGAGGAAGA TCTGCATCAC
            TCGAAGTTGT CCTTACTCAC ACTCCTTGTC TTCGACTAGA GTCTCCTTCT AGACGTAGTG

NotI
              H   H   H       *   ---------
361         CACCATCACC ATTAAGCGGC CGC
            GTGGTAGTGG TAATTCGCCG GCG
```

Fig. 1 (cont.)

3-106

```
     E  L  Q  L  V  E  S  G  G  G  V  V  Q  P  G  R  S  L  R  L
1    GAGCTGCAGC TGGTCGAGTC TGGGGGAGGC GTGGTCCAGC CTGGGAGGTC CCTGAGACTC
     CTCGACGTCG ACCAGCTCAG ACCCCCTCCG CACCAGGTCG GACCCTCCAG GGACTCTGAG

S  C  A  A  S  G  F  T  F  S    S  Y  G  M  H  W  V  R  Q  A
61   TCCTGTGCAG CCTCTGGATT CACCTTCAGT AGCTATGGCA TGCACTGGGT CCGCCAGGCT
     AGGACACGTC GGAGACCTAA GTGGAAGTCA TCGATACCGT ACGTGACCCA GGCGGTCCGA
                                     └──────── VH-CDR1 ────────┘

VH-CDR2
     P  G  K  G  L  E  W  V  A    V  I  S  Y  D  G  S  N  K  Y  Y
121  CCAGGCAAGG GGCTGGAGTG GGTGGCAGTT ATATCATATG ATGGAAGTAA TAAATACTAC
     GGTCCGTTCC CCGACCTCAC CCACCGTCAA TATAGTATAC TACCTTCATT ATTTATGATG

A  D  S  V  K  G  R    F  T  I  S  R  D  N  S  K  N  T  L  Y
181  GCAGACTCCG TGAAGGGCCG ATTCACCATC TCCAGAGACA ATTCCAAGAA CACGCTGTAT
     CGTCTGAGGC ACTTCCCGGC TAAGTGGTAG AGGTCTCTGT TAAGGTTCTT GTGCGACATA
     └──────────────────┘
```

Fig. 6

```
        L  Q  M  N  S  L  R     S  E  D     T  A  V  Y  Y  C  A     R  L  S
241   CTGCAAATGA ACAGCCTGAG ATCTGAGGAC ACGGCCGTGT ATTACTGTGC GAGGCTCAGC
      GACGTTTACT TGTCGGACTC TAGACTCCTG TGCCGGCACA TAATGACACG CTCCGAGTCG

VH-CDR3
        P  Y  C  T  N  G  V  C  W  D     A  F  D  I     W  G  Q     G  T  M
301   CCGTATTGTA CTAATGGTGT ATGCTGGGAT GCTTTTGATA TCTGGGGCCA AGGGACAATG
      GGCATAACAT GATTACCACA TACGACCCTA CGAAAACTAT AGACCCCGGT TCCCTGTTAC

V  T  V  S  S  G  G     G  G  S     G  G  G  G     S  G  G     G  G  S
361   GTCACCGTCT CCTCAGGTGG TGGCGGTTCT GGCGGCGGCG GCTCCGGTGG TGGTGGTTCT
      CAGTGGCAGA GGAGTCCACC ACCGCCAAGA CCGCCGCCGC CGAGGCCACC ACCACCAAGA

E  L  Q  M  T  Q  S     P  S  S     L  S  A  S     V  G  D     R  V  S
421   GAGCTCCAGA TGACCCAGTC TCCATCCTCC CTGTCTGCAT CTGTCGGAGA CAGAGTCTCC
      CTCGAGGTCT ACTGGGTCAG AGGTAGGAGG GACAGACGTA GACAGCCTCT GTCTCAGAGG
```

Fig. 6 (cont.)

```
           VL-CDR1
      I  T  C  R  A  S  Q   T  I  S   N  Y  L  N    W  Y  Q  L  K  P
481   ATCACTTGTC GGGCAAGTCA GACCATTAGC AATTATTAA ATTGGTATCA ACTGAAGCCA
      TAGTGAACAG CCCGTTCAGT CTGGTAATCG TTAATAATT TAACCATAGT TGACTTCGGT

VL-CDR2
      G  K  A  P  K  L  L  I  Y   A  A  S  T  L  Q  S   E  V  P  T
541   GGGAAAGCCC CTAAGCTCCT GATCTATGCT GCATCCACTT TGCAAAGTGA GGTCCCAACC
      CCCTTTCGGG GATTCGAGGA CTAGATACGA CGTAGGTGAA ACGTTTCACT CCAGGGTTGG

R  F  S  G  S  G  S  G  T  D  F  T  L  T  I  S  G   L  H  P
601   AGGTTCAGTG GCAGTGGGTC TGGGACAGAT TTCACTCTCA CCATCAGTGG TCTGCATCCT
      TCCAAGTCAC CGTCACCCAG ACCCTGTCTA AAGTGAGAGT GGTAGTCACC AGACGTAGGA

VL-CDR3
      E  D  F  A  T  Y  Y  C   Q  Q  F  N  S  Y  P  R  T   F  G  Q
661   GAAGATTTTG CAACTTACTA CTGTCAACAG TTTAATAGTT ATCCTCGAAC GTTCGGCCAA
      CTTCTAAAAC GTTGAATGAT GACAGTTGTC AAATTATCAA TAGGAGCTTG CAAGCCGGTT

G  T  K  V  E  I  K
721   GGGACCAAGG TGGAAATCAA A
      CCCTGGTTCC ACCTTTAGTT T
```

Fig. 6 (cont.)

3-114

```
     E  L  Q  L  V  E  S  G  G       G  L  V  K  P  G  R  S     L  R  L
1    GAGCTGCAGC TGGTCGAGTC TGGGGGAGGC TTGGTAAAGC CAGGGCGGTC     CCTGAGACTC
     CTCGACGTCG ACCAGCTCAG ACCCCCTCCG AACCATTTCG GTCCCGCCAG     GGACTCTGAG

S  C  T  A  S  G  F     T  F  G                            VH-CDR1
                                              D  Y  A  M  S     W  F  R  Q  A
61   TCCTGTACAG CTTCTGGATT CACCTTTGGT         GATTATGCTA TGAGCTGGTT CCGCCAGGCT
     AGGACATGTC GAAGACCTAA GTGGAAACCA         CTAATACGAT ACTCGACCAA GGCGGTCCGA

P  G  K  G  L  E  W  V  G  F     I  R  S  K  A  Y  G       VH-CDR2
                                                                 G  T  T
121  CCAGGGAAGG GGCTGGAGTG GGTAGGTTTC ATTAGAAGCA AAGCTTATGG     TGGGACAACA
     GGTCCCTTCC CCGACCTCAC CCATCCAAAG TAATCTTCGT TTCGAATACC     ACCCTGTTGT

E  Y  A  A  S  V  K  G  R  F  T  I  S  R  D  D  S  K  S  I
181  GAATACGCCG CGTCTGTGAA AGGCAGATTC ACCATCTCAA GAGATGATTC CAAAAGCATC
     CTTATGCGGC GCAGACACTT TCCGTCTAAG TGGTAGAGTT CTCTACTAAG GTTTTCGTAG
```

Fig. 7

```
        A   Y   L   Q   M   N   S   L   K   T   E   D   T   A   V   Y   Y   C   T   P
241  GCCTATCTGC AAATGAACAG CCTGAAAACC GAGGACACAG CCGTGTATTA CTGTACTCCA
     CGGATAGACG TTTACTTGTC GGACTTTTGG CTCCTGTGTC GGCACATAAT GACATGAGGT
                                    ┌─────────────────────────────────────────────┐
        Q   L   W   L   L   Q   D   │ A   F   D   I   W   G   Q   G   T   M   V   T   V
301  CAGCTATGGT TACTACAAGA TGCTTTTTGAT ATCTGGGGCC AAGGGACAAT GGTCACCGTC
     GTCGATACCA ATGATGTTCT ACGAAAACTA TAGACCCCGG TTCCCTGTTA CCAGTGGCAG
                          VH-CDR3
                                    └─────────────────────────────────────────────┘
        S   S   G   G   G   G   S   G   G   G   G   S   G   G   G   G   S   E   L   Q
361  TCCTCAGGTG GTGGCGGTTC TGGCGGCGGC GGCTCCGGTG GTGGTGGTTC TGAGCTCCAG
     AGGAGTCCAC CACCGCCAAG ACCGCCGCCG CCGAGGCCAC CACCACCAAG ACTCGAGGTC

M   T   Q   S   P   S   S   L   S   A   S   V   G   D   R   V   T   I   T   C
421  ATGACCCAGT CTCCATCCTC CCTGTCTGCA TCTGTAGGAG ATAGAGTCAC CATCACTTGC
     TACTGGGTCA GAGGTAGGAG GGACAGACGT AGACATCCTC TATCTCAGTG GTAGTGAACG
                                    ┌─────────────────────────────────────────────┐
        R   A   S   Q   G   I   S   │ N   Y   L   A   │ W   Y   Q   Q   K   P   G   K   V
481  CGGGCGAGTC AGGGCATTAG CAATTATTTA GCCTGGTATC AGCAGAAACC AGGGAAAGTT
     GCCCGCTCAG TCCCGTAATC GTTAATAAAT CGGACCATAG TCGTCTTTGG TCCCTTTCAA
                          VL-CDR1
                                    └─────────────────────────────────────────────┘
```

Fig. 7 (cont.)

```
            P   K   L   L   I   Y   A   A   S   T   L   Q   S   G   V   P   S   R   F   S
541         CCTAAGCTCC TGATCTATGC TGCATCCACT TTGCAATCAG GGGTCCCATC TCGGTTCAGT
            GGATTCGAGG ACTAGATACG ACGTAGGTGA AACGTTAGTC CCCAGGGTAG AGCCAAGTCA

G   S   G   S   G   T   D   F   T   L   T   I   S   S   L   Q   P   E   D   F
601         GGCAGTGGAT CTGGGACAGA TTTCACTCTC ACCATCAGCA GTCTGCAACC TGAAGATTTT
            CCGTCACCTA GACCCTGTCT AAAGTGAGAG TGGTAGTCGT CAGACGTTGG ACTTCTAAAA

A   T   Y   Y   C   Q   Q   S   Y   S   T   P   P   T   F   G   Q   G   T   K
661         GCAACTTACT ACTGTCAACA GAGTTACAGT ACCCCTCCGA CGTTCGGCCA AGGGACCAAG
            CGTTGAATGA TGACAGTTGT CTCAATGTCA TGGGGAGGCT GCAAGCCGGT TCCCTGGTTC

L   E   I   K
721         CTGGAGATCA AA
            GACCTCTAGT TT
```

VL-CDR2 box covers: L Q S G V P S R F S region nucleotides
VL-CDR3 box covers: Q Q S Y S T P P T region nucleotides

Fig. 7 (cont.)

3-148

```
     E  L  Q  L  V  E  S     G  P  G     L  V  K  P     S  G  T     L  S  L
  1  GAGCTGCAGC TGGTCGAGTC TGGGCCCAGGA CTGGTGAAGC CTTCGGGGAC CCTGTCCCTC
     CTCGACGTCG ACCAGCTCAG ACCCGGGTCCT GACCACTTCG GAAGCCCCTG GGACAGGGAG

T  C  A  V  S  G  G     S  I  S     S  R  N  W     S  W     V  R  Q
 61  ACCTGCGCTG TCTCTGGTGG CTCCATCAGC AGTAGAAACT GGTGGAGTTG GGTCCGCCAG
     TGGACGCGAC AGAGACCACC GAGGTAGTCG TCATCTTTGA CCACCTCAAC CCAGGCGGTC
                                      └─────────VH-CDR1──────────┘

P  P  G  K     G  L  E  W  I  G     D  I  Y  H  S  G  S     T  N  Y
121  CCCCCAGGGA AGGGGCTGGA GTGGATTGGT GATATCTATC ATAGTGGGAG CACCAACTAC
     GGGGGTCCCT TCCCCGACCT CACCTAACCA CTATAGATAG TATCACCCTC GTGGTTGATG
                                      └──────────────VH-CDR2

N  P  S  L  K  S     R     V  T  I     S  V  D  K  S  K  N     Q  F  S
181  AACCCGTCCC TCAAGAGTCG AGTCACCATA TCAGTAGACA AGTCCAAGAA CCAGTTCTCC
     TTGGGCAGGG AGTTCTCAGC TCAGTGGTAT AGTCATCTGT TCAGGTTCTT GGTCAAGAGG
     ────────────────┘
```

Fig. 8

```
        L  K  L  S  S  V  T     A  A  D     T  A  V  Y  Y  C  A     S  G  Y
241     CTGAAGCTGA GCTCTGTGAC CGCCGCGGAC ACGGCCGTGT ATTACTGTGC GAGTGGGTAT
        GACTTCGACT CGAGACACTG GCGGCGCCTG TGCCGGCACA TAATGACACG CTCACCCATA

VH-CDR3
        T  S  C  R  D  A  F     D  I  W     G  Q  G  T     M  V  T  V  S  S
301     ACCAGCTGTC GTGATGCTTT TGATATCTGG GGCCAAGGGA CAATGGTCAC CGTCTCCTCA
        TGGTCGACAG CACTACGAAA ACTATAGACC CCGGTTCCCT GTTACCAGTG GCAGAGGAGT

G  G  G  S  G  G     G  G  S     G  G  G  G  S     E  L  V  M  T
361     GGTGGTGGTG GTTCTGGCGG CGGCGGCTCC GGTGGTGGTG GCTCCGAGCT GGTGATGACT
        CCACCACCAC CAAGACCGCC GCCGCCGAGG CCACCACCAC CGAGGCTCGA CCACTACTGA

Q  S  P  S  S  L  S     A  S  V     G  D  R  V  T  I  T     C  R  A
421     CAGTCTCCAT CCTCCCTGTC TGCATCTGTA GGAGACAGAG TCACCATCAC TTGCCGGGCG
        GTCAGAGGTA GGAGGGACAG ACGTAGACAT CCTCTGTCTC AGTGGTAGTG AACGGCCCGC

VL-CDR1
        S  Q  G  I  G  N  Y     L  A  W     Y  Q  Q  K  P  G  Q     P  P  K
481     AGTCAGGGCA TTGGCAATTA TTTAGCCTGG TATCAGCAGA AACCAGGGCA GCCTCCTAAG
        TCAGTCCCGT AACCGTTAAT AAATCGGACC ATAGTCGTCT TTGGTCCCGT CGGAGGATTC
```

Fig. 8 (cont.)

```
              M   L   I   Y   W   A   S   I   R   E   S   G   V   P   D   R   F   S   G   S
541          ATGCTCATTT ACTGGGCATC AATCCGGGAA TCCGGGGTCC CTGACCGATT CAGTGGCAGC
             TACGAGTAAA TGACCCGTAG TTAGGCCCTT AGGCCCCAGG GACTGGCTAA GTCACCGTCG
                                  VL-CDR2

G   S   G   T   D   F   T   L   T   I   S   S   L   Q   A   E   D   V   A   V
601          GGGTCTGGGA CAGACTTCAC TCTCACCATC AGCAGCCTGC AGGCTGAAGA TGTGGCAGTT
             CCCAGACCCT GTCTGAAGTG AGAGTGGTAG TCGTCGGACG TCCGACTTCT ACACCGTCAA

Y   Y   C   Q   Q   Y   S   N   P   Q   T   F   G   Q   G   T   K   V   E
661          TACTACTGTC AGCAATATTA TAGTAATCCT CAGACGTTCG GCCAAGGGAC CAAGGTGGAA
             ATGATGACAG TCGTTATAAT ATCATTAGGA GTCTGCAAGC CGGTTCCCTG GTTCCACCTT
                              VL-CDR3

I   K
721          ATCAAA
             TAGTTT
```

Fig. 8 (cont.)

3-190

```
      E  L  Q  L  V  E  W      G  A  G      L  L  K  P  S  E  T      L  S  L
  1   GAGCTGCAGC TGGTCGAGTG GGGCGCAGGA CTGTTGAAGC CTTCGGAGAC CCTGTCCCTC
      CTCGACGTCG ACCAGCTCAC CCCGCGTCCT GACAACTTCG GAAGCCTCTG GGACAGGAG

T  C  A  V  Y  G  G      S  F  S      G  Y  Y  W  S      W  I  R  Q  P
 61   ACCTGCGCTG TCTATGGTGG GTCCTTCAGT GGTTACTACT GGAGCTGGAT CCGCCAGCCC
      TGGACGCGAC AGATACCACC CAGGAAGTCA CCAATGATGA CCTCGACCTA GGCGGTCGGG
                                        ┌─────────────────────────────
                                        │         VH-CDR1
                                        └─────────────────────────────

P  G  K  G  L  E  W      I  G  E      I  N  H  S  G  S  T      N  Y  N
121   CCAGGGAAGG GGCTGGAGTG GATTGGGGAA ATCAATCATA GTGGAAGCAC CAACTACAAC
      GGTCCCTTCC CCGACCTCAC CTAACCCCTT TAGTTAGTAT CACCTTCGTG GTTGATGTTG
      ──────────────────────────────────────────────────────────────────
                                                    VH-CDR2

P  S  L  K  S  R  V      T  I  S      V  D  T  S  K  N  Q      F  S  L
181   CCGTCCCTCA AGAGTCGAGT CACCATATCA GTAGACACGT CCAAGAACCA GTTCTCCCTG
      GGCAGGGAGT TCTCAGCTCA GTGGTATAGT CATCTGTGCA GGTTCTTGGT CAAGAGGAC
                                ──────
```

Fig. 9

```
              K   L   S   S   V   T   A       A   D   T       A   V   Y   Y   C   A   R       G   R   G
241   AAGCTGAGCT CTGTGACCGC CGCGGACACG GCTGTGTATT ACTGTGCGAG AGGCCGAGGC
      TTCGACTCGA GACACTGGCG GCGCCTGTGC CGACACATAA TGACACGCTC TCCGGCTCCG

VH-CDR3
              R   F   L   G   W   L   L       G   G   S       N   W   F   D   P   W   G       Q   G   T
301   CGATTTTTGG GGTGGTTATT AGGGGGCTCC AACTGGTTCG ACCCCTGGGG CCAGGGAACC
      GCTAAAAACC CCACCAATAA TCCCCGAGG  TTGACCAAGC TGGGGACCCC GGTCCCTTGG

L   V   T   V   S   S   G       G   G   G       S   G   G   G   G   S   G       G   G   G
361   CTGGTCACCG TCTCCTCAGG TGGTGGCGGT TCTGGCGGCG GCGGCTCCGG TGGTGGTGGT
      GACCAGTGGC AGAGGAGTCC ACCACCGCCA AGACCGCCGC CGCCGAGGCC ACCACCACCA

S   E   L   V   M   T   Q       S   P   S       S   L   S   A   S   V   G       D   R   V
421   TCTGAGCTCG TGATGACCCA GTCTCCATCC TCCCTGTCTG CATCTGTAGG AGACAGAGTC
      AGACTCGAGC ACTACTGGGT CAGAGGTAGG GAGGACAGAC GTAGACATCC TCTGTCTCAG

VL-CDR1
              T   I   T   C   R   A   S       Q   G   I       S   N   Y   L   N   W   Y       Q   Q   K
481   ACCATCACTT GCCGGGCGAG TCAGGGCATT AGCAATTATT TAAATTGGTA TCAGCAGAAA
      TGGTAGTGAA CGGCCCGCTC AGTCCCGTAA ATTTAACCAT AGTCGTCTTT
```

Fig. 9 (cont.)

```
              P   G   K   A   P   K   L   L   I   Y   D   A   S   N   L   E   T   G   V   P
541           CCAGGGAAAG CCCCTAAGCT CCTGATCTAC GATGCATCCA ATTTGGAAAC AGGGGTCCCA
              GGTCCCTTTC GGGGATTCGA GGACTAGATG CTACGTAGGT TAAACCTTTG TCCCCAGGGT
                                                └──────────VL-CDR2──────────┘

S   R   F   S   G   S   G   S   G   T   D   F   T   L   T   I   S   S   L   Q
601           TCAAGGTTCA GTGGCAGTGG ATCTGGGACA GATTTCACTC TCACCATCAG CAGTCTGCAA
              AGTTCCAAGT CACCGTCACC TAGACCCTGT CTAAAGTGAG AGTGGTAGTC GTCAGACGTT

P   E   D   F   A   T   Y   Y   C   Q   Q   S   Y   S   T   P   Y   T   F   G
661           CCTGAAGATT TTGCAACTTA CTACTGTCAA CAGAGTTACA GTACCCCGTA CACTTTTGGC
              GGACTTCTAA AACGTTGAAT GATGACAGTT GTCTCAATGT CATGGGGCAT GTGAAAACCG
                                             └──────────VL-CDR3──────────┘

Q   G   T   K   V   D   I   K
721           CAGGGGACCA AAGTGGATAT CAAA
              GTCCCCTGGT TTCACCTATA GTTT
```

Fig. 9 (cont.)

3-271

```
      E   L   Q   L   V   E   W   G   A   G       L   L   K   P   S   E   T       L   S   L
  1   GAGCTGCAGC TGGTCGAGTG GGGCGCAGGA            CTGTTGAAGC CTTCGGAGAC            CCTGTCCCTC
      CTCGACGTCG ACCAGCTCAC CCCGCGTCCT            GACAACTTCG GAAGCCTCTG            GGACAGGAG

T   C   A   V   Y   G   G       S   F   S         G   Y   Y   W   S       W   I   R   Q   P
 61   ACCTGCGCTG TCTATGGTGG GTCCTTCAGT            GGTTACTACT GGAGCTGGAT            CCGCCAGCCC
      TGGACGCGAC AGATACCACC CAGGAAGTCA            CCAATGATGA CCTCGACCTA            GGCGGTCGGG

┌──VH-CDR1──┐
                                                                        ┌──VH-CDR2
      P   G   K   G   L   E   W       I   G   E       I   N   H   S   G   S   T       N   Y   N
121   CCAGGGAAGG GGCTGGAGTG GATTGGGGAA            ATCAATCACA GTGGAAGCAC            CAACTACAAC
      GGTCCCTTCC CCGACCTCAC CTAACCCCTT            TAGTTAGTGT CACCTTCGTG            GTTGATGTTG
                                                                                                VH-CDR2┘

P   S   L   K   S   R   V       T   I   S:  V   D   T   S       K   N   Q       F   S   L
181   CCGTCCCTCA AGAGTCGAGT CACCATATCA            GTAGACACGT CCAAGAACCA            GTTCTCCCTG
      GGCAGGGAGT TCTCAGCTCA GTGGTATAGT            CATCTGTGCA GGTTCTTGGT            CAAGAGGGAC
```

Fig. 10

```
           K  L  S  S  V  T  A  A  D  T  A  V  Y  Y  C  A  R    G  P  D
241     AAGCTGAGCT CTGTGACCGC CGCGGACACG GCTGTGTATT ACTGTGCGAG AGGCCCTGAC
        TTCGACTCGA GACACTGGCG GCGCCTGTGC CGACACATAA TGACACGCTC TCCGGGACTG

VH-CDR3
           R  M  G  H  G  F  D  I  W  G  Q  G  T  M  V  T  V    S  S  G
301     CGAATGGGGC ATGGTTTTGA TATCTGGGGC CAAGGGACAA TGGTCACCGT CTCCTCAGGT
        GCTTACCCCG TACCAAAACT ATAGACCCCG GTTCCCTGTT ACCAGTGGCA GAGGAGTCCA

G  G  G  S  G  G  G  G  S  G  G  G  S  E  L  Q    M  T  Q
361     GGTGGTGGTT CTGGCGGCGG CGGCTCCGGT GGTGGTGGTT CTGAGCTCCA GATGACCCAG
        CCACCACCAA GACCGCCGCC GCCGAGGCCA CCACCACCAA GACTCGAGGT CTACTGGGTC

S  P  S  S  L  S  A  S  V  G  D  R  V  T  I  T  C    R  A  S
421     TCTCCATCCT CCCTGTCTGC ATCTGTAGGA GACAGAGTCA CCATCACTTG CCGGGCAAGT
        AGAGGTAGGA GGGACAGACG TAGACATCCT CTGTCTCAGT GGTAGTGAAC GGCCCGTTCA

VL-CDR1
           Q  S  I  S  S  Y  L  N  W  Y  Q  Q  K  S  G  K  A  P  K  L
481     CAGAGCATTA GCAGCTATTT AAATTGGTAT CAGCAGAAAT CAGGGAAAGC CCCTAAGCTC
        GTCTCGTAAT CGTCGATAAA TTTAACCATA GTCGTCTTTA GTCCCTTTCG GGGATTCGAG
```

Fig. 10 (cont.)

|     |       |       | VL-CDR2 |       |       |       |       |       |       |       |
|-----|-------|-------|---------|-------|-------|-------|-------|-------|-------|-------|
|     | L     | I     | Y       | A     | A     | S     | S     | L     | Q     | S     | G     | V     | P     | S     | R     | F     | S     | G     | S     | G     |
| 541 | CTGATCTATG | CTGCATCCAG | TTTGCAAAGT | GGGGTCCCAT | CAAGGTTCAG | TGGCAGTGGA |
|     | GACTAGATAC | GACGTAGGTC | AAACGTTTCA | CCCCAGGGTA | GTTCCAAGTC | ACCGTCACCT |

|     | S     | G     | T     | D     | F     | T     | L     | T     | I     | S     | S     | L     | Q     | P     | E     | D     | F     | A     | T     | Y     |
|-----|-------|-------|-------|-------|-------|-------|-------|-------|-------|-------|-------|-------|-------|-------|-------|-------|-------|-------|-------|-------|
| 601 | TCTGGGACAG | ATTTCACTCT | CACCATCAGT | AGTCTGCAAC | CTGAAGATTT | TGCAACTTAT |
|     | AGACCCTGTC | TAAAGTGAGA | GTGGTAGTCA | TCAGACGTTG | GACTTCTAAA | ACGTTGAATA |

|     |       |       |       | VL-CDR3 |       |       |       |       |       |       |
|-----|-------|-------|-------|---------|-------|-------|-------|-------|-------|-------|
|     | Y     | C     | Q     | Q       | S     | Y     | S     | S     | P     | W     | T     | F     | G     | Q     | G     | T     | K     | V     | E     | I     |
| 661 | TACTGTCAAC | AGAGTTACAG | TAGCCCGTGG | ACATTCGGCC | AAGGACCAA | GGTGGAGATC |
|     | ATGACAGTTG | TCTCAATGTC | ATCGGGCACC | TGTAAGCCGG | TTCCCTGGTT | CCACCTCTAG |

|     | K   |
|-----|-----|
| 721 | AAA |
|     | TTT |

Fig. 10 (cont.)

3-550

```
     E   L   Q   L   V   E   S           G   P   G           L   V   K   P   S   Q   T           L   S   L
  1  GAGCTGCAGC TGGTCGAGTC CCTCGAAGC CCTCGCAGAC CCTCTCACTC
     CTCGACGTCG ACCAGCTCAG GGAGCGTTCG GGAGCGTCTG GGAGAGTGAG

T   C   A   I   S   G   D           S   V   S           ┌─────────────VH-CDR1─────────────┐
                                                             │ S   N   S   A   A   W   N           W   I   R │
 61  ACCTGTGCCA TCTCCGGGGA CAGTGTCTCT                        │AGCAACAGTG CTGCTTGGAA              │CTGGATCAGG
     TGGACACGGT AGAGGCCCCT GTCACAGAGA                        │TCGTTGTCAC GACGAACCTT              │GACCTAGTCC
                                                             └──────────────────────────────────┘

Q   S   P   S   R   G   L           E   W   L           G   R   T   Y   Y   R   S           ┌──VH-CDR2──┐
                                                                                                  │ K   W   Y │
                                                                                                  │CAAGTGGTAT │
121  CAGTCCCCAT CGAGAGGCCT TGAGTGGCTG GGAAGGACAT ACTACAGGTC │CAAGTGGTAT
     GTCAGGGGTA GCTCTCCGGA ACTCACCGAC CCTTCCTGTA TGATGTCCAG │GTTCACCATA
                                                             └───────────┘

┌──────────N   D   Y   A   V   S   V   K   S   R──────────┐  I   T   I   N   P   D   T           S   K   N
     │                                                          │
181  │AATGATTATG CAGTATCTGT GAAAAGTCGA                          │ATAACCATCA ACCCAGACAC ATCCAAGAAC
     │TTACTAATAC GTCATAGACA CTTTTCAGCT                          │TATTGGTAGT TGGGTCTGTG TAGGTTCTTG
     └──────────────────────────────────────────────────────────┘
```

Fig. 11

```
       Q   F   S   L   Q   L   N   S   V   T   P   E   D   T   A   V   Y   Y   C   A
241    CAGTTCTCCC TGCAGCTGAA CTCTGTGACT CCCGAGGACA CGGCTGTGTA TTACTGTGCA
       GTCAAGAGGG ACGTCGACTT GAGACACTGA GGGCTCCTGT GCCGACACAT AATGACACGT
                                                                    VH-CDR3
       R   D   R   R   I   A   A   R   Q       Y   Y   G   M   D   V   W   G   Q   G
301    AGAGATCGTC GACGTATAGC AGCTCGTCAA TACTACGGTA TGGACGTCTG GGGCCAAGGG
       TCTCTAGCAG CTGCATATCG TCGAGCAGTT ATGATGCCAT ACCTGCAGAC CCCGGTTCCC

T   T   V   T   V   S   S   G   G   G   G   S   G   G   G   G   S   G   G   G
361    ACCACGGTCA CCGTCTCCTC AGGTGGTGGT GGTTCTGGCG GCGGCGGCTC CGGTGGTGGT
       TGGTGCCAGT GGCAGAGGAG TCCACCACCA CCAAGACCGC CGCCGCCGAG GCCACCACCA

G   S   E   L   V   L   T   Q   S   P   G   T   L   S   L   S   P   G   E   R
421    GGTTCTGAGC TCGTGTTGAC ACAGTCTCCA GGCACCCTGT CTTTGTCTCC AGGGGAAAGA
       CCAAGACTCG AGCACAACTG TGTCAGAGGT CCGTGGGACA GAAACAGAGG TCCCCTTTCT
                                  VL-CDR1
       A   T   L   S   C   R   A   S   Q   S   V   S   S   N   Y   L   A   W   Y   Q
481    GCCACCCTCT CCTGCAGGGC AAGTCAGAGT GTTAGCAGCA ACTACTTAGC CTGGTACCAG
       CGGTGGGAGA GGACGTCCCG TTCAGTCTCA CAATCGTCGT TGATGAATCG GACCATGGTC
```

Fig. 11 (cont.)

```
            Q   K   P   G   Q   A   P   R   L   L   I   Y   G   A   S   S   R   A   T   G
541         CAGAAACCTG GCCAGGCTCC CAGGCTCCTC CAGGCTCCTC ATCTATGGTG CATCCAGCAG GGCCACTGGC
            GTCTTTGGAC CGGTCCGAGG GTCCGAGGAG GTCCGAGGAG TAGATACCAC GTAGGTCGTC CCGGTGACCG
                                                                    └─ VL-CDR2 ─┘

I   P   D   R   F   S   G   S   G   S   G   T   D   F   T   L   T   I   S   S
601         ATCCCAGACA GGTTCAGTGG CAGCGGGTCT GGGACAGATT TCACTCTCAC CATCAGCAGC
            TAGGGTCTGT CCAAGTCACC GTCGCCCAGA CCCTGTCTAA AGTGAGAGTG GTAGTCGTCG

L   Q   P   E   D   V   A   T   Y   Y   C   Q   K   Y   N   S   A   P   L   T
661         CTGCAGCCTG AAGATGTTGC AACTTATTAC TGTCAAAAGT ATAACAGTGC CCCTCTCACT
            GACGTCGGAC TTCTACAACG TTGAATAATG ACAGTTTCA TATTGTCACG GGGAGAGTGA
                                                        └─ VL-CDR3 ─┘

F   G   G   G   T   K   V   E   I   K
721         TTCGGGCGGAG GGACCAAGGT GGAAATCAAA
            AAGCCCGCCTC CCTGGTTCCA CCTTTAGTTT
```

Fig. 11 (cont.)

4-10

```
      E  L  Q  L  V  E  S  G  G  G  L  V  Q  P  G  G  S  L  R  L
  1   GAGCTGCAGC TGGTCGAGTC TGGGGGAGGC TTGGTACAGC CTGGGGGGTC CCTGAGACTC
      CTCGACGTCG ACCAGCTCAG ACCCCCTCCG AACCATGTCG GACCCCCCAG GGACTCTGAG

S  C  A  A  S  G  F  T  F  S    S  Y  A  M  G    W  V  R  Q  A
 61   TCCTGTGCAG CCTCTGGATT CACCTTTAGC AGCTATGCCA TGGGCTGGGT CCGCCAGGCT
      AGGACACGTC GGAGACCTAA GTGGAAATCG TCGATACGGT ACCCGACCCA GGCGGTCCGA
                                      └─── VH-CDR1 ───┘

P  G  K  G  L  E  W  V  S  A  V  S  G  S  G  G  S    T  Y  Y
121   CCAGGGAAGG GGCTGGAGTG GGTCTCAGCT GTTAGTGGTA GTGGTGGTAG CACATACTAC
      GGTCCCTTCC CCGACCTCAC CCAGAGTCGA CAATCACCAT CACCACCATC GTGTATGATG
                                                                └─ VH-CDR2

A  D  S  V  K  G  R    F  T  I  S  R  D  N  S  K  N    T  L  Y
181   GCAGACTCCG TGAAGGGCCG GTTCACCATC TCCAGAGACA ATTCCAAGAA CACGCTGTAT
      CGTCTGAGGC ACTTCCCGGC CAAGTGGTAG AGGTCTCTGT TAAGGTTCTT GTGCGACATA
```

Fig. 12

```
              L  Q  M  N  S  L  R     A  E  D     T  A  V  Y  Y  C  A
241      CTGCAAATGA ACAGCCTGAG AGCCGAGGAC ACGGCCGTAT ATTACTGTGC
         GACGTTTACT TGTCGGACTC TCGGCTCCTG TGCCGGCATA TAATGACACG

┌VH-CDR3─────────────────────────────────────────────────┐
             F  L  G  H     Y  Y  G  M  D  V     W  G  Q  G     T  T  V
301      TTCCTGGGCC ACTACTACGG TATGGACGTC TGGGGCCAAG GAACCACGGT
         AAGGACCCGG TGATGATGCC ATACCTGCAG ACCCCGGTTC CTTGGTGCCA

S  G  G  G  S     G  G  G  G     S  G  G  G  S     E
361      TCAGGTGGTG GTGGTTCTGG CGGCGGCGGC GCCGCCGCCG GCTCCGAGATG
         AGTCCACCAC CACCAAGACC GCCGCCGCCG CGGCGGCGGC CGAGGTCTAC

T  Q  S  P  S  S  L     S  A  S     V  G  D  R  V  T  I
421      ACCCAGTCTC CATCCTCCCT GTCTGCATCT GTAGGAGACA GAGTCACCAT
         TGGGTCAGAG GTAGGAGGGA CAGACGTAGA CATCCTCTGT CTCAGTGGTA

┌VL-CDR1──────────────────────────────┐
             A  S     Q  S  I  S  S     Y  L  N     W  Y  Q  Q     K  P
481      GCAAGTCAGA GCATTAGCAG CTATTTAAAT TGGTATCAGC AGAAACCAGG
         CGTTCAGTCT CGTAATCGTC GATAAATTTA ACCATAGTCG TCTTTGGTCC
```

Fig. 12 (cont.)

```
                    ┌──────────────────────────────────────────────────────┐
        K  L  L  I  Y │ A  A  S  S  L  Q │ S  G  V  P  S  R  F  S  G
541     AAGCTCCTGA TCTATGCTGC ATCCAGTTTG CAAAGTGGAG TCCCATCAAG GTTCAGCGGC
        TTCGAGGACT AGATACGACG TAGGTCAAAC GTTTCACCTC AGGGTAGTTC CAAGTCGCCG
                    │      VL-CDR2       │

S  G  S  G  T  E  F  T  L  T  I  S  S  L  Q  P  E  D  F  A
601     AGTGGGATCTG GGACAGAGTT CACTCTCACA ATCAGCAGCC TGCAGCCTGA AGATTTTGCA
        TCACCCTAGAC CCTGTCTCAA GTGAGAGTGT TAGTCGTCGG ACGTCGGACT TCTAAAACGT

┌──────────────────────────────────┐
        T  Y  Y  C │ L  Q  H  N  A  Y  P  Y  T │ F  G  Q  G  T  K  V
661     ACTTATTACT GTCTTCAGCA TAATGCTTAC CCGTACACTT TCGGCCAGGG GACCAAGGTG
        TGAATAATGA CAGAAGTCGT ATTACGAATG GGCATGTGAA AGCCGGTCCC CTGGTTCCAC
                    │            VL-CDR3           │

E  I  K
721     GAAATCAAA
        CTTTAGTTT
```

Fig. 12 (cont.)

4-48

```
      E   L   Q   L   V   E   S       G   P   V       L   V   K   P       T   D   T       L   T   L
  1   GAGCTGCAGC TGGTCGAGTC TGGTCCTGTG CTGGTGAAAC CCACAGATAC CCTCACGCTG
      CTCGACGTCG ACCAGCTCAG ACCAGGACAC GACCACTTTG GGTGTCTATG GGAGTGCGAC

VH-CDR1
      T   C   T   V   S   G   F       S   L   N       N   P   R   M   G   V   S       W   I   R
 61   ACTTGCACCG TCTCTGGGTT CTCACTCAAT AATCCTAGAA TGGGTGTGAG CTGGATCCGT
      TGAACGTGGC AGAGACCCAA GAGTGAGTTA TTAGGATCTT ACCCACACTC GACCTAGGCA

VH-CDR2
      Q   P   P   G   K   T   L       E   W   L   A       H   I   F   P   S   D       A   K   A
121   CAGCCCCCAG GAAGACCCT GGAGTGGCTT GCACACATTT TTCCGAGTGA CGCAAAAGCC
      GTCGGGGGTC CCTTCTGGGA CCTCACCGAA CGTGTGTAAA AAGGCTCACT GCGTTTTCGG

H   S   A   S   L   K   S       R   L   T       I   S   K   D       T   S   K       S   Q   V
181   CACAGTGCAT CTCTGAAGAG CAGGCTCACC ATCTCCAAGG ACACCTCCAA AAGCCAGGTG
      GTGTCACGTA GAGACTTCTC GTCCGAGTGG TAGAGGTTCC TGTGGAGGTT TTCGGTCCAC
```

Fig. 13

```
              V  P  T  M  T  N  M  D  P  V  D  T  A  T  Y  Y  C  A  R  I
241           GTCCCTACCA TGACCAACAT GGACCCTGTG GACACAGCCA CATATTACTG TGCACGGATA
              CAGGGATGGT ACTGGTTGTA CCTGGGACAC CTGTGTCGGT GTATAATGAC ACGTGCCTAT

VH-CDR3
              L  G  E  Y  P  P  A  W  F  D  P  W  G  Q  G  T  L  V  T
301           TTGGGGGAAT ACTATCCCCC AGCCTGGTTC GACCCCTGGG GCCAGGGAAC CCTGGTCACC
              AACCCCCTTA TGATAGGGGG TCGGACCAAG CTGGGGACCC CGGTCCCTTG GGACCAGTGG

V  S  S  G  G  G  G  S  G  G  G  G  S  G  G  G  G  S  E  L
361           GTCTCCTCAG GTGGTGGTGG TTCTGGCGGC GGCGGCTCCG GTGGTGGTGG CACCGAGCTC
              CAGAGGAGTC CACCACCACC AAGACCGCCG CCGCCGAGGC CACCACCACC GTGGCTCGAG

V  M  T  Q  S  P  D  S  L  A  V  S  L  G  E  R  A  T  I  N
421           GTGATGACAC AGTCTCCAGA CTCCCTGGCT GTGTCTCTGG GCGAGAGGGC CACCATCAAC
              CACTACTGTG TCAGAGGTCT GAGGGACCGA CACAGAGACC CGCTCTCCCG GTGGTAGTTG

VL-CDR1
              C  K  S  S  Q  S  V  L  Y  S  S  N  N  K  N  Y  L  A  W  Y
481           TGCAAGTCCA GCCAGAGTGT TTTATACAGC TCCAACAATA AGAACTACTT AGCTTGGTAC
              ACGTTCAGGT CGGTCTCACA AAATATGTCG AGGTTGTTAT TCTTGATGAA TCGAACCATG
```

Fig. 13 (cont.)

```
          Q  Q  K  P  G  Q  P  P  K  L  L  I  Y  W  A  S  T  R  E  S
541  CAGCAGAAAC CAGGACAGCC TCCTAAGCTG CTCATTTACT GGGCATCTAC CCGGGAATCC
     GTCGTCTTTG GTCCTGTCGG AGGATTCGAC GAGTAAATGA CCCGTAGATG GGCCCTTAGG
                                                 └─VL-CDR2─────────────┘

G  V  P  D  R  F  S  G  S  G  S  G  T  D  F  T  L  T  I  S
601  GGGGTCCCTG ACCGATTCAG TGGCAGCGGG TCTGGGACAG ATTTCACTCT CACCATCAGC
     CCCCAGGGAC TGGCTAAGTC ACCGTCGCCC AGACCCTGTC TAAAGTGAGA GTGGTAGTCG

┌─VL-CDR3
          S  L  Q  A  E  D  V  A  V  Y  Y  C  Q  Q  Y  L  K  I  P  Y
661  AGCCTGCAGG CTGAAGACGT GGCAGTTTAT TACTGTCAGC AATATTTGAA AATCCCTTAT
     TCGGACGTCC GACTTCTGCA CCGTCAAATA ATGACAGTCG TTATAAACTT TTAGGGAATA

T  F  G  Q  G  T  K  V  E  I  K
721  ACTTTTGGCC AGGGGACCAA GGTGGAGATC AAA
     TGAAAACCGG TCCCCTGGTT CCACCTCTAG TTT
     ────────┘
```

Fig. 13 (cont.)

Figure 16:
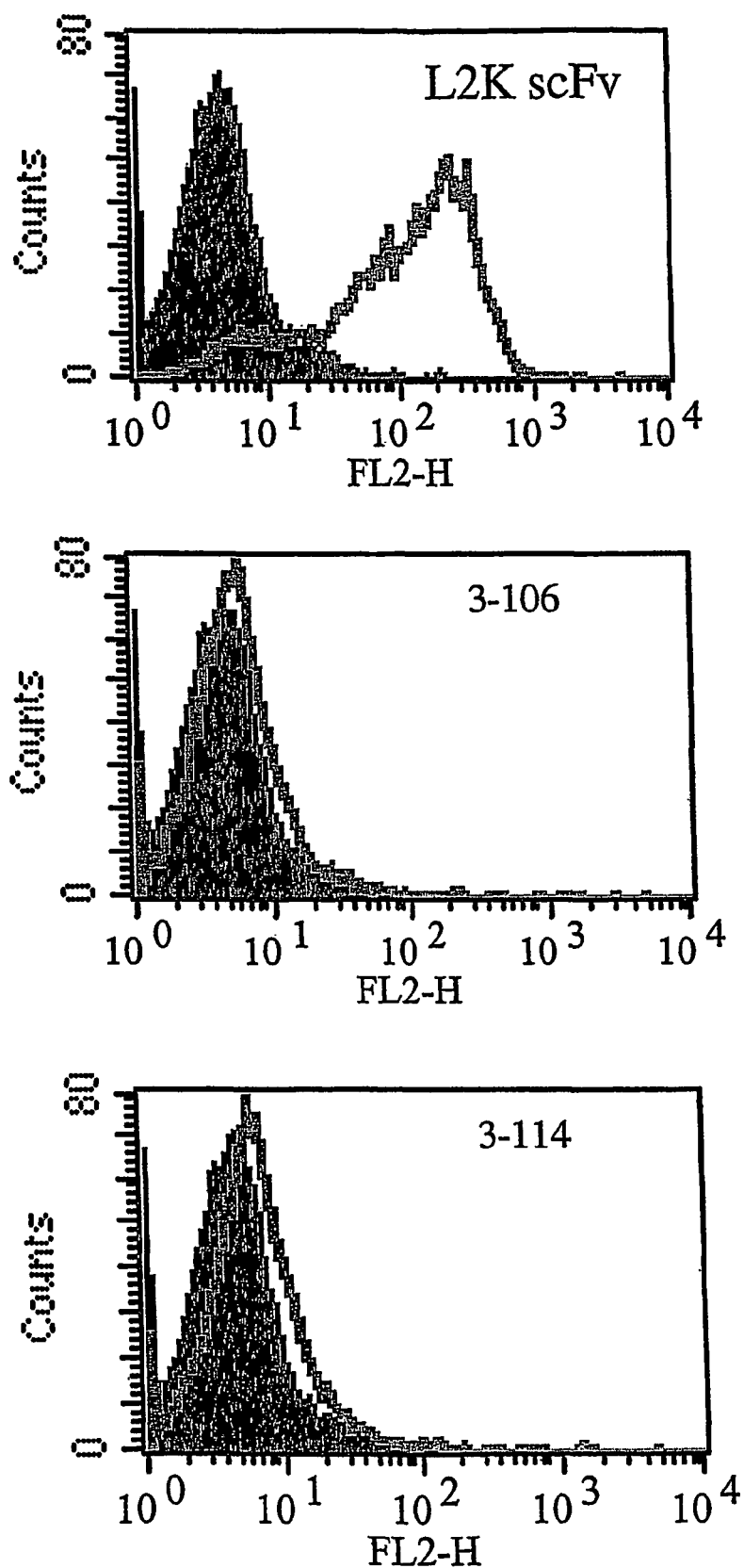

Fig. 16 (cont.)   Jurkat
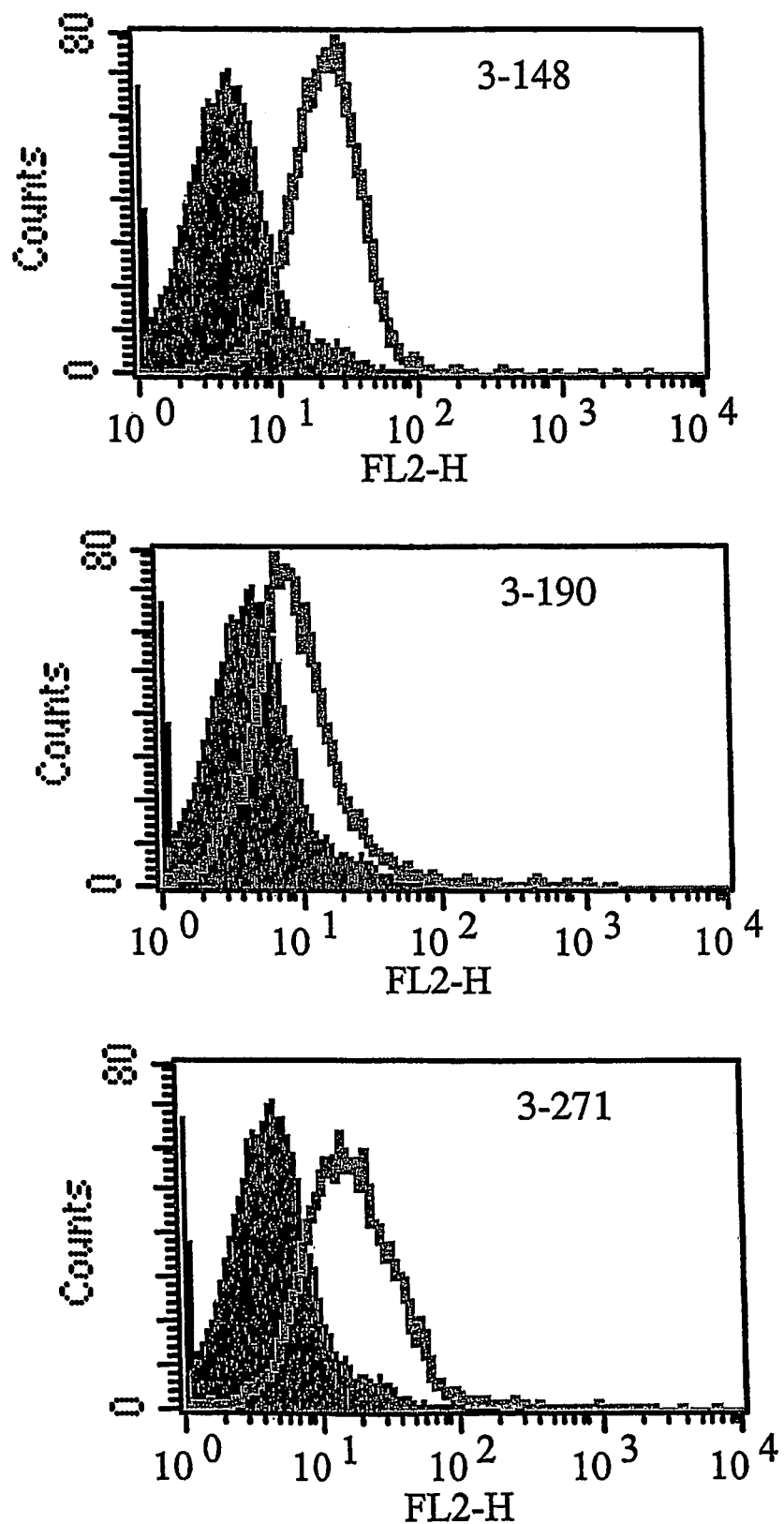

Fig. 16 (cont.) Jurkat
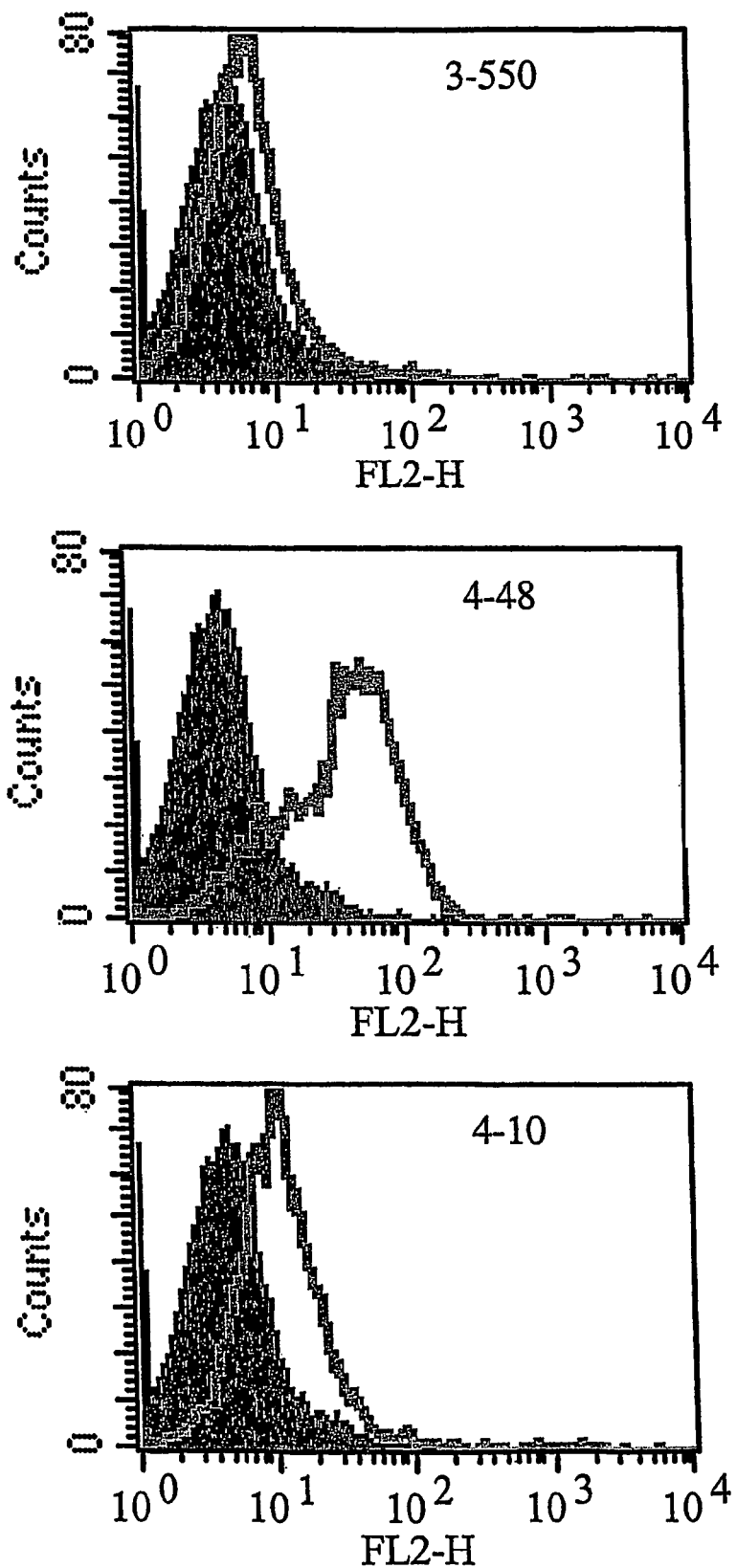

Fig. 16 (cont.) Jurkat
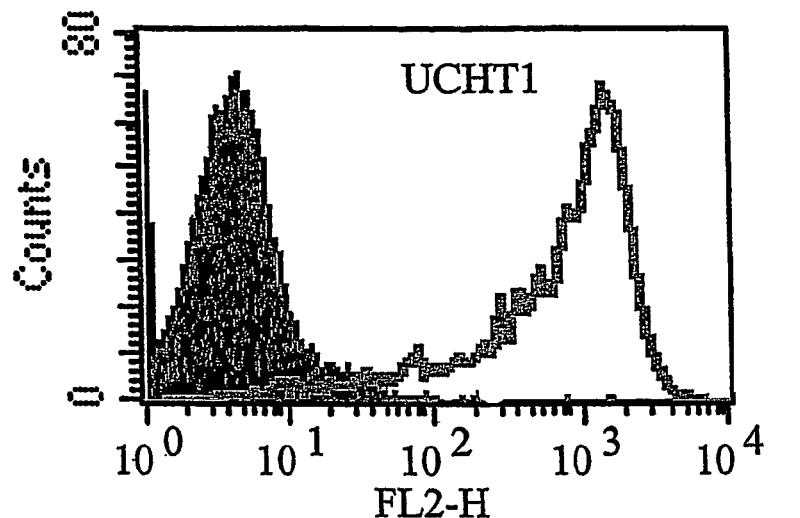
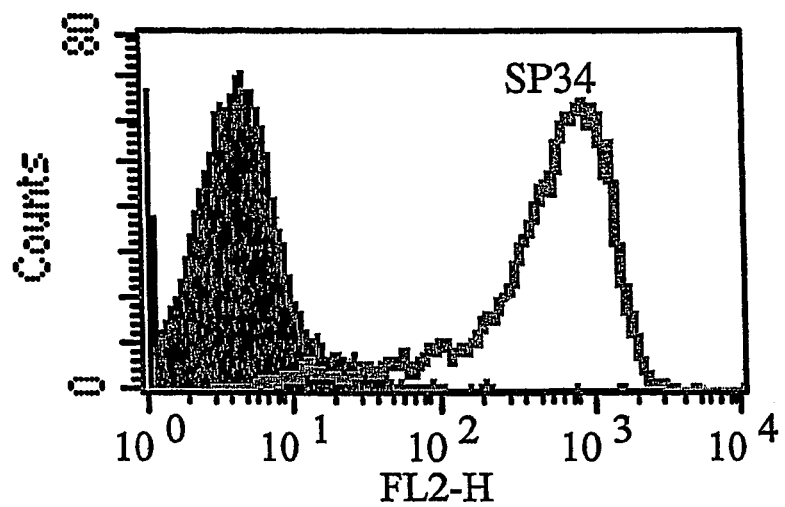
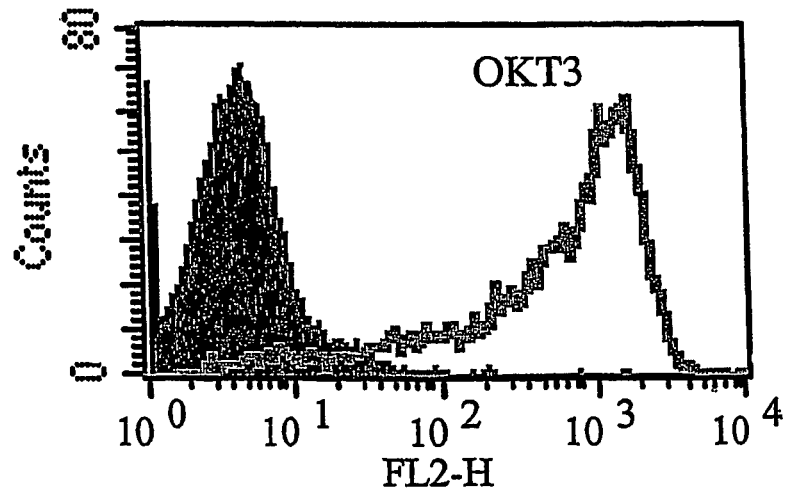

Figure 17:
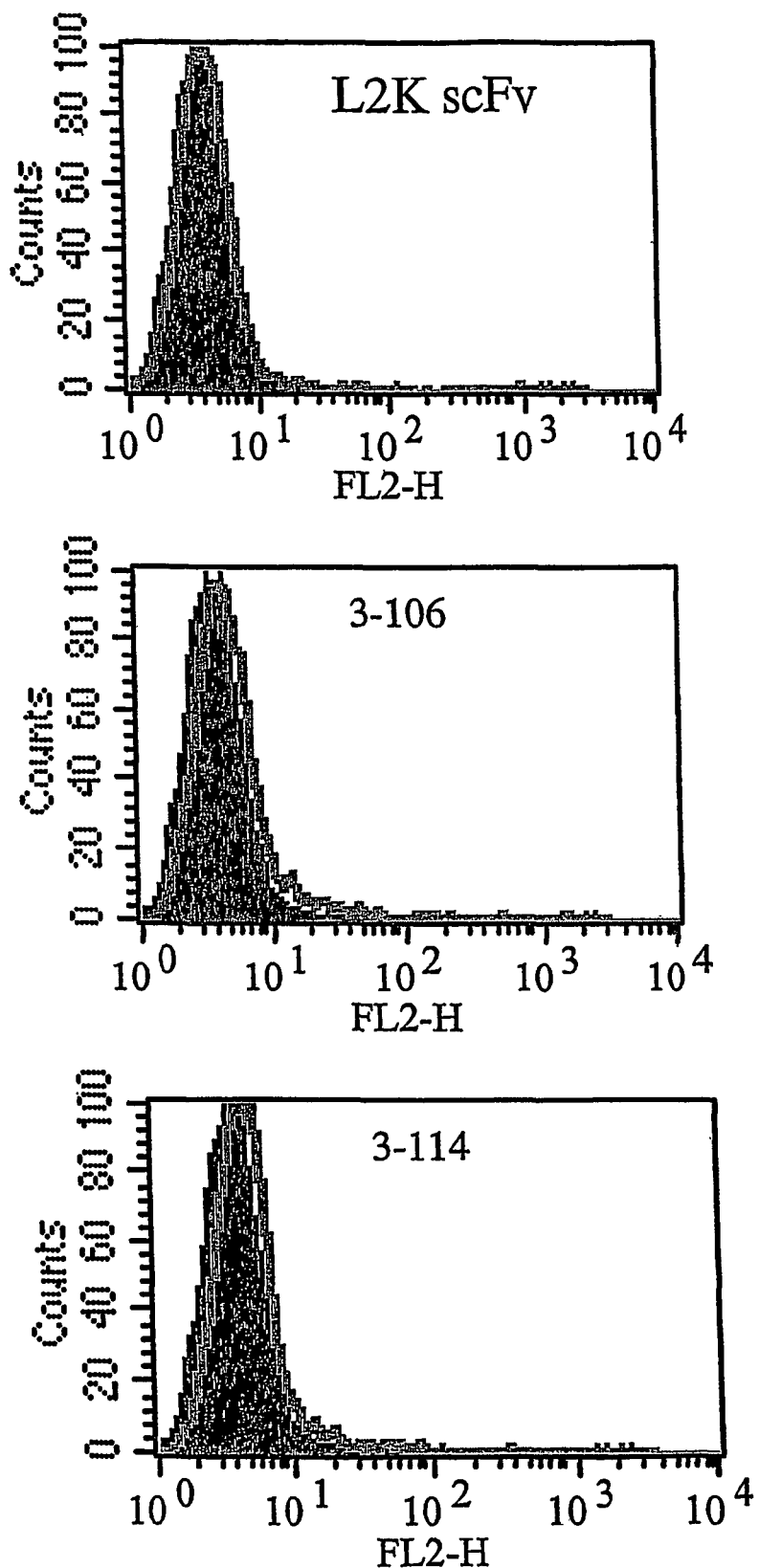

Fig. 17 (cont.)  CHO
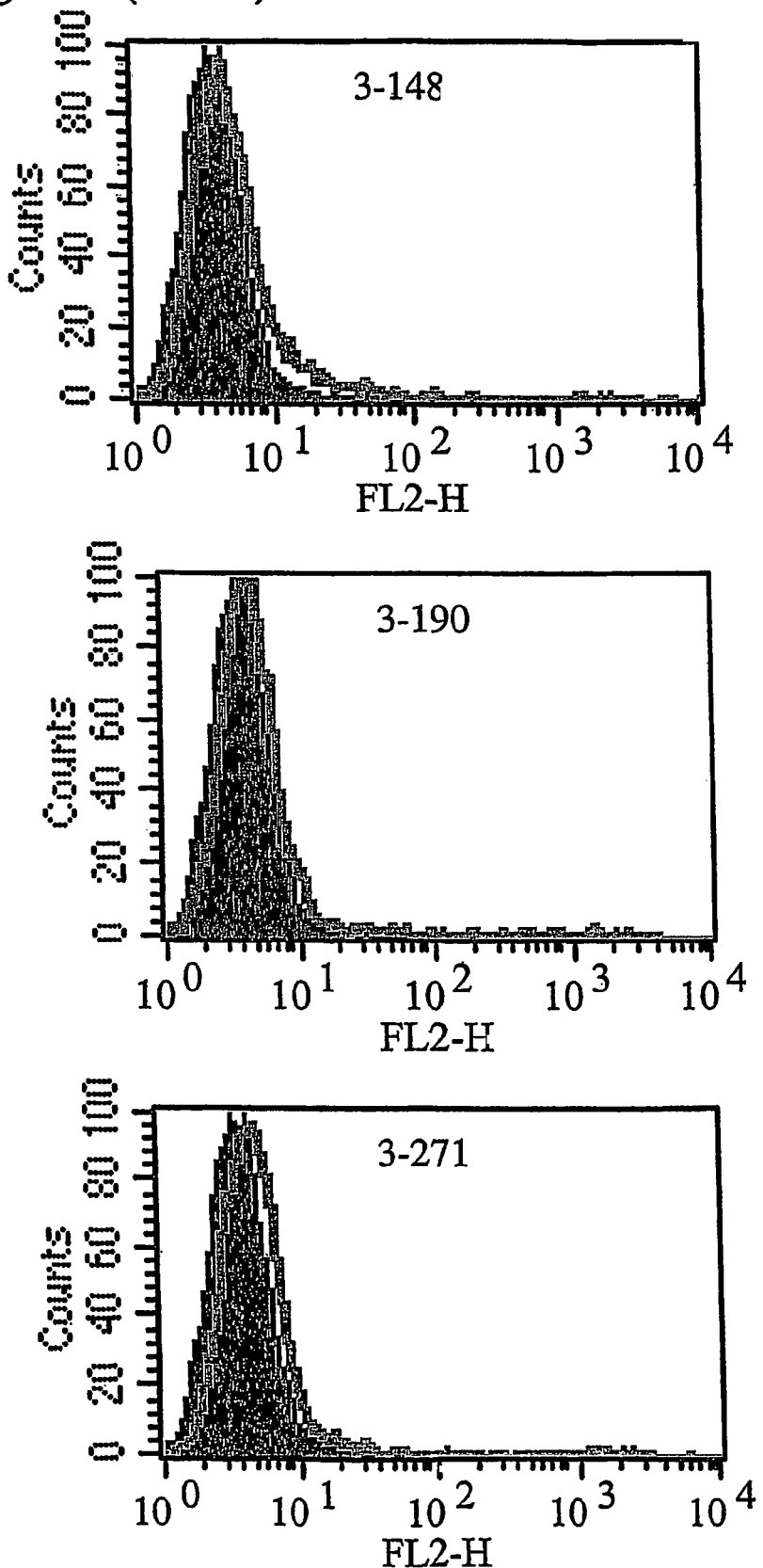

Fig. 17 (cont.) CHO
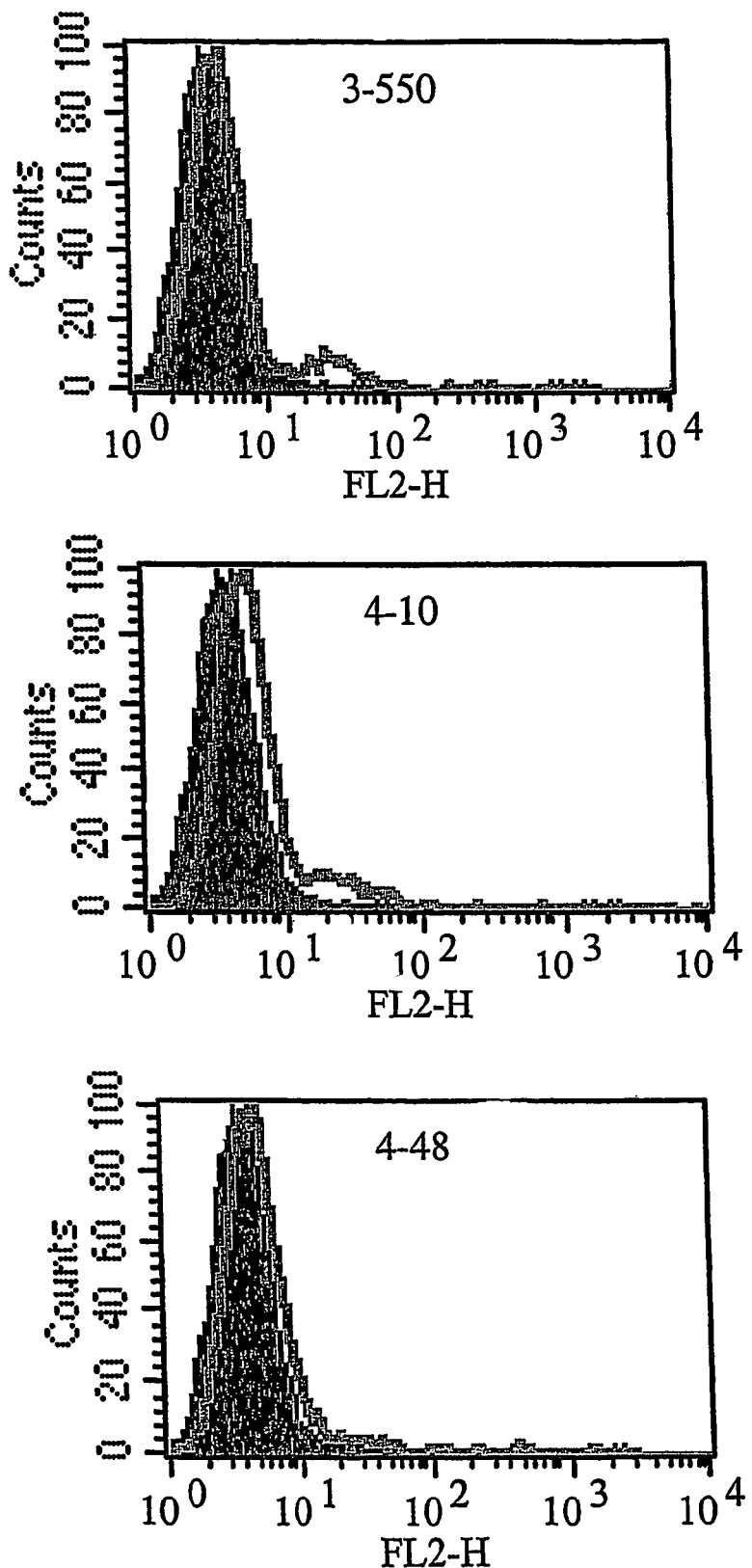

Fig. 17 (cont.) CHO
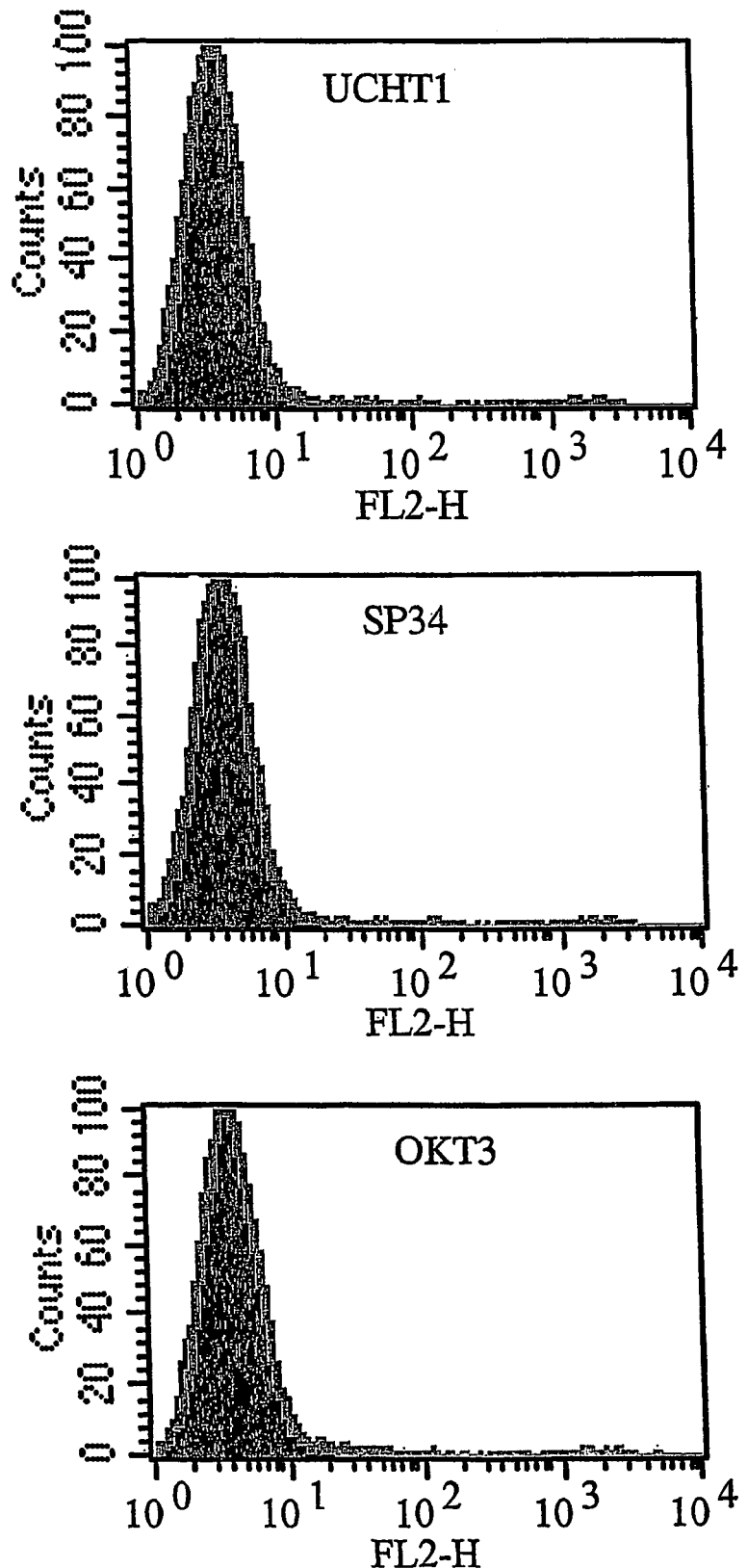

Figure 18:
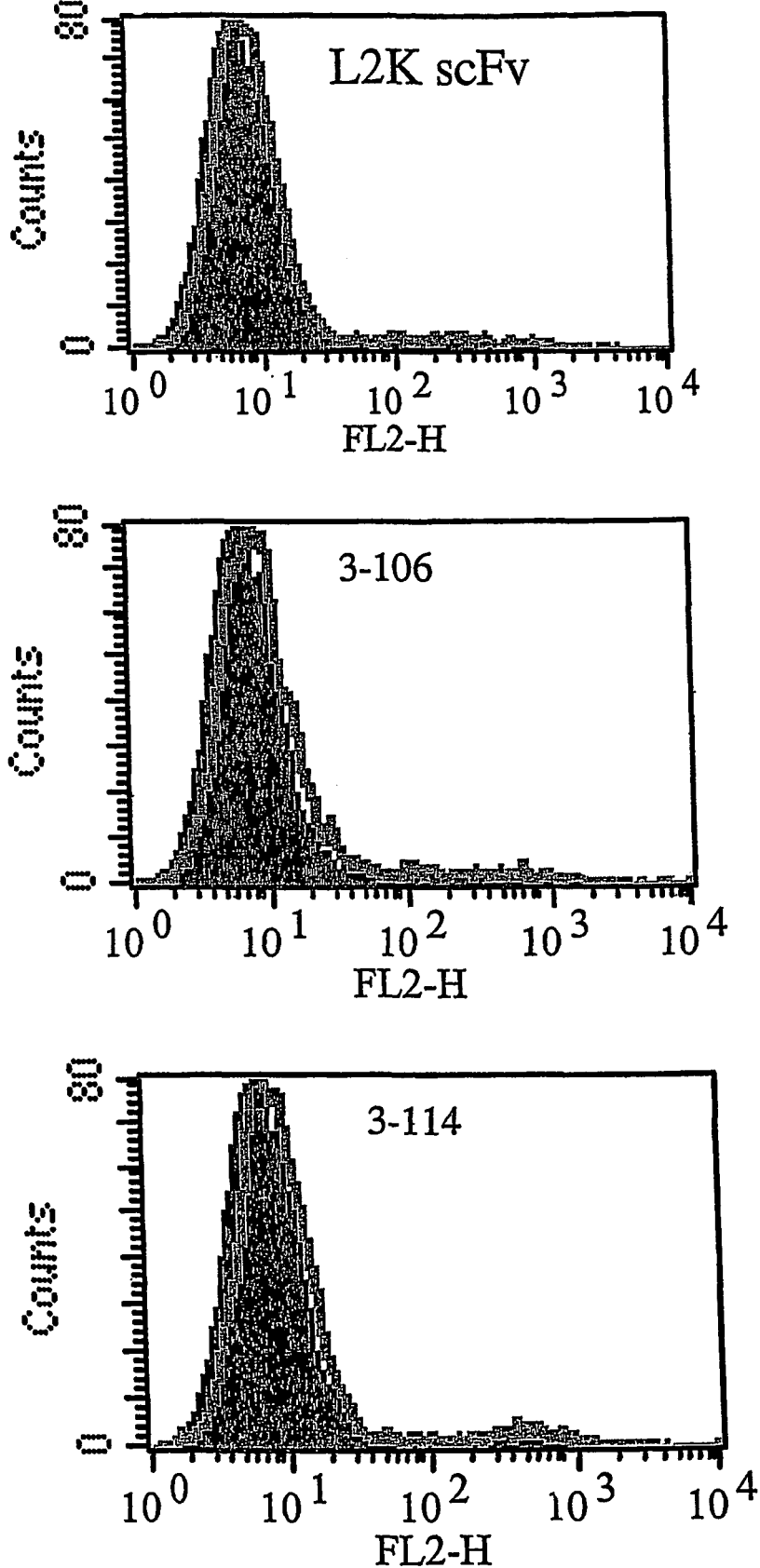

Fig. 18 (cont.)  KatoIII
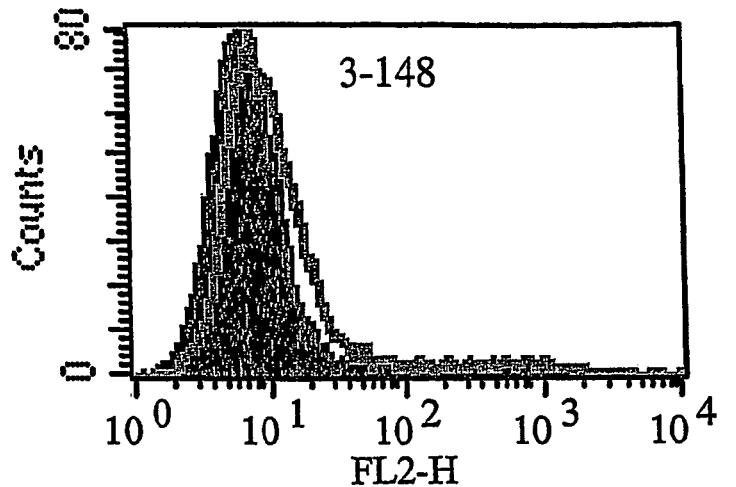
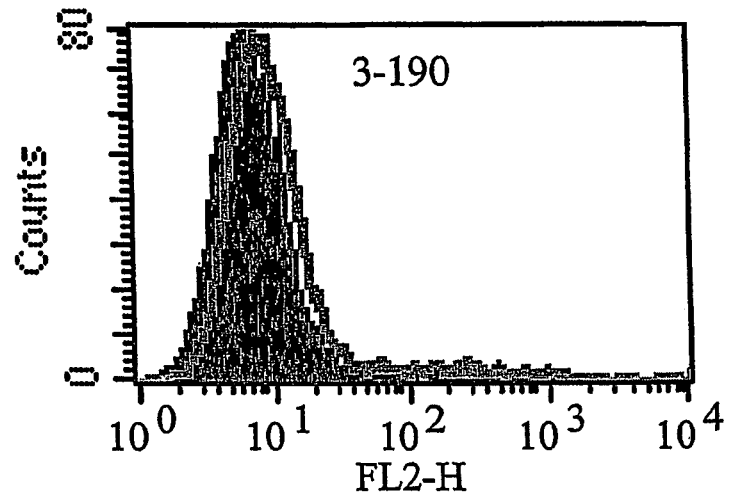
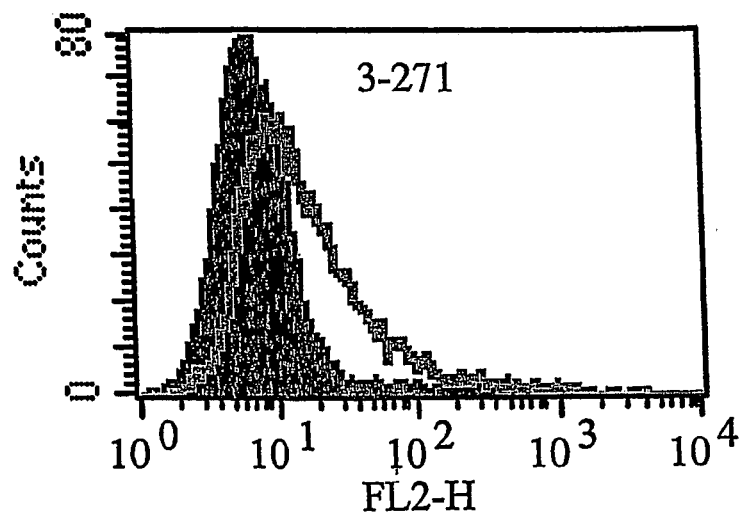

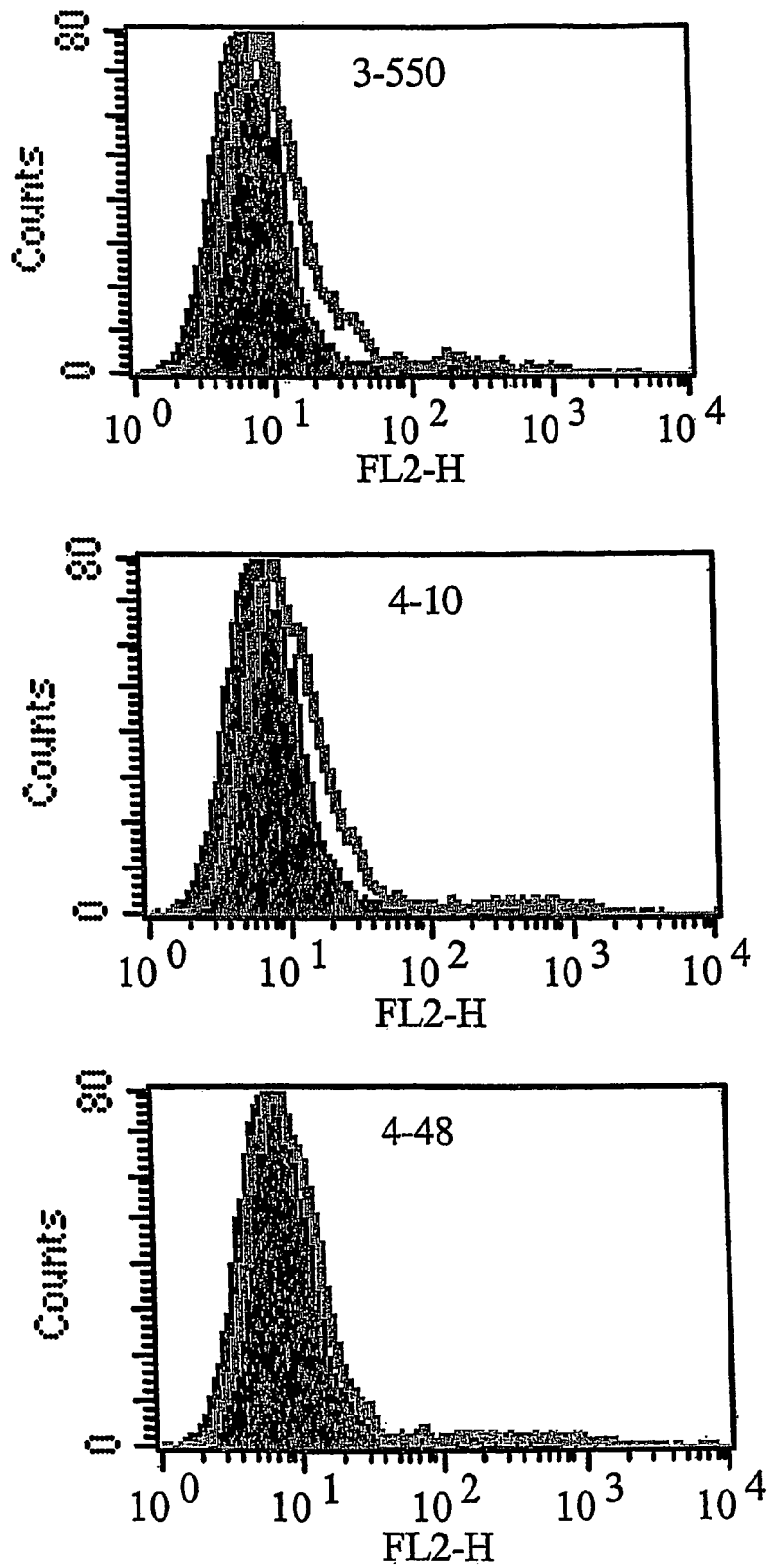
Fig. 18 (cont.)   KatoIII

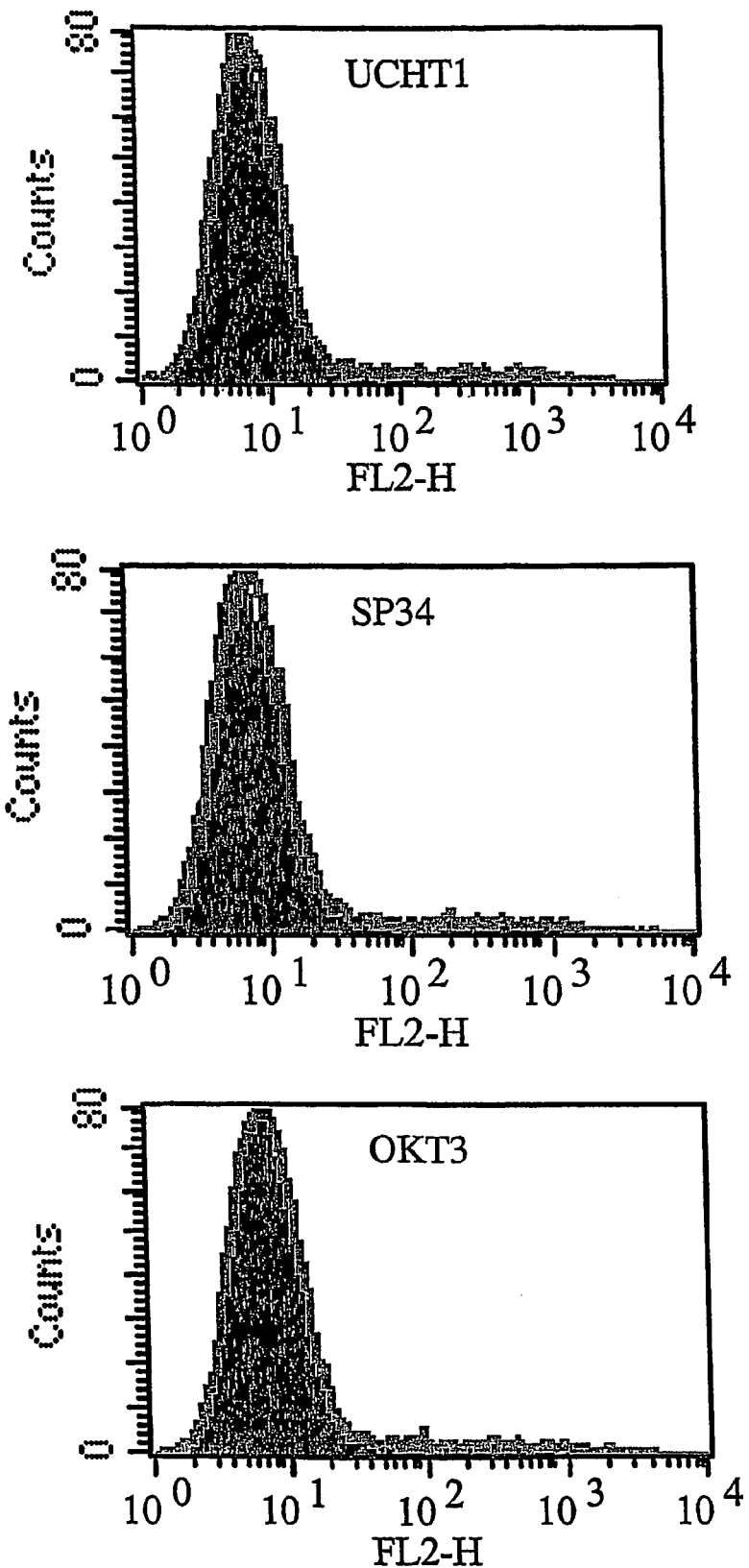
Fig. 18(cont.) KatoIII

Fig. 19    Jurkat
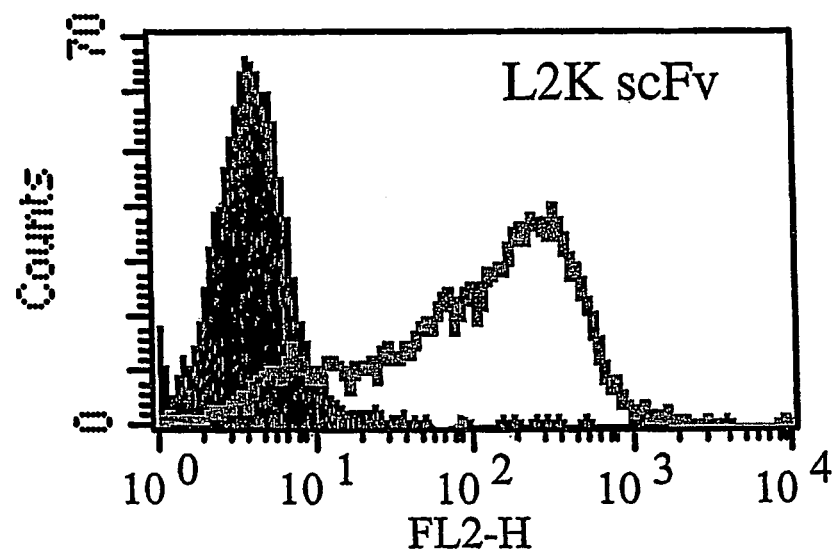
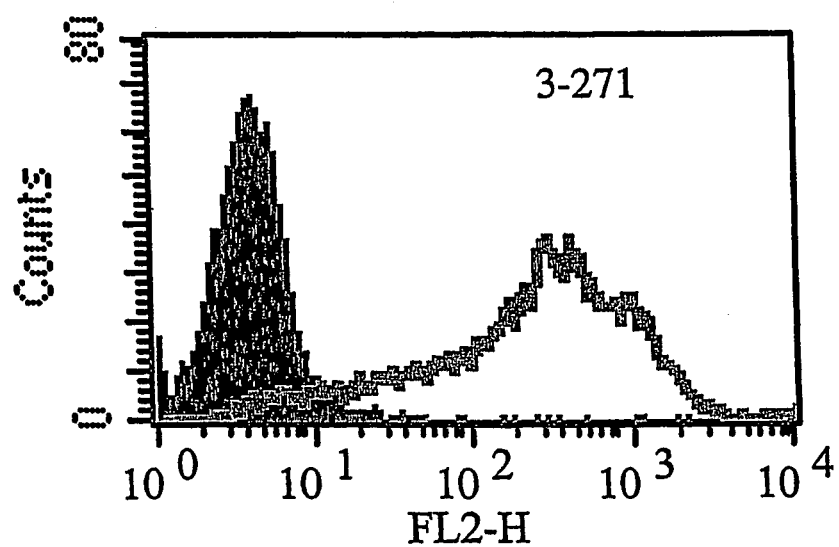

Fig. 19 (cont.) Jurkat
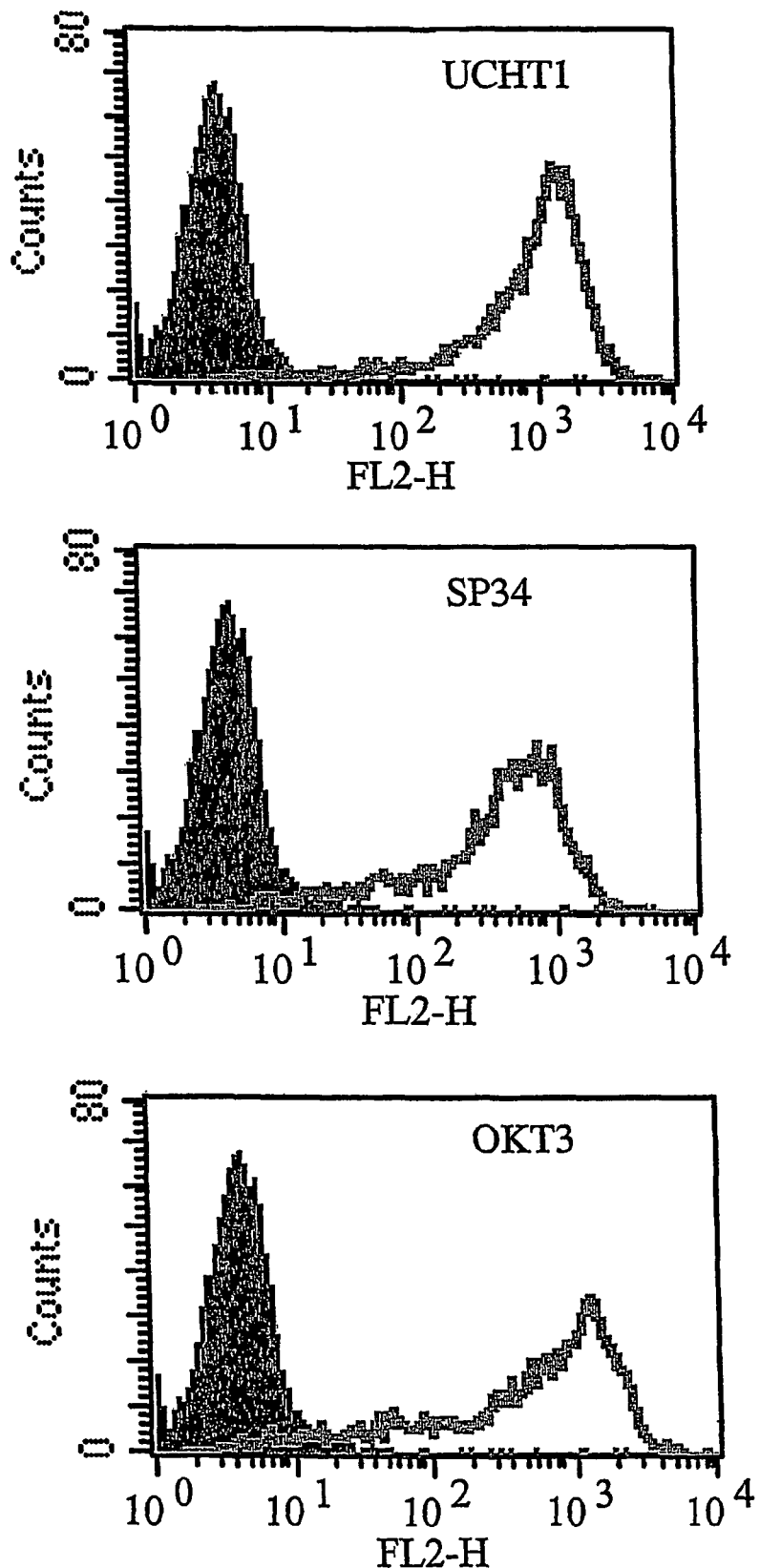

Fig. 20    CHO
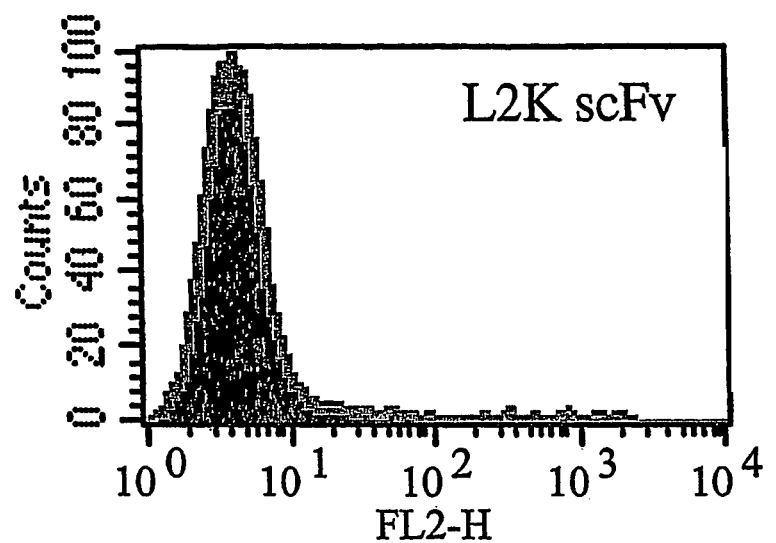
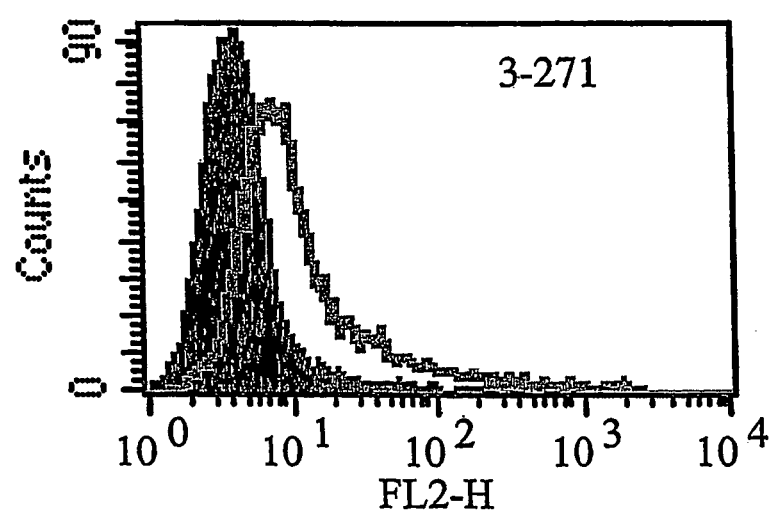

Fig. 20 (cont.) CHO
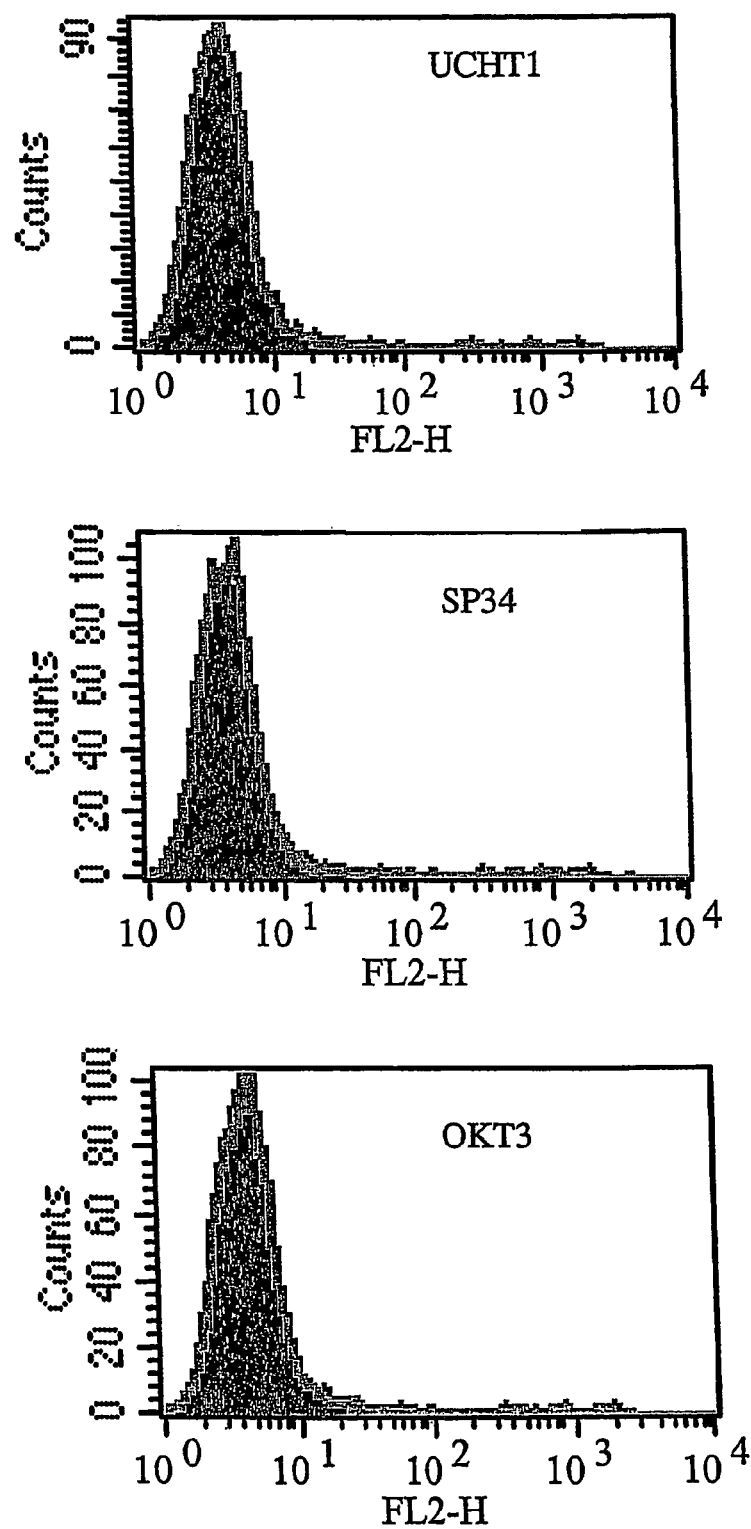

Fig. 21     CHO/CD3e-g
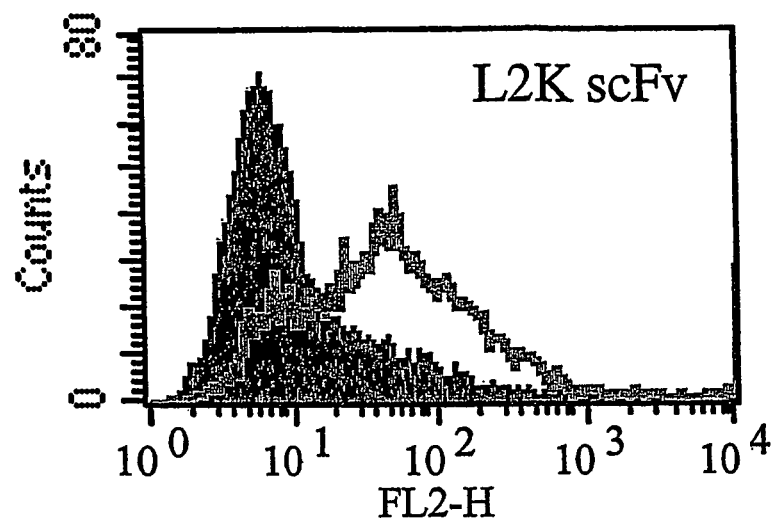
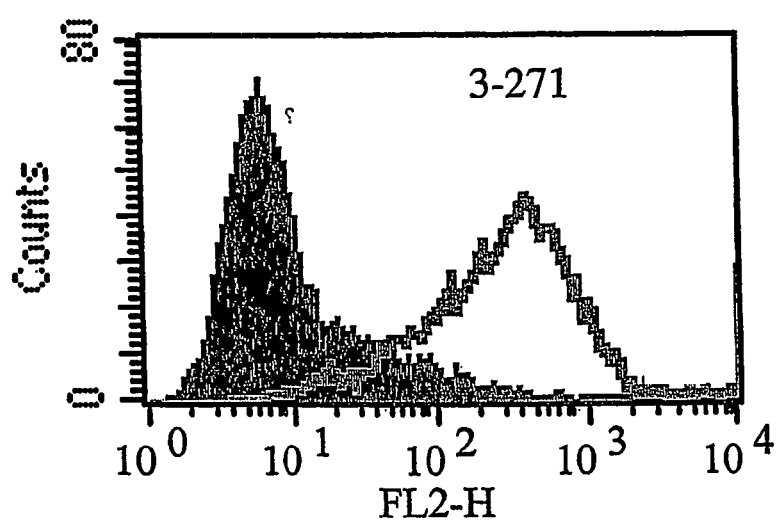

Fig. 21 (cont.) CHO/CD3e-g
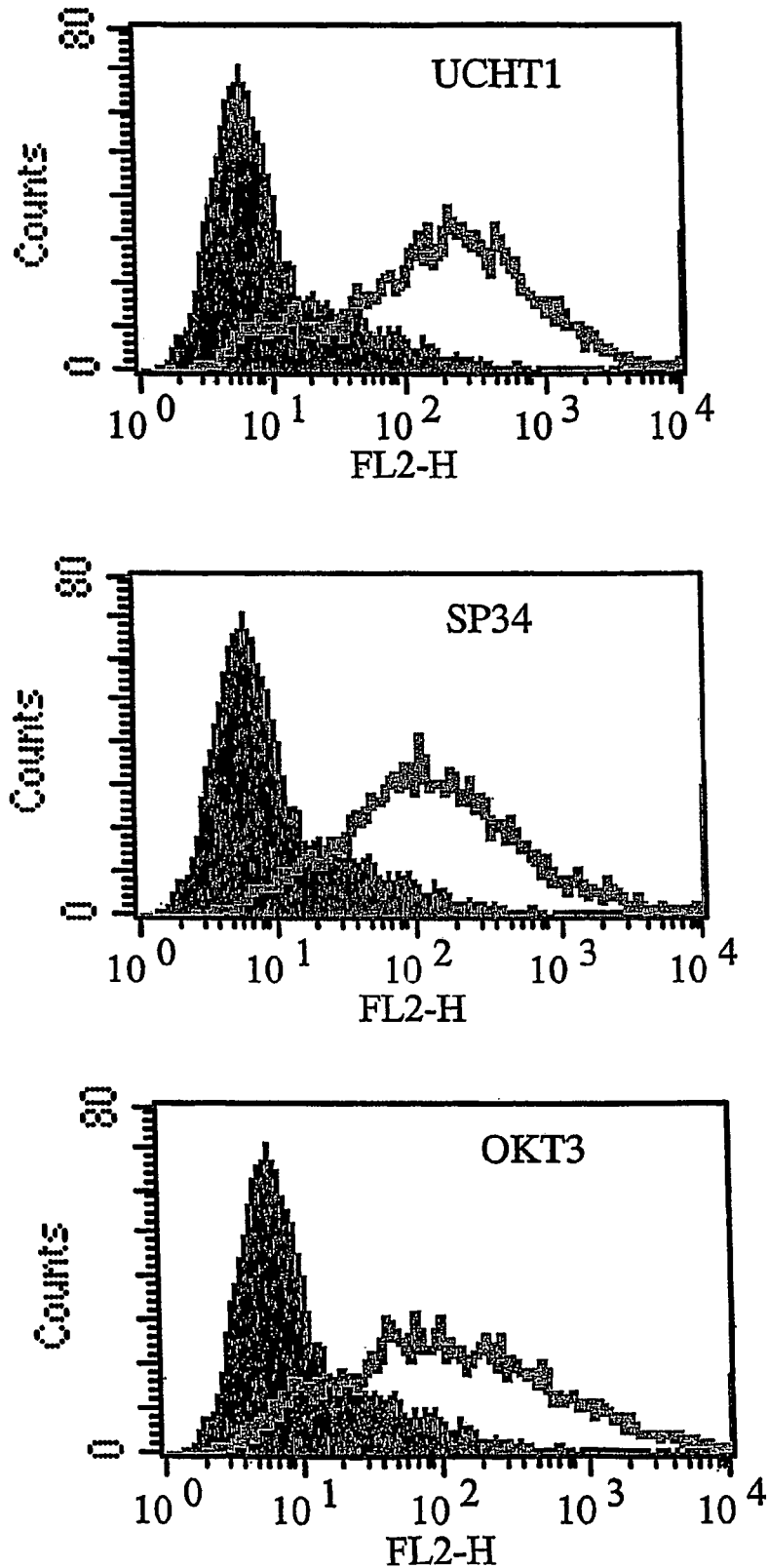

EpCAM 5-10

```
      E   V   Q   L   L   E   Q   S   G   A   E   L   V   R   P   G   T   S   V   K
  1   GAGGTGCAGC TGCTCGAGCA GTCTGGAGCT GAGCTGGTAA GGCCTGGGAC TTCAGTGAAG
      CTCCACGTCG ACGAGCTCGT CAGACCTCGA CTCGACCATT CCGGACCCTG AAGTCACTTC

I   S   C   K   A   S   G   Y   A   F   T   N   Y   W   L   G   W   V   K   Q
 61   ATATCCTGCA AGGCTTCTGG ATACGCCTTC ACTAACTACT GGCTAGGTTG GGTAAAGCAG
      TATAGGACGT TCCGAAGACC TATGCGGAAG TGATTGATGA CCGATCCAAC CCATTTCGTC

R   P   G   H   G   L   E   W   I   G   D   I   F   P   G   S   G   N   I   H
121   AGGCCTGGAC ATGGACTTGA GTGGATTGGA GATATTTTCC CTGGAAGTGG TAATATCCAC
      TCCGGACCTG TACCTGAACT CACCTAACCT CTATAAAAGG GACCTTCACC ATTATAGGTG

Y   N   E   K   F   K   G   K   A   T   L   T   A   D   K   S   S   S   T   A
181   TACAATGAGA AGTTCAAGGG CAAAGCCACA CTGACTGCAG ACAAATCTTC GAGCACAGCC
      ATGTTACTCT TCAAGTTCCC GTTTCGGTGT GACTGACGTC TGTTTAGAAG CTCGTGTCGG
```

Fig. 22

```
           Y  M  Q  L  S  S  L     T  F  E     D  S  A  V  Y  F  C     A  R  L
241        TATATGCAGC TCAGTAGCCT   GACATTTGAG  GACTCTGCTG TCTATTTCTG   TGCAAGACTG
           ATATACGTCG AGTCATCGGA   CTGTAAACTC  CTGAGACGAC AGATAAAGAC   ACGTTCTGAC

R  N  W  D  E  P  M     D  Y  W     G  Q  G  T  T  V  T     V  S  S
301        AGGAACTGGG ACGAGCCTAT   GGACTACTGG  GGCCAAGGGA CCACGGTCAC   CGTCTCCTCA
           TCCTTGACCC TGCTCGGATA   CCTGATGACC  CCGGTTCCCT GGTGCCAGTG   GCAGAGGAGT

G  G  G  G  S     G  G  G  G     S  G  G  G  G  S     E  L  V  M  T
361        GGTGGTGGTG GTTCTGGCGG   CGGCGGCTCC  GGTGGTGGTG GTTCTGAGCT   CGTGATGACA
           CCACCACCAC CAAGACCGCC   GCCGCCGAGG  CCACCACCAC CAAGACTCGA   GCACTACTGT

Q  S  P  S  S  L  T     V  T  A     G  E  K  V  T  M  S     C  K  S
421        CAGTCTCCAT CCTCCCTGAC   TGTGACAGCA  GGAGAGAAGG TCACTATGAG   CTGCAAGTCC
           GTCAGAGGTA GGAGGGACTG   ACACTGTCGT  CCTCTCTTCC AGTGATACTC   GACGTTCAGG

S  Q  S  L  L  N  S     G  N  Q     K  N  Y  L  T  W  Y     Q  Q  K
481        AGTCAGAGTC TGTTAAACAG   TGGAAATCAA  AAGAACTACT TGACCTGGTA   CCAGCAGAAA
           TCAGTCTCAG ACAATTTGTC   ACCTTTAGTT  TTCTTGATGA ACTGGACCAT   GGTCGTCTTT
```

Fig. 22 (cont.)

```
         P  G  Q  P  P  K  L  L  I  Y  W  A  S  T  R  E  S     G  V  P
541   CCAGGGCAGC CTCCTAAACT GTTGATCTAC TGGGCATCCA CTAGGGAATC TGGGGTCCCT
      GGTCCCGTCG GAGGATTTGA CAACTAGATG ACCCGTAGGT GATCCCTTAG ACCCCAGGGA

D  R  F  T  G  S  G     S  G  T     D  F  T  L  T  I  S  S  V  Q
601   GATCGCTTCA CAGGCAGTGG ATCTGGAACA GATTTCACTC TCACCATCAG CAGTGTGCAG
      CTAGCGAAGT GTCCGTCACC TAGACCTTGT CTAAAGTGAG AGTGGTAGTC GTCACACGTC

A  E  D  L  A  V  Y  Y  C  Q     N  D  Y  S     Y  P  L  T  F  G
661   GCTGAAGACC TGGCAGTTTA TTACTGTCAG AATGATTATA GTTATCCGCT CACGTTCGGT
      CGACTTCTGG ACCGTCAAAT AATGACAGTC TTACTAATAT CAATAGGCGA GTGCAAGCCA

A  G  T  K  L  E  I  K
721   GCTGGGACCA AGCTTGAGAT CAAA
      CGACCCTGGT TCGAACTCTA GTTT
```

Fig. 22 (cont.)

CD19

```
     Q  V  Q  L  Q  Q  S     G  A  E     L  V  R  P  G  S  S     V  K  I
  1  CAGGTGCAGC TGCAGCAGTC TGGGGCTGAG CTGGTGAGGC CTGGGTCCTC AGTGAAGATT
     GTCCACGTCG ACGTCGTCAG ACCCCGACTC GACCACTCCG GACCCAGGAG TCACTTCTAA

S  C  K  A  S  G  Y     A  F  S     S  Y  W  M  N  W  V     K  Q  R
 61  TCCTGCAAGG CTTCTGGCTA TGCATTCAGT AGCTACTGGA TGAACTGGGT GAAGCAGAGG
     AGGACGTTCC GAAGACCGAT ACGTAAGTCA TCGATGACCT ACTTGACCCA CTTCGTCTCC

P  G  Q  G  L  E  W     I  G  Q     I  W  P  G  D  G  D     T  N  Y
121  CCTGGACAGG GTCTTGAGTG GATTGGACAG ATTTGGCCTG GAGATGGTGA TACTAACTAC
     GGACCTGTCC CAGAACTCAC CTAAACCTGTC TAAACCGGAC CTCTACCACT ATGATTGATG

N  G  K  F  K  G  K     A  T  L     T  A  D  E  S  S  S     T  A  Y
181  AATGGAAAGT TCAAGGGTAA AGCCACTCTG ACTGCAGACG AATCCTCCAG CACAGCCTAC
     TTACCTTTCA AGTTCCCATT TCGGTGAGAC TGACGTCTGC TTAGGAGGTC GTGTCGGATG
```

Fig. 23

```
      M  Q  L  S    L  A      S  E  D      S  A  V  Y    F  C  A      R  R  E
241   ATGCAACTCA GCAGCCTAGC ATCTGAGGAC TCTGCGGTCT ATTTCTGTGC AAGACGGGAG
      TACGTTGAGT CGTCGGATCG TAGACTCCTG AGACGCCAGA TAAAGACACG TTCTGCCCTC

T  T  T  V    G  R  Y    Y  A      M  D  Y  W    G  Q  G      T  T  V
301   ACTACGACGG TAGGCCGTTA TTACTATGCT ATGGACTACT GGGGCCAAGG GACCACGGTC
      TGATGCTGCC ATCCGGCAAT AATGATACGA TACCTGATGA CCCCGGTTCC CTGGTGCCAG

T  V  S  S    G  G  G    G  S      G  G  G  G    S  G  G  G      G  S  D
361   ACCGTCTCCT CCGGTGGTGG GGGCGGGGCT CCGGTGGTGG TGGTTCTGAT
      TGGCAGAGGA GGCCACCACC CCCGCCCCGA GGCCACCACC ACCAAGACTA

I  Q  L  T    Q  S  P    A  S  L    A  V  S  L    G  Q  R      A  T  I
421   ATCCAGCTGA CCCAGTCTCC AGCTTCTTTG GCTGTGTCTC TAGGGCAGAG GGCCACCATC
      TAGGTCGACT GGGTCAGAGG TCGAAGAAAC CGACACAGAG ATCCCGTCTC CCGGTGGTAG

S  C  K  A    S  Q  S    V  D  Y    D  G  D  S    Y  L  N      W  Y  Q
481   TCCTGCAAGG CCAGCCAAAG TGTTGATTAT GATGGTGATA GTTATTTGAA CTGGTACCAA
      AGGACGTTCC GGTCGGTTTC ACAACTAATA CTACCACTAT CAATAAACTT GACCATGGTT
```

Fig. 23 (cont.)

```
              Q   I   P   G   Q   P   P       K   L   L       I   Y   D   A   S   N   L       V   S   G
    541   CAGATTCCAG GACAGCCACC CAAACTCCTC ATCTATGATG CATCCAATCT AGTTTCTGGG
          GTCTAAGGTC CTGTCGGTGG GTTTGAGGAG TAGATACTAC GTAGGTTAGA TCAAAGACCC

I   P   P   R   F   S   G       S   G   S       G   T   D   F   T   L   N       I   H   P
    601   ATCCCACCCA GGTTTAGTGG CAGTGGGTCT GGGACAGACT TCACCCTCAA CATCCATCCT
          TAGGGTGGGT CCAAATCACC GTCACCCAGA CCCTGTCTGA AGTGGGAGTT GTAGGTAGGA

V   E   K   V   D   A   A       T   Y   H       C   Q   Q   S       T   E   D       P   W   T
    661   GTGGAGAAGG TGGATGCTGC AACCTATCAC TGTCAGCAAA GTACTGAGGA TCCGTGGACG
          CACCTCTTCC ACCTACGACG TTGGATAGTG ACAGTCGTTT CATGACTCCT AGGCACCTGC

F   G   G   G   T   K   L       E   I   K
    721   TTCGGTGGAG GGACCAAGCT CGAGATCAAA
          AAGCCACCTC CCTGGTTCGA GCTCTAGTTT
```

Fig. 23 (cont.)

```
      Q   V   Q   L   R   Q   P   G   A   E   L   V   K   P   G   A   S   V   K   M
  1   CAGGTGCAAC TGCGGCAGCC TGGGGCTGAG CTGGTGAAGC CTGGGGCCTC AGTGAAGATG
      GTCCACGTTG ACGCCGTCGG ACCCCGACTC GACCACTTCG GACCCCGGAG TCACTTCTAC

S   C   K   A   S   G   Y   T   F   T   S   Y   N   M   H   W   V   K   Q   T
 61   TCCTGCAAGG CTTCTGGCTA CACATTTACC AGTTACAATA TGCACTGGGT AAAGCAGACA
      AGGACGTTCC GAAGACCGAT GTGTAAATGG TCAATGTTAT ACGTGACCCA TTTCGTCTGT

P   G   Q   G   L   E   W   I   G   A   I   Y   P   G   N   G   D   T   S   Y
121   CCTGGACAGG GCCTGGAATG GATTGGAGCT ATTTATCCAG GAAATGGTGA TACTTCCTAC
      GGACCTGTCC CGGACCTTAC CTAACCTCGA TAAATAGGTC CTTTACCACT ATGAAGGATG

N   Q   K   F   K   G   K   A   T   L   T   A   D   K   S   S   S   T   A   Y
181   AATCAGAAGT TCAAAGGCAA GGCCACATTG ACTGCAGACA AATCCTCCAG CACAGCCTAC
      TTAGTCTTCA AGTTTCCGTT CCGGTGTAAC TGACGTCTGT TTAGGAGGTC GTGTCGGATG
```

Fig. 24

```
       M   Q   L   S       S   L   T       S   E   D       S   A   V   Y       Y   C   A       R   S   H
241    ATGCAGCTCA GCAGTCTGAC ATCTGAGGAC TCTGCGGTCT ATTACTGTGC AAGATCGCAC
       TACGTCGAGT CGTCAGACTG TAGACTCCTG AGACGCCAGA TAATGACACG TTCTAGCGTG

Y   G   S   N   Y   V   D       Y   F   D       Y   W   G   Q       G   T   L       V   T   V
301    TACGGTAGTA ACTACGTAGA CTACTTTGAC TACTGGGGCC AAGGCACACT AGTCACAGTC
       ATGCCATCAT TGATGCATCT GATGAAACTG ATGACCCCGG TTCCGTGTGA TCAGTGTCAG

S   T   G   G   G   S       G   G   G       G   S   G       G   G   S       Q   I   V
361    TCGACAGGTG GTGGTGGTTC TGGCGGGGGC GGCTCCGGTG GTGGTGCTTC TCAAATTGTT
       AGCTGTCCAC CACCACCAAG ACCGCCCCCG CCGAGGCCAC CACCACCAAG AGTTTAACAA

L   S   Q   S       P   A   I       L   S   A       S   P   G   E       K   V   T       M   T   C
421    CTCTCCCAGT CTCCAGCAAT CCTTTCTGCA TCTCCAGGGG AGAAGGTCAC AATGACTTGC
       GAGAGGGTCA GAGGTCGTTA GGAAAGACGT AGAGGTCCCC TCTTCCAGTG TTACTGAAACG
```

Fig. 24 (cont.)

```
        R   A   S   S       L   S           F   M   H       W   Y   Q   Q       K   P   G       S   S   P
481     AGGGCCAGCT CAAGTTTAAG TTTCATGCAC TGGTACCAGC AGAAGCCAGG ATCCTCCCCC
        TCCCGGTCGA GTTCAAATTC AAAGTACGTG ACCATGGTCG TCTTCGGTCC TAGGAGGGGG

K   P   W   I       Y   A   T       S   N   L       A   S   G   V       P   A   R       F   S   G
541     AAACCCTGGA TTTATGCCAC ATCCAACCTG GCTTCTGGAG TCCCTGCTCG CTTCAGTGGC
        TTTGGGACCT AAATACGGTG TAGGTTGGAC CGAAGACCTC AGGGACGAGC GAAGTCACCG

S   G   S   G       T   S   Y       S   L   T       I   S   R   V       E   A   E       D   A   A
601     AGTGGGTCTG GAACCTCTTA CTCTCTCACA ATCAGCAGAG TGGAGGCTGA AGATGCTGCC
        TCACCCAGAC CCTGGAGAAT GAGAGAGTGT TAGTCGTCTC ACCTCCGACT TCTACGACGG

T   Y   F   C       H   Q   W       S   S   N       P   L   F       G   A   G       T   K   V
661     ACTTATTTCT GCCATCAGTG GAGTAGTAAC CCGCTCACGT TCGGTGCTGG GACAAAGGTG
        TGAATAAAGA CGGTAGTCAC CTCATCATTG GGCGAGTGCA AGCCACGACC CTGTTTCCAC

E   I   K
721     GAAATAAAAA
        CTTTATTTT
```

Fig. 24 (cont.)

```
          Q   L   E   Q   S   G   P       E   L   K   K   P   G   E       T   V   T   I   S   C
  1   CAGCTGGAGC AGTCTGGACC TGAACTGAAG AAGCCTGGAG AGACAGTCAC GATCTCCTGC
      GTCGACCTCG TCAGACCTGG ACTTGACTTC TTCGGACCTC TCTGTCAGTG CTAGAGGACG

K   A   S   G   Y   T   F       T   K   F   G   M   N   W       V   K   Q   A   P   G
 61   AAGGCTTCTG GGTATACCTT CACGAAGTTC GGAATGAACT GGGTGAAGCA GGCTCCAGGA
      TTCCGAAGAC CCATATGGAA GTGCTTCAAG CCTTACTTGA CCCACTTCGT CCGAGGTCCT

K   G   L   K   W   M   G       W   I   H   T   S   T   G       E   P   T   Y   S   D
121   AAGGGTTTAA AGTGGATGGG CTGGATACAC ACCTCCACTG GAGAGCCAAC ATATTCTGAT
      TTCCCAAATT TCACCTACCC GACCTATGTG TGGAGGTGAC CTCTCGGTTG TATAAGACTA

D   F   K   G   R   F   A       F   S   L   E   T   S   A       S   T   A   Y   L   R
181   GACTTCAAGG GACGGGTTGC CTTCTCTTTG GAAACGTCTG CCAGCACTGC CTATTTGCGG
      CTGAAGTTCC CTGCCAAACG GAAGAGAAAC CTTTGCAGAC GGTCGTGACG GATAAACGCC
```

Fig. 25

```
           I  N  N  L  K  N  E     D  M  A     K  Y  F  C     A  R  G     G  P  Y
241  ATCAACAACC TCAAAAATGA GGACATGGCT AAATACTTCT GTGCCAGAGG TGGTCCTTAC
     TAGTTGTTGG AGTTTTTACT CCTGTACCGA TTTATGAAGA CACGGTCTCC ACCAGGAATG

V  R  G  A     L  D  Y     W  G  Q     G  T  S  V     T  V  S     S  G  G
301  GTAAGGGGTG CTTTGGACTA CTGGGGTCAA GGAACCTCAG TCACCGTCTC CTCCGGTGGT
     CATTCCCCAC GAAACCTGAT GACCCCAGTT CCTTGGAGTC AGTGGCAGAG GAGGCCACCA

G  G  S  G     G  G  G  G     S  G  G     G  G  S  D     I  L  L     I  Q  S
361  GGTGGTTCTG GCGGCGGCGG CTCCGGTGGT GGTGGTTCTG ACATTATCCT GATCCAATCT
     CCACCAAGAC CGCCGCCGCC GAGGCCACCA CCACCAAGAC TGTAATAGGA CTAGGTTAGA

P  P  S  L     A  V  S     L  G  Q     R  A  T  I     S  C  R     T  S  E
421  CCACCTTCTT TGGCTGTGTC TCTAGGGCAG AGGGCCACCA TCTCCTGCAG AACCAGCGAA
     GGTGGAAGAA ACCGACACAG AGATCCCGTC TCCCGGTGGT AGAGGACGTC TTGGTCGCTT
```

Fig. 25 (cont.)

```
            N  V  D  G  Y  G  I     S  F  I     N  W  Y     Q  K  P     G  Q  P
481  AATGTTGACG GATACGGCAT TAGTTTATA AACTGGTACC AACAGAAGCC AGGACAGCCA
     TTACAACTGC CTATGCCGTA ATCAAAATAT TTGACCATGG TTGTCTTCGG TCCTGTCGGT

P  K  L  L  I  Y  A     A  S  H     Q  G  S  G     V  P  A     R  F  S
541  CCCAAACTCC TCATCTATGC TGCATCCCAC CAAGGATCCG GGGTCCCTGC CAGATTTAGT
     GGGTTTGAGG AGTAGATACG ACGTAGGGTG GTTCCTAGGC CCCAGGGACG GTCTAAATCA

G  S  G  S  G     T  D  F     S  L     N  I  H  P     L  E  E     D  D  T
601  GGCAGTGGGT CTGGACACAGA CTTCAGCCTC AACATCCATC CTTTGGAGGA GGATGATACT
     CCGTCACCCA GACCCTGTCT GAAGTCGGAG TTGTAGGTAG GAAACCTCCT CCTACTATGA

A  M  Y  F  C  H  Q     S  K  K     V  P  W  T     F  G  G     G  T  K
661  GCAATGTATT TCTGTCACCA AAGTAAGAAG GTTCCGTGGA CGTTCGGTGG AGGCACCAAG
     CGTTACATAA AGACAGTGGT TTCATTCTTC CAAGGCACCT GCAAGCCACC TCCGTGGTTC

L  E  I  K
721  CTGGAAATCA AA
     GACCTTTAGT TT
```

Fig. 25 (cont.)

HUMAN-ANTI-HUMAN CD3 BINDING MOLECULES

CROSS-REFERENCE TO RELATED APPLICATIONS

This application is a national phase application under 35 U.S.C. §371 of International Application No. PCT/EP2004/005684 filed 26 May 2004, which claims priority to European Application No. 03012132.1 filed 31 May 2003.

INCORPORATION BY REFERENCE OF SEQUENCE LISTING SUBMITTED ON A COMPACT DISC

The Sequence Listing is submitted on one compact disc (Copy 1), together with a duplicate thereof (Copy 2), each created on Oct. 28, 2005, and each containing one 249 kb file entitled "VOSS011.TXT" The material contained on the compact disc is specifically incorporated herein by reference.

The present invention relates to a method for the preparation of a human binding molecule, fragment or derivative thereof which specifically binds to the human CD3 complex. Furthermore, the invention relates to human binding molecules specifically binding to the human CD3 complex and means comprising said human binding molecules.

A variety of documents is cited throughout this specification. The disclosure content of said documents is herewith incorporated by reference.

Human CD3 antigen denotes an antigen which is expressed on T cells as part of the multimolecular T cell receptor complex (TCR) and which consists of three different chains: CD3-ε, CD3-δ and CD3-γ. Clustering of CD3 on T cells, e.g., by immobilized antibodies specific for the CD3 molecule leads to T cell activation similar to the engagement of the T cell receptor but independent of its clone-typical specificity. The individual proteins of the CD3 complex are referred to as δ, γ (both glycosylated) and ε (non-glycosylated). In the TCR/CD3 complex, CD3-ε exists as a dimer with either the CD3-δ or the CD3-γ signaling subunit. Upon dimerization with either the CD3-δ or the CD3-γ subunit, solely expressed, i.e. monomeric, CD3-ε undergoes a conformational change into its natural conformation (Kastrup, Scand. J. Immunol. 56 (2002), 436-42).

Owing to its central role in the modulation of T cell activity, the TCR/CD3 complex has been the subject of much research aimed at developing molecules capable of binding TCR/CD3. Much of this work has focused on the development of anti-TCR/CD3 monoclonal antibodies.

The prior art exemplifies antibodies with specificity for the human CD3 antigen. One such CD3 specific antibody is the murine monoclonal antibody OKT3 (proprietary name ORTHOCLONE®). OKT3 was the first monoclonal antibody drug approved by the FDA (approved in 1986). OKT3 has been described in the literature as a potent T cell mitogen (Van Wauve, J. Immunol. 124 (1980), 2708-18) as well as a potent T cell killer (Wong Transplantation 50 (1990), 683-9). OKT3 exhibits both of these activities in a time-dependent fashion; following early activation of T cells leading to cytokine release, upon further administration OKT3 later blocks all known T cell functions. It is due to this later blocking of T cell function that OKT3 has found such wide application as an immunosuppressant in therapy regimens for reduction or even abolition of allograft tissue rejection.

OKT3 reverses allograft tissue rejection most probably by blocking the function of all T cells which play a major role in acute rejection. OKT3 reacts with and blocks the function of the CD3 complex in the membrane of human T cells which is associated with the antigen recognition structure of T cells (TCR) and is essential for signal transduction. Which subunit of the TCR/CD3 is bound by OKT3 has been the subject of multiple studies. Though some evidence has pointed to a specificity of OKT3 for the ε-subunit of the TCR/CD3 complex (Tunnacliffe, Int. Immunol. 1 (1989), 546-50). Further evidence has shown that OKT3 binding of the TCR/CD3 complex requires other subunits of this complex to be present (Salmeron, J; Immunol. 147 (1991), 3047-52). The evidence relating to the exact epitope bound by OKT3 remains, then, ultimately inconclusive.

Patients treated with OKT3 experience a rapid and concomitant decrease in the number of circulating CD2+, CD3+, CD4+ and CD8+ cells within minutes following administration. This decrease in the number of CD3+ T cells results from the specific interaction between OKT3 and the CD3 surface antigen, ubiquitous on all T cells.

Other well known antibodies specific for the CD3 molecule are listed in Tunnacliffe, Int. Immunol. 1 (1989), 546-50. As indicated above, such CD3 specific antibodies are able to induce various T cell responses such as lymphokine production (Von Wussow, J. Immunol. 127 (1981), 1197; Palacious, J. Immunol. 128 (1982), 337), proliferation (Van Wauve, J. Immunol. 124 (1980), 2708-18) and suppressor-T cell induction (Kunicka, in "Lymphocyte Typing II" 1 (1986), 223). That is, depending on the experimental conditions, CD3 specific monoclonal antibody can either inhibit or induce cytotoxicity (Leewenberg, J. Immunol. 134 (1985), 3770; Phillips, J. Immunol. 136 (1986) 1579; Platsoucas, Proc. Natl. Acad. Sci. USA 78 (1981), 4500; Itoh, Cell. Immunol. 108 (1987), 283-96; Mentzer, J. Immunol. 135 (1985), 34; Landegren, J. Exp. Med. 155 (1982), 1579; Choi (2001), Eur. J. Immunol. 31, 94-106; Xu (2000), Cell Immunol. 200, 16-26; Kimball (1995), Transpl. Immunol. 3, 212-221).

Another serious problem hampering the therapeutic use of, especially, murine monoclonal antibodies in humans is the mounting of a humoral immune response against such antibodies, resulting in the production of human anti-mouse antibodies ("HAMAs"). HAMAs are typically generated during the second week of treatment with the murine antibody and neutralize the murine antibodies, thereby blocking their ability to bind to their intended target. The HAMA response can depend on a number of factor % including the nature of the murine constant ("Fc") antibody regions, the nature of the murine variable ("V") regions, human Ig allotypes, unusual glycosylation of the murine antibody, the patient's MHC haplotype, the specificity of the murine antibody, whether the murine antibody binds to a surface antigen or a soluble antigen, whether the murine antibody forms immune complexes with the antigen, complement activation by the murine antibody, the ability of the murine antibody to bind the Fc receptor as well as the state of inflammation and/or cytokine release.

The prior art contains various approaches to reducing or preventing the production of HAMAs by modifying monoclonal antibodies.

One approach to reducing the immunogenicity of antibodies is by humanization, as for example described in WO 91/09968 and U.S. Pat. No. 6,407,213. In general, humanization entails substitutions of non-human antibody sequences for corresponding human sequences, as for example is the case with CDR-grafting. In CDR-grafting, murine CDRs are inserted into human framework regions. However, being of murine origin, the grafted CDR regions can themselves lead to the production of HAMAs. Furthermore, CDR-grafting may affect the folding properties of the CDR regions, as the latter are at least partially dependent on amino acids in the original framework. Such alterations in the folding properties of the CDR regions can decrease the binding affinity and bioactivity of the CDR-grafted molecules. To ensure that the grafted CDR regions can fold into a conformation sufficient for the desired binding, certain murine amino acid residues considered important for the proper conformation of the amino acid residues within the CDR regions are reintroduced into the human framework region. However, such reintroduction can itself contribute to a production of HAMAs.

Another approach to reducing the immunogenicity of such antibodies is by deimmunization, as for example described in WO 92/10755, WO 00/34317, WO 98/52976, WO 02/079415, WO 02/012899 and WO 02/069232. In general, deimmunization entails carrying out substitutions of amino acids within potential T cell epitopes. In this way, the likelihood that a given sequence will give rise to T cell epitopes upon intracellular protein processing is reduced. However, deimmunization procedures such as those indicated above are purely predictive in nature, based as they are on theoretical approaches. For instance, predictions of potential T cell epitopes are made based on lists of known MHC haplotypes which are representative but incomplete. Therefore, it is impossible to ensure that removal of all predicted T cell epitopes will truly result in a fully deimmunized molecule.

Furthermore, both humanization and deimmunization approaches often lead to a significantly decreased binding affinity and therefore bioactivity with respect to the non-modified species.

Despite the numerous disadvantages indicated above, recent literature indicates in the specific context of CD3 specific antibodies—that humanization still represents the most feasible and promising mode of decreasing immunogenicity (Chatenoud, Nature Reviews 3 (2003), 123-32).

Thus, the technical problem underlying the present invention was to provide means and methods for binding molecules with specificity for the human CD3 complex which avoid the disadvantages of immunogenicity of molecules known in the art.

The solution to said technical problem is achieved by providing the embodiments characterized in the claims.

Accordingly, the present invention relates to a method for the preparation of a human binding molecule, fragment or derivative thereof which specifically binds to the human CD3 complex, said method comprising the steps of
(a) selecting molecules specifically binding to/interacting with the extracellular domain of the recombinant ε-chain; expressed independent of the human CD3 complex in the absence of other members of said CD3 complex, from a population of candidate polypeptides encoded by a library;
(b) selecting molecules from a population identified in step (a) for binding to the human CD3 complex; and
(c) preparation of said selected binding molecule.

The term "human binding molecule" defines a molecule of human source, i.e. of human origin. Said "human binding molecule" relates, for example, to (an) antibody molecule(s) or (a) fragment(s) thereof or to (a) specifically binding peptide(s) or protein(s) which is/are characterized by its/their ability to bind to the human CD3 complex, in particular to CD3 c chain. As defined herein above, the CD3 complex is a part of the T-cell receptor (TCR).

The term "binding to/interacting with" as used in the context of the present invention defines a binding/interaction of at least two "antigen-interaction-sites" with each other. The term "antigen-interaction-site" defines, in accordance with the present invention, a motif of a polypeptide which is able to specifically interact with a specific antigen or a specific group of antigens. Said binding/interaction is also understood to define a "specific recognition". The term "specifically recognizing" means in accordance with this invention that the antibody molecule is capable of specifically interacting with and/or binding to at least two, preferably at least three, more preferably at least four amino acids of the human CD3 antigen as defined herein. Said term relates to the specificity of the antibody molecule, i.e. to its ability to discriminate between the specific regions of the human CD3 molecule as defined herein. The specific interaction of the antigen-interaction-site with its Specific antigen may result in the initiation of a signal, e.g. due to the induction of a change of the conformation of the antigen, an oligomerization of the antigen, etc. Further, said binding may be exemplified by the specificity of a "lock-and-key-principle". Thus, specific motifs in the amino acid sequence of the antigen-interaction-site and the antigen bind to each other as a result of their primary, secondary or tertiary structure as well as the result of secondary modifications of said structure. The specific interaction of the antigen-interaction-site with its specific antigen may result as well in a simple binding of said site to the antigen.

The term "specific interaction" as used in accordance with the present invention means that the binding molecule does not or does not significantly cross-react with (poly)peptides which have similar structure as those bound by the binding molecule, and which are expressed by the same cells as the (poly)peptide of interest. Cross-reactivity of a panel of binding molecules under investigation may be tested, for example, by assessing binding of said panel of binding molecules under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999).

Examples for the specific interaction of an antigen-interaction-site with a specific antigen comprise the specificity of a ligand for its receptor. Said definition particularly comprises the interaction of ligands which induce a signal upon binding to its specific receptor. Examples for corresponding ligands comprise cytokines which interact/bind with/to their specific cytokine-receptors. Also particularly comprised by said definition is the binding of an antigen-interaction-site to antigens such as antigens of the selectin family, integrins and of the family of growth factors like EGF. Another example for said interaction, which is also particularly comprised by said definition, is the interaction of an antigenic determinant (epitope) with the antigenic binding site of an antibody.

The term "binding to/interacting with" may also relate to a conformational epitope, a structural epitope or a discontinuous epitope consisting of two regions of the human CD3 molecule or parts thereof. In the context of this invention, a conformational epitope is defined by two or more discrete amino acid sequences which are separated in the primary sequence, but which come together on the surface when the polypeptide folds to the native protein (Sela, (1969) Science 166, 1365 and Laver, (1990) Cell 61, 553-6).

The term "discontinuous epitope" means in context of the invention non-linear epitopes that are assembled from residues from distant portions of the polypeptide chain. These residues come together on the surface when the polypeptide chain folds into a three-dimensional structure to constitute a conformational/structural epitope.

The binding molecules of the present invention are also envisaged to specifically bind to/interact with a conformational/structural epitope(s) composed of and/or comprising at least two regions of the human CD3 complex, or composed of/comprising individual components, like CD3-ε, CD3-δ and CD3-γ and/or combinations of said components, such as CD3-ε/CD3-δ or CD3-ε/CD3-γ. Furthermore, it is envisaged that said conformational/structural epitope(s) described herein comprises individual parts/regions/stretches of at least two regions of a single component of the human CD3 complex, preferably at least two parts/regions/stretches of CD3-ε, even more preferably of the extracellular domain of CD3-ε.

Specificity of the human binding molecules obtained by the method of this invention can be determined experimentally by methods known in the art and methods as disclosed and described herein. Such methods comprise, but are not limited to Western blots, ELISA-, EIA-1, RIA-, ECL-, IRMA-tests and peptide scans.

According to the present invention "human binding molecules" are (poly)peptides which specifically bind to the human CD3 complex and/or its individual components. The term "(poly)peptide" as used herein describes a group of molecules which comprise the group of peptides, as well as the group of polypeptides. The group of peptides is consisting of molecules with up to 30 amino acids, the group of polypeptides is consisting of molecules with consisting of more than 30 amino acids. Most preferably, said "human binding molecules" are selected from the group of antibodies, antibody fragments, antibody derivatives, specific binding peptides and specific binding proteins. Said antibody fragments are known in the art and comprise, but are not limited to, Fab-fragments, F(ab$_2$)' fragments, Fv fragments and the like. As will be detailed below, particular preferred fragments of antibodies in context of this invention are scFv fragments. Antibody derivatives comprise but are not limited to labeled antibodies/antibody fragments as well as chemically modified antibody molecules/antibody fragments. Therefore, fragments or derivatives of the recited human binding molecules also relate to (poly)peptides which are parts of the above defined (poly)peptides or which are modified posttranslationally or by chemical/biochemical or molecular biological methods. Corresponding methods are known in the art and are described, inter alia, in laboratory manuals (see Sambrook et al.; Molecular Cloning: A Laboratory Manual; Cold Spring Harbor Laboratory Press, 2nd edition 1989 and 3rd edition 2001; Gerhardt et al.; Methods for General and Molecular Bacteriology; ASM Press, 1994; Lefkovits; Immunology Methods Manual: The Comprehensive Sourcebook of Techniques; Academic Press, 1997; Golemis; Protein-Protein Interactions: A Molecular Cloning Manual; Cold Spring Harbor Laboratory Press, 2002).

The recited extracellular domain of the recombinant ε-chain of the CD3 complex is known in the art and relates, in accordance with this invention, to the term "extracellular domain of recombinant ε-chain" and/or to the term "extracellular domain of human CD3-ε". Said extracellular domain comprises the amino acid positions 23 to 126 of the known human CD3-ε, as documented in NM_000733/NP_000724 Homo sapiens CD3E [gi:4502670/gi:450267]. In accordance with the present invention, a particular preferred extracellular domain of human CD3-ε is encoded by a nucleic acid molecule as shown in SEQ ID NO. 140. It is also envisaged that only parts of the extracellular domain of human CD3ε-chain are employed in the method of the present invention. Yet, it is to be understood that the method of the present invention may also be carried out with recombinantly expressed extracellular domains of CD3ε-chain which are homologous or mutated in relation to the extracellular domain shown in SEQ ID NO: 141. For example, the method of the present invention may be carried out with recombinantly expressed extracellular domains of CD3ε-chains which are genetic variants, for example allelic variants, of the extracellular domain of the human CD3ε chain. Such variants also comprise CD3ε-chains from closely related primates. Preferably, said primate CD3ε-chains, respectively their extracellular domains shown an homology to the human CD3ε-chain of at least 80%, more preferably of at least 90%, most preferably of at least 95%.

For the step of selection of binding molecules of the present inventive method; said ε-chain is expressed independent of the human CD3 complex in the absence of other members of said CD3 complex. In the absence of other members of the complex the ε-chain is folded without any support in its folding by said other members. Consequently, the antigenicity of some domains of the ε-chain is different from the antigenicity of said other domains when the ε-chain is expressed in the context of the CD3 complex. The cloning and expression of the CD3ε-chain is exemplified in the appended Example 1.

The selection recited in steps (a) and (b) of the method of the invention particularly comprises the selection of binding molecules by affinity selection. Methods for affinity selection are known in the art (see Golemis, loc cit.; Rehm, Der Experimentator: Proteinbiochemie/Proteomics, Spektrum Akademischer Verlag, 2002; Lottspeich and Zorbas, Bioanalytik, Spektrum Akademischer Verlag, 1998). One embodiment of a corresponding method is described in appended Example 2. The term "population of candidate polypeptides" defines the population of polypeptides from which the binding molecules are selected from. In accordance with the present invention said polypeptides are encoded by a library. Thus, said population may be a peptide library as well as a population of peptides encoded by a library. Examples for said libraries comprise DNA-libraries such as cDNA-libraries and RNA-libraries, see, inter alia, Hoogenboom (2000) Immun Today 21, 371-378. The preparation of a cDNA-library is exemplified in the appended examples.

One population of candidate polypeptides is described in the appended examples as peptides encoded by a library derived from human cells, wherein the genes of said library encode human antibody molecules. Human antibody molecules encoded by said genes with specificity for the human CD3 complex are not expressed by mature B cells in the human body. This is because of the above discussed lack of T helper cell signals for self-reactive B cells (specific for autoantigens) since the necessary self-reactive T helper cells have been eliminated during the intrathymic clonal deletion of self-reactive pre-T cells.

Identification of autoantigen-specific human antibodies from a library derived from such human B cells is therefore highly unlikely. When considering the human CD3 antigen, ubiquitously expressed throughout the entire T cell compartment, this likelihood is decreased even further. Human B cells which, by chance or accident, produce and surface-display an Ig with specificity for human CD3, and which by binding of the human CD3 antigen activate $CD8^+$ T cells, will be killed by the very $CD8^+$ cells they themselves activate (Itoh, Cellular Immunol. 108 (1987) 313-22; Hoffman, J. Immunol. 135 (1985), 5-8). The subpopulation of B cells bearing anti-human CD3 specific antibodies on their surface therefore becomes depleted below its already naturally low level within the entire B cell compartment. A random cross-section of B cells from the B cell compartment, such as is used in constructing a diverse antibody library, is thus all the less likely to comprise B cells producing antibody specific for human CD3. This explains the difficulty in identifying antibodies of human origin against the autoantigen human CD3 using antibody library techniques.

Said obstacle has been surprisingly overcome by the present invention which resulted in the preparation of binding molecules with specificity for the human CD3 complex, wherein said binding molecules themselves are human derived/of human origin. Due to the human source of the binding molecule, said molecules are most preferably non-immunogenic (or at least minimally immunogenic) for the human immune system under physiological conditions.

The term "preparation" as used in the present specification and in particular in the above described inventive method, defines method steps such as recovery of a peptide from a binding partner, i.e. from the ε-chain of the human CD3 complex, the purification of said peptide as well as their corresponding isolation, their further determination (like sequencing), the isolation/generation of corresponding encoding nucleic acid molecules as well as their expansion (general reproduction, recombinant reproduction, chemical synthesis, in-vitro translation etc). Corresponding techniques are detailed below and also shown in the appended examples.

A particularly surprising advantage of the present invention is the provision of human binders (in particular antibody binders) against the human CD3 antigen, which overcome several major limitations in the field of antibody technology.

In general, it is known that developing B cells which exhibit a binding specificity for autoantigens are naturally selected against before the mature B cells are released into the bloodstream. As such, human B cells in the blood which produce monoclonal antibody against human antigen make up an exceedingly small proportion of the peripheral B cell compartment. Identification of autoantigen-specific human antibodies from an antibody library derived from such human B cells is therefore highly unlikely. When considering the human CD3 antigen, ubiquitously expressed throughout the entire T cell compartment, this likelihood is decreased even further. Human B cells which, by chance or accident, produce and surface-display an Ig with specificity for human CD3, and which by binding of the human CD3 antigen activate CD8+ T cells, will be killed by the very CD8+ cells they themselves activate (i.e. redirected lysis) (Itoh, Cellular Immunol. 108 (1987) 313-22; Hoffman, J. Immunol. 135 (1985), 5-8). The subpopulation of B cells bearing anti-human CD3 antibodies on their surface therefore becomes depleted below its already naturally low level within the entire B cell compartment. A random cross-section of B cells from the B cell compartment, such as is used in constructing a diverse antibody library, is thus all the less likely to comprise B cells producing antibody specific for human CD3. This explains the difficulty in identifying antibodies of human origin against the autoantigen human CD3 using antibody library techniques.

The above mentioned hurdles are surprisingly overcome by the method of the present invention, in particular by using an appropriate protein for selection of antibodies from a library, in particular from an antibody library. In accordance with this invention, solely expressed recombinant CD3-epsilon protein is used for selection of a CD3 binder, in particular an antibody binder from a diverse library, e.g. an antibody library derived from human B cells. Without being bound by theory, it is believed that the conformation adopted by solely expressed recombinant CD3-epsilon protein differs from that adopted in its natural form, that is, the form in which the CD3-epsilon subunit of the TCR/CD3 complex exists as part of a noncovalent complex with either the CD3-delta or the CD3-gamma subunit of the TCR/CD3 complex (Kastrup, Scand. J. Immunol. 56 (2002) 436-42). Were natural CD3-epsilon in its complexed form to be used as an antigen for selection of antibodies from an antibody library, the probability of identifying an antibody specifically binding to this protein would be very low. This is because the cells generating antibodies with binding specificity for natural CD3-epsilon are preferentially depleted in vivo from the compartment used to construct the antibody library. However, when solely expressed recombinant CD3-epsilon protein is used as an antigen for selection of antibodies from an antibody library, antibodies specific for this antigen are identified from the library. This is due to the fact that solely expressed recombinant CD3-epsilon protein does not exist in vivo; it is not an autoantigen. Consequently, subpopulations of B cells expressing antibodies specific for this protein have not been depleted in vivo; an antibody library constructed from such B cells would contain genetic material for antibodies specific for solely expressed recombinant CD3-epsilon protein.

A major advantage according to the invention is that binders, like antibodies identified from (antibody) libraries as specific binders of solely expressed recombinant CD3-epsilon are also able to specifically bind CD3-epsilon in its natural, complexed form. This is especially surprising, given the failure of natural, complexed CD3-epsilon to identify specific antibodies when this protein is used as the selection antigen for human antibody libraries. According to the invention, the recombinant form of CD3-epsilon thus acts as a surrogate antigen which can be used to identify human antibodies to the human CD3 antigen. Such antibodies would normally remain unidentifiable using naturally-expressed human CD3 antigen in its complexed form.

In a further embodiment, the invention relates to the above described method, further comprising a step (d), relating to the identification of the nucleic acid sequence encoding the human CD3 binding molecule in the library.

As mentioned above, said identification may comprise the sequence-analysis of the amino acid sequence of the selected polypeptide or the sequence-analysis of the nucleic acid molecule coding for the selected polypeptide. Methods for said analysis are known in the art. Furthermore, examples for said identification are described in the appended examples 2.8 and 3.2.

In accordance with the present invention, the recited library which encodes the candidate polypeptides may be derived from a DNA-library or an RNA-library. Particularly comprised by said definition are cDNA-libraries.

Further in accordance with the invention the library which encodes the candidate polypeptides is derived from primary or secondary lymphatic organs of humans. Said sources particularly comprise fetuses. Examples for said lymphatic organs are spleen, lymph nodes, MALT (mucosa associated lymphatic tissues), bone marrow, blood, proliferative disorder tissue, tonsil, umbilical cord blood and inflammatory tissue.

As pointed out above, in the method of the invention said selection of the human binding molecules may be effected by exposing the human binding molecules to immobilized recombinant, solely expressed ε-chain, expressed independent of the human CD3 complex in the absence of other members of said CD3 complex. The recombinant ε-chain may be immobilized or adsorbed on a solid support/surface. Examples for said solid support/surface are known in the art and comprise, inter alia, polymeric surfaces, such as polystyrene, polypropylene as well as specifically coated surfaces like PolySorp™, MaxiSorp™, MultiSorp™, etc.

According to a preferred embodiment of the method of the invention, the selection step of the method of the invention comprises a phage display method. Phage display technology has been described in the literature, for example in Hoogenboom, Methods Mol Biol 178 (2002), 1-37, Pini, Curr Protein Prep Sci 1 (2000), 155-69. A description of the selection of phage-displayed antibodies is described e.g. in Mutuberria, J. Immunol. Methods 231 (1999), 65-81. Phage display methology is also described in WO 99/25818 and is also exemplified in the appended examples.

As mentioned above and illustrated in the appended examples, the human binding molecule, fragment or derivative thereof, which is prepared/isolated by the method of the invention is preferably an antibody molecule, antibody fragment or derivative thereof or a construct comprising at least one antibody, antibody fragment or derivative thereof which specifically binds to the human CD3 complex.

Said antibody is preferably a monoclonal antibody. The term "antibody fragment or derivative thereof" relates to single chain antibodies, or fragment thereof, synthetic antibodies, antibody fragments, such as Fab, a F(ab$_2$)', Fv or scFv fragments etc., or a chemically modified derivative of any of these. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit.

According to a further preferred embodiment of the method of the invention, said method for the production of human anti-human CD3 binding molecules further comprises the steps of:

I: (a) taking the VH and/or VL region/s of at least one of the isolated human CD3 binders and (i) inserting mutations resulting in amino acid substitutions (e.g. as described in Barbas III, TIBTECH 14 (1996) 230; Schier, J. Mol. Biol. 263 (1996) 551, Hawkins, J. Mol. Biol. 226 (1992) 889) and/or (ii) shuffling a repertoire of human V-regions to the VH or VL of said human CD3 binders (e.g. as described in Raum, Cancer Immunol Immunother 50 (2001) 141-150) and/or
(b) grafting at least one CDR of at least one of the isolated human CD3 binders into the corresponding position/s of the variable regions of a human antibody library (e.g. principle of inserting predetermined CDR/s into the context of human antibody libraries e.g. as described in Rader, PNAS 95 (1998) 8910-5, Steinberger, J Biol Chem 17 (2000) 36073-8)
and
II: subjecting the resulting library/ies to further selection on human CD3 antigen or parts thereof (e.g. for the purpose of affinity maturation). The CD3 antigen or parts thereof used for selection may be expressed (naturally or via transfection) on cells (e.g. T cells, see Tunnacliffe, International Immunology 1 (1989) 546) or isolated from a natural source (e.g. immunoprecipitated from human T cells following the method as described e.g. by Leo, PNAS 84 (1997) 1374-1378 adapted to human CD3) or produced as recombinant protein (as described e.g. in the present invention or by Tunnacliffe, Immunol. Lett. 21 (1989) 243, Kastrup, Scand. J. Immunol. 56 (2002) 436-442), Kim, J. Mol. Biol. 302 (2000) 899-916 adapted to human CD3) or synthesized as peptide.

The term "antibody fragment or derivative thereof" particularly relates to (poly)peptide constructs comprising at least one CDR The complementary determining region (CDR) dictates the antigen specificity of the response and plays a central role in initiating activation. However, this interaction, by itself, is not sufficient to fully activate naïve T cells: After the initial T cell stimulation there have to be further, antigen-independent co-stimulatory signals.

It is particularly envisaged by the invention that said derivative of an antibody is an scFv. The term "scFv fragment" (single-chain Fv fragment) is well understood in the art. ScFvs are preferred in context of this invention, due to their small size and the possibility of recombinantly producing these antibody fragments.

According to a preferred embodiment of the invention said human binding molecule specifically binding to the human CD3 complex is an antibody molecule, antibody fragment, derivative thereof or antibody construct comprising at least one further antigen-interaction-site and/or at least one further effector domain.

Examples for the recited "further effector domain" comprise signal inducing domains of molecules, wherein the initiation of said signal results in the uptake of the molecule into the cell, cell death, cell proliferation or cell stimulation. Examples of such effector domains comprise, but are not limited to, B7.1, Fas-ligand, cytokines (like IL2), NKG-2D, NKD-46, OX40L, or 4.1BBL. Corresponding binding molecules comprise bispecific constructs in molecular format as described e.g. in WO 99/54440 as well as molecular formats as described in WO 00/06605.

Preferably said bispecific constructs are bispecific single chain antibody construct. The term "single-chain" as used in accordance with the present invention means that said first and second domain of the bispecific single chain construct are covalently linked, preferably in the form of a co-linear amino acid sequence encodable by a single nucleic acid molecule.

Preferably it is envisaged that said antibody molecule, antibody fragment, derivative thereof or construct is humanized and/or deimmunized in an additional step.

Since the domain specifically binding to/interacting with the human CD3 complex is a human (poly)peptide or human (poly)peptide fragment it is envisaged that only parts of said at least one further antigen-interaction-site and/or at least one further effector domain which are non-human derived are humanized. The non-human derived domains of said antibody molecule, antibody fragment, derivative thereof or construct may be also or alternatively be deimmunized. Furthermore, the fusion of human derived domains to non-human derived domains, preferably by the linker referred above, may result in immunogenic epitopes. Corresponding epitopes at said junctions between human derived domains and non-human derived domains may also be deleted by deimmunization. Methods for the humanization of antibodies and antibody constructs are known in the art and described e.g. in EP-A1 0 239 400, WO 90/07861, Welt (2003) Clin Cancer Res 9, 1338-1346. Methods for the deimunization of (poly)peptides and (poly)peptide constructs are known in the art and described e.g. in WO 02/079415, WO021069232 or WO00/34317.

Further in accordance with the invention said further antigen-interaction-site of the human binding molecule specific for human CD3 complex and as described herein is, in addition, specific for one or more cell surface molecule.

The term "cell surface molecule" as used herein denotes molecules which are presented or/and attached on/to the surface of a cell. Examples for said cell surface molecules are membrane and transmembrane proteins (including modified variants, such as glycosylated variants), molecules attached to said proteins or the cell surface as well as glycosylated moieties such as for example lipids. Attachment is to be understood as being effected by way of an integral membrane protein, a GPI-linked (glycosyl phosphatidyl inositol-linked)

protein, a proteinaceous or non-proteinaceous moiety bound covalently or non-covalently to another carrier molecule such as sugar moieties or ganglioside moieties. Preferably said cell surface molecule is a tumor-specific marker. A tumor-specific marker is a tumor-associated cell surface antigen which is either found exclusively on tumor cells or is overexpressed on tumor cells as compared to non-malignant cells. Tumor-associated cell surface antigens can be expressed not only on tumor cells but also on cells/tissue which are/is not essential for survival or which can be replenished by stem cells not expressing tumor-associated cell surface antigen. Furthermore, tumor-associated cell surface antigen can be expressed on malignant cells and non-malignant cells but is better accessible by a therapeutic agent of interest on malignant cells. Examples of over-expressed tumor-associated cell surface antigens are Her2/neu, EGF-Receptor, Her-3 and Her-4. An example of a tumor-associated cell surface antigen which is tumor specific is EGFRV-III. An example of a tumor-associated cell surface antigen which is presented on a cell which is non-essential for survival is PSMA. Examples of tumor-associated cell surface antigens which are presented on cells which are replenished are CD19, CD20 and CD33. An example of a tumor-associated cell surface antigen which is better accessible in a malignant state than in a non-malignant state is EpCAM.

It is envisaged and documented herein that said at least one further antigen-interaction-site is a domain which is derived from an antibody or antibody construct.

Preferably, said domain which is an antibody-derived region comprises a polypeptide sequence which corresponds to at least one variable region of an antibody. More preferably, said at least one further antigen-interaction-site is a further scFv. A particularly preferred molecular format of the invention provides a polypeptide construct wherein the antibody-derived region comprises one $V_H$ and one $V_L$ region.

The term "bispecific single chain antibody construct" relates to a construct comprising one domain consisting of (at least one) variable region(s) (or parts thereof) as defined above capable of specifically interacting with/binding to human CD3/human CD3 complex and comprising a second domain consisting of (at least one) variable region(s) (or parts thereof) as defined above capable of specifically interacting with/binding to a further antigen.

Said binding/interaction is also understood to define a "specific recognition". The term "specifically recognizing" means in accordance with this invention that the antibody molecule is capable of specifically interacting with and/or binding to at least two amino acids of each of the human target molecule as defined herein. Said term relates to the specificity of the antibody molecule, i.e. to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Further, said binding may be exemplified by the specificity of a "key-lock-principle". Thus, specific motifs in the amino acid sequence of the antigen-interaction-site and the antigen bind to each other as a result of their primary, secondary or tertiary structure as well as the result of secondary modifications of said structure. The specific interaction of the antigen-interaction-site with its specific antigen may result as well in a simple binding of said site to the antigen.

The term "specific interaction", as used in accordance with the present invention means that the bispecific single chain construct does not or essentially does not cross-react with (poly)peptides of similar structures. Cross-reactivity of a panel of bispecific single chain construct under investigation may be tested, for example, by assessing binding of said panel of bispecific single chain construct under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999) to the (poly)peptide of interest as well as to a number of more or less (structurally and/or functionally) closely related (poly)peptides. Only those antibodies that bind to the (poly)peptide/protein of interest but do not or do not essentially bind to any of the other (poly)peptides are considered specific for the (poly)peptide/protein of interest. Examples for the specific interaction of an antigen-interaction-site with a specific antigen comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens like antigens of the selectin family, integrins and of the family of growth factors like EGF. An other example for said interaction, which is also particularly comprised by said definition, is the interaction of an antigenic determinant (epitope) with the antigenic binding site of an antibody.

The term "binding to/interacting with" may also relate to a conformational epitope, a structural epitope or a discontinuous epitope consisting of two regions of the human target molecules or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Laver, (1990) Cell 61, 553-6).

The term "discontinuous epitope" means in context of the invention non-linear epitopes that are assembled from residues from distant portions of the polypeptide chain. These residues come together on the surface of the molecule when the polypeptide chain folds into a three-dimensional structure to constitute a conformational/structural epitope.

According to the present invention the term "variable region" used in the context with Ig-derived antigen-interaction comprises fragments and derivatives of (poly)peptides which at least comprise one CDR derived from an antibody, antibody fragment or derivative thereof. It is envisaged by the invention, that said at least one CDR is preferably a CDR3, more preferably the CDR3 of the heavy chain of an antibody (CDR-H3). However, other antibody derived CDRs are also particularly comprised by the term "variable region"

The "specific binding" of an antibody is characterized primarily by two parameters: a qualitative parameter (the binding epitope, or where the antibody binds) and a quantitative parameter (the binding affinity, or how strongly it binds where it does). Which epitope is bound by an antibody can advantageously be determined by e.g. known FACS methodology, peptide-spot epitope mapping, mass spectroscopy. The strength of antibody binding to a particular epitope may be advantageously be determined by e.g. known BIAcore and/or ELISA methodologies. A combination of such techniques allows the calculation of a signal:noise ratio as a representative measure of binding specificity. In such a signal:noise ratio, the signal represents the strength of antibody binding to the epitope of interest, whereas the noise represents the strength of antibody binding to other, non-related epitopes differing from the epitope of interest. In general, any time an antibody binds more frequently and/or strongly to one epitope than another epitope, such antibody may be said to bind the former epitope specifically. Preferably, a signal: noise ratio for an epitope of interest which is about 50-fold higher than for other epitopes different from the epitope of interest may be taken as an indication that the antibody evaluated binds the epitope of interest in a specific manner, i.e. is a "specific binder".

A part of a variable region may be at least one CDR ("Complementary Determining Region"), most preferably at least the CDR3 region. Said two domains/regions in the single chain antibody construct are preferably covalently connected to one another as a single chain. This connection can be effected either directly (domain1 interacting with CD3-domain2 interacting with the further antigen or domain1 interacting with the further antigen-domain2 interacting with CD3) or through an additional polypeptide linker sequence (domain1-linker sequence-domain2 or domain2-linker sequence-domain1). In the event that a linker is used, this linker is preferably of a length and sequence sufficient to ensure that each of the first and second domains can, independently from one another, retain their differential binding specificities. Most preferably and as documented in the appended examples, the "bispecific single chain antibody construct" is a bispecific single chain Fv (bscFv). Bispecific single chain molecules are known in the art and are described in WO 99/54440, Mack, J. Immunol. (1997), 158, 3965-3970, Mack, PNAS, (1995), 92, 7021-7025; Kufer, Cancer Immunol. Immunother., (1997), 45, 193-197; Löffler, Blood, (2000), 95, 6, 2098-2103; Brühl, Immunol., (2001), 166, 2420-2426. Distinct examples for such bispecific single chain antibody construct are provided herein below and illustrated in the appended examples.

In accordance with the invention, said at least one further antigen-interaction-site specifically binds to/interacts with an antigen selected from the group consisting of EpCAM, CCR5, CD19, EphA2, HER-2 neu, HER-3, HER-4, EGFR, PSMA, CEA, MUC-1 (mucin), MUC2, MUC3, MUC4, MUC5$_{AC}$, MUC5$_B$, MUC7, βhCG, Lewis-Y, CD20, CD22, CD52, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1., Plasma Cell Antigen, (membrane-bound) IgE, Melanoma Chondroitin Sulfate Proteoglycan (MCSP), CCR8, TNF-alpha precursor, STEAP, STEAP II, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, L6, SAS, CD63, Tu, TF, Le$^a$, Sialyl Le$^a$, Le$^b$, Le$^x$, Sialyl Le$^x$ and polyfucosyl-Le$^x$.

Optionally the method of the invention may further comprise the step of recombinant expression of the binding molecule, fragment or derivative thereof encoded by a nucleic acid sequence selected from the group consisting of:
(a) the identified nucleic acid sequence;
(b) a nucleic acid sequence hybridizing with the complementary strand of the identified nucleic acid sequence under stringent hybridization conditions;
(c) a nucleic acid sequence which is degenerate as a result of the genetic code to a nucleotide sequence of any one of (a) and (b).

The term "hybridizing" as used herein refers to polynucleotides which are capable of hybridizing to the recited nucleic acid sequence or parts thereof. Therefore, said nucleic acid sequence may be useful as probes in Northern or Southern Blot analysis of RNA or DNA preparations, respectively, or can be used as oligonucleotide primers in PCR analysis dependent on their respective size. Preferably, said hybridizing polynucleotides comprise at least 10, more preferably at least 15 nucleotides while a hybridizing polynucleotide of the present invention to be used as a probe preferably comprises at least 100, more preferably at least 200, or most preferably at least 500 nucleotides.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Sambrook et al. (loc cit.) and other standard laboratory manuals known by the person skilled in the art or as recited above. Preferred in accordance with the present inventions are polynucleotides which are capable of hybridizing to the polyriucleotides of the invention or parts thereof, under stringent hybridization conditions.

"Stringent hybridization conditions" refer, i.e. to an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Also contemplated are nucleic acid molecules that hybridize to the polynucleotides of the invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M NaH$_2$PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). It is of note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The recited nucleic acid molecules may be, e.g., DNA, cDNA, RNA or synthetically produced DNA or RNA or a recombinantly produced chimeric nucleic acid molecule comprising any of those polynucleotides either alone or in combination.

The invention further relates to a method, wherein said optional step of recombinant expression of the binding molecule, fragment or derivative thereof encoded by a nucleic acid sequence comprises the preparation of a vector comprising said nucleic acid sequence.

Many suitable vectors are known to those skilled in molecular biology, the choice of which would depend on the function desired and would include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

Also in accordance with the invention said vector further comprises a nucleic acid sequence which is a regulatory sequence operably linked to said identified nucleic acid sequence.

The term "regulatory sequence" refers to DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes control sequences generally include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a arrangement/configuration wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is preferably an expression vector. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic hosts comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Besides elements which are responsible for the initiation of transcription such regulatory elements may also comprise transcription termination signals, such as the SV40-poly-A site or the tk-poly-A site, downstream of the polynucleotide. Furthermore, depending on the expression system used, leader sequences capable of directing the polypeptide to a cellular compartment or secreting it into the medium may be added to the coding sequence of the recited nucleic acid sequence and are well known in the art; see also, e.g., the appended examples. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product see supra. In this context, suitable expression vectors are known in the art such as Okayama-Berg cDNA expression vector pcDV1 (Pharmacia), pCDM8, pRc/CMV, pcDNA1, pcDNA3 (Invitrogene), pEF-DHFR and pEF-ADA (Raum et al. Cancer Immunol Immunother (2001) 50(3), 141-150) or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended examples.

An alternative expression system which could be used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia larvae*. The coding sequence of a recited nucleic acid molecule may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia* larvae in which the protein of the invention is expressed (Smith, J. Virol. 46 (1983), 584; Engelhard, Proc. Nat. Acad. Sot USA 91 (1994), 3224-3227).

Additional regulatory elements may include transcriptional as well as translational enhancers. Advantageously, the above-described vectors of the invention comprises a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable marker are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907).

This embodiment is particularly useful for simple and rapid screening of cells, tissues and organisms containing a recited vector.

As described above, the recited nucleic acid molecule can be used alone or as part of a vector to express the encoded polypeptide in cells, for, e.g., gene therapy. The nucleic acid molecules or vectors containing the DNA sequence(s) encoding any one of the above described human binding molecules is introduced into the cells which in turn produce the polypeptide of interest. Gene therapy, which is based on introducing therapeutic genes into cells by ex-vivo or in-vivo techniques is one of the most important applications of gene transfer. Suitable vectors, methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957, U.S. Pat. No. 5,580,859; U.S. Pat. No. 5,589, 466; or Schaper, Current Opinion in Biotechnology 7 (1996), 635-640. The recited nucleic acid molecules and vectors may be designed for direct introduction or for introduction via liposomes, or viral vectors (e.g., adenoviral, retroviral) into the cell. Preferably, said cell is a germ line cell, embryonic cell, or egg cell or derived therefrom, most preferably said cell is a stem cell. An example for an embryonic stem cell can be, inter alia, a stem cell as described in, Nagy, Proc. Natl. Acad. Sci. USA 90 (1993), 8424-8428.

In accordance with the above, the present invention relates to method to derive vectors, particularly plasmids, cosmids, viruses and bacteriophages used conventionally in genetic engineering that comprise a nucleic acid molecule encoding the polypeptide sequence of a human binding molecule. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotes, whereas calcium phosphate treatment or electroporation may be used for other cellular hosts; see Sambrook, supra. The recited vector may be the pEF-Neo, pEF-DHFR or pEF-ADA. The vectors pEF-DHFR and pEF-ADA have been described in the art, e.g. in Mack, PNAS (1995) 92, 7021-7025 and Raum, Cancer Immunol Immunother (2001) 50(3), 141-150.

It is further envisaged that the method of the invention further comprises the step of transforming a host with the above described vector.

Said host may be produced by introducing said at least one of the above described vector or at least one of the above described nucleic acid molecules into the host. The presence of said at least one vector or at least one nucleic acid molecule in the host may mediate the expression of a gene encoding the above described human binding molecule. The described nucleic acid molecule or vector which is introduced in the host may either integrate into the genome of the host or it may be maintained extrachromosomally.

The host can be any prokaryotes or eukaryotic cell.

The term "prokaryote" is meant to include all bacteria which can be transformed or transfected with a DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

Preferably, said host is a bacteria, an insect, fungal, plant or animal cell. It is particularly envisaged that the recited host may be a mammalian cell, more preferably a human cell or human cell line. Particularly preferred host cells comprise CHO cells, COS cells, myeloma cell lines like SP2/0 or NS/0.

It is further envisaged that the method of the invention may comprise the step of isolation and/or purification of the recombinantly expressed human binding molecule, fragment or derivative thereof. Said method consequently comprises the step of culturing a recited host under conditions allowing the expression of the recited human binding molecule and recovering said binding molecule from the culture. The transformed hosts can be grown in fermentors and cultured according to techniques known in the art to achieve optimal cell growth. The human binding molecule can then be isolated from the culture medium, cellular lysates, or cellular membrane fractions. The isolation and purification of the, say, microbially expressed human binding molecules may be effected by any conventional means such as, for example, preparative chromatographic separations and immunological separations such as those involving the use of monoclonal or polyclonal antibodies directed, for example against a tag of the human binding molecule or as described in the appended examples.

The conditions for the culturing of a host which allow the expression are known in the art to depend on the host system and the expression system/vector used in such process. The parameters to be modified in order to achieve conditions allowing the expression of a recombinant polypeptide are known in the art. Thus, suitable conditions can be determined by the person skilled in the art in the absence of further inventive input.

Once expressed, the human binding molecule can be purified according to standard procedures of the art, including ammonium sulfate precipitation, affinity columns, column chromatography, gel electrophoresis and the like; see, Scopes, "Protein Purification", Springer-Verlag, N.Y. (1982). Substantially pure polypeptides of at least about 90 to 95% homogeneity are preferred, and 98 to 99% or more homogeneity are most preferred, for pharmaceutical uses. Once purified, partially or to homogeneity as desired, the human binding molecules may then be used therapeutically (including extracorporeally) or in developing and performing assay procedures. Furthermore, examples for methods for the recovery human binding molecules from a culture are described in detail in the appended examples.

In a preferred embodiment of the method of the invention, said method further comprises the step of formulating the human binding molecule as a pharmaceutical composition, which optionally further comprises a pharmaceutically acceptable carrier or diluent.

The term "pharmaceutical composition" as well as the terms "pharmaceutically acceptable carrier" and "pharmaceutically acceptable diluent" are defined in more detail herein below.

In an alternative embodiment the present invention relates to a human binding molecule specifically binding to/interacting with the human CD3 complex, whereby said binding molecule is an antibody molecule, antibody fragment or derivative thereof or an antibody construct.

As described herein above, the method of the invention provides means for the preparation/isolation of a human binding molecule of the invention. Said particular human binding molecule of the invention is an antibody molecule, antibody fragment or derivative thereof or an antibody construct.

The terms "antibody molecule", "antibody fragment or derivative thereof" and "antibody construct" have been defined in the context of the above described method of the invention. In line with said definitions the antibody fragment or derivative thereof or an antibody construct of the invention comprises at least one CDR of a human antibody with specificity for the human CD3 complex, preferably at least one CDR3, which provides the capacity of the binding molecule to bind to/interact with the human CD3 complex.

The human binding molecule of the invention may comprise an additional domain which may be used for the isolation/preparation of the molecule. Examples for said additional domain comprise label and tags. Said tag may be selected from the group consisting of: His-tag, Flag-tag, Myc-tag, HA-tag, GST-tag, T100™, VSV-G, V5, S-tag™, HSV, CFP, RFP, YFP, GFP, BFP, Cellulose binding domain (CBD), Maltose binding protein (MBP), NusA-tag, thioredoxin (Trx), DsbA, DabC and a biotinylation sequence.

A human binding molecule wherein said derivative of an antibody is an scFv is particularly envisaged by the present invention.

As also discussed herein above, the terms "antibody fragment or derivative thereof" and "antibody construct" relate, inter alia, to scFv constructs. The intramolecular orientation of the $V_H$-domain and the $V_L$-domain, which are linked to each other by a linker-domain, in the scFv format is not decisive for binding molecules of the invention. Thus, scFvs with both possible arrangements ($V_H$-domain-linker domain-$V_L$-domain; $V_L$-domain-linker domain-$V_H$-domain) are particular embodiments of the human binding molecule of the invention.

A corresponding format of the human binding molecule of the invention is described in the appended example 3.2.

A human binding molecule of the invention is characterized as an antibody molecule, antibody fragment or derivative thereof or an antibody construct, which comprises a variable $V_H$-region as encoded by a nucleic acid molecule as shown in a SEQ ID NO selected from the group consisting of SEQ ID NOs: 1, 17, 33, 49, 65, 81, 97 and 113 or a variable $V_H$-region having an amino acid sequence as shown in a SEQ ID NO selected from the group consisting of SEQ ID NOs: 2, 18, 34, 50, 66, 82, 98 and 114.

Alternatively, the human binding molecule of the invention is characterized as an antibody molecule, antibody fragment or derivative thereof or an antibody construct, which comprises a variable $V_L$-region as encoded by a nucleic acid molecule as shown in a SEQ ID NO selected from the group consisting of SEQ ID NOs: 9, 25, 41, 57, 73, 89, 105 and 121 or a variable $V_L$-region having an amino acid sequence as shown in a SEQ ID NO selected from the group consisting of SEQ ID NOs: 10, 26, 42, 58, 74, 90, 106 and 122.

The human binding molecule of the invention may also comprise at least one CDR3 of a $V_H$-region as encoded by a nucleic acid molecule as shown in SEQ ID NOs: 7, 23, 39, 55, 71, 87, 103 or 119 or at least one CDR3 amino acid sequence of an $V_H$-region as shown in SEQ ID NOs: 8, 24, 40, 56, 72, 88, 104 or 120 and/or wherein said antibody molecule comprises at least one CDR3 of an $V_L$-region as encoded by a nucleic acid molecule as shown in SEQ ID NOs: 15, 31, 47, 63, 79, 95, 111 or 127 or at least one CDR3 amino acid sequence of a $V_L$-region as shown in SEQ ID NOs: 16, 32, 48, 64, 80, 96, 112 or 128.

Alternatively the human binding molecule of the invention may also comprise at least one CDR2 of an $V_H$-region as encoded by a nucleic acid molecule as shown in SEQ ID NOs: 5, 21, 37, 53, 69, 85, 101 or 117 or at least one CDR2 amino acid sequence of an $V_H$-region as shown in SEQ ID NOs: 6, 22, 38, 54, 70, 86, 102 or 118 and/or wherein said antibody molecule comprises at least one CDR2 of an $V_L$-region as encoded by a nucleic acid molecule as shown in SEQ ID NOs: 13, 29, 45, 61, 77, 93, 109 or 125 or at least one CDR2 amino acid sequence of an $V_L$-region as shown in SEQ ID NOs: 14, 30, 46, 62, 78, 94, 110 or 126.

A further alternative human binding molecule of the invention is characterized as an antibody molecule, antibody fragment or derivative thereof or an antibody construct, which comprises at least one CDR1 of an $V_H$-region as encoded by a nucleic acid molecule as shown in SEQ ID NOs: 3, 19, 35, 51, 67, 83, 99 or 115 or at least one CDR1 amino acid sequence of an $V_H$-region as shown in SEQ ID NOs: 4, 20, 36, 52, 68, 84, 100 or 116 and/or wherein said antibody molecule comprises at least one CDR1 of an $V_L$-region as encoded by a nucleic acid molecule as shown in SEQ ID NOs: 11, 27, 43, 59, 75, 91, 107 or 123 or at least one CDR1 amino acid sequence of an $V_L$-region as shown in SEQ ID NOs: 12, 28, 44, 60, 76, 92, 108 or 124.

It is further envisaged by the present invention that the human binding molecule additionally comprises at least one further antigen-interaction-site and/or at least one further effector domain.

The invention also relates to multispecific binding molecules. Bi-, tri-, tetra- as well as oligo-specific binding molecule are particularly comprised. The term "further effector domain" has been defined and exemplified herein above.

Human binding molecules of the invention, which comprise at least one further antigen-interaction-site and/or at least one further effector domain, may be humanized and/or deimmunized.

As noted herein above only non-human derived domains of the binding molecule may be humanized. Furthermore, immunogenic epitopes, at the junctions between human derived domains and non-human derived domains and in non-human derived domains may be deleted by deimmunization. Methods for the humanization and or deimmunization of corresponding domains are known by the person skilled in the art and some possible methods have been discussed herein above.

In one embodiment of the human binding molecule of the invention, said at least one further antigen-interaction-site is specific for one or more cell surface molecule.

The terms "cell surface molecule" and "tumor marker/tumor specific marker" have been defined herein above. Preferably said cell surface molecule is a tumor specific marker. Examples for said tumor specific markers are TAG72, PSMA, CD44v6, CEA, Her2-neu, Her-3, Her-4, Lewis Y. Further markers have been described above.

It is also envisaged that said at least one further antigen-interaction-site is a domain which is derived from an antibody or antibody construct.

Preferably, said domain which is an antibody-derived region comprises a polypeptide sequence which corresponds to at least one variable region of an antibody. More preferably, said at least one further antigen-interaction-site is a further scFv. A particularly preferred molecular format of the invention provides a polypeptide construct wherein the antibody-derived region comprises one $V_H$ and one $V_L$ region.

The intramolecular orientation (N-terminal or C-terminal) of the different antigen interaction-sites (domains) in the human binding molecule is not decisive for the invention as long as said different antigen interaction-sites specifically bind to/interact with its specific antigens. Consequently, in the case of a bispecific binding molecule the domain specific for the human CD3 complex may be N-terminal (and the further antigen-interaction-site C-terminal) as well as C-terminal (and the further antigen-interaction-site N-terminal).

Preferably said at least one further antigen-interaction-site is a further scFv. In the particular format of an scFv the orientation of the $V_H$-domain and the $V_L$-domain in the domain of the further antigen-interaction-site is not decisive for the present invention. Thus, scFvs with both possible arrangements in the portion of the further antigen-interaction-site ($V_H$-domain-linker domain-$V_L$-domain; $V_L$-domain-linker domain-$V_H$-domain) are particular embodiments of the human binding molecule of the invention. Accordingly, for a corresponding bispecific human binding molecule said permutation of domains results in eight possible constructs for one specific human binding molecule.

In accordance with the invention said at least one further antigen-interaction-site specifically binds to/interacts with an antigen selected from the group consisting of EpCAM, CCR5, CD19, EphA2, HER-2 neu, HER-3, HER-4, EGFR, PSMA, CEA, TAG-72, MUC-1 (mucin), MUC2, MUC3, MUC4, $MUC5_{AC}$, $MUC5_B$, MUC7, βhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, STEAP II, mesothelin, A33 Antigen, Prostate Stem Cell Antigen (PSCA), Ly-6, desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, L6, SAS, CD63, Tu, TF, $Le^a$, Sialyl $Le^a$, $Le^b$, $Le^x$, Sialyl $Le^x$ and polyfucosyl-$Le^x$.

In the following tables 1 to 8, specific bispecific constructs comprising as one specificity the human anti-human CD3 binder as described herein are provided. The following tables 1 and 2 relate to the above described embodiment of the present invention and describe specific human anti-human CD3×CD19 constructs. The following tables 3 and 4 relate to the above described embodiment of the present invention and describe specific human anti-human CD3×EpCAM constructs. The following tables 5 and 6 relate to the above described embodiment of the present invention and describe specific human anti-human CD3×CCR5 constructs. The following tables 7 and 8 relate to the above-described embodiment of the present invention and describe specific human anti-human CD3×CD20 constructs. In this context, it is of note that tables 1, 3, 5 and 7 relate to nucleic acid sequences encoding the corresponding bispecific constructs, whereas tables 2, 4, 6 and 8, respectively, show the corresponding proteinaceous sequences.

The following tables 1, 3, 5 and 7 depict selected nucleic acid molecules encoding specific constructs of the inventions.

TABLE 1

| Construct | SEQ ID NO in construct portion . . . | | | | | | | h anti-hCD3 construct/ Specificity (N -> C)/ Domain Arrangement |
| | A | B | C | D | E | F | G | |
|---|---|---|---|---|---|---|---|---|
| 1 nuc | 9 | 174 | 1 | 176 | 129 | 174 | 131 | 3-106/CD3xCD19/LHHL |
| 2 nuc | 1 | 174 | 9 | 176 | 129 | 174 | 131 | 3-106/CD3xCD19/HLHL |
| 3 nuc | 9 | 174 | 1 | 176 | 131 | 174 | 129 | 3-106/CD3xCD19/LHLH |
| 4 nuc | 1 | 174 | 9 | 176 | 131 | 174 | 129 | 3-106/CD3xCD19/HLLH |
| 5 nuc | 131 | 174 | 129 | 176 | 1 | 174 | 9 | 3-106/CD19xCD3/LHHL |
| 6 nuc | 129 | 174 | 131 | 176 | 1 | 174 | 9 | 3-106/CD19xCD3/HLHL |
| 7 nuc | 131 | 174 | 129 | 176 | 9 | 174 | 1 | 3-106/CD19xCD3/LHLH |
| 8 nuc | 129 | 174 | 131 | 176 | 9 | 174 | 1 | 3-106/CD19xCD3/HLLH |
| 9 nuc | 25 | 174 | 17 | 176 | 129 | 174 | 131 | 3-114/CD3xCD19/LHHL |
| 10 nuc | 17 | 174 | 25 | 176 | 129 | 174 | 131 | 3-114/CD3xCD19/HLHL |
| 11 nuc | 25 | 174 | 17 | 176 | 131 | 174 | 129 | 3-114/CD3xCD19/LHLH |
| 12 nuc | 17 | 174 | 25 | 176 | 131 | 174 | 129 | 3-114/CD3xCD19/HLLH |
| 13 nuc | 131 | 174 | 129 | 176 | 17 | 174 | 25 | 3-114/CD19xCD3/LHHL |
| 14 nuc | 129 | 174 | 131 | 176 | 17 | 174 | 25 | 3-114/CD19xCD3/HLHL |
| 15 nuc | 131 | 174 | 129 | 176 | 25 | 174 | 17 | 3-114/CD19xCD3/LHLH |
| 16 nuc | 129 | 174 | 131 | 176 | 25 | 174 | 17 | 3-114/CD19xCD3/HLLH |
| 17 nuc | 41 | 174 | 33 | 176 | 129 | 174 | 131 | 3-148/CD3xCD19/LHHL |
| 18 nuc | 33 | 174 | 41 | 176 | 129 | 174 | 131 | 3-148/CD3xCD19/HLHL |
| 19 nuc | 41 | 174 | 33 | 176 | 131 | 174 | 129 | 3-148/CD3xCD19/LHLH |
| 20 nuc | 33 | 174 | 41 | 176 | 131 | 174 | 129 | 3-148/CD3xCD19/HLLH |
| 21 nuc | 131 | 174 | 129 | 176 | 33 | 174 | 41 | 3-148/CD19xCD3/LHHL |
| 22 nuc | 129 | 174 | 131 | 176 | 33 | 174 | 41 | 3-148/CD19xCD3/HLHL |
| 23 nuc | 131 | 174 | 129 | 176 | 41 | 174 | 33 | 3-148/CD19xCD3/LHLH |

TABLE 1-continued

| Construct | SEQ ID NO in construct portion . . . | | | | | | | h anti-hCD3 construct/ Specificity (N -> C)/ Domain Arrangement |
|---|---|---|---|---|---|---|---|---|
| | A | B | C | D | E | F | G | |
| 24 nuc | 129 | 174 | 131 | 176 | 41 | 174 | 33 | 3-148/CD19xCD3/HLLH |
| 25 nuc | 57 | 174 | 49 | 176 | 129 | 174 | 131 | 3-190/CD3xCD19/LHHL |
| 26 nuc | 49 | 174 | 57 | 176 | 129 | 174 | 131 | 3-190/CD3xCD19/HLHL |
| 27 nuc | 57 | 174 | 49 | 176 | 131 | 174 | 129 | 3-190/CD3xCD19/LHLH |
| 28 nuc | 49 | 174 | 57 | 176 | 131 | 174 | 129 | 3-190/CD3xCD19/HLLH |
| 29 nuc | 131 | 174 | 129 | 176 | 49 | 174 | 57 | 3-190/CD19xCD3/LHHL |
| 30 nuc | 129 | 174 | 131 | 176 | 49 | 174 | 57 | 3-190/CD19xCD3/HLHL |
| 31 nuc | 131 | 174 | 129 | 176 | 57 | 174 | 49 | 3-190/CD19xCD3/LHLH |
| 32 nuc | 129 | 174 | 131 | 176 | 57 | 174 | 49 | 3-190/CD19xCD3/HLLH |
| 33 nuc | 73 | 174 | 65 | 176 | 129 | 174 | 131 | 3-271/CD3xCD19/LHHL |
| 34 nuc | 65 | 174 | 73 | 176 | 129 | 174 | 131 | 3-271/CD3xCD19/HLHL |
| 35 nuc | 73 | 174 | 65 | 176 | 131 | 174 | 129 | 3-271/CD3xCD19/LHLH |
| 36 nuc | 65 | 174 | 73 | 176 | 131 | 174 | 129 | 3-271/CD3xCD19/HLLH |
| 37 nuc | 131 | 174 | 129 | 176 | 65 | 174 | 73 | 3-271/CD19xCD3/LHHL |
| 38 nuc | 129 | 174 | 131 | 176 | 65 | 174 | 73 | 3-271/CD19xCD3/HLHL |
| 39 nuc | 131 | 174 | 129 | 176 | 73 | 174 | 65 | 3-271/CD19xCD3/LHLH |
| 40 nuc | 129 | 174 | 131 | 176 | 73 | 174 | 65 | 3-271/CD19xCD3/HLLH |
| 41 nuc | 89 | 174 | 81 | 176 | 129 | 174 | 131 | 3-550/CD3xCD19/LHHL |
| 42 nuc | 81 | 174 | 89 | 176 | 129 | 174 | 131 | 3-550/CD3xCD19/HLHL |
| 43 nuc | 89 | 174 | 81 | 176 | 131 | 174 | 129 | 3-550/CD3xCD19/LHLH |
| 44 nuc | 81 | 174 | 89 | 176 | 131 | 174 | 129 | 3-550/CD3xCD19/HLLH |
| 45 nuc | 131 | 174 | 129 | 176 | 81 | 174 | 89 | 3-550/CD19xCD3/LHHL |
| 46 nuc | 129 | 174 | 131 | 176 | 81 | 174 | 89 | 3-550/CD19xCD3/HLHL |
| 47 nuc | 131 | 174 | 129 | 176 | 89 | 174 | 81 | 3-550/CD19xCD3/LHLH |
| 49 nuc | 105 | 174 | 97 | 176 | 129 | 174 | 131 | 4-10/CD3xCD19/LHHL |
| 50 nuc | 97 | 174 | 105 | 176 | 129 | 174 | 131 | 4-10/CD3xCD19/HLHL |
| 51 nuc | 105 | 174 | 97 | 176 | 131 | 174 | 129 | 4-10/CD3xCD19/LHLH |
| 52 nuc | 97 | 174 | 105 | 176 | 131 | 174 | 129 | 4-10/CD3xCD19/HLLH |
| 53 nuc | 131 | 174 | 129 | 176 | 97 | 174 | 105 | 4-10/CD19xCD3/LHHL |
| 54 nuc | 129 | 174 | 131 | 176 | 97 | 174 | 105 | 4-10/CD19xCD3/HLHL |
| 55 nuc | 131 | 174 | 129 | 176 | 105 | 174 | 97 | 4-10/CD19xCD3/LHLH |
| 56 nuc | 129 | 174 | 131 | 176 | 105 | 174 | 97 | 4-10/CD19xCD3/HLLH |
| 57 nuc | 121 | 174 | 113 | 176 | 129 | 174 | 131 | 4-48/CD3xCD19/LHHL |
| 58 nuc | 113 | 174 | 121 | 176 | 129 | 174 | 131 | 4-48/CD3xCD19/HLHL |
| 59 nuc | 121 | 174 | 113 | 176 | 131 | 174 | 129 | 4-48/CD3xCD19/LHLH |
| 60 nuc | 113 | 174 | 121 | 176 | 131 | 174 | 129 | 4-48/CD3xCD19/HLLH |
| 61 nuc | 131 | 174 | 129 | 176 | 113 | 174 | 121 | 4-48/CD19xCD3/LHHL |
| 62 nuc | 129 | 174 | 131 | 176 | 113 | 174 | 121 | 4-48/CD19xCD3/HLHL |
| 63 nuc | 131 | 174 | 129 | 176 | 121 | 174 | 113 | 4-48/CD19xCD3/LHLH |
| 64 nuc | 129 | 174 | 131 | 176 | 121 | 174 | 113 | 4-48/CD19xCD3/HLLH |

TABLE 3

| Construct | SEQ ID NO in construct portion . . . | | | | | | | h anti-hCD3 construct/ Specificity (N -> C)/ Domain Arrangement |
|---|---|---|---|---|---|---|---|---|
| | A | B | C | D | E | F | G | |
| 65 nuc | 9 | 174 | 1 | 176 | 133 | 174 | 135 | 3-106/CD3xEpCAM/LHHL |
| 66 nuc | 1 | 174 | 9 | 176 | 133 | 174 | 135 | 3-106/CD3xEpCAM/HLHL |
| 67 nuc | 9 | 174 | 1 | 176 | 135 | 174 | 133 | 3-106/CD3xEpCAM/LHLH |
| 68 nuc | 1 | 174 | 9 | 176 | 135 | 174 | 133 | 3-106/CD3xEpCAM/HLLH |
| 69 nuc | 135 | 174 | 133 | 176 | 1 | 174 | 9 | 3-106/EpCAMxCD3/LHHL |
| 70 nuc | 133 | 174 | 135 | 176 | 1 | 174 | 9 | 3-106/EpCAMxCD3/HLHL |
| 71 nuc | 135 | 174 | 133 | 176 | 9 | 174 | 1 | 3-106/EpCAMxCD3/LHLH |
| 72 nuc | 133 | 174 | 135 | 176 | 9 | 174 | 1 | 3-106/EpCAMxCD3/HLLH |
| 73 nuc | 25 | 174 | 17 | 176 | 133 | 174 | 135 | 3-114/CD3xEpCAM/LHHL |
| 74 nuc | 17 | 174 | 25 | 176 | 133 | 174 | 135 | 3-114/CD3xEpCAM/HLHL |
| 75 nuc | 25 | 174 | 17 | 176 | 135 | 174 | 133 | 3-114/CD3xEpCAM/LHLH |
| 76 nuc | 17 | 174 | 25 | 176 | 135 | 174 | 133 | 3-114/CD3xEpCAM/HLLH |
| 77 nuc | 135 | 174 | 133 | 176 | 17 | 174 | 25 | 3-114/EpCAMxCD3/LHHL |
| 78 nuc | 133 | 174 | 135 | 176 | 17 | 174 | 25 | 3-114/EpCAMxCD3/HLHL |
| 79 nuc | 135 | 174 | 133 | 176 | 25 | 174 | 17 | 3-114/EpCAMxCD3/LHLH |
| 80 nuc | 133 | 174 | 135 | 176 | 25 | 174 | 17 | 3-114/EpCAMxCD3/HLLH |
| 81 nuc | 41 | 174 | 33 | 176 | 133 | 174 | 135 | 3-148/CD3xEpCAM/LHHL |
| 82 nuc | 33 | 174 | 41 | 176 | 133 | 174 | 135 | 3-148/CD3xEpCAM/HLHL |
| 83 nuc | 41 | 174 | 33 | 176 | 135 | 174 | 133 | 3-148/CD3xEpCAM/LHLH |
| 84 nuc | 33 | 174 | 41 | 176 | 135 | 174 | 133 | 3-148/CD3xEpCAM/HLLH |
| 85 nuc | 135 | 174 | 133 | 176 | 33 | 174 | 41 | 3-148/EpCAMxCD3/LHHL |
| 86 nuc | 133 | 174 | 135 | 176 | 33 | 174 | 41 | 3-148/EpCAMxCD3/HLHL |
| 87 nuc | 135 | 174 | 133 | 176 | 41 | 174 | 33 | 3-148/EpCAMxCD3/LHLH |
| 88 nuc | 133 | 174 | 135 | 176 | 41 | 174 | 33 | 3-148/EpCAMxCD3/HLLH |

TABLE 3-continued

| Construct | SEQ ID NO in construct portion... | | | | | | | h anti-hCD3 construct/ Specificity (N -> C)/ Domain Arrangement |
|---|---|---|---|---|---|---|---|---|
| | A | B | C | D | E | F | G | |
| 89 nuc | 57 | 174 | 49 | 176 | 133 | 174 | 135 | 3-190/CD3xEpCAM/LHHL |
| 90 nuc | 49 | 174 | 57 | 176 | 133 | 174 | 135 | 3-190/CD3xEpCAM/HLHL |
| 91 nuc | 57 | 174 | 49 | 176 | 135 | 174 | 133 | 3-190/CD3xEpCAM/LHLH |
| 92 nuc | 49 | 174 | 57 | 176 | 135 | 174 | 133 | 3-190/CD3xEpCAM/HLLH |
| 93 nuc | 135 | 174 | 133 | 176 | 49 | 174 | 57 | 3-190/EpCAMxCD3/LHHL |
| 94 nuc | 133 | 174 | 135 | 176 | 49 | 174 | 57 | 3-190/EpCAMxCD3/HLHL |
| 95 nuc | 135 | 174 | 133 | 176 | 57 | 174 | 49 | 3-190/EpCAMxCD3/LHLH |
| 96 nuc | 133 | 174 | 135 | 176 | 57 | 174 | 49 | 3-190/EpCAMxCD3/HLLH |
| 97 nuc | 73 | 174 | 65 | 176 | 133 | 174 | 135 | 3-271/CD3xEpCAM/LHHL |
| 98 nuc | 65 | 174 | 73 | 176 | 133 | 174 | 135 | 3-271/CD3xEpCAM/HLHL |
| 99 nuc | 73 | 174 | 65 | 176 | 135 | 174 | 133 | 3-271/CD3xEpCAM/LHLH |
| 100 nuc | 65 | 174 | 73 | 176 | 135 | 174 | 133 | 3-271/CD3xEpCAM/HLLH |
| 101 nuc | 135 | 174 | 133 | 176 | 65 | 174 | 73 | 3-271/EpCAMxCD3/LHHL |
| 102 nuc | 133 | 174 | 135 | 176 | 65 | 174 | 73 | 3-271/EpCAMxCD3/HLHL |
| 103 nuc | 135 | 174 | 133 | 176 | 73 | 174 | 65 | 3-271/EpCAMxCD3/LHLH |
| 104 nuc | 133 | 174 | 135 | 176 | 73 | 174 | 65 | 3-271/EpCAMxCD3/HLLH |
| 105 nuc | 89 | 174 | 81 | 176 | 133 | 174 | 135 | 3-550/CD3xEpCAM/LHHL |
| 106 nuc | 81 | 174 | 89 | 176 | 133 | 174 | 135 | 3-550/CD3xEpCAM/HLHL |
| 107 nuc | 89 | 174 | 81 | 176 | 135 | 174 | 133 | 3-550/CD3xEpCAM/LHLH |
| 108 nuc | 81 | 174 | 89 | 176 | 135 | 174 | 133 | 3-550/CD3xEpCAM/HLLH |
| 109 nuc | 135 | 174 | 133 | 176 | 81 | 174 | 89 | 3-550/EpCAMxCD3/LHHL |
| 110 nuc | 133 | 174 | 135 | 176 | 81 | 174 | 89 | 3-550/EpCAMxCD3/HLHL |
| 111 nuc | 135 | 174 | 133 | 176 | 89 | 174 | 81 | 3-550/EpCAMxCD3/LHLH |
| 112 nuc | 133 | 174 | 135 | 176 | 89 | 174 | 81 | 3-550/EpCAMxCD3/HLLH |
| 113 nuc | 105 | 174 | 97 | 176 | 133 | 174 | 135 | 4-10/CD3xEpCAM/LHHL |
| 114 nuc | 97 | 174 | 105 | 176 | 133 | 174 | 135 | 4-10/CD3xEpCAM/HLHL |
| 115 nuc | 105 | 174 | 97 | 176 | 135 | 174 | 133 | 4-10/CD3xEpCAM/LHLH |
| 116 nuc | 97 | 174 | 105 | 176 | 135 | 174 | 133 | 4-10/CD3xEpCAM/HLLH |
| 117 nuc | 135 | 174 | 133 | 176 | 97 | 174 | 105 | 4-10/EpCAMxCD3/LHHL |
| 118 nuc | 133 | 174 | 135 | 176 | 97 | 174 | 105 | 4-10/EpCAMxCD3/HLHL |
| 119 nuc | 135 | 174 | 133 | 176 | 105 | 174 | 97 | 4-10/EpCAMxCD3/LHLH |
| 120 nuc | 133 | 174 | 135 | 176 | 105 | 174 | 97 | 4-10/EpCAMxCD3/HLLH |
| 121 nuc | 121 | 174 | 113 | 176 | 133 | 174 | 135 | 4-48/CD3xEpCAM/LHHL |
| 122 nuc | 113 | 174 | 121 | 176 | 133 | 174 | 135 | 4-48/CD3xEpCAM/HLHL |
| 123 nuc | 121 | 174 | 113 | 176 | 135 | 174 | 133 | 4-48/CD3xEpCAM/LHLH |
| 124 nuc | 113 | 174 | 121 | 176 | 135 | 174 | 133 | 4-48/CD3xEpCAM/HLLH |
| 125 nuc | 135 | 174 | 133 | 176 | 113 | 174 | 121 | 4-48/EpCAMxCD3/LHHL |
| 126 nuc | 133 | 174 | 135 | 176 | 113 | 174 | 121 | 4-48/EpCAMxCD3/HLHL |
| 127 nuc | 135 | 174 | 133 | 176 | 121 | 174 | 113 | 4-48/EpCAMxCD3/LHLH |
| 128 nuc | 133 | 174 | 135 | 176 | 121 | 174 | 113 | 4-48/EpCAMxCD3/HLLH |

TABLE 5

| Construct | SEQ ID NO in construct portion... | | | | | | | h anti-hCD3 construct/ Specificity (N -> C)/ Domain Arrangement |
|---|---|---|---|---|---|---|---|---|
| | A | B | C | D | E | F | G | |
| 129 nuc | 9 | 174 | 1 | 176 | 196 | 174 | 198 | 3-106/CD3xCCR5/LHHL |
| 130 nuc | 1 | 174 | 9 | 176 | 196 | 174 | 198 | 3-106/CD3xCCR5/HLHL |
| 131 nuc | 9 | 174 | 1 | 176 | 198 | 174 | 196 | 3-106/CD3xCCR5/LHLH |
| 132 nuc | 1 | 174 | 9 | 176 | 198 | 174 | 196 | 3-106/CD3xCCR5/HLLH |
| 133 nuc | 198 | 174 | 196 | 176 | 1 | 174 | 9 | 3-106/CCR5xCD3/LHHL |
| 134 nuc | 196 | 174 | 198 | 176 | 1 | 174 | 9 | 3-106/CCR5xCD3/HLHL |
| 135 nuc | 198 | 174 | 196 | 176 | 9 | 174 | 1 | 3-106/CCR5xCD3/LHLH |
| 136 nuc | 196 | 174 | 198 | 176 | 9 | 174 | 1 | 3-106/CCR5xCD3/HLLH |
| 137 nuc | 25 | 174 | 17 | 176 | 196 | 174 | 198 | 3-114/CD3xCCR5/LHHL |
| 138 nuc | 17 | 174 | 25 | 176 | 196 | 174 | 198 | 3-114/CD3xCCR5/HLHL |
| 139 nuc | 25 | 174 | 17 | 176 | 198 | 174 | 196 | 3-114/CD3xCCR5/LHLH |
| 140 nuc | 17 | 174 | 25 | 176 | 198 | 174 | 196 | 3-114/CD3xCCR5/HLLH |
| 141 nuc | 198 | 174 | 196 | 176 | 17 | 174 | 25 | 3-114/CCR5xCD3/LHHL |
| 142 nuc | 196 | 174 | 198 | 176 | 17 | 174 | 25 | 3-114/CCR5xCD3/HLHL |
| 143 nuc | 198 | 174 | 196 | 176 | 25 | 174 | 17 | 3-114/CCR5xCD3/LHLH |
| 144 nuc | 196 | 174 | 198 | 176 | 25 | 174 | 17 | 3-114/CCR5xCD3/HLLH |
| 145 nuc | 41 | 174 | 33 | 176 | 196 | 174 | 198 | 3-148/CD3xCCR5/LHHL |
| 146 nuc | 33 | 174 | 41 | 176 | 196 | 174 | 198 | 3-148/CD3xCCR5/HLHL |
| 147 nuc | 41 | 174 | 33 | 176 | 198 | 174 | 196 | 3-148/CD3xCCR5/LHLH |
| 148 nuc | 33 | 174 | 41 | 176 | 198 | 174 | 196 | 3-148/CD3xCCR5/HLLH |
| 149 nuc | 198 | 174 | 196 | 176 | 33 | 174 | 41 | 3-148/CCR5xCD3/LHHL |
| 150 nuc | 196 | 174 | 198 | 176 | 33 | 174 | 41 | 3-148/CCR5xCD3/HLHL |
| 151 nuc | 198 | 174 | 196 | 176 | 41 | 174 | 33 | 3-148/CCR5xCD3/LHLH |
| 152 nuc | 196 | 174 | 198 | 176 | 41 | 174 | 33 | 3-148/CCR5xCD3/HLLH |

TABLE 5-continued

| Construct | A | B | C | D | E | F | G | h anti-hCD3 construct/ Specificity (N -> C)/ Domain Arrangement |
|---|---|---|---|---|---|---|---|---|
| 153 nuc | 57 | 174 | 49 | 176 | 196 | 174 | 198 | 3-190/CD3xCCR5/LHHL |
| 154 nuc | 49 | 174 | 57 | 176 | 196 | 174 | 198 | 3-190/CD3xCCR5/HLHL |
| 155 nuc | 57 | 174 | 49 | 176 | 198 | 174 | 196 | 3-190/CD3xCCR5/LHLH |
| 156 nuc | 49 | 174 | 57 | 176 | 198 | 174 | 196 | 3-190/CD3xCCR5/HLLH |
| 157 nuc | 198 | 174 | 196 | 176 | 49 | 174 | 57 | 3-190/CCR5xCD3/LHHL |
| 158 nuc | 196 | 174 | 198 | 176 | 49 | 174 | 57 | 3-190/CCR5xCD3/HLHL |
| 159 nuc | 198 | 174 | 196 | 176 | 57 | 174 | 49 | 3-190/CCR5xCD3/LHLH |
| 160 nuc | 196 | 174 | 198 | 176 | 57 | 174 | 49 | 3-190/CCR5xCD3/HLLH |
| 161 nuc | 73 | 174 | 65 | 176 | 196 | 174 | 198 | 3-271/CD3xCCR5/LHHL |
| 162 nuc | 65 | 174 | 73 | 176 | 196 | 174 | 198 | 3-271/CD3xCCR5/HLHL |
| 163 nuc | 73 | 174 | 65 | 176 | 198 | 174 | 196 | 3-271/CD3xCCR5/LHLH |
| 164 nuc | 65 | 174 | 73 | 176 | 198 | 174 | 196 | 3-271/CD3xCCR5/HLLH |
| 165 nuc | 198 | 174 | 196 | 176 | 65 | 174 | 73 | 3-271/CCR5xCD3/LHHL |
| 166 nuc | 196 | 174 | 198 | 176 | 65 | 174 | 73 | 3-271/CCR5xCD3/HLHL |
| 167 nuc | 198 | 174 | 196 | 176 | 73 | 174 | 65 | 3-271/CCR5xCD3/LHLH |
| 168 nuc | 196 | 174 | 198 | 176 | 73 | 174 | 65 | 3-271/CCR5xCD3/HLLH |
| 169 nuc | 89 | 174 | 81 | 176 | 196 | 174 | 198 | 3-550/CD3xCCR5/LHHL |
| 170 nuc | 81 | 174 | 89 | 176 | 196 | 174 | 198 | 3-550/CD3xCCR5/HLHL |
| 171 nuc | 89 | 174 | 81 | 176 | 198 | 174 | 196 | 3-550/CD3xCCR5/LHLH |
| 172 nuc | 81 | 174 | 89 | 176 | 198 | 174 | 196 | 3-550/CD3xCCR5/HLLH |
| 173 nuc | 198 | 174 | 196 | 176 | 81 | 174 | 89 | 3-550/CCR5xCD3/LHHL |
| 174 nuc | 196 | 174 | 198 | 176 | 81 | 174 | 89 | 3-550/CCR5xCD3/HLHL |
| 175 nuc | 198 | 174 | 196 | 176 | 89 | 174 | 81 | 3-550/CCR5xCD3/LHLH |
| 176 nuc | 196 | 174 | 198 | 176 | 89 | 174 | 81 | 3-550/CCR5xCD3/HLLH |
| 177 nuc | 105 | 174 | 97 | 176 | 196 | 174 | 198 | 4-10/CD3xCCR5/LHHL |
| 178 nuc | 97 | 174 | 105 | 176 | 196 | 174 | 198 | 4-10/CD3xCCR5/HLHL |
| 179 nuc | 105 | 174 | 97 | 176 | 198 | 174 | 196 | 4-10/CD3xCCR5/LHLH |
| 180 nuc | 97 | 174 | 105 | 176 | 198 | 174 | 196 | 4-10/CD3xCCR5/HLLH |
| 181 nuc | 198 | 174 | 196 | 176 | 97 | 174 | 105 | 4-10/CCR5xCD3/LHHL |
| 182 nuc | 196 | 174 | 198 | 176 | 97 | 174 | 105 | 4-10/CCR5xCD3/HLHL |
| 183 nuc | 198 | 174 | 196 | 176 | 105 | 174 | 97 | 4-10/CCR5xCD3/LHLH |
| 184 nuc | 196 | 174 | 198 | 176 | 105 | 174 | 97 | 4-10/CCR5xCD3/HLLH |
| 185 nuc | 121 | 174 | 113 | 176 | 196 | 174 | 198 | 4-48/CD3xCCR5/LHHL |
| 186 nuc | 113 | 174 | 121 | 176 | 196 | 174 | 198 | 4-48/CD3xCCR5/HLHL |
| 187 nuc | 121 | 174 | 113 | 176 | 198 | 174 | 196 | 4-48/CD3xCCR5/LHLH |
| 188 nuc | 113 | 174 | 121 | 176 | 198 | 174 | 196 | 4-48/CD3xCCR5/HLLH |
| 189 nuc | 198 | 174 | 196 | 176 | 113 | 174 | 121 | 4-48/CCR5xCD3/LHHL |
| 190 nuc | 196 | 174 | 198 | 176 | 113 | 174 | 121 | 4-48/CCR5xCD3/HLHL |
| 191 nuc | 198 | 174 | 196 | 176 | 121 | 174 | 113 | 4-48/CCR5xCD3/LHLH |
| 192 nuc | 196 | 174 | 198 | 176 | 121 | 174 | 113 | 4-48/CCR5xCD3/HLLH |

TABLE 7

| Construct | A | B | C | D | E | F | G | h anti-hCD3 construct/ Specificity (N -> C)/ Domain Arrangement |
|---|---|---|---|---|---|---|---|---|
| 193 nuc | 9 | 174 | 1 | 176 | 200 | 174 | 202 | 3-106/CD3xCD20/LHHL |
| 194 nuc | 1 | 174 | 9 | 176 | 200 | 174 | 202 | 3-106/CD3xCD20/HLHL |
| 195 nuc | 9 | 174 | 1 | 176 | 202 | 174 | 200 | 3-106/CD3xCD20/LHLH |
| 196 nuc | 1 | 174 | 9 | 176 | 202 | 174 | 200 | 3-106/CD3xCD20/HLLH |
| 197 nuc | 202 | 174 | 200 | 176 | 1 | 174 | 9 | 3-106/CD20xCD3/LHHL |
| 198 nuc | 200 | 174 | 202 | 176 | 1 | 174 | 9 | 3-106/CD20xCD3/HLHL |
| 199 nuc | 202 | 174 | 200 | 176 | 9 | 174 | 1 | 3-106/CD20xCD3/LHLH |
| 200 nuc | 200 | 174 | 202 | 176 | 9 | 174 | 1 | 3-106/CD20xCD3/HLLH |
| 201 nuc | 25 | 174 | 17 | 176 | 200 | 174 | 202 | 3-114/CD3xCD20/LHHL |
| 202 nuc | 17 | 174 | 25 | 176 | 200 | 174 | 202 | 3-114/CD3xCD20/HLHL |
| 203 nuc | 25 | 174 | 17 | 176 | 202 | 174 | 200 | 3-114/CD3xCD20/LHLH |
| 204 nuc | 17 | 174 | 25 | 176 | 202 | 174 | 200 | 3-114/CD3xCD20/HLLH |
| 205 nuc | 202 | 174 | 200 | 176 | 17 | 174 | 25 | 3-114/CD20xCD3/LHHL |
| 206 nuc | 200 | 174 | 202 | 176 | 17 | 174 | 25 | 3-114/CD20xCD3/HLHL |
| 207 nuc | 202 | 174 | 200 | 176 | 25 | 174 | 17 | 3-114/CD20xCD3/LHLH |
| 208 nuc | 200 | 174 | 202 | 176 | 25 | 174 | 17 | 3-114/CD20xCD3/HLLH |
| 209 nuc | 41 | 174 | 33 | 176 | 200 | 174 | 202 | 3-148/CD3xCD20/LHHL |
| 210 nuc | 33 | 174 | 41 | 176 | 200 | 174 | 202 | 3-148/CD3xCD20/HLHL |
| 211 nuc | 41 | 174 | 33 | 176 | 202 | 174 | 200 | 3-148/CD3xCD20/LHLH |
| 212 nuc | 33 | 174 | 41 | 176 | 202 | 174 | 200 | 3-148/CD3xCD20/HLLH |
| 213 nuc | 202 | 174 | 200 | 176 | 33 | 174 | 41 | 3-148/CD20xCD3/LHHL |
| 214 nuc | 200 | 174 | 202 | 176 | 33 | 174 | 41 | 3-148/CD20xCD3/HLHL |
| 215 nuc | 202 | 174 | 200 | 176 | 41 | 174 | 33 | 3-148/CD20xCD3/LHLH |
| 216 nuc | 200 | 174 | 202 | 176 | 41 | 174 | 33 | 3-148/CD20xCD3/HLLH |

TABLE 7-continued

| Construct | A | B | C | D | E | F | G | h anti-hCD3 construct/Specificity (N -> C)/Domain Arrangement |
|---|---|---|---|---|---|---|---|---|
| 217 nuc | 57 | 174 | 49 | 176 | 200 | 174 | 202 | 3-190/CD3xCD20/LHHL |
| 218 nuc | 49 | 174 | 57 | 176 | 200 | 174 | 202 | 3-190/CD3xCD20/HLHL |
| 219 nuc | 57 | 174 | 49 | 176 | 202 | 174 | 200 | 3-190/CD3xCD20/LHLH |
| 220 nuc | 49 | 174 | 57 | 176 | 202 | 174 | 200 | 3-190/CD3xCD20/HLLH |
| 221 nuc | 202 | 174 | 200 | 176 | 49 | 174 | 57 | 3-190/CD20xCD3/LHHL |
| 222 nuc | 200 | 174 | 202 | 176 | 49 | 174 | 57 | 3-190/CD20xCD3/HLHL |
| 223 nuc | 202 | 174 | 200 | 176 | 57 | 174 | 49 | 3-190/CD20xCD3/LHLH |
| 224 nuc | 200 | 174 | 202 | 176 | 57 | 174 | 49 | 3-190/CD20xCD3/HLLH |
| 225 nuc | 73 | 174 | 65 | 176 | 200 | 174 | 202 | 3-271/CD3xCD20/LHHL |
| 226 nuc | 65 | 174 | 73 | 176 | 200 | 174 | 202 | 3-271/CD3xCD20/HLHL |
| 227 nuc | 73 | 174 | 65 | 176 | 202 | 174 | 200 | 3-271/CD3xCD20/LHLH |
| 228 nuc | 65 | 174 | 73 | 176 | 202 | 174 | 200 | 3-271/CD3xCD20/HLLH |
| 229 nuc | 202 | 174 | 200 | 176 | 65 | 174 | 73 | 3-271/CD20xCD3/LHHL |
| 230 nuc | 200 | 174 | 202 | 176 | 65 | 174 | 73 | 3-271/CD20xCD3/HLHL |
| 231 nuc | 202 | 174 | 200 | 176 | 73 | 174 | 65 | 3-271/CD20xCD3/LHLH |
| 232 nuc | 200 | 174 | 202 | 176 | 73 | 174 | 65 | 3-271/CD20xCD3/HLLH |
| 233 nuc | 89 | 174 | 81 | 176 | 200 | 174 | 202 | 3-550/CD3xCD20/LHHL |
| 234 nuc | 81 | 174 | 89 | 176 | 200 | 174 | 202 | 3-550/CD3xCD20/HLHL |
| 235 nuc | 89 | 174 | 81 | 176 | 202 | 174 | 200 | 3-550/CD3xCD20/LHLH |
| 236 nuc | 81 | 174 | 89 | 176 | 202 | 174 | 200 | 3-550/CD3xCD20/HLLH |
| 237 nuc | 202 | 174 | 200 | 176 | 81 | 174 | 89 | 3-550/CD20xCD3/LHHL |
| 238 nuc | 200 | 174 | 202 | 176 | 81 | 174 | 89 | 3-550/CD20xCD3/HLHL |
| 239 nuc | 202 | 174 | 200 | 176 | 89 | 174 | 81 | 3-550/CD20xCD3/LHLH |
| 240 nuc | 200 | 174 | 202 | 176 | 89 | 174 | 81 | 3-550/CD20xCD3/HLLH |
| 241 nuc | 105 | 174 | 97 | 176 | 200 | 174 | 202 | 4-10/CD3xCD20/LHHL |
| 242 nuc | 97 | 174 | 105 | 176 | 200 | 174 | 202 | 4-10/CD3xCD20/HLHL |
| 243 nuc | 105 | 174 | 97 | 176 | 202 | 174 | 200 | 4-10/CD3xCD20/LHLH |
| 244 nuc | 97 | 174 | 105 | 176 | 202 | 174 | 200 | 4-10/CD3xCD20/HLLH |
| 245 nuc | 202 | 174 | 200 | 176 | 97 | 174 | 105 | 4-10/CD20xCD3/LHHL |
| 246 nuc | 200 | 174 | 202 | 176 | 97 | 174 | 105 | 4-10/CD20xCD3/HLHL |
| 247 nuc | 202 | 174 | 200 | 176 | 105 | 174 | 97 | 4-10/CD20xCD3/LHLH |
| 248 nuc | 200 | 174 | 202 | 176 | 105 | 174 | 97 | 4-10/CD20xCD3/HLLH |
| 249 nuc | 121 | 174 | 113 | 176 | 200 | 174 | 202 | 4-48/CD3xCD20/LHHL |
| 250 nuc | 113 | 174 | 121 | 176 | 200 | 174 | 202 | 4-48/CD3xCD20/HLHL |
| 251 nuc | 121 | 174 | 113 | 176 | 202 | 174 | 200 | 4-48/CD3xCD20/LHLH |
| 252 nuc | 113 | 174 | 121 | 176 | 202 | 174 | 200 | 4-48/CD3xCD20/HLLH |
| 253 nuc | 202 | 174 | 200 | 176 | 113 | 174 | 121 | 4-48/CD20xCD3/LHHL |
| 254 nuc | 200 | 174 | 202 | 176 | 113 | 174 | 121 | 4-48/CD20xCD3/HLHL |
| 255 nuc | 202 | 174 | 200 | 176 | 121 | 174 | 113 | 4-48/CD20xCD3/LHLH |
| 256 nuc | 200 | 174 | 202 | 176 | 121 | 174 | 113 | 4-48/CD20xCD3/HLLH |

Nucleic acid constructs are as defined in Tables 1, 3, 5 and 7. Each nucleic acid construct in each of Tables 1, 3, 5 and 7 comprises 7 distinct nucleic acid modules, denoted A-G. Nucleic acid modules A-G are directly and covalently linked to one another in a single contiguous nucleotide chain by phosphate glycoside bonds in the order A-B-C-D-E-F-G, with nucleic acid module A at the 5'-end and nucleic acid module G at the 3'-end of a respective nucleic acid construct. Nucleic acid modules A, C, E and G denote encoding regions for antibody variable domains which can be either VH or VL domains of antibodies having specificity for different antigens. Each construct comprises nucleic acid modules encoding a VH and VL region from a human antibody or fragment thereof having specificity for human CD3 as well as a VH and VL region from an antibody or fragment thereof having specificity for one of the human antigens CD19, EpCAM, CCR5 or CD20.

If nucleic acid module A encodes a VH antibody domain, then nucleic acid module C encodes a VL protein domain, and vice versa. If nucleic acid module E encodes a VH antibody domain, then nucleic acid module G encodes a VL protein domain, and vice versa.

Nucleic acid molecules encoding VH domains of human antibodies or fragments thereof having specificity for the human CD3 antigen can be selected from the sequences as set out in SEQ ID NOs: 1, 17, 33, 49, 65, 81, 97 or 113. Nucleic acid molecules encoding VL domains of human antibodies or fragments thereof having specificity for the human CD3 antigen can be selected from the sequences as set out in SEQ ID NOs: 9, 25, 41, 57, 73, 89, 105, 121. Nucleic acid molecules encoding VH and VL domains of an antibody or fragment thereof having specificity for the CD19 antigen have the nucleic acid sequences as set out in SEQ ID NOs: 129 and 131, respectively. Nucleic acid molecules encoding VH and VL domains of an antibody or fragment thereof having specificity for the EpCAM antigen have the nucleic acid sequences as set out in SEQ ID NOs: 133 and 135, respectively. Nucleic acid molecules encoding VH and VL domains of an antibody or fragment thereof having specificity for the CCR5 antigen have the nucleic acid sequences as set out in SEQ ID NOs: 196 and 198, respectively. Nucleic acid molecules encoding VH and VL domains of an antibody or fragment thereof having specificity for the CD20 antigen have the nucleic acid sequences as set out in SEQ ID NOs: 200 and 202, respectively.

Pairs of nucleic acids encoding antibody variable domains denoted by the nucleic acid module pairs NC and E/G are joined by additional linking nucleic acid modules, wherein nucleic acid module B serves to directly link the module pair A/C and nucleic acid module F serves to directly link the module pair E/G. Nucleic acid modules B and F each have the nucleotide sequence as set out in SEQ ID NO: 174.

The combination of nucleic acid modules A-B-C and the combination of nucleic acid modules E-F-G each respectively constitute one scFv fragment of an antibody having specificity for either the human CD3 antigen or for any of the human antigens CD19, EpCAM, CCR5 or CD20. The respective groups of nucleic acid modules A-B-C and E-F-G are connected to one another through nucleic acid module D, having the nucleotide sequence as set out in SEQ ID NO: 176. Nucleic acid module D serves to connect the 3'-end of nucleic acid module C with the 5'-end of nucleic acid module E.

Especially preferred nucleic acid constructs encoding bispecific single chain binding molecules comprising human anti-CD3 portions are (with corresponding SEQ ID NOs in parentheses) 20nuc (SEQ ID NO: 205), 21nuc (SEQ ID NO: 215), 28nuc (SEQ ID NO: 207), 29nuc (SEQ ID NO: 217), 36nuc (SEQ ID NO: 209), 37nuc (SEQ ID NO: 219), 52nuc (SEQ ID NO: 211), 53nuc (SEQ ID NO: 221), 60nuc (SEQ ID NO: 213), 61nuc (SEQ ID NO: 223), 82nuc (SEQ ID NO: 225), 85nuc (SEQ ID NO: 235), 90nuc (SEQ ID NO: 227), 93nuc (SEQ ID NO: 237), 98nuc (SEQ ID NO: 229), 101nuc (SEQ ID NO: 239), 114nuc (SEQ ID NO: 231), 117nuc (SEQ ID NO: 241), 122nuc (SEQ ID NO: 233), 125nuc (SEQ ID NO: 243), 149nuc (SEQ ID NO: 251), 157nuc (SEQ ID NO: 249), 213nuc (SEQ ID NO: 247) and 221nuc (SEQ ID NO: 245).

Proteinaceous constructs as encoded, inter alia, by the nucleic acid molecules shown in Tables 1, 3, 5 and 7 (as detailed above) are shown and illustrated in the corresponding tables 2, 4, 6 and 8.

TABLE 2

| Construct | SEQ ID NO in construct portion . . . | | | | | | | h anti-hCD3 construct/ Specificity (N -> C)/ Domain Arrangement |
| | A | B | C | D | E | F | G | |
|---|---|---|---|---|---|---|---|---|
| 1 prot | 10 | 175 | 2 | 177 | 130 | 175 | 132 | 3-106/CD3xCD19/LHHL |
| 2 prot | 2 | 175 | 10 | 177 | 130 | 175 | 132 | 3-106/CD3xCD19/HLHL |
| 3 prot | 10 | 175 | 2 | 177 | 132 | 175 | 130 | 3-106/CD3xCD19/LHLH |
| 4 prot | 2 | 175 | 10 | 177 | 132 | 175 | 130 | 3-106/CD3xCD19/HLLH |
| 5 prot | 132 | 175 | 130 | 177 | 2 | 175 | 10 | 3-106/CD19xCD3/LHHL |
| 6 prot | 130 | 175 | 132 | 177 | 2 | 175 | 10 | 3-106/CD19xCD3/HLHL |
| 7 prot | 132 | 175 | 130 | 177 | 10 | 175 | 2 | 3-106/CD19xCD3/LHLH |
| 8 prot | 130 | 175 | 132 | 177 | 10 | 175 | 2 | 3-106/CD19xCD3/HLLH |
| 9 prot | 26 | 175 | 18 | 177 | 130 | 175 | 132 | 3-114/CD3xCD19/LHHL |
| 10 prot | 18 | 175 | 26 | 177 | 130 | 175 | 132 | 3-114/CD3xCD19/HLHL |
| 11 prot | 26 | 175 | 18 | 177 | 132 | 175 | 130 | 3-114/CD3xCD19/LHLH |
| 12 prot | 18 | 175 | 26 | 177 | 132 | 175 | 130 | 3-114/CD3xCD19/HLLH |
| 13 prot | 132 | 175 | 130 | 177 | 18 | 175 | 26 | 3-114/CD19xCD3/LHHL |
| 14 prot | 130 | 175 | 132 | 177 | 18 | 175 | 26 | 3-114/CD19xCD3/HLHL |
| 15 prot | 132 | 175 | 130 | 177 | 26 | 175 | 18 | 3-114/CD19xCD3/LHLH |
| 16 prot | 130 | 175 | 132 | 177 | 26 | 175 | 18 | 3-114/CD19xCD3/HLLH |
| 17 prot | 42 | 175 | 34 | 177 | 130 | 175 | 132 | 3-148/CD3xCD19/LHHL |
| 18 prot | 34 | 175 | 42 | 177 | 130 | 175 | 132 | 3-148/CD3xCD19/HLHL |
| 19 prot | 42 | 175 | 34 | 177 | 132 | 175 | 130 | 3-148/CD3xCD19/LHLH |
| 20 prot | 34 | 175 | 42 | 177 | 132 | 175 | 130 | 3-148/CD3xCD19/HLLH |
| 21prot | 132 | 175 | 130 | 177 | 34 | 175 | 42 | 3-148/CD19xCD3/LHHL |
| 22 prot | 130 | 175 | 132 | 177 | 34 | 175 | 42 | 3-148/CD19xCD3/HLHL |
| 23 prot | 132 | 175 | 130 | 177 | 42 | 175 | 34 | 3-148/CD19xCD3/LHLH |
| 24 prot | 130 | 175 | 132 | 177 | 42 | 175 | 34 | 3-148/CD19xCD3/HLLH |
| 25 prot | 58 | 175 | 50 | 177 | 130 | 175 | 132 | 3-190/CD3xCD19/LHHL |
| 26 prot | 50 | 175 | 58 | 177 | 130 | 175 | 132 | 3-190/CD3xCD19/HLHL |
| 27 prot | 58 | 175 | 50 | 177 | 132 | 175 | 130 | 3-190/CD3xCD19/LHLH |
| 28 prot | 50 | 175 | 58 | 177 | 132 | 175 | 130 | 3-190/CD3xCD19/HLLH |
| 29 prot | 132 | 175 | 130 | 177 | 50 | 175 | 58 | 3-190/CD19xCD3/LHHL |
| 30 prot | 130 | 175 | 132 | 177 | 50 | 175 | 58 | 3-190/CD19xCD3/HLHL |
| 31 prot | 132 | 175 | 130 | 177 | 58 | 175 | 50 | 3-190/CD19xCD3/LHLH |
| 32 prot | 130 | 175 | 132 | 177 | 58 | 175 | 50 | 3-190/CD19xCD3/HLLH |
| 33 prot | 74 | 175 | 66 | 177 | 130 | 175 | 132 | 3-271/CD3xCD19/LHHL |
| 34 prot | 66 | 175 | 74 | 177 | 130 | 175 | 132 | 3-271/CD3xCD19/HLHL |
| 35 prot | 74 | 175 | 66 | 177 | 132 | 175 | 130 | 3-271/CD3xCD19/LHLH |
| 36 prot | 66 | 175 | 74 | 177 | 132 | 175 | 130 | 3-271/CD3xCD19/HLLH |
| 37 prot | 132 | 175 | 130 | 177 | 66 | 175 | 74 | 3-271/CD19xCD3/LHHL |
| 38 prot | 130 | 175 | 132 | 177 | 66 | 175 | 74 | 3-271/CD19xCD3/HLHL |
| 39 prot | 132 | 175 | 130 | 177 | 74 | 175 | 66 | 3-271/CD19xCD3/LHLH |
| 40 prot | 130 | 175 | 132 | 177 | 74 | 175 | 66 | 3-271/CD19xCD3/HLLH |
| 41 prot | 90 | 175 | 82 | 177 | 130 | 175 | 132 | 3-550/CD3xCD19/LHHL |
| 42 prot | 82 | 175 | 90 | 177 | 130 | 175 | 132 | 3-550/CD3xCD19/HLHL |
| 43 prot | 90 | 175 | 82 | 177 | 132 | 175 | 130 | 3-550/CD3xCD19/LHLH |
| 44 prot | 82 | 175 | 90 | 177 | 132 | 175 | 130 | 3-550/CD3xCD19/HLLH |
| 45 prot | 132 | 175 | 130 | 177 | 82 | 175 | 90 | 3-550/CD19xCD3/LHHL |
| 46 prot | 130 | 175 | 132 | 177 | 82 | 175 | 90 | 3-550/CD19xCD3/HLHL |
| 47 prot | 132 | 175 | 130 | 177 | 90 | 175 | 82 | 3-550/CD19xCD3/LHLH |
| 48 prot | 130 | 175 | 132 | 177 | 90 | 175 | 82 | 3-550/CD19xCD3/HLLH |
| 49 prot | 106 | 175 | 98 | 177 | 130 | 175 | 132 | 4-10/CD3xCD19/LHHL |
| 50 prot | 98 | 175 | 106 | 177 | 130 | 175 | 132 | 4-10/CD3xCD19/HLHL |
| 51 prot | 106 | 175 | 98 | 177 | 132 | 175 | 130 | 4-10/CD3xCD19/LHLH |
| 52 prot | 98 | 175 | 106 | 177 | 132 | 175 | 130 | 4-10/CD3xCD19/HLLH |
| 53 prot | 132 | 175 | 130 | 177 | 98 | 175 | 106 | 4-10/CD19xCD3/LHHL |
| 54 prot | 130 | 175 | 132 | 177 | 98 | 175 | 106 | 4-10/CD19xCD3/HLHL |
| 55 prot | 132 | 175 | 130 | 177 | 106 | 175 | 98 | 4-10/CD19xCD3/LHLH |
| 56 prot | 130 | 175 | 132 | 177 | 106 | 175 | 98 | 4-10/CD19xCD3/HLLH |

TABLE 2-continued

| Construct | SEQ ID NO in construct portion . . . | | | | | | | h anti-hCD3 construct/ Specificity (N -> C)/ Domain Arrangement |
|---|---|---|---|---|---|---|---|---|
| | A | B | C | D | E | F | G | |
| 57 prot | 122 | 175 | 114 | 177 | 130 | 175 | 132 | 4-48/CD3xCD19/LHHL |
| 58 prot | 114 | 175 | 122 | 177 | 130 | 175 | 132 | 4-48/CD3xCD19/HLHL |
| 59 prot | 122 | 175 | 114 | 177 | 132 | 175 | 130 | 4-48/CD3xCD19/LHLH |
| 60 prot | 114 | 175 | 122 | 177 | 132 | 175 | 130 | 4-48/CD3xCD19/HLLH |
| 61 prot | 132 | 175 | 130 | 177 | 114 | 175 | 122 | 4-48/CD19xCD3/LHHL |
| 62 prot | 130 | 175 | 132 | 177 | 114 | 175 | 122 | 4-48/CD19xCD3/HLHL |
| 63 prot | 132 | 175 | 130 | 177 | 122 | 175 | 114 | 4-48/CD19xCD3/LHLH |
| 64 prot | 130 | 175 | 132 | 177 | 122 | 175 | 114 | 4-48/CD19xCD3/HLLH |

TABLE 4

| Construct | SEQ ID NO in construct portion . . . | | | | | | | h anti-hCD3 construct/ Specificity (N -> C)/ Domain Arrangement |
|---|---|---|---|---|---|---|---|---|
| | A | B | C | D | E | F | G | |
| 65 prot | 10 | 175 | 2 | 177 | 134 | 175 | 136 | 3-106/CD3xEpCAM/LHHL |
| 66 prot | 2 | 175 | 10 | 177 | 134 | 175 | 136 | 3-106/CD3xEpCAM/HLHL |
| 67 prot | 10 | 175 | 2 | 177 | 136 | 175 | 134 | 3-106/CD3xEpCAM/LHLH |
| 68 prot | 2 | 175 | 10 | 177 | 136 | 175 | 134 | 3-106/CD3xEpCAM/HLLH |
| 69 prot | 136 | 175 | 134 | 177 | 2 | 175 | 10 | 3-106/EpCAMxCD3/LHHL |
| 70 prot | 134 | 175 | 136 | 177 | 2 | 175 | 10 | 3-106/EpCAMxCD3/HLHL |
| 71 prot | 136 | 175 | 134 | 177 | 10 | 175 | 2 | 3-106/EpCAMxCD3/LHLH |
| 72 prot | 134 | 175 | 136 | 177 | 10 | 175 | 2 | 3-106/EpCAMxCD3/HLLH |
| 73 prot | 26 | 175 | 18 | 177 | 134 | 175 | 136 | 3-114/CD3xEpCAM/LHHL |
| 74 prot | 18 | 175 | 26 | 177 | 134 | 175 | 136 | 3-114/CD3xEpCAM/HLHL |
| 75 prot | 26 | 175 | 18 | 177 | 136 | 175 | 134 | 3-114/CD3xEpCAM/LHLH |
| 76 prot | 18 | 175 | 26 | 177 | 136 | 175 | 134 | 3-114/CD3xEpCAM/HLLH |
| 77 prot | 136 | 175 | 134 | 177 | 18 | 175 | 26 | 3-114/EpCAMxCD3/LHHL |
| 78 prot | 134 | 175 | 136 | 177 | 18 | 175 | 26 | 3-114/EpCAMxCD3/HLHL |
| 79 prot | 136 | 175 | 134 | 177 | 26 | 175 | 18 | 3-114/EpCAMxCD3/LHLH |
| 80 prot | 134 | 175 | 136 | 177 | 26 | 175 | 18 | 3-114/EpCAMxCD3/HLLH |
| 81 prot | 42 | 175 | 34 | 177 | 134 | 175 | 136 | 3-148/CD3xEpCAM/LHHL |
| 82 prot | 34 | 175 | 42 | 177 | 134 | 175 | 136 | 3-148/CD3xEpCAM/HLHL |
| 83 prot | 42 | 175 | 34 | 177 | 136 | 175 | 134 | 3-148/CD3xEpCAM/LHLH |
| 84 prot | 34 | 175 | 42 | 177 | 136 | 175 | 134 | 3-148/CD3xEpCAM/HLLH |
| 85 prot | 136 | 175 | 134 | 177 | 34 | 175 | 42 | 3-148/EpCAMxCD3/LHHL |
| 86 prot | 134 | 175 | 136 | 177 | 34 | 175 | 42 | 3-148/EpCAMxCD3/HLHL |
| 87 prot | 136 | 175 | 134 | 177 | 42 | 175 | 34 | 3-148/EpCAMxCD3/LHLH |
| 88 prot | 134 | 175 | 136 | 177 | 42 | 175 | 34 | 3-148/EpCAMxCD3/HLLH |
| 89 prot | 58 | 175 | 50 | 177 | 134 | 175 | 136 | 3-190/CD3xEpCAM/LHHL |
| 90 prot | 50 | 175 | 58 | 177 | 134 | 175 | 136 | 3-190/CD3xEpCAM/HLHL |
| 91 prot | 58 | 175 | 50 | 177 | 136 | 175 | 134 | 3-190/CD3xEpCAM/LHLH |
| 92 prot | 50 | 175 | 58 | 177 | 136 | 175 | 134 | 3-190/CD3xEpCAM/HLLH |
| 93 prot | 136 | 175 | 134 | 177 | 50 | 175 | 58 | 3-190/EpCAMxCD3/LHHL |
| 94 prot | 134 | 175 | 136 | 177 | 50 | 175 | 58 | 3-190/EpCAMxCD3/HLHL |
| 95 prot | 136 | 175 | 134 | 177 | 58 | 175 | 50 | 3-190/EpCAMxCD3/LHLH |
| 96 prot | 134 | 175 | 136 | 177 | 58 | 175 | 50 | 3-190/EpCAMxCD3/HLLH |
| 97 prot | 74 | 175 | 66 | 177 | 134 | 175 | 136 | 3-271/CD3xEpCAM/LHHL |
| 98 prot | 66 | 175 | 74 | 177 | 134 | 175 | 136 | 3-271/CD3xEpCAM/HLHL |
| 99 prot | 74 | 175 | 66 | 177 | 136 | 175 | 134 | 3-271/CD3xEpCAM/LHLH |
| 100 prot | 66 | 175 | 74 | 177 | 136 | 175 | 134 | 3-271/CD3xEpCAM/HLLH |
| 101 prot | 136 | 175 | 134 | 177 | 66 | 175 | 74 | 3-271/EpCAMxCD3/LHHL |
| 102 prot | 134 | 175 | 136 | 177 | 66 | 175 | 74 | 3-271/EpCAMxCD3/HLHL |
| 103 prot | 136 | 175 | 134 | 177 | 74 | 175 | 66 | 3-271/EpCAMxCD3/LHLH |
| 104 prot | 134 | 175 | 136 | 177 | 74 | 175 | 66 | 3-271/EpCAMxCD3/HLLH |
| 105 prot | 90 | 175 | 82 | 177 | 134 | 175 | 136 | 3-550/CD3xEpCAM/LHHL |
| 106 prot | 82 | 175 | 90 | 177 | 134 | 175 | 136 | 3-550/CD3xEpCAM/HLHL |
| 107 prot | 90 | 175 | 82 | 177 | 136 | 175 | 134 | 3-550/CD3xEpCAM/LHLH |
| 108 prot | 82 | 175 | 90 | 177 | 136 | 175 | 134 | 3-550/CD3xEpCAM/HLLH |
| 109 prot | 136 | 175 | 134 | 177 | 82 | 175 | 90 | 3-550/EpCAMxCD3/LHHL |
| 110 prot | 134 | 175 | 136 | 177 | 82 | 175 | 90 | 3-550/EpCAMxCD3/HLHL |
| 111 prot | 136 | 175 | 134 | 177 | 90 | 175 | 82 | 3-550/EpCAMxCD3/LHLH |
| 112 prot | 134 | 175 | 136 | 177 | 90 | 175 | 82 | 3-550/EpCAMxCD3/HLLH |
| 113 prot | 106 | 175 | 98 | 177 | 134 | 175 | 136 | 4-10/CD3xEpCAM/LHHL |
| 114 prot | 98 | 175 | 106 | 177 | 134 | 175 | 136 | 4-10/CD3xEpCAM/HLHL |
| 115 prot | 106 | 175 | 98 | 177 | 136 | 175 | 134 | 4-10/CD3xEpCAM/LHLH |
| 116 prot | 98 | 175 | 106 | 177 | 136 | 175 | 134 | 4-10/CD3xEpCAM/HLLH |
| 117 prot | 136 | 175 | 134 | 177 | 98 | 175 | 106 | 4-10/EpCAMxCD3/LHHL |
| 118 prot | 134 | 175 | 136 | 177 | 98 | 175 | 106 | 4-10/EpCAMxCD3/HLHL |
| 119 prot | 136 | 175 | 134 | 177 | 106 | 175 | 98 | 4-10/EpCAMxCD3/LHLH |
| 120 prot | 134 | 175 | 136 | 177 | 106 | 175 | 98 | 4-10/EpCAMxCD3/HLLH |

TABLE 4-continued

| Con-struct | SEQ ID NO in construct portion ... | | | | | | | h anti-hCD3 construct/Specificity (N -> C)/ Domain Arrangement |
|---|---|---|---|---|---|---|---|---|
| | A | B | C | D | E | F | G | |
| 121 prot | 122 | 175 | 114 | 177 | 134 | 175 | 136 | 4-48/CD3xEpCAM/LHHL |
| 122 prot | 114 | 175 | 122 | 177 | 134 | 175 | 136 | 4-48/CD3xEpCAM/HLHL |
| 123 prot | 122 | 175 | 114 | 177 | 136 | 175 | 134 | 4-48/CD3xEpCAM/LHLH |
| 124 prot | 114 | 175 | 122 | 177 | 136 | 175 | 134 | 4-48/CD3xEpCAM/HLLH |
| 125 prot | 136 | 175 | 134 | 177 | 114 | 175 | 122 | 4-48/EpCAMxCD3/LHHL |
| 126 prot | 134 | 175 | 136 | 177 | 114 | 175 | 122 | 4-48/EpCAMxCD3/HLHL |
| 127 prot | 136 | 175 | 134 | 177 | 122 | 175 | 114 | 4-48/EpCAMxCD3/LHLH |
| 128 prot | 134 | 175 | 136 | 177 | 122 | 175 | 114 | 4-48/EpCAMxCD3/HLLH |

TABLE 6

| Construct | SEQ ID NO in construct portion ... | | | | | | | h anti-hCD3 construct/Specificity (N -> C)/ Domain Arrangement |
|---|---|---|---|---|---|---|---|---|
| | A | B | C | D | E | F | G | |
| 129 prot | 10 | 175 | 2 | 177 | 197 | 175 | 199 | 3-106/CD3xCCR5/LHHL |
| 130 prot | 2 | 175 | 10 | 177 | 197 | 175 | 199 | 3-106/CD3xCCR5/HLHL |
| 131 prot | 10 | 175 | 2 | 177 | 199 | 175 | 197 | 3-106/CD3xCCR5/LHLH |
| 132 prot | 2 | 175 | 10 | 177 | 199 | 175 | 197 | 3-106/CD3xCCR5/HLLH |
| 133 prot | 199 | 175 | 197 | 177 | 2 | 175 | 10 | 3-106/CCR5xCD3/LHHL |
| 134 prot | 197 | 175 | 199 | 177 | 2 | 175 | 10 | 3-106/CCR5xCD3/HLHL |
| 135 prot | 199 | 175 | 197 | 177 | 10 | 175 | 2 | 3-106/CCR5xCD3/LHLH |
| 136 prot | 197 | 175 | 199 | 177 | 10 | 175 | 2 | 3-106/CCR5xCD3/HLLH |
| 137 prot | 26 | 175 | 18 | 177 | 197 | 175 | 199 | 3-114/CD3xCCR5/LHHL |
| 138 prot | 18 | 175 | 26 | 177 | 197 | 175 | 199 | 3-114/CD3xCCR5/HLHL |
| 139 prot | 26 | 175 | 18 | 177 | 199 | 175 | 197 | 3-114/CD3xCCR5/LHLH |
| 140 prot | 18 | 175 | 26 | 177 | 199 | 175 | 197 | 3-114/CD3xCCR5/HLLH |
| 141 prot | 199 | 175 | 197 | 177 | 18 | 175 | 26 | 3-114/CCR5xCD3/LHHL |
| 142 prot | 197 | 175 | 199 | 177 | 18 | 175 | 26 | 3-114/CCR5xCD3/HLHL |
| 143 prot | 199 | 175 | 197 | 177 | 26 | 175 | 18 | 3-114/CCR5xCD3/LHLH |
| 144 prot | 197 | 175 | 199 | 177 | 26 | 175 | 18 | 3-114/CCR5xCD3/HLLH |
| 145 prot | 42 | 175 | 34 | 177 | 197 | 175 | 199 | 3-148/CD3xCCR5/LHHL |
| 146 prot | 34 | 175 | 42 | 177 | 197 | 175 | 199 | 3-148/CD3xCCR5/HLHL |
| 147 prot | 42 | 175 | 34 | 177 | 199 | 175 | 197 | 3-148/CD3xCCR5/LHLH |
| 148 prot | 34 | 175 | 42 | 177 | 199 | 175 | 197 | 3-148/CD3xCCR5/HLLH |
| 149 prot | 199 | 175 | 197 | 177 | 34 | 175 | 42 | 3-148/CCR5xCD3/LHHL |
| 150 prot | 197 | 175 | 199 | 177 | 34 | 175 | 42 | 3-148/CCR5xCD3/HLHL |
| 151 prot | 199 | 175 | 197 | 177 | 42 | 175 | 34 | 3-148/CCR5xCD3/LHLH |
| 152 prot | 197 | 175 | 199 | 177 | 42 | 175 | 34 | 3-148/CCR5xCD3/HLLH |
| 153 prot | 58 | 175 | 50 | 177 | 197 | 175 | 199 | 3-190/CD3xCCR5/LHHL |
| 154 prot | 50 | 175 | 58 | 177 | 197 | 175 | 199 | 3-190/CD3xCCR5/HLHL |
| 155 prot | 58 | 175 | 50 | 177 | 199 | 175 | 197 | 3-190/CD3xCCR5/LHLH |
| 156 prot | 50 | 175 | 58 | 177 | 199 | 175 | 197 | 3-190/CD3xCCR5/HLLH |
| 157 prot | 199 | 175 | 197 | 177 | 50 | 175 | 58 | 3-190/CCR5xCD3/LHHL |
| 158 prot | 197 | 175 | 199 | 177 | 50 | 175 | 58 | 3-190/CCR5xCD3/HLHL |
| 159 prot | 199 | 175 | 197 | 177 | 58 | 175 | 50 | 3-190/CCR5xCD3/LHLH |
| 160 prot | 197 | 175 | 199 | 177 | 58 | 175 | 50 | 3-190/CCR5xCD3/HLLH |
| 161 prot | 74 | 175 | 66 | 177 | 197 | 175 | 199 | 3-271/CD3xCCR5/LHHL |
| 162 prot | 66 | 175 | 74 | 177 | 197 | 175 | 199 | 3-271/CD3xCCR5/HLHL |
| 163 prot | 74 | 175 | 66 | 177 | 199 | 175 | 197 | 3-271/CD3xCCR5/LHLH |
| 164 prot | 66 | 175 | 74 | 177 | 199 | 175 | 197 | 3-271/CD3xCCR5/HLLH |
| 165 prot | 199 | 175 | 197 | 177 | 66 | 175 | 74 | 3-271/CCR5xCD3/LHHL |
| 166 prot | 197 | 175 | 199 | 177 | 66 | 175 | 74 | 3-271/CCR5xCD3/HLHL |
| 167 prot | 199 | 175 | 197 | 177 | 74 | 175 | 66 | 3-271/CCR5xCD3/LHLH |
| 168 prot | 197 | 175 | 199 | 177 | 74 | 175 | 66 | 3-271/CCR5xCD3/HLLH |
| 169 prot | 90 | 175 | 82 | 177 | 197 | 175 | 199 | 3-550/CD3xCCR5/LHHL |
| 170 prot | 82 | 175 | 90 | 177 | 197 | 175 | 199 | 3-550/CD3xCCR5/HLHL |
| 171 prot | 90 | 175 | 82 | 177 | 199 | 175 | 197 | 3-550/CD3xCCR5/LHLH |
| 172 prot | 82 | 175 | 90 | 177 | 199 | 175 | 197 | 3-550/CD3xCCR5/HLLH |
| 173 prot | 199 | 175 | 197 | 177 | 82 | 175 | 90 | 3-550/CCR5xCD3/LHHL |
| 174 prot | 197 | 175 | 199 | 177 | 82 | 175 | 90 | 3-550/CCR5xCD3/HLHL |
| 175 prot | 199 | 175 | 197 | 177 | 90 | 175 | 82 | 3-550/CCR5xCD3/LHLH |
| 176 prot | 197 | 175 | 199 | 177 | 90 | 175 | 82 | 3-550/CCR5xCD3/HLLH |
| 177 prot | 106 | 175 | 98 | 177 | 197 | 175 | 199 | 4-10/CD3xCCR5/LHHL |
| 178 prot | 98 | 175 | 106 | 177 | 197 | 175 | 199 | 4-10/CD3xCCR5/HLHL |
| 179 prot | 106 | 175 | 98 | 177 | 199 | 175 | 197 | 4-10/CD3xCCR5/LHLH |
| 180 prot | 98 | 175 | 106 | 177 | 199 | 175 | 197 | 4-10/CD3xCCR5/HLLH |
| 181 prot | 199 | 175 | 197 | 177 | 98 | 175 | 106 | 4-10/CCR5xCD3/LHHL |
| 182 prot | 197 | 175 | 199 | 177 | 98 | 175 | 106 | 4-10/CCR5xCD3/HLHL |
| 183 prot | 199 | 175 | 197 | 177 | 106 | 175 | 98 | 4-10/CCR5xCD3/LHLH |
| 184 prot | 197 | 175 | 199 | 177 | 106 | 175 | 98 | 4-10/CCR5xCD3/HLLH |

TABLE 6-continued

| Construct | SEQ ID NO in construct portion . . . | | | | | | | h anti-hCD3 construct/ Specificity (N -> C)/ Domain Arrangement |
|---|---|---|---|---|---|---|---|---|
| | A | B | C | D | E | F | G | |
| 185 prot | 122 | 175 | 114 | 177 | 197 | 175 | 199 | 4-48/CD3xCCR5/LHHL |
| 186 prot | 114 | 175 | 122 | 177 | 197 | 175 | 199 | 4-48/CD3xCCR5/HLHL |
| 187 prot | 122 | 175 | 114 | 177 | 199 | 175 | 197 | 4-48/CD3xCCR5/LHLH |
| 188 prot | 114 | 175 | 122 | 177 | 199 | 175 | 197 | 4-48/CD3xCCR5/HLLH |
| 189 prot | 199 | 175 | 197 | 177 | 114 | 175 | 122 | 4-48/CCR5xCD3/LHHL |
| 190 prot | 197 | 175 | 199 | 177 | 114 | 175 | 122 | 4-48/CCR5xCD3/HLHL |
| 191 prot | 199 | 175 | 197 | 177 | 122 | 175 | 114 | 4-48/CCR5xCD3/LHLH |
| 192 prot | 197 | 175 | 199 | 177 | 122 | 175 | 114 | 4-48/CCR5xCD3/HLLH |

TABLE 8

| Construct | SEQ ID NO in construct portion . . . | | | | | | | h anti-hCD3 construct/ Specificity (N -> C)/ Domain Arrangement |
|---|---|---|---|---|---|---|---|---|
| | A | B | C | D | E | F | G | |
| 193 prot | 10 | 175 | 2 | 177 | 201 | 175 | 203 | 3-106/CD3xCD20/LHHL |
| 194 prot | 2 | 175 | 10 | 177 | 201 | 175 | 203 | 3-106/CD3xCD20/HLHL |
| 195 prot | 10 | 175 | 2 | 177 | 203 | 175 | 201 | 3-106/CD3xCD20/LHLH |
| 196 prot | 2 | 175 | 10 | 177 | 203 | 175 | 201 | 3-106/CD3xCD20/HLLH |
| 197 prot | 203 | 175 | 201 | 177 | 2 | 175 | 10 | 3-106/CD20xCD3/LHHL |
| 198 prot | 201 | 175 | 203 | 177 | 2 | 175 | 10 | 3-106/CD20xCD3/HLHL |
| 199 prot | 203 | 175 | 201 | 177 | 10 | 175 | 2 | 3-106/CD20xCD3/LHLH |
| 200 prot | 201 | 175 | 203 | 177 | 10 | 175 | 2 | 3-106/CD20xCD3/HLLH |
| 201 prot | 26 | 175 | 18 | 177 | 201 | 175 | 203 | 3-114/CD3xCD20/LHHL |
| 202 prot | 18 | 175 | 26 | 177 | 201 | 175 | 203 | 3-114/CD3xCD20/HLHL |
| 203 prot | 26 | 175 | 18 | 177 | 203 | 175 | 201 | 3-114/CD3xCD20/LHLH |
| 204 prot | 18 | 175 | 26 | 177 | 203 | 175 | 201 | 3-114/CD3xCD20/HLLH |
| 205 prot | 203 | 175 | 201 | 177 | 18 | 175 | 26 | 3-114/CD20xCD3/LHHL |
| 206 prot | 201 | 175 | 203 | 177 | 18 | 175 | 26 | 3-114/CD20xCD3/HLHL |
| 207 prot | 203 | 175 | 201 | 177 | 26 | 175 | 18 | 3-114/CD20xCD3/LHLH |
| 208 prot | 201 | 175 | 203 | 177 | 26 | 175 | 18 | 3-114/CD20xCD3/HLLH |
| 209 prot | 42 | 175 | 34 | 177 | 201 | 175 | 203 | 3-148/CD3xCD20/LHHL |
| 210 prot | 34 | 175 | 42 | 177 | 201 | 175 | 203 | 3-148/CD3xCD20/HLHL |
| 211 prot | 42 | 175 | 34 | 177 | 203 | 175 | 201 | 3-148/CD3xCD20/LHLH |
| 212 prot | 34 | 175 | 42 | 177 | 203 | 175 | 201 | 3-148/CD3xCD20/HLLH |
| 213 prot | 203 | 175 | 201 | 177 | 34 | 175 | 42 | 3-148/CD20xCD3/LHHL |
| 214 prot | 201 | 175 | 203 | 177 | 34 | 175 | 42 | 3-148/CD20xCD3/HLHL |
| 215 prot | 203 | 175 | 201 | 177 | 42 | 175 | 34 | 3-148/CD20xCD3/LHLH |
| 216 prot | 201 | 175 | 203 | 177 | 42 | 175 | 34 | 3-148/CD20xCD3/HLLH |
| 217 prot | 58 | 175 | 50 | 177 | 201 | 175 | 203 | 3-190/CD3xCD20/LHHL |
| 218 prot | 50 | 175 | 58 | 177 | 201 | 175 | 203 | 3-190/CD3xCD20/HLHL |
| 219 prot | 58 | 175 | 50 | 177 | 203 | 175 | 201 | 3-190/CD3xCD20/LHLH |
| 220 prot | 50 | 175 | 58 | 177 | 203 | 175 | 201 | 3-190/CD3xCD20/HLLH |
| 221 prot | 203 | 175 | 201 | 177 | 50 | 175 | 58 | 3-190/CD20xCD3/LHHL |
| 222 prot | 201 | 175 | 203 | 177 | 50 | 175 | 58 | 3-190/CD20xCD3/HLHL |
| 223 prot | 203 | 175 | 201 | 177 | 58 | 175 | 50 | 3-190/CD20xCD3/LHLH |
| 224 prot | 201 | 175 | 203 | 177 | 58 | 175 | 50 | 3-190/CD20xCD3/HLLH |
| 225 prot | 74 | 175 | 66 | 177 | 201 | 175 | 203 | 3-271/CD3xCD20/LHHL |
| 226 prot | 66 | 175 | 74 | 177 | 201 | 175 | 203 | 3-271/CD3xCD20/HLHL |
| 227 prot | 74 | 175 | 66 | 177 | 203 | 175 | 201 | 3-271/CD3xCD20/LHLH |
| 228 prot | 66 | 175 | 74 | 177 | 203 | 175 | 201 | 3-271/CD3xCD20/HLLH |
| 229 prot | 203 | 175 | 201 | 177 | 66 | 175 | 74 | 3-271/CD20xCD3/LHHL |
| 230 prot | 201 | 175 | 203 | 177 | 66 | 175 | 74 | 3-271/CD20xCD3/HLHL |
| 231 prot | 203 | 175 | 201 | 177 | 74 | 175 | 66 | 3-271/CD20xCD3/LHLH |
| 232 prot | 201 | 175 | 203 | 177 | 74 | 175 | 66 | 3-271/CD20xCD3/HLLH |
| 233 prot | 90 | 175 | 82 | 177 | 201 | 175 | 203 | 3-550/CD3xCD20/LHHL |
| 234 prot | 82 | 175 | 90 | 177 | 201 | 175 | 203 | 3-550/CD3xCD20/HLHL |
| 235 prot | 90 | 175 | 82 | 177 | 203 | 175 | 201 | 3-550/CD3xCD20/LHLH |
| 236 prot | 82 | 175 | 90 | 177 | 203 | 175 | 201 | 3-550/CD3xCD20/HLLH |
| 237 prot | 203 | 175 | 201 | 177 | 82 | 175 | 90 | 3-550/CD20xCD3/LHHL |
| 238 prot | 201 | 175 | 203 | 177 | 82 | 175 | 90 | 3-550/CD20xCD3/HLHL |
| 239 prot | 203 | 175 | 201 | 177 | 90 | 175 | 82 | 3-550/CD20xCD3/LHLH |
| 240 prot | 201 | 175 | 203 | 177 | 90 | 175 | 82 | 3-550/CD20xCD3/HLLH |
| 241 prot | 106 | 175 | 98 | 177 | 201 | 175 | 203 | 4-10/CD3xCD20/LHHL |
| 242 prot | 98 | 175 | 106 | 177 | 201 | 175 | 203 | 4-10/CD3xCD20/HLHL |
| 243 prot | 106 | 175 | 98 | 177 | 203 | 175 | 201 | 4-10/CD3xCD20/LHLH |
| 244 prot | 98 | 175 | 106 | 177 | 203 | 175 | 201 | 4-10/CD3xCD20/HLLH |
| 245 prot | 203 | 175 | 201 | 177 | 98 | 175 | 106 | 4-10/CD20xCD3/LHHL |
| 246 prot | 201 | 175 | 203 | 177 | 98 | 175 | 106 | 4-10/CD20xCD3/HLHL |
| 247 prot | 203 | 175 | 201 | 177 | 106 | 175 | 98 | 4-10/CD20xCD3/LHLH |
| 248 prot | 201 | 175 | 203 | 177 | 106 | 175 | 98 | 4-10/CD20xCD3/HLLH |

TABLE 8-continued

| Construct | SEQ ID NO in construct portion... | | | | | | h anti-hCD3 construct/ Specificity (N -> C)/ |
| --- | --- | --- | --- | --- | --- | --- | --- |
| | A | B | C | D | E | F | G Domain Arrangement |
| 249 prot | 122 | 175 | 114 | 177 | 201 | 175 | 203 4-48/CD3xCD20/LHHL |
| 250 prot | 114 | 175 | 122 | 177 | 201 | 175 | 203 4-48/CD3xCD20/HLHL |
| 251 prot | 122 | 175 | 114 | 177 | 203 | 175 | 201 4-48/CD3xCD20/LHLH |
| 252 prot | 114 | 175 | 122 | 177 | 203 | 175 | 201 4-48/CD3xCD20/HLLH |
| 253 prot | 203 | 175 | 201 | 177 | 114 | 175 | 122 4-48/CD20xCD3/LHHL |
| 254 prot | 201 | 175 | 203 | 177 | 114 | 175 | 122 4-48/CD20xCD3/HLHL |
| 255 prot | 203 | 175 | 201 | 177 | 122 | 175 | 114 4-48/CD20xCD3/LHLH |
| 256 prot | 201 | 175 | 203 | 177 | 122 | 175 | 114 4-48/CD20xCD3/HLLH |

Protein constructs are as defined in Tables 2, 4, 6 and 8. Each protein construct in each of the Tables 2, 4, 6 and 8 comprises 7 distinct protein modules, denoted A: G. Protein modules A-G are directly and covalently linked to one another in a single contiguous polypeptide chain by peptide bonds in the order A-B-C-D-E-F-G, with protein module A at the N-terminus and protein module G at the C-terminus. Protein modules A, C, E and G denote antibody variable domains which can be either VH or VL domains of antibodies having specificity for the different antigens. Each construct protein modules encoding a VH and VL region from a human antibody or fragment thereof having specificity for human CD3 as well as a VH and VL region from an antibody or fragment thereof having specificity for one of the human antigens CD19, EpCAM, CCR5 or CD20.

If protein module A is a VH antibody domain, then protein module C is a VL protein domain, and vice versa. If protein module E is a VH antibody domain, then protein module G is a VL protein domain, and vice versa.

VH domains of human antibodies or fragments thereof having specificity for the human CD3 antigen can be selected from the amino acid sequences as set out in SEQ ID NOs: 2, 18, 34, 50, 66, 82, 98 or 114. VL domains of human antibodies or fragments thereof having specificity for the human CD3 antigen can be selected from the amino acid sequences as set out in SEQ ID NOs: 10, 26, 42, 58, 74, 90, 106 or 122. Protein molecules encoding VH and VL domains of an antibody or fragment thereof having specificity for the CD19 antigen have the amino acid sequences as set out in SEQ ID NOs: 130 and 132, respectively. Protein molecules encoding VH and VL domains of an antibody or fragment thereof having specificity for the EpCAM antigen have the amino acid sequences as set out in SEQ ID NOs: 134 and 136, respectively. Protein molecules encoding VH and VL domains of an antibody or fragment thereof having specificity for the CCR5 antigen have the amino acid sequences as set out in SEQ ID NOs: 197 and 199, respectively. Protein molecules encoding VH and VL domains of an antibody or fragment thereof having specificity for the CD20 antigen have the amino acid sequences as set out in SEQ ID NOs: 201 and 203, respectively.

Pairs of antibody variable domains denoted by the protein module pairs A/C and E/G are joined by additional linking protein modules, wherein protein module B serves to directly link the module pair A/C and protein module F serves to directly link the module pair E/G. Protein modules B and F each have the amino acid sequence as set out in SEQ ID NO: 175.

The combination of protein modules A-B-C and the combination of protein modules E-F-G each respectively constitute one scFv fragment of an antibody having specificity for either the human CD3 antigen or for any of the human antigens CD19, EpCAM, CCR5 or CD20. The respective groups of protein modules A-B-C and E-F-G are connected to each other through protein module D, having the amino acid sequence as set out in SEQ ID NO: 177. Protein module D serves to connect the C-terminal end of protein module C with the N-terminal end of protein module E.

Especially preferred bispecific single chain binding molecules comprising human anti-CD3 portions are (with corresponding SEQ ID NOs in parentheses): 20prot (SEQ ID NO: 206), 21prot (SEQ ID NO: 216), 28prot (SEQ ID NO: 208), 29prot (SEQ ID NO: 218), 36prot (SEQ ID NO: 210), 37prot (SEQ ID NO: 220), 52prot (SEQ ID NO: 212), 53prot (SEQ ID NO: 222), 60prot (SEQ ID NO: 214), 61prot (SEQ ID NO: 224), 82prot (SEQ ID NO: 226), 85prot (SEQ ID NO: 236), 90prot (SEQ ID NO: 228), 93prot (SEQ ID NO: 238), 98prot (SEQ ID NO: 230), 101prot (SEQ ID NO: 240), 114prot (SEQ ID NO: 232), 117prot (SEQ ID NO: 242), 122prot (SEQ ID NO: 234), 125prot (SEQ ID NO: 244), 149prot (SEQ ID NO: 252), 157prot (SEQ ID NO: 250), 213prot (SEQ ID NO: 248) and 221prot (SEQ ID NO: 246).

Accordingly, in one embodiment of the inventive human binding molecule specifically binding to human CD3/human CD3 complex comprises a further antigen binding site, said further antigen binding site specifically binds to/interacts with the CD19 molecule.

Preferably, the corresponding human binding molecule of the invention comprises an amino acid sequence selected from the group of:
(a) an amino acid sequence corresponding to construct 1 prot to 64prot of table 2 herein above;
(b) (an amino acid sequence encoded by a nucleic acid sequence corresponding to construct 1nuc to 64nuc of table 1 herein above;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

It is of note that the nucleic acid sequences referred to in (c) herein above specifically code for human anti-human CD3 bispecific constructs with a second specificity for CD19, preferably human CD19.

Particular preferred human anti-human CD3×CD19 constructs (nucleic acid and protein) are depicted in SEQ ID NOs: 205, 206, 207, 208, 209, 210, 211, 212, 213 and 214. Also envisaged are constructs in the format CD19×human anti-human CD3. Illustrative and preferred examples of said constructs (nucleic acid and protein) are shown in SEQ ID NOs.: 215, 216, 217, 218, 219, 220, 221, 222, 223 and 224.

In an alternative embodiment of the human binding molecule of the invention said further antigen binding site specifically binds to/interacts with the EpCAM molecule. The term "EpCAM" defines a cell surface molecule also known as 17-1, GA733, CO17-1a, EGP, KS1-4, KSA, ESA, Epithelial cell adhesion molecule, etc. (see, e.g. Helrich, Int. J. Cancer 76 (1998), 232-9; Staib, Int. J. Cancer 92 (2001), 79-87).

Accordingly, in one embodiment of the inventive human binding molecule specifically binding to human CD3/human CD3 complex comprises a further antigen binding site, said further antigen binding site specifically binds to/interacts with the EpCAM molecule. Preferably, the corresponding human binding molecule comprises an amino acid sequence selected from the group of:
(a) an amino acid sequence corresponding to construct 65prot to 128prot of table 4 as shown above;
(b) an amino acid sequence encoded by a nucleic acid sequence corresponding to construct 65nuc to 128nuc of table 3 as shown above;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

It is of note that the nucleic acid sequences referred to in (c) herein above specifically code for human anti-human CD3 bispecific constructs with a second specificity for EpCAM, preferably human EpCAM.

Particular preferred human anti-human CD3×EpCAM constructs (nucleic acid and protein) are depicted in SEQ ID NOs: 225, 226, 227, 228, 229, 230, 231, 232, 233 and 234. Also envisaged are constructs in the format EpCAM×human anti-human CD3. Illustrative and preferred examples of said constructs (nucleic acid and protein) are shown in SEQ ID NOs.: 235, 236, 237, 238, 239, 240, 241, 242, 243 or 244.

In a further alternative embodiment of the human binding molecule of the invention, it comprises a further antigen binding site, said further antigen binding site being capable of specifically binding to/interacting with the CCR5 molecule. Therefore, it is envisaged that a human binding molecule of the invention comprises an amino acid sequence selected from the group of:
(6) an amino acid sequence corresponding to construct 129prot to 192prot of table 6 herein above;
(b) an amino acid sequence encoded by a nucleic acid sequence corresponding to construct 129nuc to 192nuc of table 5 herein above;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

It is of note that the nucleic acid sequences referred to in (c) herein above specifically code for human anti-human CD3 bispecific constructs with a second specificity for CCR5.

Particular preferred human anti-human CD3×CCR5 constructs (nucleic acid and protein) are depicted in SEQ ID NOs: 249, 250, 251 and 252.

Moreover, in an alternative embodiment of the human binding molecule of the invention, having at least two binding specificities, comprises a binding specificity for human CD3/CD3 complex and a further antigen binding site, further antigen binding site specifically binding to/interacting with the CD20 molecule, preferably the human CD20 molecule.

Accordingly, it is also envisaged that a human binding molecule of the invention comprises an amino acid sequence selected from the group of:
(a) an amino acid sequence corresponding to construct 193prot to 256prot of table 8 shown herein above;
(b) an amino acid sequence encoded by a nucleic acid sequence corresponding to construct 193nuc to 256nuc of table 7 shown herein above;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of any one of (b) and (c).

It is of note that the nucleic acid sequences referred to in (c) herein above specifically code for human anti-human CD3 bispecific constructs with a second specificity for CD20, preferably human CD20.

Particular preferred constructs (nucleic acid and protein) in the format CD20×human anti-human CD3 are shown in SEQ ID NOs.: 245, 246, 247 and 248.

The invention also relates to an above characterized human binding molecule, wherein said binding molecule is obtainable by a method of the invention.

Further, the invention relates to a nucleic acid sequence encoding a human binding molecule described herein. Said nucleic acid molecule may be a naturally nucleic acid molecule as well as a recombinant nucleic acid molecule. The nucleic acid molecule of the invention may, therefore, be of natural origin, synthetic or semi-synthetic. It may comprise DNA, RNA as well as PNA and it may be a hybrid thereof.

Thus, the present invention relates, in a preferred embodiment, to a nucleic acid molecule comprising a nucleotide sequence selected from the group consisting of:
(a) a nucleotide sequence encoding the mature form of a protein comprising the amino acid sequence of human binding molecule of the invention, preferably as given in SEQ ID Nos: 181, 183, 185, 187, 189, 191, 193, 195, 206, 208, 210, 212, 214, 216, 218, 220, 222, 224, 226, 228, 230, 232, 234, 236, 238, 240, 242, 244, 246, 248, 250 or 252;
(b) a nucleotide sequence comprising or consisting of the DNA sequence as given in SEQ ID NOs: 180, 182, 184, 186, 188, 190, 192, 194, 205, 207, 209, 211, 213, 215, 217, 219, 221, 223, 225, 227, 229, 231, 233, 235, 237, 239, 241, 243, 245, 247, 249 or 251;
(c) a nucleotide sequence hybridizing with the complementary strand of a nucleotide sequence as defined in (b) under stringent hybridization conditions;
(d) a nucleotide sequence encoding a protein derived from the protein encoded by a nucleotide sequence of (a) or (b) by way of substitution, deletion and/or addition of one or several amino acids of the amino acid sequence encoded by the nucleotide sequence of (a) or (b);
(e) a nucleotide sequence encoding a protein having an amino acid sequence at least 60%, preferably 70%, more preferably 80%, most preferably 90% identical to the amino acid sequence encoded by the nucleotide sequence of (a) or (b);
(f) a nucleotide sequence which is degenerate as a result of the genetic code to a nucleotide sequence of any one of (a) to (e);

The above mentioned nucleic acid SEQ ID NOs: 180, 182, 184, 186, 188, 190, 192 and 194 relate to specific human anti-human CD3-binders of the present invention in scFv format. The corresponding protein sequences are shown in SEQ ID NOs: 181, 183, 185, 187, 189, 191, 193 and 195. As detailed above, the SEQ ID NOs: 206, 208, 210, 212, 214, 216, 218, 220, 222, 224, 226, 228, 230, 232, 234, 236, 238, 240, 242, 244, 246, 248, 250 and 252 relate to exemplified, bispecific protein constructs comprising, as one specificity, the human anti-human CD3 binding molecule of the invention. Corresponding encoding nucleic acid sequences are given in SEQ ID NOs: 205, 207, 209, 211, 213, 215, 217, 219, 221, 223, 225, 227, 229, 231, 233, 235, 237, 239, 241, 243, 245, 247, 249 or 251, respectively.

The term "mature form of the protein" defines, in the context of the present invention a protein translated from its corresponding mRNA and optionally subsequently modified.

The term "hybridizing" has been defined in the context of the present invention herein above.

It is evident to the person skilled in the art that regulatory sequences may be added to the nucleic acid molecule of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecule may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that the polynucleotide of the invention can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

Said nucleic acid molecule(s) may be a recombinantly produced chimeric nucleic acid molecule comprising any of the aforementioned nucleic acid molecules either alone or in combination. Preferably, the nucleic acid molecule is part of a vector. Examples for suitable vectors have been described herein above.

Preferably said vector of the invention comprises a nucleic acid sequence which is a regulatory sequence operably linked to said nucleic acid sequence encoding a human binding molecule of the invention.

It is envisaged that the vector of the invention is an expression vector wherein the nucleic acid molecule encodes a human binding molecule of the invention.

The terms "control sequence" and "operably linked", as well as examples for suitable vector systems have been described herein above.

The present invention furthermore relates to host containing at least one vector or at least one nucleic acid molecule of the invention.

Said host may be produced by introducing said at least one vector or at least one nucleic acid molecule into the host. The presence of said at least one vector or at least one nucleic acid molecule in the host may mediate the expression of a gene encoding a human binding molecule of the invention.

The nucleic acid molecule or vector of the invention which is present in the host may either be integrated into the genome of the host or it may be maintained extrachromosomally.

Suitable hosts are discussed herein above. Yet, the host can be any prokaryote or eukaryotic cell. In a preferred embodiment the host is a bacteria, an insect, fungal, plant or animal cell. Preferably it is envisaged that the host of the invention may be a mammalian cell, more preferably a human cell or human cell line. Particularly preferred host cells comprise CHO cells, COS cells, myeloma cell lines like SP2/0 or NS/0.

A method for the production of such host is exemplified in the appended examples. An alternative embodiment of the invention relates to a process for the production of a human binding molecule of the invention, said process comprising culturing a host of the invention under conditions allowing the expression of the polypeptide construct and recovering the produced polypeptide construct from the culture.

The transformed hosts can be grown in fermentors and cultured according to techniques known in the art to achieve optimal cell growth. The polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

The conditions for the culturing of a host which allow the expression are known in the art and discussed herein above. The same holds true for procedures for the purification/recovery of said polypeptide constructs.

The invention also provides for a composition comprising a human binding molecule(s) of the invention or as produced by the method of the invention. The compositions of the invention, which are pharmaceutical compositions may be administered simultaneously or in a non-simultaneous way with an above defined proteinaceous compound capable of mediating an activation signal for immune effector cells.

In the light of the present invention, said "proteinaceous compounds" providing an activation signal for immune effector cells" may be, e.g. an activation signal for T cells. Preferred formats of proteinaceous compounds comprise bispecific antibodies and fragments or derivatives thereof, e.g. bispecific scFv. Preferably, said activation signal for T cells may be provided via the T cell receptor (TCR), more preferably via CD3 molecule of the TCR. Proteinaceous compounds can comprise, but are not limited to, scFv fragments specific for CD3, scFv fragments specific for the T cell receptor or superantigens. Superantigens directly bind to certain subfamilies of T cell receptor variable regions in an MHC-independent manner thus mediating the primary T cell activation signal. The proteinaceous compound may also provide an activation signal for an immune effector cell which is a non-T cell. Examples of immune effector cells which are non-T cells comprise, inter alia, B cells and NK cells.

The present invention also relates to compositions which are pharmaceutical compositions comprising these aforementioned human binding molecule(s), nucleic acid molecule(s), vector(s) or host(s) of the invention and, optionally, the described proteinaceous compound capable of an activation signal for immune effector cells.

The compositions of the invention, which are pharmaceutical compositions may be administered simultaneously or in a non-simultaneous way with an above defined proteinaceous compound capable of mediating an activation signal for immune effector cells.

In a further preferred embodiment of the invention the composition, which is a pharmaceutical composition, further comprises suitable formulations of carrier, stabilizers and/or excipients.

In accordance with this invention, the term "pharmaceutical composition" relates to a composition for administration to a patient, preferably a human patient. In preferred embodiment, the pharmaceutical composition comprises a composition for parenteral, intraluminal, intra-arterial, intrathecal or transdermal administration. Also envisaged is direct injection into a tissue, for example into a tumor. It is in particular envisaged that said pharmaceutical composition is administered to a patient via infusion or injection. Administration of the suitable compositions may be effected by different ways, e.g., by intravenous, intraperitoneal, subcutaneous, intramuscular, topical or intradermal administration. The pharmaceutical composition of the present invention may further comprise a pharmaceutically acceptable carrier. Examples of suitable pharmaceutical carriers are well known in the art and include, phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A preferred dosage for administration might be in the range of 0.24 μg to 48 mg units per kilogram of body weight per day, preferably 0.24 μg to 24 mg, more preferably 0.24 μg to 2.4 mg even more preferably 0.24 μg to 0.24 μg and most preferably 0.24 μg to 240 μg units per kg body weight per day. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous bispecific single chain antibody constructs or nucleic acid molecules or vectors encoding the same (as described in this invention), further biologically active agents, depending on the intended use of the pharmaceutical composition. Such agents might be drugs acting on the gastro-intestinal system, drugs acting as cytostatica, drugs preventing hyperurikemia, drugs inhibiting immunoreactions (e.g. corticosteroids), drugs acting on the circulatory system and/or agents such as T-cell co-stimulatory molecules or cytokines known in the art.

Possible indications for administration of the human binding molecule(s) of the invention are tumorous diseases, especially epithelial cancers/carcinomas such as breast cancer, colon cancer, prostate cancer, ovarian cancer or lung cancer or other tumorous diseases like haematological tumors, gliomas, sarcomas, osteosarcomas, head and neck cancer, skin cancer, cancers of the genitor-urinary tract, endometrial cancer, cervix cancer, kidney cancer, gastric cancer, cancer of the small intestine, liver cancer, pancreas cancer, gall bladder cancer, cancers of the bile duct, esophageal cancer, cancer of the salivatory glands or cancer of the thyroid gland. The administration of the human binding molecule(s) of the invention of the invention is especially indicated for minimal residual disease, which is characterized by the local and non-local reoccurrence of the tumor caused by the survival of single cells. Further possible indications for administration of the constructs of the invention may comprise autoimmune diseases, especially T cell mediated autoimmune diseases, inflammatory diseases, infectious diseases, especially bacterial and fungal infections, viral diseases, allergic reactions, parasitic reactions, graft versus host disease, host versus graft disease, transplant rejection.

The invention further envisages co-administration protocols with other compounds, e.g. bispecific antibody constructs, targeted toxins or other compounds, which act via T cells. The clinical regimen for co-administration of the inventive compound(s) may encompass co-administration at the same time, before or after the administration of the other component.

The human binding molecule of the invention may also be modified or derivatized. Corresponding modifications may comprise the use of recombinant DNA technologies to improve the binding specificity, avidity, half life etc of the inventive human binding molecule.

A possible approach to demonstrate the efficacy/activity of the inventive constructs is an in vivo model. A suitable model may be a mouse model. Illustratively, such models may be chosen from mouse models expressing human CD3 and human EpCAM, chimeric mouse models expressing human CD3 and mouse models into which human tumors have been transplanted or tumor cells injected or chimeric mouse models into which human PBMCs have been injected. Preferred models for such assays are nude mice.

As detailed herein, the pharmaceutical composition of the invention may be administered to a patient in need of medical intervention (preferably a human patient). The pharmaceutical composition may administered alone or in combination with other medicaments/pharmaceutical compositions. These further medicaments/pharmaceutical compositions may be administered simultaneously or non-simultaneously with the pharmaceutical composition of the invention.

Alternatively the present invention relates in a preferred embodiment to a composition, which is a diagnostic composition further comprising, optionally, means and methods for detection.

A further alternative embodiment of the invention relates to the use of a human binding molecule of the invention or as produced by a process of the invention, a nucleic acid molecule of the invention, a vector of the invention or a host of the invention for the preparation of a pharmaceutical composition for the prevention, treatment or amelioration of a proliferative disease, a tumorous disease, an inflammatory disease, an immunological disorder, an autoimmune disease, an infectious disease, viral disease, allergic reactions, parasitic reactions, graft-versus-host diseases or host-versus-graft diseases.

In particular, the pharmaceutical composition of the present invention may be particularly useful in preventing, ameliorating and/or treating cancer, B-cell malignancies, acute myeloid leukaemia, chronic myeloid leukemia, leukemias, arthritis, asthma, allergies or other autoimmune disorders/diseases.

The term "immunological disorders" relates to autoimmune diseases, skin diseases, allergic diseases, inflammatory diseases, diabetes, transplant rejections and graft versus host disease, wherein said autoimmune disease is selected from the group consisting of type I diabetes and rheumatoid arthritis.

Said skin diseases, may comprise psoriatic lesions, psoriasis, atrophic dermatitis, atopic dermatitis, skin inflammation and the like. Inflammatory disease mentioned hereinabove is selected from the group consisting of inflammatory joint diseases, inflammatory renal diseases, inflammatory bowel diseases. In particular, said inflammatory bowel disease may comprise Morbus Crohn, sarcoidosis, systemic sclerosis, collagenosis, myositis, neuritis. Inflammatory renal diseases may comprise nephritis, glomerulonephritis, lupus nephritis, or IgA nephropathy and inflammatory joint disease may comprise (chronic) arthritis.

Said autoimmune disease is selected from the group consisting of Pemphigus vulgaris, Bullous pemphigoid, Goodpasture's syndrome, autoimmune haemolytic anemia (AIHA), rheumatoid arthritis, Systemic Lupus erythematosus, Grave's disease (autoimmune hyperthyroidism), contact dermatitis, Myasthenia gravis, juvenile diabetes, Sjogren's syndrome, autoimmune thyroiditis, primary hypoadrenalism (Addison's disease), thrombocytopenic purpura, Morbus Wegener (granulomatosis), pemphigus foliaceous and celiac disease.

Autoimmune diseases are generally divided into three types: B-cell dominant, T-cell dominant or combinational types. Pathogenic phenotypes of B-cell dominant autoimmune diseases are caused by autoantibodies produced by autoreactive B-cells, while those of the T-cell dominant type are caused by tissue damage mediated by activated T-cells. These T-cells are activated by other cells presenting autoreactive peptide-MHC complexes on their surface. Yet, these distinctions are not perspicuous, since B-cells and T-cells cooperate with and depend on each other in each type of autoimmune disease. Autoimmune diseases are classified as combinatorial when both autoreactive B- and T-cells contribute directly to the pathogenesis observed ("Immunobiology", 4th edt. (1999), Chapter 13 pp 489-536, Janeway, C. A., Travers, P., Walport, M., Capra, J. D. eds and "Harrison's Principles in Internal Medicine",14th edt, Fauci, Braunwald, Isselbacher, Wilson, Martin, Kasper, Hauser, Longo, eds).

The pathogenic effects of autoreactive B cells are caused by the secreted autoreactive antibodies. Antibody-mediated autoimmune diseases can be differentiated into two major groups based on their immunopathogenic mechanism. The first group comprises autoimmune responses against cell-surface or extracellular matrix antigens, while the second group consists of immune-complex diseases.

Examples of the first group of antibody-mediated autoimmune diseases are autoimmune hemolytic anemia, autoimmune thrombocytopenic purpura, myasthenia gravis, Goodpasture's syndrome, immunologically mediated blistering diseases like Pemphigus vulgaris and pemphigus foliaceus, and acute rheumatic fever. Examples of the second group comprise mixed essential cryoglobulinemia, subacute bacterial endocarditis, and several rheumatic autoimmune diseases Possible indications for administration of the human binding molecule of the invention are tumorous diseases especially epithelial cancers/carcinomas such as mamma carcinoma, colon carcinoma, prostate carcinoma, ovarial carcinoma or lung carcinoma or other tumorous diseases like haematological tumors, glioma, sarcoma or osteosarcoma. Preferably, the constructs of the invention may be administered in non-small cell lung cancer, prostate cancer, adenocarcinoma, squamous and adenocarcinomas of the cervix, breast cancer, squamous cell carcinoma of the head and neck, small cell lung cancer, colorectal and pancreatic carcinoma or colon carcinoma.

Preferably said tumorous disease is epithelial cancer or a minimal residual cancer.

Indications for administration of pharmaceutical compositions of the invention providing to a subject a human binding molecules with specificity for the human CD3 complex and at least one further second target domain are exemplified in table 9.

TABLE 9

Indications for preferred second target domains

| Preferred second target domains | Exemplified disorders/ malignancies to be treated |
|---|---|
| CD19 (Kvalheim, Bone Marrow Transplant 1988, 3(1):31-41; Dörken, Lancet 1974 Dec 14; 2(7894):1463) | Various B cell malignancies: Various B cell malignancies: |
| CD30 (Wahl, Cancer Res 2002, 62(13):3736-42) | Hodgkin lymphoma |
| CD33 (Maslak, Expert Opin Investig Drugs 2000, 9(6):1197-205; Stadtmauer, Curr Oncol Rep 2002, 4(5):375-80) | AML (acute myeloic leukemia) |
| CD33 (Lopez-Karpovitch, Rev Invest Clin 1997, 49(1):31-6) | CML (chronic myeloic leukemia) |
| CD25 (Dahmoush, Cancer 2002, 96(2):110-6; Savoie, Curr Treat Options Oncol 2001, 2(3):217-24) | Certain T-cell and B-cell leukemias |
| CD19 (Issacs, Arthritis Rheum 2001, 44(9):1998-2008), CCR5 (Bruhl, J Immunol 2001, 166(4):2420-6), TNF-alpha precursor (Wollheim, Expert Opin Investig Drugs 2002, 11(7):947-53) | Rheumatoid arthritis |
| CD19 (Sato, J Immunol 2000, 165(11):6635-43, CCR5 (Zapico, Genes Immun 2000; 1(4):288-9), CD30 (Okumura, J Clin Endocrinol Metab 1997, 82(6):1757-60) | Autoimmune diseases |
| CCR8(Owen, Pulm Pharmacol Ther 2001; 14(3):193-202) | Asthma |
| IgE (membrane bound) (Lustgarten, Eur J Immunol 1995, 25(10):2985-91) | Allergy |
| EpCAM (Naundorf, Int J Cancer 2002, 100(1):101-10), EGFR (Liu, Br J Cancer 2000, 82(12):1991-9), CEA (Stewart, Cancer Immunol Immunother 1999, 47(6):299-306; Durbin, Proc Natl Acad Sci USA 1994, 91(10):4313-7), TAG-72 (tumor associated glycoprotein =>sTn antigen) (Kashmiri, Crit Rev Oncol Hematol 2001, 38(1):3-16), Sonic Hedgehog (Shh) (Lacour, Br J Dermatol 2002, 146 Suppl 61:17-9; Tojo, Br J Dermatol 2002, 146(1):69-73) | Pan-carcinoma |
| Her-2 (Arteaga, Semin Oncol 2002, 29(3 Suppl 11):4-10; Wester, Acta Oncol 2002; 41(3):282-8) | Mamma carcinoma and other carcinomas |

TABLE 9-continued

Indications for preferred second target domains

| Preferred second target domains | Exemplified disorders/ malignancies to be treated |
|---|---|
| EGFR (Bonner, Semin Radiat Oncol 2002, 12:11-20; Kiyota, Oncology 2002; 63 (1): 92-8), CD44v6 related to stage of carcinoma (Rodrigo, Am J Clin Pathol 2002, 118(1):67-72; Fonseca, J Surg Oncol 2001, 76(2):115-20) | Squamous cell carcinoma |
| PSMA (Fracasso, Prostate 2002, 53(1):9-23), STEAP (Hubert, Proc Natl Acad Sci USA 1999, 96(25):14523-8), PSCA (prostate stem cell antigen) (Jalkut, Curr Opin Urol 2002, 12(5):401-6) | Prostate cancer |
| CEA (Stewart, Cancer Immunol Immunother 1999, 47(6):299-306; Durbin, Proc Natl Acad Sci USA 1994, 91(10):4313-7), TAG-72 (tumor associated glycoprotein =>sTn antigen) (Kashmiri, Crit Rev Oncol Hematol 2001, 38(1):3-16), | Adenocarcinoma |
| MUC-1 (mucin) (Couto, Adv Exp Med Biol 1994; 353:55-9) | Breast cancer |
| ganglioside GD3 (Brezicka, Lung Cancer 2000, 28(1):29-36; Shepard, Semin Oncol 2001, 28(2 Suppl 4):30-7) | SCLC (small cell lung cancer) |
| mesothelin (Scholler, Proc Natl Acad Sci USA 1999, 96(20):11531-6; Brinkmann, Int J Cancer 1997, 71(4):638-44), CA-125 (Hogdall, Anticancer Res 2002, 22(3):1765-8), Muellerian Inhibitory Substance (MIS) Receptor Type II (Stephen, Clin Cancer Res 2002, 8(8):2640-6) | Ovarian cancer |
| LY-6 (Eshel, Int J Cancer 2002, 98(6):803-10), desmoglein 4 (Tomson, Clin Exp Metastasis 1996, 14(6):501-11) | Head and Neck cancer |
| Lewis-Y(Power, Cancer Immunol Immunother 2001, 50(5):241-50) | Epithelial cancers |
| E-cadherin neoepitope (Becker, Surg Oncol 2000, 9(1):5-11) | Gastric cancers |
| MUC-1 (mucin) (Hanski, Cancer Res 1993, 53(17):4082-8), Lewis-Y (Flieger, Clin Exp Immunol 2001, 123(1):9-14; Power, Cancer Immunol Immunother 2001, 50(5):241-50), A33 antigen (Heath, Proc Natl Acad Sci USA 1997, 94(2):469-74) | Colon carcinoma |
| Carbonic anhydrase IX (MN/CA IX) (Uemura, Br J Cancer 1999, 81(4):741-6 | Renal cell carcinoma |
| Carbonic anhydrase IX (MN/CA IX) (Longcaster, Cancer Res 2001, 61(17):6394-9) | Cervix carcinoma |
| Carbonic anhydrase IX (MN/CA IX) (Chia, J Clin Oncol 2001, 19(16):3660-8) | Breast carcinoma |
| Carbonic anhydrase IX (MN/CA IX) (Beasley, Cancer Res 2001, 61(13):5262-7) | Head and neck squamous cell carcinoma |
| CA19-9 marker (Brockmann, Anticancer Res 2000, 20(6D):4941-7) | Pancreas carcinoma |
| Fetal AchR (acetylcholine receptor) (Gattenloehner, Am J Pathol 1998, 152(2):437-44) | Rhabdomyosarcoma |
| EGFR (Kuan, Brain Tumor Pathol 2000; 17(2):71-8) | Glioma |
| Wue-1 Plasma cell antigen (Greiner, Virchows Arch 2000, 437(4):372-9) | Multiple Myeloma |
| ganglioside GD3 (Dippold, Cancer Res 1984, 44(2):806-10; Scott, J Clin Oncol 2001, 19(19):3976-87), MCSP (melanoma chondroitin sulfate proteoglycan) (Pluschke, Proc Natl Acad Sci USA 1996, 93(18):9710-5; Geiser, Cancer Res 1999, 59(4):905-10) | Melanoma |
| CD44v6 (Rodrigo, Am J Clin Pathol 2002, 118(1):67-72; Fonseca, J Surg Oncol 2001, 76(2):115-20) | Metastatic disease |
| CD20 (Chu, 2002, Leuk. Lymphoma 43, 23335-23337) | Non-Hodgkin's lymphoma |

It is envisaged by the present invention that the human binding molecules, nucleic acid molecules and vectors of the invention are administered either alone or in any combination using standard vectors and/or gene delivery systems, and optionally together with a pharmaceutically acceptable carrier or excipient. Subsequent to administration, said nucleic acid molecules or vectors may be stably integrated into the genome of the subject.

On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying the above identified diseases.

Furthermore, it is possible to use a pharmaceutical composition of the invention which comprises nucleic acid molecules or vectors of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). Further methods for the delivery of nucleic acids comprise particle-mediated gene transfer as, e.g., described in Verma, Gene Ther. 15 (1998), 692-699.

Furthermore the invention relates to a method for the prevention, treatment or amelioration of a proliferative disease, a tumorous disease, an inflammatory disease, an immunological disorder, an autoimmune disease, an infectious disease, viral disease, allergic reactions, parasitic reactions, graft-versus-host diseases or host-versus-graft diseases in a subject in the need thereof, said method comprising the step of administration of an effective amount of a human binding molecule of the invention or as produced by a process of the invention, a nucleic acid molecule of the invention, a vector of the invention or a host of the invention.

Preferably said subject is a human.

The method for the prevention, treatment or amelioration of the invention may comprise the co-administration of an above defined proteinaceous compound capable of an activation signal for immune effector cells to the subject. The co-administration may be a simultaneous co-administration or a non-simultaneous co-administration.

Finally, the present invention relates to a kit comprising a human binding molecule of the invention or as produced by a process of the invention, a nucleic acid molecule of the invention, a vector of the invention or a host of the invention. It is also envisaged that the kit of this invention comprises a pharmaceutical composition as described herein above, either alone or in combination with further medicaments to be administered to a patient in need of medical treatment or intervention.

The Figures show:

Throughout the following figure legends as well as the appended examples, the abbreviation "Hu" shall denote "Human".

FIG. 1: DNA and protein sequences of the mouse C kappa domain with a C-terminally attached His6-tag. Numbers indicate the nucleotide (nt) positions, amino acids (aa) are presented in single letter code. The relevant restriction sites for cloning this DNA-fragment into a translational fusion protein with scFvs are shown (BsiWI, NotI).

FIG. 2: CD3-specific ELISA-analysis of periplasmic preparations containing scFv protein fragments from the selection of huLIB-ST (phage pool 1). Periplasmic preparations of soluble scFv protein fragments were added to wells of an ELISA-plate, which had been coated with a soluble recombinant CD3-epsilon antigen. Detection of scFv-fragments bound to immobilized recombinant human CD3 epsilon antigen was carried out using a biotinylated anti-mouse kappa antibody (Southern Biotech, 1 µg/ml PBS) detected with horseradish peroxidase-conjugated avidine (Dako, 1 µg/ml PBS). The ELISA was developed by an ABTS di[3-ethylbenzthiazoline sulfonate (6)] diammonium salt)-substrate solution as described in Example 3. The OD-values (y axis) were measured at 405 nm by an ELISA reader. Clone numbers are presented on the x axis, where the first number of the clone number indicates the round of panning in which the respective clone was obtained, while the second number indicates the respective clone of this round.

Figure 3:
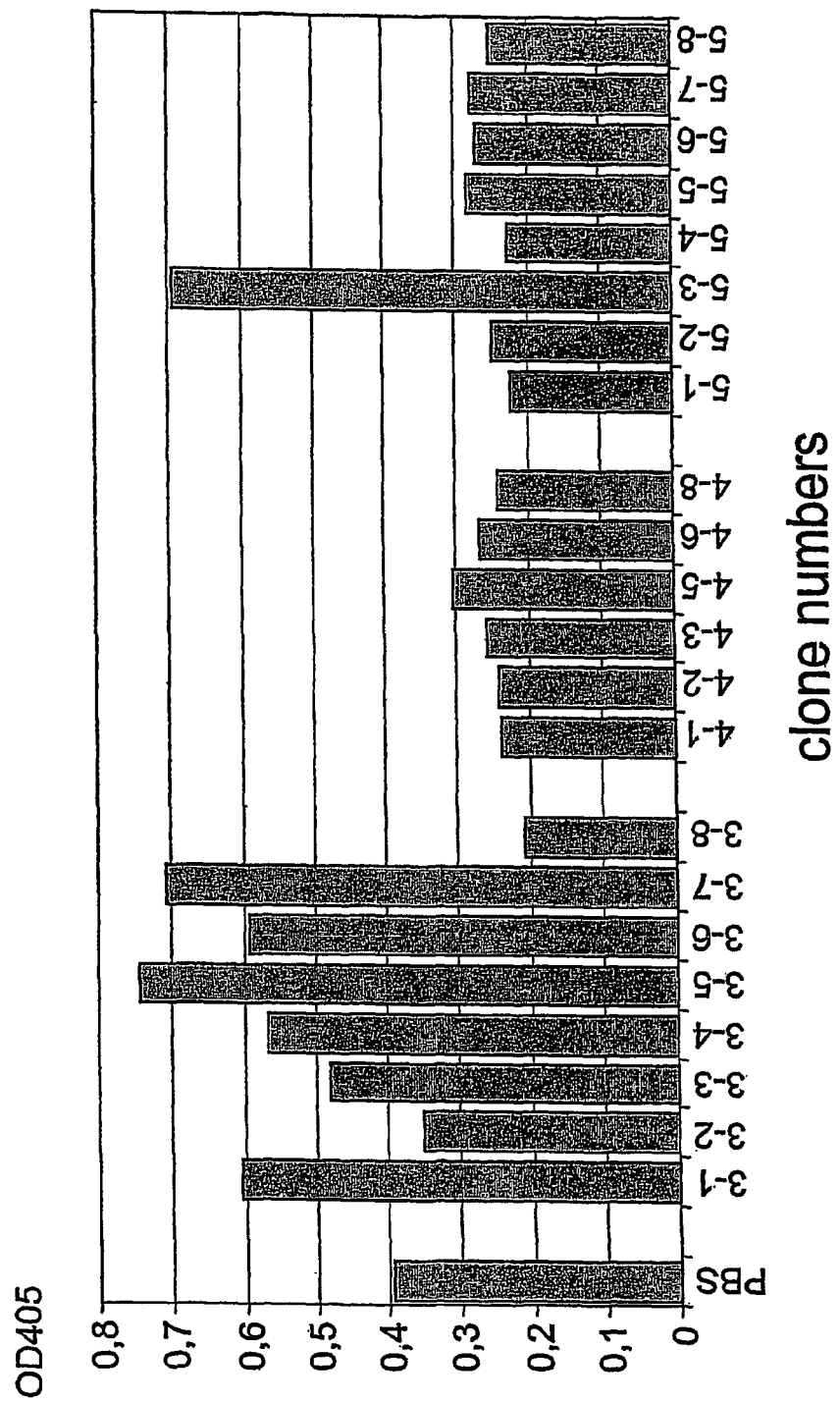

FIG. 3: CD3-specific ELISA-analysis of periplasmic preparations containing scFv protein fragments from the selection of huLIB-ST (phage pool 2). Periplasmic preparations of soluble scFv protein fragments were added to wells of an ELISA-plate that had been coated with soluble recombinant CD3-epsilon antigen. Detection of scFv-fragments bound to immobilized recombinant human CD3 epsilon antigen was carried out using a biotinylated anti-mouse kappa antibody (Southern Biotech, 1 µg/ml PBS) detected with horseradish peroxidase-conjugated avidine (Dako, 1 µg/ml PBS). The ELISA was developed by an ABTS-substrate solution as described in example 3. The OD-values (Y-axis) were measured at 405 nm by an ELISA-reader. Clone numbers are presented on the X-axis, where the first number of the clone number indicates the round of panning in which the respective clone was obtained, while the second number indicates the respective clone of this round.

Figure 4:
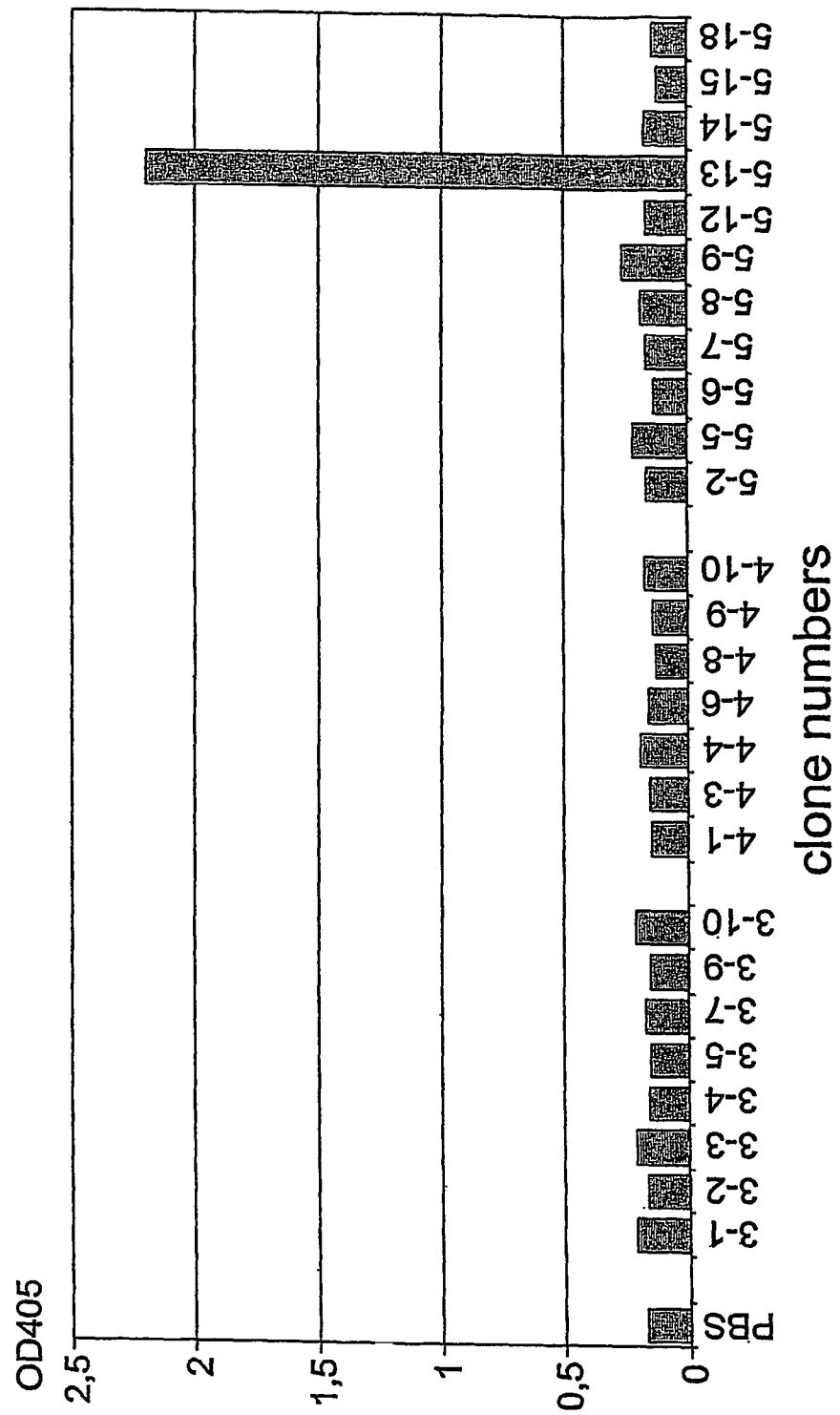

FIG. 4: CD3-specific ELISA-analysis of periplasmic preparations containing scFv protein fragments from the selection of huLIB-STE (phage pool 3). Periplasmic preparations of soluble scFv protein fragments were added to wells of an ELISA-plate that had been coated with soluble recombinant CD3-epsilon antigen. Detection of scFv-fragments bound to immobilized recombinant human CD3 epsilon antigen, was carried out using a biotinylated anti-mouse kappa antibody (Southern Biotech, 1 µg/ml PBS) detected with horseradish Peroxidase-conjugated avidine (Dako, 1 µg/ml PBS). The ELISA was developed by an ABTS-substrate solution as described in Example 3. The OD-values (Y-axis) were measured at 405 nm by an ELISA-reader. Clone numbers are presented on the X-axis, where the first number of the clone number indicates the round of panning in which the respective clone was obtained, while the second number indicates the respective clone of this round.

Figure 5:
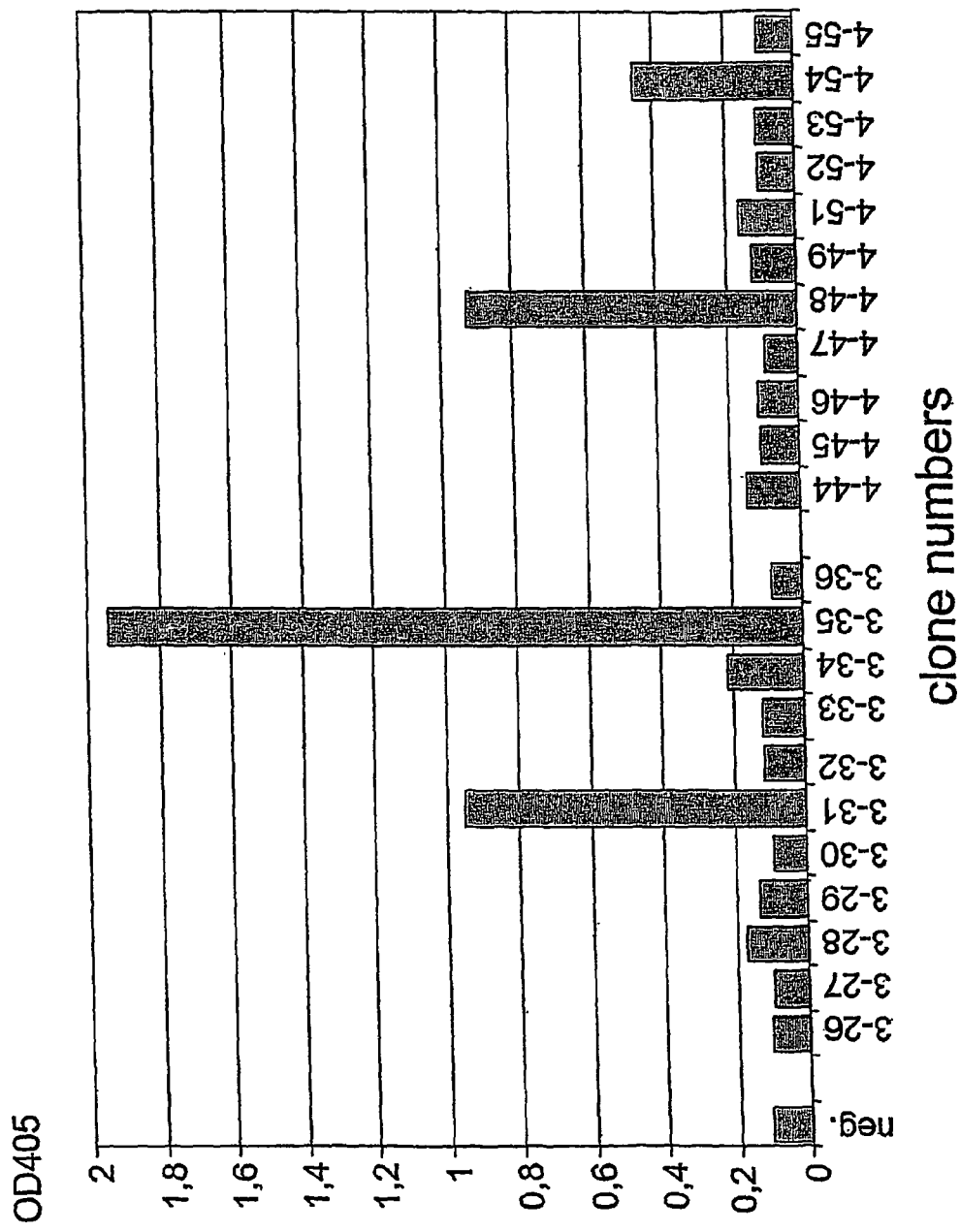

FIG. 5: CD3-specific ELISA-analysis of periplasmic preparations containing scFv protein fragments from the selection of huLIB-STE (phage pool 4). Periplasmic preparations of soluble scFv protein fragments were added to wells of an ELISA-plate that had been coated with soluble recombinant CD3-epsilon antigen. Detection of scFv-fragments bound to immobilized recombinant human CD3 epsilon antigen was carried out using an anti-Flag-tag antibody (M2 Sigma 1 µg/ml PBS) detected with horseradish peroxidase-conjugated polyclonal anti-mouse antibody (Dako 1 µg/ml PBS). The ELISA was developed by an ABTS-substrate solution as described in Example 3. The OD-values (Y-axis) were measured at 405 nm by an ELISA-reader. Clone numbers are presented on the X-axis, where the first number of the clone number indicates the round of panning in which the respective clone was obtained, while the second number indicates the respective clone of this round.

FIG. 6: DNA and protein sequences of the human scFv fragment 3-106. Numbers indicate the nucleotide (nt) positions, amino acids (aa) are presented in single letter code. The coding region of the DNA sequence for the V-region of the heavy chain starts at nt 1 and ends at nt 375 followed by a $(G_4S_1)_3$-linker. The coding region of the DNA sequence for the V-region of the kappa (light) chain starts at nt 421 and ends at nt 741. Complementarity determining regions (CDRs) are indicated by boxes surrounding the relevant nt and aa positions (according to the Kabat definition for CDRs).

FIG. 7: DNA and protein sequences of the human scFv fragment 3-114. Numbers indicate the nucleotide (nt) positions, amino acids (aa) are presented in single letter code. The coding region of the DNA sequence for the V-region of the heavy chain starts at nt 1 and ends at nt 366 followed by a $(G_4S_1)_3$-linker. The coding region of the DNA sequence for the V-region of the kappa (light) chain starts at nt 412 and ends at nt 732. Complementarity determining regions (CDRs) are indicated by boxes surrounding the relevant nt and aa positions (according to the Kabat definition for CDRs).

FIG. 8: DNA and protein sequences of the human scFv fragment 3-148. Numbers indicate the nucleotide (nt) positions, amino acids (aa) are presented in single letter code. The coding region of the DNA sequence for the V-region of the heavy chain starts at nt 1 and ends at nt 360 followed by a $(G_4S_1)_3$-linker. The coding region of the DNA sequence for the V-region of the kappa (light) chain starts at nt 406 and ends at nt 726. Complementarity determining regions (CDRs) are indicated by boxes surrounding the relevant nt and aa positions (according to the Kabat definition for CDRs).

FIG. 9: DNA and protein sequences of the human scFv fragment 3-190. Numbers indicate the nucleotide (nt) positions, amino acids (aa) are presented in single letter code. The coding region of the DNA sequence for the V-region of the heavy chain starts at nt 1 and ends at nt 378 followed by a $(G_4S_1)_3$-linker. The coding region of the DNA sequence for the V-region of the kappa (light) chain starts at nt 424 and ends at nt 744. Complementarity determining regions (CDRs) are indicated by boxes surrounding the relevant nt and aa positions (according to the Kabat definition for CDRs).

FIG. 10: DNA and protein sequences of the human scFv fragment 3-271. Numbers indicate the nucleotide (nt) positions, amino acids (aa) are presented in single letter code. The coding region of the DNA sequence for the V-region of the heavy chain starts at nt 1 and ends at nt 357 followed by a $(G_4S_1)_3$-linker. The coding region of the DNA sequence for the V-region of the kappa (light) chain starts at nt 403 and ends at nt 723. Complementarity determining regions (CDRs) are indicated by boxes surrounding the relevant nt and aa positions (according to the Kabat definition for CDRs).

FIG. 11: DNA and protein sequences of the human scFv fragment 3-550. Numbers indicate the nucleotide (nt) positions, amino acids (aa) are presented in single letter code. The coding region of the DNA sequence for the V-region of the heavy chain starts at nt 1 and ends at nt 381 followed by a $(G_4S_1)_3$-linker. The coding region of the DNA sequence for the V-region of the kappa (light) chain starts at nt 427 and ends at nt 750. Complementarity determining regions (CDRs) are indicated by boxes surrounding the relevant nt and aa positions (according to the Kabat definition for CDRs).

FIG. 12: DNA and protein sequence of the human scFv fragment 4-10. Numbers indicate the nucleotide (nt) positions, amino acids (aa) are presented in single letter code. The coding region of the DNA sequence for the V-region of the heavy chain starts at nt 1 and ends at nt 363 followed by a $(G_4S_1)_3$-linker. The coding region of the DNA sequence for the V-region of the kappa (light) chain starts at nt 409 and ends at nt 729. Complementarity determining regions (CDRs) are indicated by boxes surrounding the relevant nt and aa positions (according to the Kabat definition for CDRs).

FIG. 13: DNA and protein sequence of the human scFv fragment 4-48. Numbers indicate the nucleotide (nt) positions, amino acids (aa) are presented in single letter code. The coding region of the DNA sequence for the V-region of the heavy chain starts at nt 1 and ends at nt 369 followed by a $(G_4S_1)_3$-linker. The coding region of the DNA sequence for the V-region of the kappa (light) chain starts at nt 415 and ends at nt 753. Complementarity determining regions (CDRs) are indicated by boxes surrounding the relevant nt and aa positions (according to the Kabat definition for CDRs).

Figure 14:
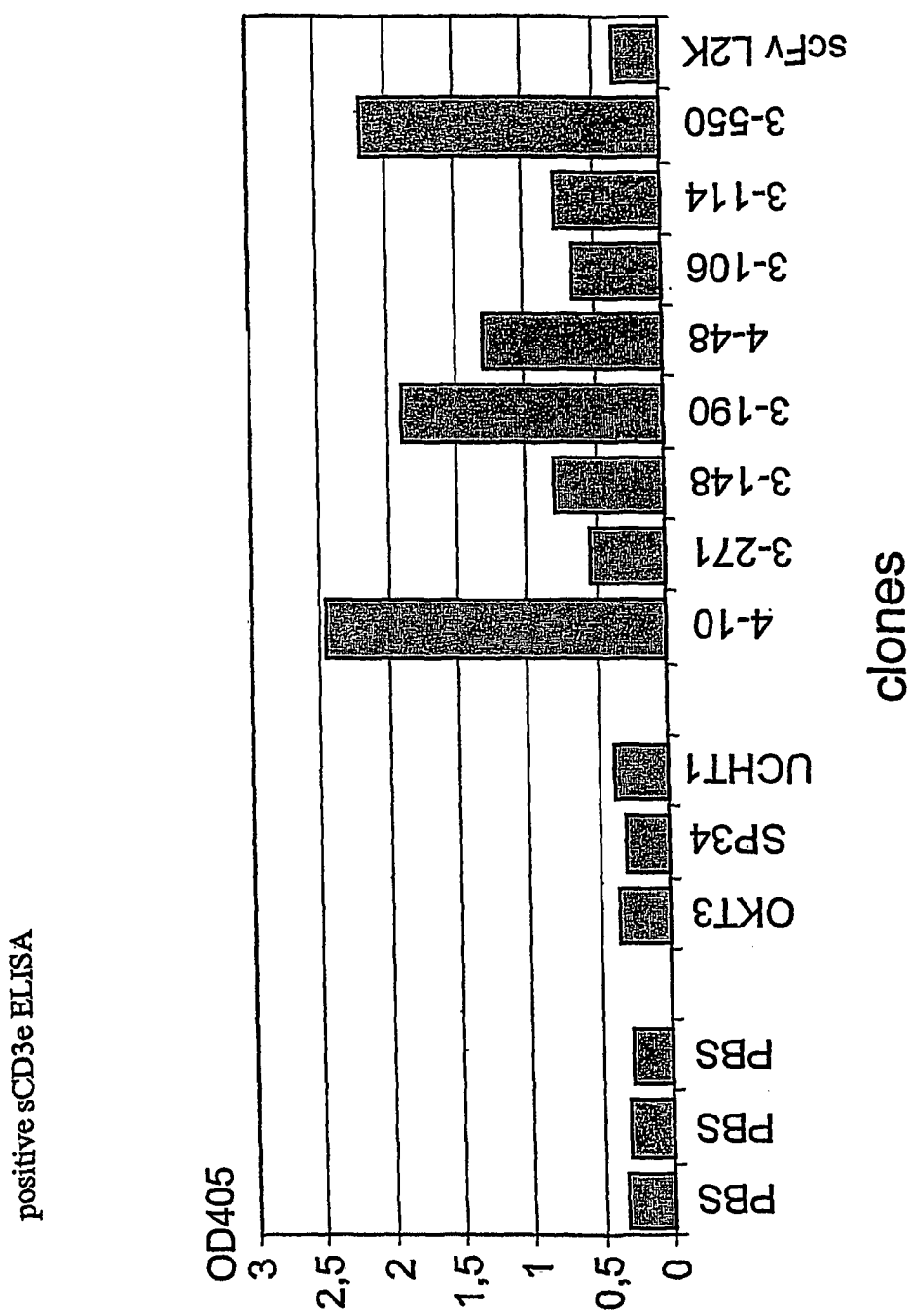

FIG. 14: CD3-specific ELISA-analysis of periplasmic preparations containing Flag-tagged scFv protein fragments from selected clones. Periplasmic preparations of soluble scFv protein fragments were added to wells of an ELISA-plate, which had been coated with soluble recombinant CD3-epsilon antigen and had been additionally blocked with PBS 3% BSA. Detection was performed by a monoclonal anti-Flag antibody followed by a peroxidase-conjugated polyclonal goat anti-mouse antibody. The ELISA was developed by an ABTS-substrate solution as described in Example 3. The OD-values (Y-axis) were measured at 405 nm by an ELISA-reader. Clone numbers are presented on the X-axis, where the first number of the clone number indicates the round of panning in which the respective clone was obtained, while the second number indicates the respective clone of this round. Periplasmic preparation from cells producing the anti-CD3 scFv L2K was included, as well as the purified anti-CD3 antibodies UCHT1, SP34 and OKT3 (concentration of each 1 µg/ml).

Figure 15:
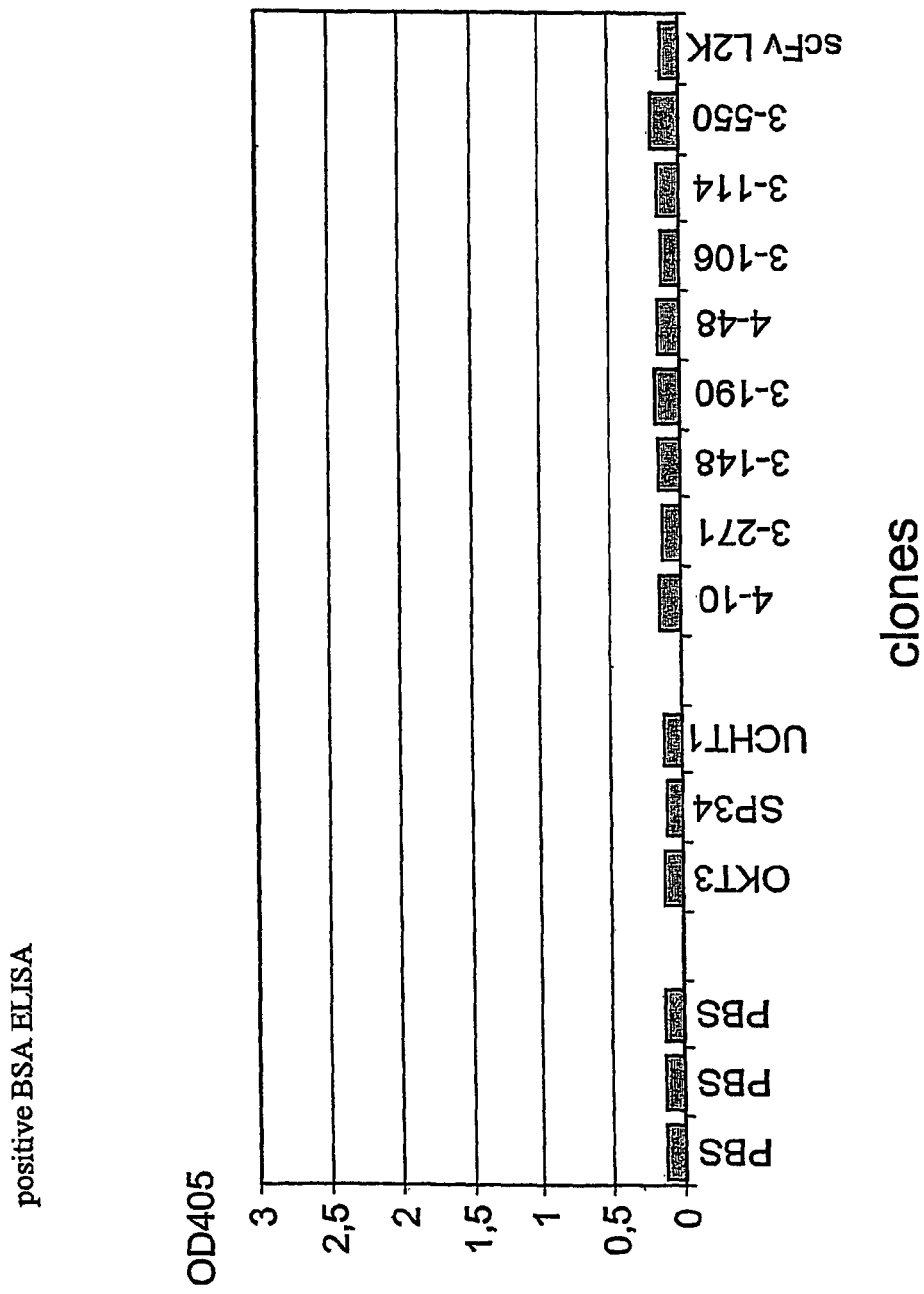

FIG. 15: ELISA-analysis of periplasmic preparations containing Flag-tagged scFv protein fragments from selected clones. The same periplasmic preparations of soluble scFv protein fragments as in FIG. 14 were added to wells of an ELISA-plate that had not been coated with soluble recombinant CD3-epsilon antigen but rather only blocked with PBS 3% BSA. Detection was performed by a monoclonal anti-Flag antibody followed by a peroxidase-conjugated polyclonal goat anti-mouse antibody. The ELISA was developed by an ABTS-substrate solution as described in example 3. The OD-values (Y-axis) were measured at 405 nm by an ELISA-reader. Clone numbers are presented on the X-axis, where the first number of the clone number indicates the round of panning in which the respective clone was obtained, while the second number indicates the respective clone of this round. Periplasmic preparation from cells producing the anti-CD3 scFv L2K was included, as well as the purified anti-CD3 antibodies UCHT1, SP34 and OKT3 (concentration of each 1 µg/ml).

FIG. 16: Flow cytometric analysis of periplasmic preparations containing Flag, tagged scFv protein fragments from selected clones (4-10, 4-48, 3-550, 3-106, 3-114, 3-148, 3-190, 3-271). Periplasmic preparations of soluble scFv protein fragments were added to CD3-positive Jurkat cells. Detection was performed by a 1.0 monoclonal anti-Flag antibody followed by a PE-labeled polyclonal anti-mouse antibody. ScFvs binding to cells was measured by an increase in fluorescence intensity as compared to cells that were incubated with PBS alone: Fluorescence intensity is blotted on the X-axis, the number of events is blotted on the Y-axis. The negative control is shown in black, the respective scFvs are shown in gray. Shifting to the right indicates positive binding to the cells. Periplasmic preparation from cells producing the anti-CD3 scFv L2K was included, as well as the purified anti-CD3 antibodies UCHT1, SP34 and OKT3 (concentration of each 5 µg/ml).

FIG. 17: Flow cytometric analysis of periplasmic preparations containing Flag-tagged scFv protein fragments from selected clones (3-106, 3-114, 3-148, 3-190, 3-271, 3-550, 4-10, 4-48). Periplasmic preparations of soluble scFv protein fragments were added to CD3-negative CHO cells. Detection was performed by a monoclonal anti-Flag antibody followed by a PE-labeled polyclonal anti-mouse antibody. Binding of scFv constructs to cells was measured by an increase in fluorescence intensity as compared to cells that were incubated with PBS alone. Fluorescence intensity is blotted on the X-axis, the number of events is blotted on the Y-axis. The negative control is shown in black, the respective scFvs are shown in gray. Shifting to the right indicates positive binding to the cells. Periplasmic preparation from cells producing the anti-CD3 scFv L2K was included, as well as the purified anti-CD3 antibodies UCHT1, SP34 and OKT3 (concentration of each 5 µg/ml).

FIG. 18: Flow cytometric analysis of periplasmic preparations containing Flag-tagged scFv protein fragments from selected clones (3-106, 3-114, 3-148, 3-190, 3-271, 3-550, 4-10, 4-48). Periplasmic preparations of soluble scFv protein fragments were added to CD3-negative KatoIII cells. Detection was performed by a monoclonal anti-Flag antibody followed by a PE-labeled polyclonal anti-mouse antibody. Binding of scFv constructs to cells was measured by an increase in fluorescence intensity as compared to cells that were incubated with PBS alone. Fluorescence intensity is blotted on the X-axis, the number of events is blotted on the Y-axis. The negative control is shown in black, the respective scFvs are shown in gray. Shifting to the right indicates positive binding to the cells. Periplasmic preparation from cells producing the anti-CD3 scFv L2K was included, as well as the purified anti-CD3 antibodies UCHT1, SP34 and OKT3 (concentration of each 5 µg/ml).

FIG. 19: Flow cytometric analysis of periplasmic preparations containing Flag-tagged 3-271 scFv protein fragments from selected clones. Periplasmic preparation of soluble 3-271 scFv protein fragments was added to CD3-positive Jurkat cells. Detection was performed by a monoclonal anti-Flag antibody followed by a PE-labeled polyclonal anti-mouse antibody. Binding of scFv constructs to cells was measured by an increase in fluorescence intensity as compared to cells that were incubated with PBS alone. Fluorescence intensity is blotted on the X-axis, the number of events is blotted on the Y-axis. The negative control is shown in black, the respective scFvs are shown in gray. Shifting to the right indicates positive binding to the cells. Periplasmic preparation from cells producing the anti-CD3 scFv L2K was included, as well as the purified anti-CD3 antibodies UCHT1, SP34 and OKT3 (concentrations of each 5 µg/ml).

FIG. 20: Flow cytometric analysis of periplasmic preparations containing Flag-tagged 3-271 scFv protein fragments from selected clones. Periplasmic preparations of soluble 3-271 scFv protein fragments was added to CD3-negative CHO cells. Detection was performed by a monoclonal anti-Flag antibody followed by a PE-labeled polyclonal anti-mouse antibody. ScFvs binding to cells was measured by an increase in fluorescence intensity as compared to cells that were incubated with PBS alone. Fluorescence intensity is blotted on the X-axis, the number of events is blotted on the Y-axis. The negative control is shown in black, the respective scFvs are shown in grey. Shifting to the right indicated positive binding to the cells. Periplasmic preparation from cells producing the anti-CD3 scFv L2K was included, as well as the purified anti-CD3 antibodies UCHT1, SP34 and OKT3 (concentration of each 5 µg/ml).

FIG. 21: Flow cytometric analysis of periplasmic preparations containing Flag-tagged 3-271 scFv protein fragments from selected clones. Periplasmic preparation of soluble 3-271 scFv protein fragments was added to CD3-epsilon and -gamma cotransfected CHO cells. Detection was performed by a monoclonal anti-Flag antibody followed by a PE-labeled polyclonal anti-mouse antibody. ScFvs binding to cells were measured by an increase in fluorescence intensity as compared to cells that were incubated with PBS alone. Fluorescence intensity is blotted on the X-axis, the number of events is blotted on the Y-axis. The negative control is shown in black, the respective scFvs are shown in grey. Shifting to the right indicates positive binding to the cells. Periplasmic preparation from cells producing the anti-CD3 scFv L2K was included, as well as the purified anti-CD3 antibodies UCHT1, SP34 and OKT3 (concentration of each 5 µg/ml).

FIG. 22: DNA and protein sequences of the anti-EpCAM scFv fragment 5-10. Numbers indicate the nucleotide (nt) positions, amino acids (aa) are presented in single letter code. The coding region of the DNA sequence for the V-region of the heavy chain starts at nt 1 and ends at nt 360 followed by a $(G_4S_1)_3$-linker. The coding region of the DNA sequence for the V-region of the kappa (light) chain starts at nt 406 and ends at nt 744.

FIG. 23: DNA and protein sequences of the anti-CD19 scFv fragment. Numbers indicate the nucleotide (nt) positions, amino acids (aa) are presented in single letter code. The coding region of the DNA sequence for the V-region of the heavy chain starts at nt 1 and ends at nt 372 followed by a $(G_4S_1)_3$-linker. The coding region of the DNA sequence for the V-region of the kappa (light) chain starts at nt 418 and ends at nt 750.

FIG. 24: DNA and protein sequences of the anti-CD20 scFv fragment. Numbers indicate the nucleotide (nt) positions, amino acids (aa) are presented in single letter code. The coding region of the DNA sequence for the V-region of the heavy chain starts at nt 1 and ends at nt 366 followed by a $(G_4S_1)_3$-linker. The coding region of the DNA sequence for the V-region of the kappa (light) chain starts at nt 412 and ends at nt 729.

FIG. 25: DNA and protein sequences of the anti-CCR5 scFv fragment. Numbers indicate the nucleotide (nt) positions, amino acids (aa) are presented in single letter code. The coding region of the DNA sequence for the V-region of the heavy chain starts at nt 1 and ends at nt 354 followed by a $(G_4S_1)_3$-linker. The coding region of the DNA sequence for the V-region of the kappa (light) chain starts at nt 399 and ends at nt 732.

Figure 26:
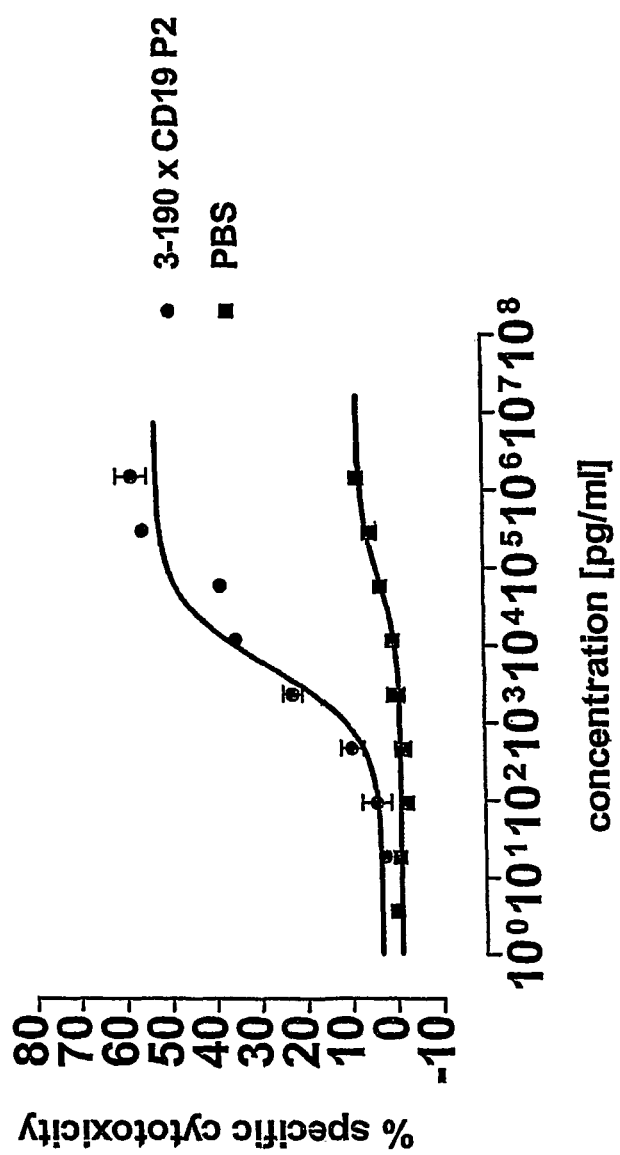

FIG. 26: Cytotoxic activity of the bispecific antibody biscFv anti-CD3 3-190×anti-CD19 as measured by fluorochrome release. Purified bispecific scFv ("biscFv") 3-190× anti-CD19 P2 (protein fraction 2 from gel filtration) was evaluated using CD19 positive fluorochrome-labeled NALM6 cells as target cells and CD3-positive CB15 T cells as effector cells (E:T ratio of 1:10). biscFv 3-190×anti-CD19 P2 was diluted in RPMI/10% FCS in a dilution series and 50 µl of the respective solution were added to the cell suspension. The same dilution series was performed using PBS as negative control, starting with the same volume as for biscFv 3-190×anti-CD19 P2. After lysis of target cells, the dye released into the incubation medium was quantitated in a fluorescence reader and compared with the fluorescence signal from a control reaction (without bispecific antibody), and the fluorescence signal was obtained for totally lysed cells. Specific cytotoxicity was calculated according to the following formula: [Fluorescence (Sample)−Fluorescence (Control)]:[Fluorescence (Total Lysis)−Fluorescence (Control)]× 100, wherein ":" denotes mathematical division. Concentrations are plotted on the X-axis, % specific toxicity on the Y-axis.

Figure 27:
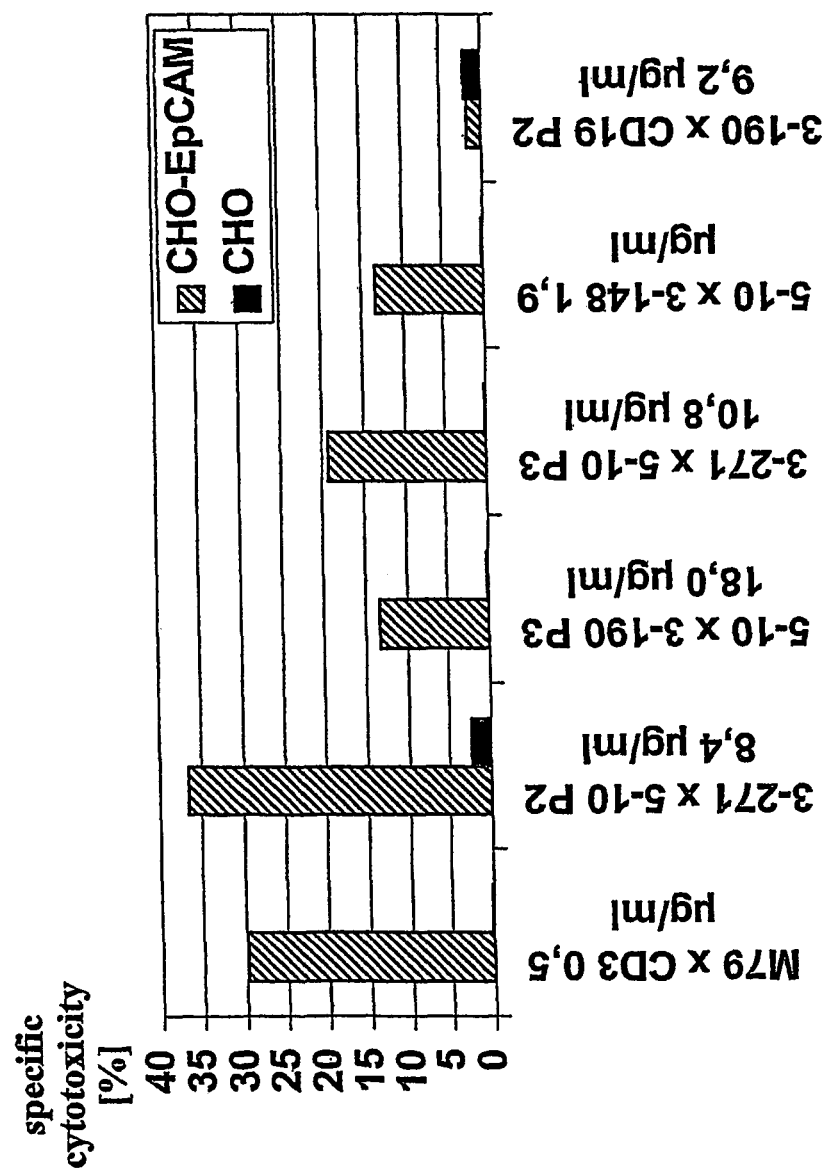

FIG. 27: Cytotoxic activity of the bispecific antibodies anti-CD3 3-271×5-10 anti-EpCAM, 5-10 anti-EpCAM×anti-CD3 3-148 and 5-10 anti-EpCAM×anti-CD3 3-190 measured by fluorochrome release. For this experiment anti-CD3 3-271×5-10 anti-EpCAM P2 (protein fraction 2 from gel filtration), anti-CD3 3-271×5-10 anti-EpCAM P3 (protein fraction 3 from gelfiltration), 5-10 anti-EpCAM×anti-CD3 3-148 (main protein fraction from gelfiltration) and 5-10 anti-EpCAM×anti-CD3 3-190 P3 (protein fraction 3 from gelfiltration) were used with EpCAM-transfected CHO and non-transfected cells as target cells and CD3-positive CB15 T cells as effector cells (E:T ratio of 1:5). Anti-CD3 3-190×anti-CD19 P2 (protein fraction 2 from gelfiltration) was included as an appropriate negative control for CD19-negative CHO-EpCAM cells. M79, an anti-EpCAM×anti-CD3 biscFv construct was used as a positive control. Untransfected CHO as well as CHO-EpCAM were labeled with PKH26. Antibody constructs were diluted in RPMI/10% FCS and added to the cell suspension. After 16 h propidium iodide (PI) was added and the cells were analyzed by flow cytometry. Cytotoxicity was measured as the ratio of PI positive cells over all target cells. The biscFv constructs are plotted on the X-axis according to the respective concentrations used for each construct, and the % specific cytotoxicity is plotted on the Y-axis.

The invention will now be described by reference to the following biological examples which are merely illustrative and are not to be construed as a limitation of scope of the present invention.

EXAMPLE 1

Procurement of the Extracellular Domain of the Human CD3-Epsilon Chain for Use as Selection Antigen in Phage Display 1.1. Cloning of the Extracellular Domain of the Human CD3 Epsilon Chain:

cDNA was isolated from human peripheral blood mononuclear cells. Preparation of the cells was performed according to standard protocols (Current Protocols in immunology (Coligan, Kruisbeek, Margulies, Shevach and Strober, John Wiley & Sons, Inc., USA, 2002)). The isolation of total RNA and cDNA synthesis by random-primed reverse transcription was performed according to standard protocols (Sambrock, Molecular Cloning; Laboratory Manual, 2nd edition, Cold Spring Harbor laboratory Press, Cold Spring Harbor, N.Y. (1989)). PCR was used to amplify the coding sequence of the extracellular domain of the human CD3 epsilon chain. The primers used in the PCR were designed so as to introduce restriction sites at the beginning and the end of the cDNA coding for the extracellular portion of the human CD3 epsilon chain (SEQ ID NO: 137 and SEQ ID NO:138). The introduced restriction sites, BsrGI and BspEI, were utilised in the following cloning procedures. The PCR product was then cloned via BsrGI and BspEI into a plasmid designated BS-Fss-Lsp derived from the Bluescript KS+ cloning vector (Stratagene Europe, Amsterdam-Zuiddoost, the Netherlands) following standard protocols. (The vector was generated by cloning a DNA fragment (SEQ ID NO: 139) via EcoRI and SalI into Bluescript KS+.) The sequence of different clones was determined by sequencing according to standard protocols. By cloning into BS-Fss-Lsp the coding sequence of a murine immunoglobulin heavy chain leader peptide was fused in-frame to the 5' end of the coding sequence for the extracellular portion of the human CD3 epsilon chain. The cDNA was then cloned via EcoRI and BspEI into another plasmid designated as BSCTI to attach a sequence to the C-terminus, coding for a pOlyhistidine tag of six consecutive histidine residues followed by a stop codon (BSCTI is described in Kufer, Cancer Immunity 1 (2001), 10). In this step the BspEI site of the cDNA was fused into an XmaI site of the plasmid thereby destroying both sites. All cloning steps were designed so as to generate an intact reading frame for the construct. The plasmid now contained a sequence coding for a protein comprising a murine immunoglobulin heavy chain leader peptide, to allow for secreted expression, followed by the extracellular domain of the human CD3 epsilon chain followed by a polyhistidine tag of six consecutive histidine residues, to allow for purification and detection via the polyhistidine tag (SEQ ID NO: 140 and SEQ ID NO: 141). This sequence was then cloned into the plasmid pFastBac1™ (Invitrogen GmbH, Karlsruhe, FRG) via EcoRI and SalI.

1.2. Expression of the Extracellular Domain of the Human CD3 Epsilon Chain in High Five™ Cells, Purification of the Recombinant Protein Expression of the extracellular domain of the human CD3 epsilon chain in High Five™ cells was performed using the Bac-to-Bac® *Baculovirus Expression System* (Invitrogen GmbH, Karlsruhe, FRG) according to the specifications of the manufacturer. 10 liters of supernatant in batches of 500 ml were produced. The construct was then purified out of the culture supernatant. Purification was performed as a two-step purification. First the diluted supernatants were loaded on ion exchange columns. The fractionated eluate was tested in an ELISA assay. To this end, an anti-human CD3 epsilon antibody (UCHT1 BD biosciences, Heidelberg, FRG) was coated (50 µl at 5 µg/ml in PBS) on a Maxisorp ELISA plate (Nunc GmbH, Wiesbaden, FRG) overnight. Unspecific binding was blocked with 1.5% BSA in PBS for 1 hour. All prior and subsequent washing steps were performed three times with 200 µl PBS. Afterwards, eluate fractions were incubated for 1 hour in the prepared cavities of the plate. Detection of the recombinant protein was performed with a horseradish peroxidase conjugated anti-H is antibody (Roche Diagnostics GmbH, Mannheim, FRG; 50 µl of antibody diluted 1:500 in 1.5% BSA in PBS). Development of the ELISA was performed with ABTS (2,2'-Azino-bis(3-Ethylbenz-thiazolin)-6-Sulfonic acid) Roche Diagnostics GmbH, Mannheim, FRG) according to the specifications of the manufacturer. Positive fractions were further purified over a cobalt-chelate column which preferentially binds histidine-tagged proteins. Eluate fractions were tested using the described ELISA assay. Positive fractions were pooled and concentrated.

EXAMPLE 2

Construction of the Combinatorial Antibody Library and Phage Display 2.1. Isolation of RNA from Selected IgD-Positive B-Cells 100 ml blood were taken from five healthy human donors. Peripheral blood mononuclear cells (PBMCs) were isolated by a ficoll-gradient according to standard methods. To select IgD-positive cells, 1 ml anti-mouse IgG-beads (CELLection™ Pan Mouse IgG Kit; DYNAL) were coated with 20 µg mouse anti-human IgD-antibody (PharMingen). Approximately $2.5 \times 10^7$ PBMCs were added to the beads and incubated at 4° C. for 15 minutes. After washing four times with 1 ml RPMI-medium (BioChrom) IgD-positive cells were released from the beads by adding 8 µl release buffer (DNase) and transferred to a fresh tube. By this method $0.9 \times 10^5$ to $3.7 \times 10^6$ IgD-positive cells could be obtained. Total RNA was isolated from IgD-positive cells using the RNeasy® Midi Kit (QIAGEN) following the manufacturers instructions. cDNA was synthesized according to standard methods (Sambrook, Cold Spring Harbor Laboratory Press 1989, Second Edition).

2.2. Isolation of RNA from PBMCs 100 ml blood from five healthy donors were taken, PBMCs were separated using a ficoll-gradient and total RNA was isolated from approximately $2.5 \times 10^7$ cells with the RNeasy® Midi Kit (QIAGEN) following the manufactures instructions. cDNA was synthesized according to standard methods (Sambrook, Cold Spring Harbor Laboratory Press 1989, Second Edition).

2.3. PCR-Amplification of Variable Regions (V-Regions)

For the isolation of light chain V-region DNA, RT-PCR was carried out using V-kappa-(5'-huVK1-Sac-2001 (SEQ ID NO: 150), 5'-huVK2/4-Sac-2001 (SEQ ID NO: 152), 5'-huVK3-Sac-2001 (SEQ ID NO: 151), 5'-huVK5-Sac-2001 (SEQ ID NO: 153), 5'-huVK6-Sac-2001 (SEQ ID NO: 154), 3'-hu-Vk-J1-SpeI-BsiWI (SEQ ID NO: 155), 3'-hu-Vk-J2/4-SpeI-BsiWI (SEQ ID NO: 156), 3'-hu-Vk-J3-SpeI-BsiWI (SEQ ID NO: 157), 3'-hu-Vk-J5-SpeI-BsiWI (SEQ ID NO: 158) and V-lambda-specific (5'-huVL1a-SacI-2001 (SEQ ID NO: 159), 5'-huVL1b-SacI-2001 (SEQ ID NO: 160), 5'-huVL2-SacI-2001 (SEQ ID NO: 161), 5'-huVL4-SacI-2001 (SEQ ID NO: 162), 5'-huVL5-SacI-2001 (SEQ ID NO: 163), 5'-huVL6-SacI-2001 (SEQ ID NO: 164), 5'-huVL3/9-SacI-2001 (SEQ ID NO: 165), 5'-huVL7/8-SacI-2001 (SEQ ID NO: 166), 3'-hu-Vlam-BlnI-SpeI-2001 (SEQ ID NO: 167), 3'-hu-Vlam2-BlnI-SpeI-2002 (SEQ ID NO: 168) primer sets. RNA from IgD positive B-cells was transcribed into cDNA (as described before) and used as template DNA in PCR reactions. Per PCR reaction, one 5'-primer was combined with one 3'-primer, wherein the 5'-kappa primer was combined with the 3'-kappa primer and the 5'-lambda primer was combined with the 3'-lambda primer. The number of different PCR reactions was determined by the number of possible combinations of 5'- and 3'-primers. The following PCR-program was used for amplification:

Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

For the isolation of VH-regions, RT-PCR was carried out in two steps. First, the heavy chain Fd-fragments of IgD were PCR-amplified using a 5'-VH-specific primer set (5'-huVH1, 3,5-XhoI-2001 (SEQ ID NO: 142), 5'-huVH2-XhoI-2001 (SEQ ID NO: 143), 5'-huVH4-XhoI-2001 (SEQ ID NO: 144), 5'-huVH4B-XhoI-2001 (SEQ ID NO: 145), 5'-huVH6-XhoI-2001 (SEQ ID NO: 146)) and a 3'-specific IgD-primer (3'-CD1 (SEQ ID NO: 147)). cDNA transcribed from RNA isolated from unselected PBMCs (as described before) was used as template. Per PCR reaction, one 5'-primer was combined with the 3'-primer; the number of different PCR reactions was determined by the number of possible combinations of 5'- and the 3'-primer. The following PCR-program was used for amplification: Denaturation at 94° C. for 15 seconds, primer annealing at 52° C. for 50 seconds and primer extension at 72° C. for 90 seconds was performed over 40 cycles, followed by final extension at 72° C. for 10 minutes.

These IgD-Fd DNA-fragments were then used as templates in a second PCR reaction using again the 5'VH-specific primer set and a set of two 3'-VH-specific primers (3'-hu-VH-BstEII-2001 (SEQ 0.1D NO: 148), 3'-hu-VH-J3-BstEII-2001 (SEQ ID NO: 149)). Per PCR reaction, one 5'-primer was combined with one 3'-primer; the number of different PCR reactions was determined by the number of possible combinations of 5'- and 3'-primers.

The following PCR-program was used for the second step: Denaturation at 94° C. for 15 seconds, primer annealing at 52° C. for 50 seconds and primer extension at. 72° C. for 90 seconds was performed over 40 cycles, followed by final extension at 72° C. for 10 minutes. Heavy chain DNA-fragments were then isolated according to standard protocols.

2.4. Library Construction

A phage display library was generally constructed based on standard procedures, as for example disclosed in "Phage Display: A Laboratory Manual"; Ed. Barbas, Burton, Scott & Silverman; Cold Spring Harbor Laboratory Press, 2001.

The primers chosen for PCR amplification gave rise to a 5'-XhoI and a 3'-BstEII recognition site for the heavy chain V-fragments and to a 5'-SacI and a 3'-SpeI recognition site for light chain V-fragments.

In two parallel reactions each 400 ng of the kappa light chain fragments (SacI-SpeI digested) were ligated with 1400 ng of the phagemid pComb3H5BHis (SacI-SpeI digested; large fragment, vector described in WO 99/25818). The two resulting antibody V-light chain libraries were then each transformed into 300 µl of electrocompetent *Escherichia coli* XL1 Blue by electroporation (2.5 kV, 0.2 cm gap cuvette, 25 FD, 200 Ohm, Biorad gene-pulser) resulting in a library size of $1.8 \times 10^8$ independent clones in total.

Kappa (light chain) DNA-fragments from the different PCR amplifications were weighted for each ligation as follows: Each 5'-primer defines a specific group. Within these groups the 3'-primers define the subgroups. The subgroups were weighted 1:2:1:1 corresponding to the primers 3'-hu-Vk-J1-SpeI-BsiWI:3'-hu-Vk-J2/4-SpeI-BsiWI:3'-hu-Vk-J3-SpeI-BsiWI: 3'-hu-Vk-J5-SpeI-BsiWI. The groups were weighted according to their germline distribution 1:1:1:0.2:0.2 corresponding to the primers 5'-huVK1-Sac-2001:5'-huVK3-Sac-2001:5'-huVK2/4-Sac-2001:5'-huVK5-Sac-2001:5'-huVK6-Sac-2001.

As described for the kappa DNA fragments, two parallel ligation reactions were carried out, each containing 400 ng of the lambda light chain fragments (SacI-SpeI digested) and 1400 ng of the phagemid pComb3H5BHis (SacI-SpeI digested). The two resulting antibody V-light chain libraries were then each transformed into 300 µl of electrocompetent *Escherichia coli* XL1 Blue by electroporation (2.5 kV, 0.2 cm gap cuvette, 25 FD, 200 Ohm; Biorad gene-pulser) resulting in a library size of $2.3 \times 10^8$ independent clones in total.

Lambda DNA-fragments from the different PCR amplifications were weighted for each ligation as follows: Each 5'-primer defines a specific group. Within these groups the 3'-primers define the subgroups. The subgroups were weighted 3:1 corresponding to the primers 3'-hu-Vlam-BlnI-SpeI-2001:3'-hu-Vlam2-BlnI-SpeI-2002. The groups were weighted according to their germline distribution 1:1:2:3:1:1:1:1 corresponding to the primers 5'-huVL1a-SacI-2001:5'-huVL1b-SacI-2001:5'-huVL2-SacI-2001:5'-huVL3/9-SacI-2001:5'-huVL4-SacI-2001:5'-huVL5-SacI-2001:5'-huVL6-SacI-2001:5'-huVL7/8-SacI-2001.

Heavy chain DNA fragments were first subcloned into pBluescript KS vector (Stratagene). To this end, eight times 400 ng of VH fragments (XhoI-BstEII digested) were each ligated with 1200 ng pBluescript KS (XhoI-BstEII digested) and transformed into electrocompetent *E. coli* XL1 Blue by electroporation as described for the light chains resulting in a library of $1.4 \times 10^9$ independent clones in total.

Heavy chain DNA-fragments from the different PCR amplifications were weighted for each ligation as follows: Each 5'-primer defines a specific group. Within these groups the 3'-primers define the subgroups. The subgroups were weighted 3:1 corresponding to the primers 3'-hu-VH-BstEII-2001:3'-hu-VH-J3-BstEII. The groups were weighted according to their germline distribution 7:1:1:1:0.3 corresponding to the primers 5'-huVH1,3,5-XhoI-2001:5'-huVH2-XhoI-2001:5'-huVH4-XhoI-2001:5'-huVH4B-XhoI-2001:5'-huVH6-XhoI-2001.

After electroporation each assay was incubated in SOC for phenotype expression. The different cultures were then separately incubated in 500 ml of SB selection medium containing 50 µg/ml Carbenicillin and 2% v/v Glucose overnight. The next day, cells of each culture were harvested by centrifugation and plasmid preparation of each culture was carried out using a commercially available plasmid preparation kit (Qiagen).

2.5. Construction of the Combinatorial Antibody Library huLIB-ST 3600 ng of this plasmid-DNA containing the VK-library (SalI-BstEII digested; large fragment) were ligated with 1200 ng of the heavy chain V-fragments (XhoI-BstEII digested, pooled in equal amounts from restriction of the eight different pBluescript/VH-plasmid preparations) and again transformed into three 300 µl aliquots of electrocompetent *E. coli* XL1 Blue by electroporation (2.5 kV, 0.2 cm gap cuvette, 25 FD, 200 Ohm) resulting in a total VH-VK scFv (single chain variable fragment) library size of $5.4 \times 10^8$ independent clones.

3600 ng of this plasmid-DNA containing the Vlambda-library (SalI-BstEII digested; large fragment) were ligated with 1200 ng of the heavy chain V-fragments (XhoI-BstEII digested, pooled in equal amounts from restriction of the eight different pBluescript/VH-plasmid preparations) and again transformed into three 300 µl aliquots of electrocompetent *E. coli*/XL1 Blue by electroporation (2.5 kV, 0.2 cm gap cuvette, 25 FD, 200 Ohm) resulting in a total VH-Vlambda scFv library size of $4.1 \times 10^8$ independent clones.

After phenotype expression and slow adaption to Carbenicillin one third of the overall kappa library and one third of the overall lambda library were each transferred into SB-Carbenicillin (50 µg/ml) selection medium; the rest was used for expansion and long term storage of the library. The VkappaNH-library and the Vlambda/VH-library were then infected with an infectious dose of $1 \times 10^{12}$ particles of helper phage VCSM13 resulting in the production and secretion of filamentous M13 phage, wherein each phage particle contained single stranded pComb3H5BHis-DNA encoding a human scFv-fragment and displayed the corresponding scFv-protein as a translational fusion to phage coat protein III.

2.6. Construction of the Combinatorial Antibody Library huLIB-STE

6 µg of this plasmid-DNA containing the VK-library (XhoI-BstEII digested; large fragment) were ligated with 2000 ng of the heavy chain V-fragments (XhoI-BstEII digested, pooled in equal amounts from restriction of the eight different pBluescript/VH-plasmid preparations) and again transformed into five 300 µl aliquots of electrocompetent *E. coli* XL1 Blue by electroporation (2.5 kV, 0.2 cm gap cuvette, 25 FD, 200 Ohm) resulting in a total VH-VK scFv (single chain variable fragment) library size of $4.3 \times 10^9$ independent clones.

6 µg of the plasmid-DNA containing the Vlambda-library (XhoI-BstEII digested; large fragment) were ligated with 2 µg of the heavy chain V-fragments (XhoI-BstEII digested, pooled in equal amounts from restriction of the eight different pBluescript/VH-plasmid preparations) and again transformed into five 300 µl aliquots of electrocompetent *E. coli* XL1 Blue by electroporation (2.5 kV, 0.2 cm gap cuvette, 25

FD, 200 Ohm) resulting in a total VH-Vlambda scFv (single chain variable fragment) library size of 4.6×10⁹ independent clones.

After phenotype expression and slow adaption to Carbenicillin one third of the overall kappa library and one third of the overall lambda library were each transferred into SB-Carbenicillin (50 µg/ml) selection medium; the rest was used for expansion and long term storage of the library. The Vkappa/VH-library and the Vlambda/VH-library were then infected with an infectious dose of 1×10¹² particles of helper phage VCSM13 resulting in the production and secretion of filamentous M13, phage, wherein each phage particle contained single stranded pComb3H5BHis-DNA encoding a human scFv-fragment and displayed the corresponding scFv-protein with the N2 domain on the phage surface as a translational fusion to phage coat protein III.

2.7. Selections

Phage libraries huLIB-ST (kappa and lambda) and huLIB-STE (kappa and lambda) carrying the cloned scFv-repertoire were each harvested from the culture supernatant by PEG8000/NaCl precipitation and centrifugation.

2.7.1. Selections with huLIB-ST

For huLIB-ST approximately 1×10¹¹ to 1×10¹² kappa phages and roughly the same amount of lambda phages were each resuspended in 150 µl of TBS/1% BSA and then pooled (=phage pool 1). For phage pool 2, approximately 1×10¹⁰ to 1×10¹¹ kappa phages and roughly the same amount of lambda phages were each resuspended in 150 µl of PBS/10% FCS and then pooled.

Selection on Recombinant Antigen (huLIB-ST Phage Pool 1).

huLIB-ST phage pool 1 was incubated with recombinant soluble human CD3 epsilon immobilized on 96 well ELISA plates. Recombinant soluble human CD3 epsilon was prepared as described in Example 1. Human CD3-epsilon normally exists in the TCR/CD3 complex as a dimer together with either the gamma or the delta subunit of the same complex. Upon dimerization with either CD3-gamma or CD3-delta, CD3-epsilon undergoes a conformational change.

The conformation of recombinant, soluble CD3-epsilon differs significantly from its native conformation in the CD3 complex (Kastrup, Scand. J. Immunol. 56 (2002), 436-42) and therefore is not significantly bound by most existing anti-CD3 antibodies (note the low ELISA signals of OKT3, SP34 and UCHT1 in binding to soluble, recombinant CD3-epsilon in FIG. 14).

scFv phage that did not specifically bind to the target antigen were eliminated by up to ten washing steps with TBS/Tween. Binding entities were eluted by using HCl-Glycine pH 2.2 and after neutralization with 2 M Tris pH 12, the eluate was used for infection of a fresh uninfected *E. coli*/XL1 Blue culture. Cells successfully transduced with a phagemid copy, encoding a human scFv-fragment, were again selected for Carbenicillin resistance and subsequently infected with VCMS13 helper phage to start the second round of antibody display and in vitro selection.

After five rounds of production and selection for antigen-binding scFv-displaying phage, plasmid DNA from *E. coli* cultures was isolated that corresponds to 3, 4 and 5 rounds of panning as well as to the unselected repertoire prior to the first round of panning.

For the production of soluble scFv-proteins two strategies were pursued:

I) ScFv-DNA fragments were excised from the plasmids (EcoRI-BsiWI), and cloned via the same restriction sites in a similar plasmid pComb3H5BFlag differing in that it adds to the expression construct (e.g. scFv) a Flag-tag (TGDYKDDDDK) instead of a His6-tag and having the phage gene III deleted.

Instead of excising the fragments from the plasmids, standard PCR amplifications of the scFv-DNA were carried out by using the previously mentioned 3'-Vkappa primers (3'-hu-Vk-J1-SpeI-BsiWI, 3'-hu-Vk-J2/4-SpeI-BsiWI, 3'-hu-Vk-J3-SpeI-BsiWI, 3'-hu-Vk-J5-SpeI-BsiWI) and the 5'-VH-primers (5'-huVH1,3,5-XhoI-2001, 5'-huVH2-XhoI-2001; 5'-huVH4-XhoI-2001, 5'-huVH4B-XhoI-2001, 5'-huVH6-XhoI-2001). The scFv-fragments were isolated and cloned via XhoI-BsiWI-(fragments) and SalI-BsiWI-restriction (expression plasmid) into the above mentioned expression vector including the Flag-tag.

II) The isolated plasmids from the phage selection rounds were cut with BsiWI and Not I and ligated with a DNA fragment (BsiWI/Not I restricted) which added, in-frame, a murine ckappa domain, a myc tag (EEQK-LISEEDL) and a His6-tag to the scFv. This ckappa/myc/His6 domain was derived by a first standard PCR using 5'-primer (5'-Mouse ckappa BsiWI (SEQ ID NO: 169)), 3'-primer (3'-Mouse-ck-myc (SEQ ID NO: 170) and murine PBMC cDNA as template. In a second standard PCR reaction the isolated product (approximately 350 bp) from the first PCR was used as template using 5'-primer (5'-Mouse ckappa BsiWI), 3'-primer (3'-myc-His6-Not (SEQ ID NO: 171), The resulting PCR-fragment was isolated (approximately 370 bp), cut with BsiWI/NotI and subcloned into a pComb3H5BHis-derivative. From this vector the ckappa/myc/His6 fragment was excised via BsiWI/NotI and used for cloning (the respective sequence is shown in FIG. 1 (SEQ ID NO: 178 and SEQ ID NO: 179)).

After ligation each pool (different rounds of panning) of plasmid DNA was transformed into 100 µl heat shock competent *E. coli* XL1 Blue and plated on Carbenicillin LB-Agar. Single colonies were grown in 5 ml LB-Carb-cultures/20 mM MgCl₂ and expression of scFv was induced after six hours by adding Isopropyl-β-D-thiogalactosid (IPTG) to a final concentration of 1 mM and then incubated at 30° C.

These cells were harvested after 20 hours by centrifugation and typically resuspended in 500 µl PBS. Through four rounds of freezing at −70° C. and thawing at 37° C. the outer membrane of the bacteria was destroyed by temperature shock so that the soluble periplasmic proteins including the scFv fusion-proteins were released into the liquid. After elimination of intact cells and cell-debris by centrifugation, the supernatant was tested by ELISA for CD3 epsilon-binding scFv-fusion-proteins.

Detection of scFv-fragments bound to immobilized recombinant human CD3 epsilon antigen was carried out using a biotinylated anti-mouse kappa antibody (Southern Biotech, 1 µg/ml PBS) detected with horseradish peroxidase-conjugated avidine (Dako, 1 µg/ml PBS). The signal was developed by adding ABTS substrate solution and detected at a wavelength of 405 nm. In contrast to PBS as negative control and most of the clones after three rounds of panning, many clones after four rounds of panning already showed significant ELISA signals. FIG. 2 is illustrative of typical ELISA results. In the selection of scFvs shown, construct 4-10 showed especially strong binding to recombinant CD3 epsilon antigen.

Sequence analysis showed that most of the positive clones from round 4 and 5 were closely related. Further investigations of different CD3 positive clones was therefore focused on clones of round three, since the sequence diversity of these was expected to be higher than for clones of rounds 4 and 5 (see Example 2.8).

Selection on Jurkat Cells and by Specific Elution with Recombinant Antigen (huLIB-ST Phage Pool 2)

huLIB-ST phage pool 2 was incubated with $2 \times 10^5$ Jurkat cells (a CD3-positive human T-cell line) for 1 hour on ice under slow agitation. These Jurkat cells had been grown in RPMI medium enriched with fetal calf serum (10%), glutamin and penicillin/streptomycin, harvested by centrifugation, washed in PBS and resuspended in PBS 10% FCS. scFv phage which did not specifically bind to the Jurkat cells were eliminated by up to five washing steps with PBS/10% FCS. Jurkat cells with bound scFv phages were then incubated with 10 µg soluble recombinant CD3 epsilon antigen for 2 hours on ice under gentle agitation. Cells were pelleted by centrifugation and the supernatant used for infection of fresh uninfected E. coli XL1 blue cells.

Cells successfully transduced with a phagemid copy encoding a human scFv-fragment were again selected for Carbenicillin resistance and subsequently infected with VCMS13 helper phage to start the second round of antibody display and in vitro selection.

After five rounds of production and selection for antigen-binding scFv-displaying phage, plasmid DNA from E. coli cultures was isolated corresponding to 3, 4 and 5 rounds of panning as well as to the unselected repertoire prior to the first round of panning.

The cloning and expression of soluble scFvs in E. coli and the processing of the periplasmic preparations were carried out as described earlier for selection of huLIB-ST on recombinant antigen. These periplasmic preparations of single clones were then tested by ELISA for CD3epsilon-binding scFv-fusion-proteins. Detection of scFv-fragments bound to immobilized recombinant human CD3 epsilon antigen was carried out using a biotinylated anti-mouse kappa antibody (Southern Biotech, 1 µg/ml PBS) detected with horseradish peroxidase-Conjugated avidine (Dako, 1 µg/ml PBS). The signal was developed by adding ABTS substrate solution and detected at a wavelength of 405 nm. Compared to PBS as negative control, FIG. 3 shows that most of the clones after panning round 3 give significantly higher ELISA signals. Only one of the clones tested after panning round 4 and 5 showed significant binding.

2.7.2. Selections with huLIB-STE

For huLIB-STE approximately $5 \times 10^{11}$ to $5 \times 10^{12}$ kappa phages and roughly the same amount of lambda phage were each resuspended in 150 µl of TBS/1% BSA and then pooled (=phage pool 3). For phage pool 4, approximately $2 \times 10^{11}$ to $2 \times 10^{12}$ kappa phages and roughly the same amount of lambda phage were each resuspended in 150 µl of PBS/10% FCS and then pooled.

Selection on Recombinant Antigen (huLIB-STE Phage Pool 3)

huLIB-STE phage pool 3 was incubated with recombinant soluble human CD3 epsilon immobilized on 96 well ELISA plates. Recombinant soluble human CD3 epsilon was prepared as described in example 1. scFv phage which did not specifically bind to the target antigen were eliminated by up to ten washing steps with TBS/Tween. Binding entities were eluted by using HCl-Glycine pH 2.2 and after neutralization with 2 M Tris pH 12, the eluate was used for infection of a fresh uninfected E. coli XL1 Blue culture. Cells successfully transduced with a phagemid copy encoding a human scFv-fragment were again selected for Carbenicillin resistance and subsequently infected with VCMS13 helper phage to start the second round of antibody display and in vitro selection. After five rounds of production and selection for antigen-binding scFv-displaying, phage, plasmid DNA from E. coli cultures were isolated corresponding to 3, 4 and 5 rounds of panning as well as to the unselected repertoire prior to the first round of panning. The cloning and expression of soluble scFvs in E. coli and the processing of the periplasmic preparations were carried out as described earlier for selection of huLIB-ST on recombinant antigen.

These periplasmic preparations of single clones were then tested by ELISA for CD3epsilon-binding scFv-fusion-proteins. Detection of scFv-fragments bound to immobilized recombinant human CD3 epsilon antigen was carried out using a biotinylated anti-mouse kappa antibody (Southern Biotech, 1 µg/ml PBS) detected with horseradish peroxidase-conjugated avidine (Dako, 1 µg/ml PBS). The signal was developed by adding ABTS substrate solution and detected at a wavelength of 405 nm. PBS as negative control and the clones after three and four rounds of panning did not show significant ELISA signals (FIG. 4): Only one clone (5-13), obtained after the fifth panning round, showed a strong signal. In further experiments positive clones could be obtained after panning round 3 and 4.

Flow cytometric analysis showed that clone 5-13 from FIG. 4 was not able to significantly bind to CD3-positive Jurkat cells. From restriction analysis of the plasmid preparations after three, four and five rounds of panning, it is probable that clones identical or at least similar to 5-13 were overgrowing other clones in rounds 4 and 5. Further investigations for different CD3-positive clones were therefore focused on clones of round three, which seems to have a higher diversity than rounds 4 and 5 (see Example 2.8).

Selection on Jurkat Cells and by Specific Elution with Recombinant Antigen (huLIB-STE Phage Pool 4)

huLIB-STE phage pool 4 was incubated with $2 \times 10^5$ Jurkat cells (a CD3-positive human T-cell line) for 1 hour on ice under slow agitation. These Jurkat cells had been grown in RPMI medium enriched with fetal calf serum (10%), glutamine and penicillin/streptomycin, harvested by centrifugation, washed in PBS and resuspended in PBS 10% FCS. scFv phage which did not specifically bind to the Jurkat cells were eliminated by up to five washing steps with PBS/10% FCS. Jurkat cells with bound scFv phages were then incubated with 10 µg (100 µl) soluble recombinant CD3-epsilon antigen for 2 hours on ice under gentle agitation. Cells were pelleted by centrifugation and the supernatant was used for infection of fresh uninfected E. coli XL1 blue cells.

Cells successfully transduced with a phagemid copy encoding a human scFv-fragment were again selected for carbenicillin resistance and subsequently infected with VCMS13 helper phage to start the second round of antibody display and in vitro selection. After five rounds of production and selection for antigen-binding scFv-displaying phages, plasmid DNA from E. coli cultures was isolated corresponding to 3, 4 and 5 rounds of panning as well as to the unselected repertoire prior to the first round of panning.

The cloning and expression of soluble scFvs in E. coli and the processing of the periplasmic preparations were carried out as described earlier for selection of huLIB-ST on recombinant antigen. These periplasmic preparations of single clones were then tested by ELISA for CD3epsilon-binding scFv-fusion-proteins. Detection of scFv-fragments bound to immobilized recombinant human CD3 epsilon antigen was carried out using an anti-Flag-tag antibody (M2 Sigma 1 µg/ml PBS) detected with horseradish peroxidase-conjugated polyclonal anti-mouse antibody (Dako) 1 µg/ml PBS). The signal was developed by adding ABTS substrate solution and detected at a wavelength of 405 nm. Compared to the negative control, some of the clones after panning round 3 and 4 show strong ELISA signals, as seen in FIG. 5. FIG. 5 is illustrative of typical ELISA results. Of particular interest in FIG. 5 is the identification of clone 4-48. This clone later showed positive binding to Jurkat CD3+ cells.

2.8. Screening of scFvs on CD3-Positive Jurkat Cells

From huLIB-ST and huLIB-STE (selections on immobilized antigen or specific elution from Jurkat cells), more than 1000 scFv-producing *E. coli* clones were isolated and used for periplasmic preparations as described in the next example. These scFv-containing periplasmic preparations were then screened for positive binding signals on Jurkat cells in flow cytometric assays as described in the next example. Binding signals of positive clones were reproduced at least twice and respective scFv DNA-sequences were determined by plasmid preparation and sequencing.

The ratio of CD3-positive clones versus high sequence diversity likely reached its highest level after round 3 of panning on immobilized, solely expressed recombinant CD3 using huLIB-ST and huLIB-STE. For this reason, most of the Clones that were screened originated from round 3.

From huLIB-ST and huLIB-STE pannings on Jurkat cells with selection by elution using recombinant CD3 antigen, periplasmic preparations ("PPPs") from scFv-producing *E. coli* clones obtained after round 3, 4 and 5 were used for screening.

EXAMPLE 3

Prokaryotic Expression as scFv: Binding to Recombinant Antigen And to Human CD3-Positive and Negative Cells 3.1. Bacterial Expression in *E. Coli* XL1 Blue As previously mentioned, *E. coli* XL1 Blue transformed with pComb3H5BHis containing a VL- and VH-segment produce soluble scFv in sufficient amounts after excision of the gene III fragment and induction with 1 mM IPTG. The scFv-chain is exported into the periplasm where it folds into a functional conformation.

For periplasmic preparations the cells were grown in SB-medium supplemented with 20 mM $MgCl_2$ and carbenicillin 50 µg/ml and redissolved in PBS after harvesting. By four rounds of freezing at −70° C. and thawing at 37° C., the outer membrane of the bacteria was destroyed by temperature shock and the soluble periplasmic proteins including the scFvs were released into the supernatant. After elimination of intact cells and cell-debris by centrifugation, the supernatant containing the human anti-human CD3-scFvs was collected and used for further examination. These crude supernatants containing scFv will be further termed PPP.

3.2. Binding to Recombinant Human CD3 Epsilon Antigen in ELISA

After screening experiments (see Example 2.8) the following human scFv clones (all FLAG-tagged) were chosen for further investigation (sequences are shown in FIGS. 6-13, corresponding to SEQ ID NOs: 180-195):

From huLIB-ST: 4-10 (SEQ ID NO: 192, 193); 3-106 (SEQ ID NO: 180, 181); 3-114 (SEQ ID NO: 182, 183); 3-148 (SEQ ID NO: 184, 185).

From huLIB-STE: 4-48 (SEQ ID NO: 194, 195); 3-190 (SEQ ID NO: 186, 187); 3-271 (SEQ ID NO: 188, 189), 3-550 (SEQ ID NO: 190, 191).

ELISA experiments were carried out by coating the recombinant CD3 epsilon on wells of 96 well plastic plates (Nunc, maxisorb) typically at 4° C. over night. The antigen was then removed, wells washed once with PBS/0.05% Tween 20 and subsequently blocked with PBS/3% BSA for at least one hour. After removal of the blocking solution, PPPs and control solutions were added to the wells and incubated for typically one hour at room temperature. The wells were then washed three times with PBS/0.05% Tween 20. Detection of scFvs and control antibodies bound to immobilized antigen was Carried out using a monoclonal murine anti-His6 or anti FLAG-tag antibody (Qiagen anti-PentaHis and M2 anti Flag Sigma, typically each at a final concentration of 1 µg/ml PBS) detected with a peroxidase-labeled polyclonal goat anti- (mouse Fab-fragment) antibody (Dianova, 1 µg/ml PBS). The signal was developed by adding ABTS substrate solution and measured at a wavelength of 405 nm. Unspecific binding of the test-samples to the blocking agent was examined by carrying out the identical assays with the identical reagents and identical timing on ELISA plates which were not coated but blocked with BSA, only. As a negative control, LK2 (a human CD3-specific svFv; described in WO 98/54440), which does not bind to the recombinant CD3 epsilon antigen, was cloned into the same phage display/expression vector pComb3H5BHis. Periplasmic preparations of L2K scFv were carried out as described for the selected scFvs.

Human CD3-specific antibodies OKT3 (Janssen Cilag GmbH), SP34 (Pharmingen) and UCHT1 (Pharmingen) were also tested for binding to the recombinant ("r") CD3-epsilon antigen (final concentrations 1 µg/ml).

FIG. 14 shows the binding, measured by ELISA, of human anti-CD3 scFvs to rCD3-epsilon. It should be remembered that, prior to this ELISA experiment, these scFv constructs have first been selected in phage display using rCD3-epsilon and then have yielded positive signals upon screening on CD3+ Jurkat cells.

As shown in FIG. 14, all of the human scFvs show significantly higher binding signals than PBS, L2K-scFv (anti-CD3) control or the anti-CD3 antibodies UCHT1, SP34 and OKT3. It can be seen that the human scFvs show different intensities of ELISA signals when binding to recombinant CD3-epsilon. For example, human scFv constructs 4-10, 3-190, 4-48 and 3-550 show significantly higher ELISA signals than do human scFv constructs 3-271 and 3-106.

To exclude the possibility that the positive binding shown in FIG. 14 might be due to binding to BSA (used as a blocking agent in the first ELISA experiment shown in FIG. 14), a second ELISA experiment was performed in parallel. In this second ELISA experiment, all parameters were identical to those in the first ELISA experiment, except that in the second ELISA experiment no coating with antigen, but only blocking with BSA took place. The results of the second ELISA experiment are shown in FIG. 15. It can clearly be seen in FIG. 15 that none of the human scFvs showing binding in FIG. 14 showed any significant binding to BSA.

Taken together with the positive binding on CD3+ Jurkat cells, the results shown in FIGS. 14 and 15 allow the conclusion that the scFvs 4-10, 3-271, 3-148, 3-190, 4-48, 3-106, 3-114, and 3-550 specifically bind to the human CD3 antigen.

3.3. Binding to CD3-Positive and -Negative Cell Lines in Flow Cytometric Analysis The test for binding to CD3-positive and -negative cell lines was also carried out with the periplasmic preparations:
From huLIB-ST: 4-10 (SEQ ID, NO: 192, 193);
    3-106 (SEQ ID NO: 180, 181);
    3-114 (SEQ ID NO: 182, 183);
    3-148 (SEQ ID NO: 184, 185).
From huLIB-STE: 4-48 (SEQ ID NO: 194, 195);
    3-190 (SEQ ID NO: 186, 187);
    3-271 (SEQ ID NO: 188, 189),
    3-550 (SEQ ID NO: 190, 191).

Positive controls: L2K scFv was again included in the experiments as well as the commercially available murine anti-human CD3 antibodies OKT3, UCHT1 and SP34. PBS was used as an appropriate negative control.

The human T-cell line Jurkat and CHO cells cotransfected with both human CD3-epsilon and human CD3-gamma (CHOe/g) were used as CD3-positive cell lines. The human gastric cancer cell line KatoIII and untransfected CHO cells were included as CD3-negative cell lines.

Cell binding assays were carried out by initially incubating between 100,000 and 200,000 cells with periplasmic preparation (PPP) containing human scFv or relevant controls. After incubation the cells were washed in PBS/1% FCS (fetal calf serum) and further incubated with 5-10 µg/ml of anti-FLAG M2 antibody. After the cells had again been washed, they were incubated with polyclonal, PE-labeled anti-mouse antibodies (Dianova) and subsequently analyzed by flow cytometry.

FIGS. 16-21 depict binding of human scFv constructs to various cell lines as measured by flow cytometric analysis. Each of figures. 16-21 contains multiple diagrams, one for each construct tested. In any given diagram, the black distribution shows fluorescence intensity for cells incubated only with PBS alone in the absence of any construct but with all appropriate detection agents as used for detection of scFvs. In this way, any fluorescence shift observed can be definitely attributed to scFv construct rather than detection agents or buffer. Shifts in fluorescence which are indicative of construct binding to the respective cell line are depicted by a gray line in each diagram. Generally, a shift of higher magnitude away from, i.e. further to the (black) control indicates stronger binding, whereas a shift of lower magnitude away from, i.e. closer to the (black) control indicates weaker binding.

FIG. 16 depicts the results of experiments measuring the binding of human scFv constructs to CD3(+) human Jurkat cells as measured by flow cytometric analysis. It can be seen that the constructs 3-148, 3-190, 3-271, 4-10 and 4-48 show clearly discernable shifts in fluorescence intensity as compared to the respective control. Constructs 3-106, 3-114 and 3-550 show only minimal, although reproducible shifts in fluorescence. The positive controls L2K scFv (anti-CD3), UCHT1, SP34 and OKT3 all show, as expected, clearly discernable shifts in fluorescence intensity as compared to the respective control. All constructs tested therefore show binding to CD3+ cells, with 3-148, 3-190, 3-271, 4-10 and 4-48 being stronger than 3-106, 3-114 and 3-550.

FIGS. 17 and 18 each show the results of the test constructs' binding to CD3(−) cells. In one case (FIG. 17), the CD3(−) cells are of non-human origin. In the other case (FIG. 18), the CD3(−) cells are of human origin. FIG. 17 depicts the results of experiments measuring the binding of human scFv constructs to CD3(−) CHO cells as measured by flow cytometric analysis. It can be seen that none of the constructs show clearly discernable shifts in fluorescence intensity as compared to the respective control, regardless of whether these constructs are scFv test constructs or the positive control constructs L2K scFv (anti-CD3), UCHT1, SP34 and OKT3. FIG. 18 depicts the results of experiments measuring the binding of human scFv constructs to CD3(−) KatoIII cells as measured by flow cytometric analysis. It can be seen that none of the constructs show clearly discernable shifts in fluorescence intensity as compared to the respective control, regardless of whether these constructs are scFv constructs to be tested or the positive control constructs L2K scFv (anti-CD3 scFv), UCHT1, SP34 and OKT3.

Comparing the results from FIG. 16 with those from either FIG. 17 or FIG. 18 indicates that the magnitudes of fluorescence shift for the constructs 3-148, 3-190, 3-271, 4-10 and 4-48 are significantly less when binding to CD3(−) cells than when binding to CD3(+) cells. Taken together with the ELISA results described above, it can therefore be concluded that at least the human scFv constructs 3-148, 3-190, 3-271, 4-10 and 4-48 bind to the native human CD3 on human CD3+ cells.

To further confirm the specificity of the scFv constructs, binding studies were also performed using CHO cells which had been cotransfected with both CD3-epsilon ("CD3-e") and CD3-gamma ("CD3-g"). Non-transfected CHO cells express neither CD3-e nor CD3-g. CHO cells transfected with both CD3-e and CD3-g express these two proteins much more weakly than do Jurkat cells. For this reason, using CHO cells transfected with CD3-e and CD3-g confers a higher degree of stringency on the binding experiments than would be possible using Jurkat cells.

FIGS. 19-21 depict the results of such binding studies as measured by flow cytometric analysis. FIG. 19 depicts the results of binding by the scFv construct 3-271 to CD3(+) Jurkat cells. FIG. 20 depicts the results of binding by the scFv construct 3-271 to CHO cells lacking CD3 antigen. FIG. 21 depicts the results of binding by the scFv construct 3-271 to CHO cells transfected with both CD3-epsilon and CD3-gamma. Therefore, the only difference between non-transfected CHO cells and CHO cells doubly transfected with CD3-epsilon and CD3-gamma is the presence of CD3-e and CD3-g on the doubly transfected cells. Considering FIGS. 19 and 21, it is clear that interaction of scFv construct 3-271 with Jurkat cells (FIG. 19) and with CHO cells doubly transfected with CD3-epsilon and CD3-gamma (FIG. 21) in each case gives rise to a strong fluorescence shift away from the control. In contrast, the interaction of scFv 3-271 with non-transfected CHO cells (FIG. 20) gives rise to no significant fluorescence shift as compared to those observed in FIGS. 19 and 21. This emphasizes the specificity for CD3 previously shown far the scFv construct 3-271.

It should not be forgotten that the human scFv construct 3-271 showed a weak signal in the ELISA experiment using recombinant CD3-epsilon as antigen (FIG. 14). Taken together with the strong binding manifested by 3-271 on CD3(+) Jurkat cells, it becomes clear that CD3 epsilon likely makes up only part of the epitope recognized by 3-271. Without being bound by theory, it is therefore believed that the epitope specifically recognized by human scFv construct 3-271 comprises CD3-epsilon as well as at least another subunit of the CD3 complex.

Similar experiments were performed for the remaining human scFv constructs, but these constructs were unable to significantly bind to CHO cells transfected with CD3-epsilon and CD3-gamma. This finding is most likely due to the lower activity of these constructs as compared to the construct 3-271 as well as to the fact that the level of expression of CD3 on the transfected CHO cells is much lower than that on Jurkat CD3+ cells. This assumption is supported by the weaker binding, in FIG. 21, of positive controls UCHT1, OKT3, SP34 and scFv 12K (anti-CD3) to the transfected CHO cells.

EXAMPLE 4

Eukaryotic Expression of Human Anti-Human CD3 Binding Specificity as Part of Bispecific Single Chain Constructs: Testing the Biological Activity as T-Cell Engagers Against Various Target Cells In order to test whether the human anti-CD3 molecules as disclosed herein above retain their biological activity in a more complicated molecular context, various bispecific single chain antibody molecules comprising anti-CD3 specificity were prepared. Each bispecific single chain antibody comprised a human scFv specifically binding to the human CD3 antigen as well as another molecular domain which specifically binds to an antigen other than the human CD3 antigen. Expression in bacteria might lead to functionally less active bispecific single chain antibodies.

Mammalian cells were used for the production of functional bispecific antibodies: To this end, the chosen human anti-human CD3 scFvs were cloned into the eukaryotic expression vector pEFDHFR (Mack, Proc. Natl. Acad. Sci. U.S.A. 92 (1995) 7021-5) already containing a target specificity, for example anti-CD19 (e.g. VH-VL as in FIG. 23), anti-EpCAM (e.g. 5-10 from WO 99/25818, e.g. VH-VL as in FIG. 22), anti-CD20(e.g. as in FIG. 24) or anti-CCR5 (e.g. as in FIG. 25).

4.1. Cloning of Bispecific Single Chain Constructs Against Human CD3 and Human CD19

In order to create a model to test the chosen human anti-human CD3 scFvs as part of a bispecific antibody, nucleic acid sequences encoding these human anti-human CD3 scFvs were cloned into a eukaryotic expression vector in translational fusion to an scFv antibody fragment directed against human CD19.

4.1.1. Construction of antiCD3-antiCD19 Bispecific Single Chain Antibodies

The pEFDHFR vector containing the DNA sequence coding for mouse anti-human CD3×anti-human CD19 was used to generate corresponding human anti-CD3 constructs wherein the human anti-CD3 portion was expressed co-linearly with and N-terminal to the anti-CD19 portion in the resulting bispecific single chain antibody construct (biscFv).

To replace the mouse anti-human CD3 specificity in VH-VL configuration with the selected human anti-human CD3 specificity, the appropriate restriction sites had to be introduced into the human anti-human CD3-constructs by PCR. The primers 5'-5BVH-BsrGI (SEQ ID NO: 172) and 3'-5BVL-BspEI (SEQ ID NO: 173) added a BsrGI-site to the 5-prime VH-domain and a BspEI-site to the 3' VL-domain, respectively.

The PCR amplified DNA-fragments were then purified. These fragments and the vector anti-human CD19 pEFDHFR were restricted with BrsGI and BspEI (NEB enzymes) and ligated after purification in an appropriate ratio. The ligation was transformed into *E. coli* XLI blue by heatshock transformation and clones were screened with the vector-specific primer leader seq and the insert-specific primer 3'-5BVL-BspEI. Positive clones were inoculated in 50 ml of SB-medium containing carbenicillin as a selection marker and were grown overnight at 37° C. in a shaker. Plasmid preparation was carried out using a commercial kit (QIAGEN plasmid midi kit) before the constructs were finally checked by sequencing.

In this way, the following biscFv-constructs were prepared:

Human anti-CD3 3-148 VH-VL×anti-CD19 VL-VH
   (nucleic acid: Table 1, Construct 20nuc; amino acid: Table 2, Construct 20prot; SEQ ID NOS: 205, 206)
Human anti-CD3 3-190 VH-VL×anti-CD19 VL-VH
   (nucleic acid: Table 1, Construct 28nuc; amino acid: Table 2, Construct 28prot; SEQ ID NOS: 207, 208)
Human anti-CD3 3-271 VH-VL×anti-CD19 VL-VH
   (nucleic acid: Table 1, Construct 36nuc; amino acid: Table 2, Construct 36prot; SEQ ID NOS: 209, 210)
Human anti-CD3 4-10 VH-VL×anti-CD19 VL-VH
   (nucleic acid: Table 1, Construct 52nuc; amino acid: Table 2, Construct 52prot; SEQ ID NOS: 211, 212)
Human anti-CD3 4-48 VH-VL×anti-CD19 VL-VH.
   (nucleic acid: Table 1, Construct 60nuc; amino acid: Table 2, Construct 60prot; SEQ ID NOS: 213, 214)

4.1.2. Construction of antiCD19-antiCD3 Bispecific Single Chain Antibodies

The pEFDHFR vector containing the DNA sequence coding for anti-human CD19×mouse-anti-human CD3 was used as a vector backbone for subcloning.

To replace the VHVL mouse anti-human CD3-epsilon specificities with the selected human anti-human CD3-specificities the appropriate restriction sites had to be introduced into the human anti-human CD3-constructs by PCR and cloning into intermediate vectors. First, to introduce an XhoI-site to clones derived from selection within the library huLIB-ST, PCR was carried out on the anti-human CD3-pComb3H5BFlag-constructs using the specific 5'-VH and 3'-VK-J-primers corresponding to their individual sequence. The amplified DNA-fragments were cloned by restriction with XhoI and BsiWI enzymes (both from Roche) into pComb3H5BFlag. Anti-human CD3-pComb3H5BFlag constructs were then digested with BspEI (NEB) and BsiWI and the approximately 750-800 bp scFv DNA-fragments were isolated. The scFv fragment 4-10 was then ligated into an intermediate cloning vector 3B10 pEFDHFRHis which had been restricted with the same enzymes. This step introduced a His-Tag followed by a SalI restriction site, the latter being necessary for the next cloning step.

Both 3B10 (anti-EpCAM)×anti-human CD3 4-10 pEFDHFR-His and the anti-CD19-bearing vector mentioned above were restricted with SalI (Roche) and BspEI(NEB). The scFv DNA fragment 4-10 His and the vector fragment of anti-CD19 pEFDHFR were isolated and then ligated in an appropriate ratio. The ligation was transformed into *E. coli* XLI blue by heatshock transformation, and clones were screened with the vector-specific primer leader seq and the insert-specific primer 3'-5BVL-BspEI. Positive clones were inoculated in 50 ml of SB-medium containing carbenicillin as a selection marker and grown overnight at 37° C. in a shaker.

Plasmid preparation was carried out using a commercial kit (QIAGEN plasmid midi kit) before the constructs were finally checked by sequencing. The isolated BspEI-BsiWI fragments of the other human CD3-specific clones (3-148, 3-190, 3-271, 4-48) were then cloned into the anti-CD19× anti-CD3 4-10 pEFDHFR via the same cloning sites in place of 4-10. Finally, the following biscFv-constructs were generated:

anti-CD19 VL-VH×human anti-CD3 3-148 VH-VL
   (nucleic acid: Table 1, Construct 21nuc; amino acid: Table 2, Construct 21prot; SEQ ID NOS: 215, 216)
anti-CD19 VL-VH×human anti-CD3 3-190 VH-VL
   (nucleic acid: Table 1, Construct 29nuc; amino acid: Table 2, Construct 29prot; SEQ ID NOS: 217, 218)
anti-CD19 VL-VH×human anti-CD3 3-271 VH-VL
   (nucleic acid: Table 1, Construct 37nuc; amino acid: Table 2, Construct 37prot; SEQ ID NOS: 219, 220)
anti-CD19 VL-VH×human anti-CD3 4-10 VH-VL
   (nucleic acid: Table 1, Construct 53nuc; amino acid: Table 2, Construct 53prot; SEQ ID NOS: 221, 222)
anti-CD19 VL-VH×human anti-CD3 4-48 VH-VL
   (nucleic acid: Table 1, Construct 61 nuc; amino acid:. Table 2, Construct 61 prot; SEQ ID NOS: 223, 224)

4.2. Cloning of Bispecific Sc-Constructs Against huCD3 and huEpCAM

4.2.1. Construction of antiCD3-antiEpCAM Bispecific Single Chain Antibodies The pEFDHFR vector containing the sequence coding for mouse anti-human CD3×5-10 (anti human-EpCAM) was used as a vector backbone for subcloning.

To replace the mouse anti-human CD3-epitope in VH/VL configuration with the selected human anti-human CD3 specificities, the appropriate restriction sites had to be introduced into the human anti-human CD3-constructs by standard PCR and DNA from the human CD3-binders as template. The primers 5'-5BVH-BsrGI (SEQ ID NO: 172) and 3'-5BVL-BspEI (SEQ ID NO: 173) added a BsrGI-site to the 5' VH-domain and a BspEI-site to the 3'-VL-domain, respectively.

The PCR-amplified DNA fragments were then purified. These fragments and the pEFDHFR vector containing the DNA-fragment coding for mouse anti-CD3×5-10 were restricted with BrsGI and BspEI (NEB enzymes) and were ligated after purification in an appropriate ratio. The ligation was transformed into *E. coli* XLI blue by heatshock transformation and clones were screened with the vector-specific primer leader sequence and the insert-specific primer 3'-5BVL-BspEI (SEQ ID NO: 173).

Positive clones were inoculated into 50 ml of SB-medium containing carbenicillin as a selection-marker and grown overnight at 37° C. in a shaker. Plasmid preparation was carried out using a commercial kit (QIAGEN plasmid midi kit) before the constructs were finally checked by sequencing. In this way, the following biscFv-constructs were generated:

Human anti-CD3 3-148 VH-VL×anti-EpCAM 5-10 VH-VL (nucleic acid: Table 3, Construct 82nuc; amino acid: Table 4, Construct 82prot; SEQ ID NOS: 225, 226)
  Human anti-CD3 3-190 VH-VL×anti-EpCAM 5-10 VH-VL (nucleic acid: Table 3, Construct 90nuc; amino acid: Table 4, Construct 90prot; SEQ ID NOS: 227, 228)
  Human anti-CD3 3-271 VH-VL×anti-EpCAM 5-10 VH-VL (nucleic acid: Table 3, Construct 98nuc; amino acid: Table 4, Construct 98prot; SEQ ID NOS: 229, 230)
  Human anti-CD3 4-10 VH-VL×anti-EpCAM 5-10 VH-VL (nucleic acid: Table 3, Construct 114nuc; amino acid: Table 4, Construct 114prot; SEQ ID NO: 231, 232)
  Human anti-CD3 4-48 VH-VL×anti-EpCAM 5-10 VH-VL (nucleic acid: Table 3, Construct 122nuc; amino acid: Table 4, Construct 122prot; SEQ ID NOS: 233, 234)

4.2.2. Construction of Anti-EpCAM×Anti-CD3 Bispecific Single Chain Antibodies The pEFDHFR, vector containing the sequence coding for mouse anti-human CD3×5-10 (anti human-EpCAM) was used as a vector backbone for subcloning. To create the desired constructs, an intermediate cloning was necessary to insert the required restriction site SalI. First, the 5' mouse anti-human CD3 scFv-domain was exchanged with another 5-10 domain to create a suitable intermediate cloning vector 5-10×5-10 pEFDHFR.

For the insert, the vector 5-10×mouse (anti-human CD3) pEFDHFR was restricted with the restriction enzymes BsrGI and BspEI. The excised and purified fragment was then ligated into the vector mentioned above, which had been restricted with the same enzymes. The resulting construct 5-10×5-10 pEFDHFR could than be used for further cloning of human anti-human CD3-epitopes at the C-terminus of 5-10 by restricting the latter with BspEI and SalI.

The chosen human anti-human CD3-specificities were taken from the pEFDHFR constructs containing the sequence mouse anti-human CD19×human anti-human CD3 which were created as described in Example 4.1.2. The 3' anti-CD3-domains were restricted from the vector with BspEI and SalI and were ligated into 5'-5-10 pEFDHFR (×BspEI-SalI) in an appropriate ratio.

The ligation was transformed into *E. coli* XLI blue by heatshock transformation, clones were screened with the vector-specific primers leader seq and EF pol. Positive clones were inoculated in 50 ml of SB-medium containing carbenicillin as a selection marker and grown overnight at 37° C. in a shaker. Plasmid preparation was carried out using a commercial kit (QIAGEN plasmid midi kit) before the constructs were finally checked by sequencing.

In this way, the following biscFv-constructs were generated:

anti-EpCAM 5-10 VL-VH×human anti-CD3 3-148 VH-VL (nucleic acid: Table 3, Construct 85nuc; amino acid: Table 4, Construct 85prot; SEQ ID NOS: 235, 236)
  anti-EpCAM 5-10 VL-VH×human anti-CD3 3-190 VH-VL (nucleic acid: Table 3, Construct 93nuc; amino acid: Table 4, Construct 93prot; SEQ ID NOS: 237, 238)
  anti-EpCAM 5-10 VL-VH×human anti-CD3 3-271 VH-VL (nucleic acid: Table 3, Construct 101 nuc; amino acid: Table 4, Construct 101prot; SEQ ID NOS: 239, 240)
  anti-EpCAM 5-10 VL-VH×human anti-CD3 4-10 VH-VL (nucleic acid: Table 3, Construct 117nuc; amino acid: Table 4, Construct 117prot; SEQ ID NOS: 241, 242)
  anti-EpCAM 5-10 VL-VH×human anti-CD3 4-48 VH-VL (nucleic acid: Table 3, Construct 125nuc; amino acid: Table 4, Construct 125prot; SEQ ID NOS: 243, 244).

Primers used for cloning of anti-target/anti-CD3 bispecific antibodies were 5'-5BVH-BsrGI (SEQ ID NO: 172) and 3'-5BVL-BspEI (SEQ ID NO: 173). The leader seq is shown in SEQ ID NO: 204.

4.3. Cloning of Bispecific Single Chain Constructs Against Human CD3 and Human CD20

Human CD3-specificities were combined with a single chain directed against the human CD20antigen in an analogous manner as described herein above for the cloning of anti-CD19 (or anti-EpCAM)×human anti-human CD3 and human anti-human CD3×anti-CD19 (or anti-EpCAM). The following examples of such constructs were generated:

anti-CD20VL-VH×human anti-CD3 3-190 VH-VL (nucleic acid: Table 7, Construct 221nuc; amino acid: Table 8, Construct 221prot; SEQ ID NOs: 245, 246)
  anti-CD20VL-VH×human anti-CD3 3-148 VH-VL (nucleic acid: Table 7, Construct 213nuc; amino acid: Table 8, Construct 213prot; SEQ ID NOs: 247, 248)

4.4. Cloning of Bispecific Single Chain Constructs Against Human CD3 and Human CCR5

Human CD3-specificities were combined with a single chain directed against the human CCR5 antigen in an analogous manner as described herein above for the cloning of anti-CD19 (or anti-EpCAM)×human anti-human CD3 and human anti-human CD3×anti-CD19 (or anti-EpCAM). The following examples are generated:

anti-CCR5VL-VH×human anti-CD3 3=190 VH-VL (nucleic acid: Table 5, Construct 157nuc; amino acid: Table 7, Construct 157prot; SEQ ID NOs: 249, 250)
  anti-CCR5VL-VH×human anti-CD3 3-148 VH-VL (nucleic acid: Table 5, Construct 149nuc; amino acid: Table 7, Construct 149prot; SEQ ID NOs: 251, 252)

4.5. Expression and Purification of the Respective Bispecific Single Chain Constructs in CHO Cells Before transfection, DHFR-negative CHO cells were grown in alpha MEM-medium ((Bio Whittaker)+10% FCS+glutamine+Penicillin/Streptomycin) containing a mix of nucleosides. The day before transfection, 4×10⁵ cells/3 ml were seeded in a sterile 6-well cell culture plastic plate and grown overnight in supplemented medium.

Transient transfection was carried out using the PolyFect® Transfection Reagent (QIAGEN) following the manufacturer's instructions. The cells were incubated for four days, followed by harvesting of the supernatants. After sedimentation of cells by centrifugation and transfer into fresh tubes, the supernatants could be tested for binding in an ELISA- and/or FACS-assay.

For stable transfection after collecting the transiently produced supernatants, CHO cells were transferred into a small cell-culture bottle (25 cm$^2$) and grown in selection medium (alpha-MEM without nucleosides). Cells were expanded (75 cm$^2$ culture flask) in this medium and finally grown in a 150 cm$^2$ cell culture flask to confluence. Cells from one 150 cm$^2$ culture flask were then transferred to plastic roller bottles with 500 ml HyQ®-medium (HyClone; serumfree, containing Penicilin/Streptomycin) and grown for 7 days before harvest of the cell culture supernatant. The cells were removed by centrifugation and the supernatant containing the expressed protein was stored at −20° C.

4.6. Purification of the Bispecific Single Chain Constructs

The single chain bispecific antibodies were isolated in a two step purification process of immobilized metal affinity chromatography (IMAC) and gel filtration. All constructs were purified according to this method. Äkta® FPLC System (Pharmacia) and Unicorn® Software were used for chromatography. All chemicals were of research grade and purchased from Sigma (Deisenhofen) or Merck (Darmstadt).

IMAC was performed using a Fractogel® column (Merck) which was loaded with $ZnCl_2$ according to the protocol provided by the manufacturer. The column was equilibrated with buffer A2 (20 mM sodium phosphate pH 7.5, 0.4 M NaCl) and the cell culture supernatant (500 ml) was applied to the column (10 ml) at a flow rate of 3 ml/min. The column was washed with buffer A2 to remove unbound sample. Bound protein was eluted using a 2 step gradient of buffer B2 (20 mM sodium phosphate pH 7.5, 0.4 M NaCl, 0.5 M Imidazol) according to the following:

Step 1: 20% buffer B2 in 6 column volumes;
Step 2: 100% buffer B2 in 6 column volumes.

Eluted protein fractions from step 2 were pooled for further purification.

Gel filtration chromatography was performed on a Sephadex S200 HiPrep column (Pharmacia) equilibrated with PBS (Gibco). Eluted protein samples (flow rate 1 ml/min) were subjected to standard SDS-PAGE and Western Blot for detection. Prior to purification, the column was calibrated for molecular weight determination (molecular weight marker kit, Sigma MW GF-200). Protein concentrations were determined using protein assay dye (MicroBCA, Pierce) and IgG (Biorad) as standard protein.

Purified bispecific protein was analyzed by SDS PAGE under reducing conditions performed with pre-cast 4-12% Bis Tris gels (Invitrogen). Sample preparation and application were performed according to the protocol provided by the manufacturer. The molecular weight was determined with MultiMark protein standard (Invitrogen). The gel was stained with colloidal Coomassie (Invitrogen protocol). Western Blot was performed using an Optitran® BA-S83 membrane and the Invitrogen Blot Module according to the protocol provided by the manufacturer. The antibodies used were directed against the His Tag (Penta His, Qiagen) and goat-anti-mouse Ig labeled with alkaline phosphatase (AP) (Sigma), and BCIP/NBT (Sigma) as substrate. The single chain bispecific antibody could be specifically detected by Western Blot.

4.7. Bioactivity of Bispecific Antibodies Specific for CD19 and CD3

Cytotoxic activity of the bispecific antibodies was determined in a fluorochrome release based cytotoxicity assay. For this experiment purified biscFv 3-190×anti-CD19 P2 (protein fraction 2 from gel filtration) was used.

CD19 positive NALM6 cells were used as target cells (1.5×10$^7$) labeled with 10 μM calcein AM (Molecular Probes, Leiden, Netherland, no. C-1430) for 30 min at 37° C. in cell culture medium. After two washes in cell culture medium, cells were counted and mixed with cells from the CD4-positive T cell clone CB15 (kindly provided by Dr. Fickenscher, University of Erlangen/Nuemberg, Germany). 2×10$^6$ CB15 cells and 2×10$^5$ Nalm6 cells were mixed per ml (E:T ratio of 1:10) and 50 μl of this suspension were used per well in a 96 well round bottom plate. biscFv 3-190×anti-CD19 P2 was diluted in RPMI/10% FCS in a dilution series and 50 μl of the respective solution were added to the cell suspension. The same dilution series was performed using PBS as negative control, starting with the same volume as for biscFv 3-190× anti-CD19 P2. A standard reaction was incubated at 37° C./5% $CO_2$ for 2 hours. After the cytotoxic reaction, the released dye in the incubation medium was quantitated in a fluorescence reader (Tecan, Crailsheim, Germany) and compared with the fluorescence signal from a control reaction (without bispecific antibody), and the fluorescence signal obtained for totally lysed cells (for 10 min in 1% saponin). On the basis of these readings, the specific cytotoxicity was calculated according to the following formula: [Fluorescence (Sample)−Fluorescence (Control)]:[Fluorescence (Total Lysis)−Fluorescence (Control)]×100.

Sigmoidal dose response curves typically had R2 values >0.97 as determined by Prism Software (GraphPad Software Inc., San Diego, USA; EC50 values calculated by the analysis program were used for comparison of bioactivity).

As shown in FIG. 26 the anti-human CD3×anti-CD19 biscFv mediated cytotoxic activity against the CD19-positive NALM6-cells using CB15 cells as effector cells. In this experiment half maximal toxicity could be obtained in the low ng/ml concentrations of the biscFv 3-190×anti-CD19. Control dilutions, with PBS instead of biscFv did not show significant cytotoxicity. Based on the results shown in FIG. 26, it can therefore be concluded that the anti-human CD3× anti-CD19 biscFv binds to the CD19 antigen on target cells and to the CD3 antigen on the effector inducing lysis of target.

4.8. Bioactivity of Bispecific Antibodies Specific for EpCAM and CD3

For this experiment anti-CD3 3-271×5-10 anti-EpCAM P2 (protein fraction 2 from gel filtration), anti-CD3 3-271×5-10 anti-EpCAM P3 (protein fraction 3 from gelfiltration), 5-10 anti-EpCAM×anti-CD3 3-148 (main protein fraction from gelfiltration) and 5-10 anti-EpCAM×anti-CD3 3-190 P3 (protein fraction 3 from gelfiltration) were evaluated with respect to their ability to mediate specific toxicity. Anti-CD3 3-190.x anti-CD19 P2 (protein fraction 2 from gelfiltration) which proved to mediate specific cytotoxicity to CD19-positive NALM6-cells (see FIG. 26) was included as an appropriate negative control for CD19-negative CHO-EpCAM cells. M79, an anti-EpCAM×anti-CD3 biscFv construct (Mack, PNAS 92 (1995), 7021-5), was used as a positive control.

CHO cells from the American Type Cell Culture Collection (ATCC, Manassas, USA) were transfected with epithelial cell adhesion molecule (EpCAM). A cell clone derived from this transfection, referred to as CHO-EpCAM cells, was used for the experiments. Untransfected CHO cells were also included in this experiment to demonstrate the EpCAM specificity of the cytotoxicity to the EpCAM-transfected cells. The CD4-positive T cell clone CB15 was kindly provided by Dr. Fickenscher, University of Erlangen/Nuemberg, Germany. Cells were cultured as recommended by the suppliers.

4.9. Flow Cytometry-Based Cytotoxicity Assay

Untransfected CHO as well as CHO-EpCAM ($1.5 \times 10^7$) cells were respectively washed free of serum two times with PBS and incubated with PKH26 dye (Sigma-Aldrich Co.) according to the manufacturer's instructions. After staining, cells were washed two times with RPMI/10% FCS. Cells were counted and mixed with CB15 effector cells. The resulting cell suspension contained 400,000 target and $2 \times 10^6$ effector cells per ml. 50 µl of the mixture was used per well in a 96 well round bottom plate. Antibody constructs were diluted in RPMI/10% FCS to the required concentration and 50 µl of this solution were added to the cell suspension. A standard reaction was incubated for 16 h at 37° C./5% $CO_2$. Propidium iodide was added to a final concentration of 1 µg/ml. After 10 min of incubation at room temperature, cells were analyzed by flow cytometry. PKH26 fluorescence was used for positive identification of target cells. Cytotoxicity was measured as ratio of PI positive over all target cells.

Specific cytotoxicity mediated by the purified biscFv-constructs was plotted in FIG. 27. This figure shows the mediation of a significant specific cytotoxicity by the anti-human CD3×anti-human EpCAM biscFvs as well as by the positive control M79×CD3 (Mack Proc Natl Acad Sci USA 92 (1995), 7021-5) on EpCAM-transfected CHO-cells. No relevant specific lysis could be obtained on non-transfected CHO cells as well as in case of the CHO-EpCAM cells irrelevant biscFv 3-190×anti CD19.

In the Cytotoxicity experiments shown in FIGS. 26 and 27 it is clearly demonstrated that the respective human anti-CD3 binders, combined with a target specificity in the context of a bispecific single chain construct, are able to mediate specific toxicity to target cells by recruiting CD3-positive effector cells. This not only corroborates the CD3 specificity of the respective human anti-CD3 constructs themselves, but also clearly demonstrates the retention of this specificity as well as T cell triggering potential within a bispecific single chain antibody format.

The invention claimed is:

1. A purified binding molecule specifically binding to/interacting with the human CD3 complex, whereby said binding molecule is an antibody molecule, antibody fragment or derivative thereof or an antibody construct, wherein said antibody molecule, antibody fragment or derivative thereof or an antibody construct comprises a CDR1, CDR2 and CDR3 region, wherein said CDR regions comprise:
   a) VH-region CDR1, CDR2 and CDR3 as encoded by a nucleic acid molecule as shown in SEQ ID NOs: 3, 5, and 7 or having the amino acid sequence as shown in SEQ ID NOs: 4, 6, and 8 and VL-region CDR1, CDR2 and CDR3 as encoded by a nucleic acid molecule as shown in SEQ ID NOs: 11, 13, 15 or having the amino acid sequence as shown in SEQ ID NOs: 12, 14, and 16;
   b) VH-region CDR1, CDR2 and CDR3 as encoded by a nucleic acid molecule as shown in SEQ ID NOs: 19, 21, and 23 or having the amino acid sequence as shown in SEQ ID NOs: 20, 22, and 24 and VL-region CDR1, CDR2 and CDR3 as encoded by a nucleic acid molecule as shown in SEQ ID NOs: 27, 29, 31 or having the amino acid sequence as shown in SEQ ID NOs: 28, 30, and 32;
   c) VH-region CDR1, CDR2 and CDR3 as encoded by a nucleic acid molecule as shown in SEQ ID NOs: 35, 37, and 39 or having the amino acid sequence as shown in SEQ ID NOs: 36, 38, and 40 and VL-region CDR1, CDR2 and CDR3 as encoded by a nucleic acid molecule as shown in SEQ ID NOs: 43, 45, 47 or having the amino acid sequence as shown in SEQ ID NOs: 44, 46, and 48;
   d) VH-region CDR1, CDR2 and CDR3 as encoded by a nucleic acid molecule as shown in SEQ ID NOs: 51, 53, and 55 or having the amino acid sequence as shown in SEQ ID NOs: 52, 54, and 56 and VL-region CDR1, CDR2 and CDR3 as encoded by a nucleic acid molecule as shown in SEQ ID NOs: 59, 61, 63 or having the amino acid sequence as shown in SEQ ID NOs: 60, 62, and 64;
   e) VH-region CDR1, CDR2 and CDR3 as encoded by a nucleic acid molecule as shown in SEQ ID NOs: 67, 69, and 71 or having the amino acid sequence as shown in SEQ ID NOs: 68, 70 and 72 and VL-region CDR1, CDR2 and CDR3 as encoded by a nucleic acid molecule as shown in SEQ ID NOs: 75, 77, 79 or having the amino acid sequence as shown in SEQ ID NOs: 76, 78, and 80;
   f) VH-region CDR1, CDR2 and CDR3 as encoded by a nucleic acid molecule as shown in SEQ ID NOs: 83, 85, and 87 or having the amino acid sequence as shown in SEQ ID NOs: 84, 86, and 88 and VL-region CDR1, CDR2 and CDR3 as encoded by a nucleic acid molecule as shown in SEQ ID NOs: 91, 93, 95 or having the amino acid sequence as shown in SEQ ID NOs: 92, 94, and 96;
   g) VH-region CDR1, CDR2 and CDR3 as encoded by a nucleic acid molecule as shown in SEQ ID NOs: 99, 101, and 103 or having the amino acid sequence as shown in SEQ ID NOs: 100, 102, and 104 and VL-region CDR1, CDR2 and CDR3 as encoded by a nucleic acid molecule as shown in SEQ ID NOs: 107, 109, 111 or having the amino acid sequence as shown in SEQ ID NOs: 108, 110, and 112; or
   h) VH-region CDR1, CDR2 and CDR3 as encoded by a nucleic acid molecule as shown in SEQ ID NOs: 115, 117, and 119 or having the amino acid sequence as shown in SEQ ID NOs: 116, 118, and 120 and VL-region CDR1, CDR2 and CDR3 as encoded by a nucleic acid molecule as shown in SEQ ID NOs: 123, 125, 127 or having the amino acid sequence as shown in SEQ ID NOs: 124, 126, and 128.

2. The human binding molecule of claim 1, wherein said derivative of an antibody is an scFv.

3. The binding molecule according to claim 1, wherein said antibody molecule, antibody fragment or derivative thereof or an antibody construct, comprises a variable VH-region as encoded by a nucleic acid molecule as shown in a SEQ ID NO selected from the group consisting of SEQ ID NOs: 1, 17, 33, 49, 65, 81, 97 and 113 or a variable VH-region having an amino acid sequence as shown in a SEQ ID NO selected from the group consisting of SEQ ID NOs: 2, 18, 34, 50, 66, 82, 98 and 114.

4. The binding molecule according to claim 1, wherein said antibody molecule, antibody fragment or derivative thereof or an antibody construct, comprises a variable VL-region as encoded by a nucleic acid molecule as shown in a SEQ ID NO selected from the group consisting of SEQ ID NOs: 9, 25, 41, 57, 73, 89, 105 and 121 or a variable VL-region having an amino acid sequence as shown in a SEQ ID NO selected from the group consisting of SEQ ID NOs: 10, 26, 42, 58, 74, 90, 106 and 122.

5. The binding molecule of claim 1, additionally comprising at least one further antigen-interaction-site and/or at least one further effector domain.

6. The binding molecule according to claim 5, which is humanized and/or deimmunized.

7. The binding molecule of claim 5, wherein said at least one further antigen-interaction-site is specific for one or more cell surface molecule.

8. The binding molecule according to claim 7, wherein said cell surface molecule is a tumor specific marker.

9. The binding molecule of claim 5, wherein said at least one further antigen-interaction-site is a scFv.

10. The binding molecule according to claim 5, wherein said at least one further antigen-interaction-site specifically binds to/interacts with an antigen selected from the group consisting of EpCAM, CCR5, CD19, EphA2, HER-2 neu, HER-3, HER-4, EGFR, PSMA, CEA, MUC-1 (mucin), MUC2, MUC3, MUC4, MUC5AC, MUC5B, MUC7, βhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6, desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; T AG-72), FAP (fibroblast activation antigen), endosialin, EGFRvIII, LG, SAS and CD63.

11. The binding molecule according to claim 10, wherein said further antigen binding site specifically binds to/interacts with the CD 19 molecule.

12. The binding molecule according to claim 11, comprising an amino acid sequence selected from the group of
(a) an amino acid sequence corresponding to construct 1prot to 64prot of table 2;
(b) an amino acid sequence encoded by a nucleic acid sequence corresponding to construct 1nuc to 64nuc of table 1;
(c) an amino acid sequence encoded by a nucleic acid sequence hybridizing with the complementary strand of a nucleic acid sequence as defined In (b) under stringent hybridization conditions; and
(d) an amino acid sequence encoded by a nucleic acid sequence which is degenerate as a result of the genetic code to a nucleotide sequence of anyone of (b) and (c).

13. The binding molecule according to claim 10, wherein said further antigen binding site specifically binds to/interacts with the EpCAM molecule.

14. The binding molecule according to claim 13, comprising an amino acid sequence selected from the group of
(a) an amino acid sequence corresponding to construct 65prot to 128prot of table 4;
(b) an amino acid sequence encoded by a nucleic acid sequence corresponding to construct 65nuc to 128nuc of in table 3;
(c) an amino acid sequence encoded by a nucleic acid sequence which is degenerate as a result of the genetic code to a nucleotide sequence of (b).

15. The binding molecule according to claim 10, wherein said further antigen binding site specifically binds to/interacts with the CCR5 molecule.

16. The binding molecule according to claim 15, comprising an amino acid sequence selected from the group of
(a) an amino acid sequence corresponding to construct 129prot to 192prot of table 6;
(b) an amino acid sequence encoded by a nucleic acid sequence corresponding to construct 129nuc to 192nuc of table 5;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of anyone of (b) and (c).

17. The binding molecule according to claim 10, wherein said further antigen binding site specifically binds to/interacts with the CD20 molecule.

18. The binding molecule according to claim 17, comprising an amino acid sequence selected from the group of
(a) an amino acid sequence corresponding to construct 193prot to 256prot of table 8;
(b) an amino acid sequence encoded by a nucleic acid sequence corresponding to construct 193nuc to 256nuc of table 7;
(c) an amino acid sequence encoded by a nucleic acid sequence hybridizing with the complementary strand of a nucleic acid sequence as defined in (b) under stringent hybridization conditions; and
(d) an amino acid sequence encoded by a nucleic acid sequence which is degenerate as a result of the genetic code to a nucleotide sequence of anyone of (b) and (c).

19. A composition comprising a binding molecule according to claim 1.

20. The composition of claim 19 which is a pharmaceutical composition further comprising, optionally, suitable formulations of carrier, stabilizers and/or excipients.

21. The composition of claim 19 which is a diagnostic composition further comprising, optionally, means and methods for detection.

22. A kit comprising a binding molecule according to any one of claims 1 to 4 or claims 5 to 10, 13 and 14.

23. The composition of claim 19, further comprising a proteinaceous compound capable of providing an activation signal for immune effector cells.

* * * * *

UNITED STATES PATENT AND TRADEMARK OFFICE
CERTIFICATE OF CORRECTION

PATENT NO. : 8,784,821 B1
APPLICATION NO. : 10/554731
DATED : July 22, 2014
INVENTOR(S) : Kufer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1579 days.

Signed and Sealed this
Fifteenth Day of September, 2015

Michelle K. Lee
*Director of the United States Patent and Trademark Office*

```
                            SEQUENCE LISTING

<160> NUMBER OF SEQ ID NOS: 252

<210> SEQ ID NO 1
<211> LENGTH: 375
<212> TYPE: DNA
<213> ORGANISM: artificial sequence
<220> FEATURE:
<223> OTHER INFORMATION: synthetic primer

<400> SEQUENCE: 1
gagctgcagc tggtcgagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag atctgaggac acggccgtgt attactgtgc gaggctcagc     300
ccgtattgta ctaatggtgt atgctgggat gcttttgata tctggggcca agggacaatg     360
gtcaccgtct cctca                                                     375

<210> SEQ ID NO 2
<211> LENGTH: 125
<212> TYPE: PRT
<213> ORGANISM: artificial sequence
<220> FEATURE:
<223> OTHER INFORMATION: synthetic peptide

<400> SEQUENCE: 2

Glu Leu Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
```

```
            85                  90                  95
Ala Arg Leu Ser Pro Tyr Cys Thr Asn Gly Val Cys Trp Asp Ala Phe
            100                 105                 110

Asp Ile Trp Gly Gln Gly Thr Met Val Thr Val Ser Ser
            115                 120                 125

<210> SEQ ID NO 3
<211> LENGTH: 15
<212> TYPE: DNA
<213> ORGANISM: artificial sequence
<220> FEATURE:
<223> OTHER INFORMATION: synthetic primer

<400> SEQUENCE: 3
agctatggca tgcac                                                    15

<210> SEQ ID NO 4
<211> LENGTH: 5
<212> TYPE: PRT
<213> ORGANISM: artificial sequence
<220> FEATURE:
<223> OTHER INFORMATION: synthetic peptide

<400> SEQUENCE: 4

Ser Tyr Gly Met His
1               5

<210> SEQ ID NO 5
<211> LENGTH: 51
<212> TYPE: DNA
<213> ORGANISM: artificial sequence
<220> FEATURE:
<223> OTHER INFORMATION: synthetic primer

<400> SEQUENCE: 5
gttatatcat atgatggaag taataaatac tacgcagact ccgtgaaggg c            51

<210> SEQ ID NO 6
<211> LENGTH: 17
<212> TYPE: PRT
<213> ORGANISM: artificial sequence
<220> FEATURE:
<223> OTHER INFORMATION: synthetic peptide

<400> SEQUENCE: 6

Val Ile Ser Tyr Asp Gly Ser Asn Lys Tyr Tyr Ala Asp Ser Val Lys
1               5                   10                  15

Gly

<210> SEQ ID NO 7
<211> LENGTH: 48
<212> TYPE: DNA
<213> ORGANISM: artificial sequence
<220> FEATURE:
<223> OTHER INFORMATION: synthetic primer

<400> SEQUENCE: 7
ctcagcccgt attgtactaa tggtgtatgc tgggatgctt ttgatatc                48

<210> SEQ ID NO 8
<211> LENGTH: 16
<212> TYPE: PRT
<213> ORGANISM: artificial sequence
<220> FEATURE:
<223> OTHER INFORMATION: synthetic peptide
```

<400> SEQUENCE: 8

Leu Ser Pro Tyr Cys Thr Asn Gly Val Cys Trp Asp Ala Phe Asp Ile
1               5                   10                  15

<210> SEQ ID NO 9
<211> LENGTH: 321
<212> TYPE: DNA
<213> ORGANISM: artificial sequence
<220> FEATURE:
<223> OTHER INFORMATION: synthetic primer

<400> SEQUENCE: 9

```
gagctccaga tgacccagtc tccatcctcc ctgtctgcat ctgtcggaga cagagtctcc    60
atcacttgtc gggcaagtca gaccattagc aattatttaa attggtatca actgaagcca   120
gggaaagccc ctaagctcct gatctatgct gcatccactt tgcaaagtga ggtcccaacc   180
aggttcagtg gcagtgggtc tgggacagat ttcactctca ccatcagtgg tctgcatcct   240
gaagattttg caacttacta ctgtcaacag tttaatagtt atcctcgaac gttcggccaa   300
gggaccaagg tggaaatcaa a                                             321
```

<210> SEQ ID NO 10
<211> LENGTH: 107
<212> TYPE: PRT
<213> ORGANISM: artificial sequence
<220> FEATURE:
<223> OTHER INFORMATION: synthetic peptide

<400> SEQUENCE: 10

Glu Leu Gln Met Thr Gln Ser Pro Ser Ser Leu Ser Ala Ser Val Gly
1               5                   10                  15

Asp Arg Val Ser Ile Thr Cys Arg Ala Ser Gln Thr Ile Ser Asn Tyr
                20                  25                  30

Leu Asn Trp Tyr Gln Leu Lys Pro Gly Lys Ala Pro Lys Leu Leu Ile
            35                  40                  45

Tyr Ala Ala Ser Thr Leu Gln Ser Glu Val Pro Thr Arg Phe Ser Gly
    50                  55                  60

Ser Gly Ser Gly Thr Asp Phe Thr Leu Thr Ile Ser Gly Leu His Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 11
<211> LENGTH: 33
<212> TYPE: DNA
<213> ORGANISM: artificial sequence
<220> FEATURE:
<223> OTHER INFORMATION: synthetic primer

<400> SEQUENCE: 11

```
cgggcaagtc agaccattag caattattta aat                                 33
```

<210> SEQ ID NO 12
<211> LENGTH: 11
<212> TYPE: PRT
<213> ORGANISM: artificial sequence
<220> FEATURE:
<223> OTHER INFORMATION: synthetic peptide

<400> SEQUENCE: 12

Arg Ala Ser Gln Thr Ile Ser Asn Tyr Leu Asn
1               5                   10

<210> SEQ ID NO 13
<211> LENGTH: 21
<212> TYPE: DNA
<213> ORGANISM: artificial sequence
<220> FEATURE:
<223> OTHER INFORMATION: synthetic primer

<400> SEQUENCE: 13
gctgcatcca ctttgcaaag t                                      21

<210> SEQ ID NO 14
<211> LENGTH: 7
<212> TYPE: PRT
<213> ORGANISM: artificial sequence
<220> FEATURE:
<223> OTHER INFORMATION: synthetic peptide

<400> SEQUENCE: 14

Ala Ala Ser Thr Leu Gln Ser
1               5

<210> SEQ ID NO 15
<211> LENGTH: 27
<212> TYPE: DNA
<213> ORGANISM: artificial sequence
<220> FEATURE:
<223> OTHER INFORMATION: synthetic primer

<400> SEQUENCE: 15
caacagttta atagttatcc tcgaacg                                27

<210> SEQ ID NO 16
<211> LENGTH: 9
<212> TYPE: PRT
<213> ORGANISM: artificial sequence
<220> FEATURE:
<223> OTHER INFORMATION: synthetic peptide

<400> SEQUENCE: 16

Gln Gln Phe Asn Ser Tyr Pro Arg Thr
1               5

<210> SEQ ID NO 17
<211> LENGTH: 366
<212> TYPE: DNA
<213> ORGANISM: artificial sequence
<220> FEATURE:
<223> OTHER INFORMATION: synthetic primer

<400> SEQUENCE: 17
gagctgcagc tggtcgagtc tgggggaggc ttggtaaagc cagggcggtc cctgagactc      60
tcctgtacag cttctggatt cacctttggt gattatgcta tgagctggtt ccgccaggct     120
ccagggaagg ggctggagtg ggtaggtttc attagaagca agcttatgg tgggacaaca      180
gaatacgccg cgtctgtgaa aggcagattc accatctcaa gagatgattc caaaagcatc     240
gcctatctgc aaatgaacag cctgaaaacc gaggacacag ccgtgtatta ctgtactcca     300
cagctatggt tactacaaga tgcttttgat atctggggcc aagggacaat ggtcaccgtc     360
tcctca                                                              366

<210> SEQ ID NO 18
<211> LENGTH: 122
<212> TYPE: PRT
<213> ORGANISM: artificial sequence
<220> FEATURE:
<223> OTHER INFORMATION: synthetic peptide

<400> SEQUENCE: 18

```
Glu Leu Gln Leu Val Glu Ser Gly Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Pro Gln Leu Trp Leu Leu Gln Asp Ala Phe Asp Ile Trp
            100                 105                 110

Gly Gln Gly Thr Met Val Thr Val Ser Ser
        115                 120
```

<210> SEQ ID NO 19
<211> LENGTH: 15
<212> TYPE: DNA
<213> ORGANISM: artificial sequence
<220> FEATURE:
<223> OTHER INFORMATION: synthetic primer

<400> SEQUENCE: 19
gattatgcta tgagc                                                    15

<210> SEQ ID NO 20
<211> LENGTH: 5
<212> TYPE: PRT
<213> ORGANISM: artificial sequence
<220> FEATURE:
<223> OTHER INFORMATION: synthetic peptide

<400> SEQUENCE: 20

```
Asp Tyr Ala Met Ser
1               5
```

<210> SEQ ID NO 21
<211> LENGTH: 57
<212> TYPE: DNA
<213> ORGANISM: artificial sequence
<220> FEATURE:
<223> OTHER INFORMATION: synthetic primer

<400> SEQUENCE: 21
ttcattagaa gcaaagctta tggtgggaca acagaatacg ccgcgtctgt gaaaggc      57

<210> SEQ ID NO 22
<211> LENGTH: 19
<212> TYPE: PRT
<213> ORGANISM: artificial sequence
<220> FEATURE:
<223> OTHER INFORMATION: synthetic peptide

<400> SEQUENCE: 22

Phe Ile Arg Ser Lys Ala Tyr Gly Gly Thr Thr Glu Tyr Ala Ala Ser
1               5                   10                  15

Val Lys Gly

<210> SEQ ID NO 23
<211> LENGTH: 33
<212> TYPE: DNA
<213> ORGANISM: artificial sequence
<220> FEATURE:
<223> OTHER INFORMATION: synthetic primer

<400> SEQUENCE: 23
cagctatggt tactacaaga tgcttttgat atc                              33

<210> SEQ ID NO 24
<211> LENGTH: 11
<212> TYPE: PRT
<213> ORGANISM: artificial sequence
<220> FEATURE:
<223> OTHER INFORMATION: synthetic peptide

<400> SEQUENCE: 24

Gln Leu Trp Leu Leu Gln Asp Ala Phe Asp Ile
1               5                   10

<210> SEQ ID NO 25
<211> LENGTH: 321
<212> TYPE: DNA
<213> ORGANISM: artificial sequence
<220> FEATURE:
<223> OTHER INFORMATION: synthetic primer

<400> SEQUENCE: 25
gagctccaga tgacccagtc tccatcctcc ctgtctgcat ctgtaggaga tagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag tctgcaacct   240
gaagattttg caacttacta ctgtcaacag agttacagta cccctccgac gttcggccaa   300
gggaccaagc tggagatcaa a                                             321

<210> SEQ ID NO 26
<211> LENGTH: 107
<212> TYPE: PRT
<213> ORGANISM: artificial sequence
<220> FEATURE:
<223> OTHER INFORMATION: synthetic peptide

<400> SEQUENCE: 26

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Thr Phe Gly Gln Gly Thr Lys Leu Glu Ile Lys
            100                 105

<210> SEQ ID NO 27
<211> LENGTH: 33
<212> TYPE: DNA
<213> ORGANISM: artificial sequence
<220> FEATURE:
<223> OTHER INFORMATION: synthetic primer

<400> SEQUENCE: 27
cgggcgagtc agggcattag caattattta gcc                            33

<210> SEQ ID NO 28
<211> LENGTH: 11
<212> TYPE: PRT
<213> ORGANISM: artificial sequence
<220> FEATURE:
<223> OTHER INFORMATION: synthetic peptide

<400> SEQUENCE: 28

Arg Ala Ser Gln Gly Ile Ser Asn Tyr Leu Ala
1               5                   10

<210> SEQ ID NO 29
<211> LENGTH: 21
<212> TYPE: DNA
<213> ORGANISM: artificial sequence
<220> FEATURE:
<223> OTHER INFORMATION: synthetic primer

<400> SEQUENCE: 29
gctgcatcca ctttgcaatc a                                         21

<210> SEQ ID NO 30
<211> LENGTH: 7
<212> TYPE: PRT
<213> ORGANISM: artificial sequence
<220> FEATURE:
<223> OTHER INFORMATION: synthetic peptide

<400> SEQUENCE: 30

Ala Ala Ser Thr Leu Gln Ser
1               5

<210> SEQ ID NO 31
<211> LENGTH: 27
<212> TYPE: DNA
<213> ORGANISM: artificial sequence
<220> FEATURE:
<223> OTHER INFORMATION: synthetic primer

<400> SEQUENCE: 31
caacagagtt acagtacccc tccgacg                                   27

<210> SEQ ID NO 32
<211> LENGTH: 9
<212> TYPE: PRT
<213> ORGANISM: artificial sequence
<220> FEATURE:
<223> OTHER INFORMATION: synthetic peptide

<400> SEQUENCE: 32

Gln Gln Ser Tyr Ser Thr Pro Pro Thr

<210> SEQ ID NO 33
<211> LENGTH: 360
<212> TYPE: DNA
<213> ORGANISM: artificial sequence
<220> FEATURE:
<223> OTHER INFORMATION: synthetic primer

<400> SEQUENCE: 33

```
gagctgcagc tggtcgagtc tggcccagga ctggtgaagc cttcggggac cctgtccctc    60
acctgcgctg tctctggtgg ctccatcagc agtagaaact ggtggagttg ggtccgccag   120
cccccaggga aggggctgga gtggattggt gatatctatc atagtgggag caccaactac   180
aacccgtccc tcaagagtcg agtcaccata tcagtagaca gtccaagaac cagttctccc   240 tgaagctga gctctgtgac cgccgcggac acggccgtgt attactgtgc gagtgggtat   300
accagctgtc gtgatgcttt tgatatctgg ggccaaggga caatggtcac cgtctcctca   360
```

<210> SEQ ID NO 34
<211> LENGTH: 120
<212> TYPE: PRT
<213> ORGANISM: artificial sequence
<220> FEATURE:
<223> OTHER INFORMATION: synthetic peptide

<400> SEQUENCE: 34

Glu Leu Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Arg
            20                  25                  30

Asn Trp Trp Ser Trp Val Arg Gln Pro Pro Gly Lys Gly Leu Glu Trp
        35                  40                  45

Ile Gly Asp Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Gly Tyr Thr Ser Cys Arg Asp Ala Phe Asp Ile Trp Gly Gln
            100                 105                 110

Gly Thr Met Val Thr Val Ser Ser
        115                 120

<210> SEQ ID NO 35
<211> LENGTH: 18
<212> TYPE: DNA
<213> ORGANISM: artificial sequence
<220> FEATURE:
<223> OTHER INFORMATION: synthetic primerc

<400> SEQUENCE: 35

```
agtagaaact ggtggagt                                                   18
```

<210> SEQ ID NO 36
<211> LENGTH: 6
<212> TYPE: PRT
<213> ORGANISM: artificial sequence
<220> FEATURE:
<223> OTHER INFORMATION: synthetic peptide

<400> SEQUENCE: 36

-continued

```
<210> SEQ ID NO 37
<211> LENGTH: 48
<212> TYPE: DNA
<213> ORGANISM: artificial sequence
<220> FEATURE:
<223> OTHER INFORMATION: synthetic primer

<400> SEQUENCE: 37
gatatctatc atagtgggag caccaactac aacccgtccc tcaagagt            48

<210> SEQ ID NO 38
<211> LENGTH: 16
<212> TYPE: PRT
<213> ORGANISM: artificial sequence
<220> FEATURE:
<223> OTHER INFORMATION: synthetic peptide

<400> SEQUENCE: 38

Asp Ile Tyr His Ser Gly Ser Thr Asn Tyr Asn Pro Ser Leu Lys Ser
1               5                   10                  15

<210> SEQ ID NO 39
<211> LENGTH: 33
<212> TYPE: DNA
<213> ORGANISM: artificial sequence
<220> FEATURE:
<223> OTHER INFORMATION: synthetic primer

<400> SEQUENCE: 39
gggtatacca gctgtcgtga tgcttttgat atc                             33

<210> SEQ ID NO 40
<211> LENGTH: 11
<212> TYPE: PRT
<213> ORGANISM: artificial sequence
<220> FEATURE:
<223> OTHER INFORMATION: synthetic peptide

<400> SEQUENCE: 40

Gly Tyr Thr Ser Cys Arg Asp Ala Phe Asp Ile
1               5                   10

<210> SEQ ID NO 41
<211> LENGTH: 321
<212> TYPE: DNA
<213> ORGANISM: artificial sequence
<220> FEATURE:
<223> OTHER INFORMATION: synthetic primer

<400> SEQUENCE: 41
gagctcgtga tgactcagtc tccatcctcc ctgtctgcat ctgtaggaga cagagtcacc    60
atcacttgcc gggcgagtca ggcattggc aattatttag cctggtatca gcagaaacca   120
gggcagcctc ctaagatgct catttactgg gcatcaatcc gggaatccgg ggtccctgac   180
cgattcagtg gcagcgggtc tgggacagac ttcactctca ccatcagcag cctgcaggct   240
gaagatgtgg cagtttacta ctgtcagcaa tattatagta atcctcagac gttcggccaa   300
gggaccaagg tggaaatcaa a                                             321

<210> SEQ ID NO 42
<211> LENGTH: 107
```

<212> TYPE: PRT
<213> ORGANISM: artificial sequence
<220> FEATURE:
<223> OTHER INFORMATION: synthetic peptide

<400> SEQUENCE: 42

Glu Leu Val Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Tyr
            20                  25                  30

Leu Ala Trp Tyr Gln Gln Lys Pro Gly Gln Pro Pro Lys Met Leu Ile
        35                  40                  45

Tyr Trp Ala Ser Ile Arg Glu Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Tyr Tyr Ser Asn Pro Gln
                85                  90                  95

Thr Phe Gly Gln Gly Thr Lys Val Glu Ile Lys
            100                 105

<210> SEQ ID NO 43
<211> LENGTH: 33
<212> TYPE: DNA
<213> ORGANISM: artificial sequence
<220> FEATURE:
<223> OTHER INFORMATION: synthetic primer

<400> SEQUENCE: 43
cgggcgagtc agggcattgg caattattta gcc                                33

<210> SEQ ID NO 44
<211> LENGTH: 11
<212> TYPE: PRT
<213> ORGANISM: artificial sequence
<220> FEATURE:
<223> OTHER INFORMATION: synthetic peptide

<400> SEQUENCE: 44

Arg Ala Ser Gln Gly Ile Gly Asn Tyr Leu Ala
1               5                   10

<210> SEQ ID NO 45
<211> LENGTH: 21
<212> TYPE: DNA
<213> ORGANISM: artificial sequence
<220> FEATURE:
<223> OTHER INFORMATION: synthetic primer

<400> SEQUENCE: 45
tgggcatcaa tccgggaatc c                                             21

<210> SEQ ID NO 46
<211> LENGTH: 7
<212> TYPE: PRT
<213> ORGANISM: artificial sequence
<220> FEATURE:
<223> OTHER INFORMATION: synthetic peptide

<400> SEQUENCE: 46

Trp Ala Ser Ile Arg Glu Ser
1               5

<210> SEQ ID NO 47
<211> LENGTH: 27
<212> TYPE: DNA
<213> ORGANISM: artificial sequence
<220> FEATURE:
<223> OTHER INFORMATION: synthetic primer

<400> SEQUENCE: 47
cagcaatatt atagtaatcc tcagacg                                27

<210> SEQ ID NO 48
<211> LENGTH: 9
<212> TYPE: PRT
<213> ORGANISM: artificial sequence
<220> FEATURE:
<223> OTHER INFORMATION: synthetic peptide

<400> SEQUENCE: 48

Gln Gln Tyr Tyr Ser Asn Pro Gln Thr
1               5

<210> SEQ ID NO 49
<211> LENGTH: 378
<212> TYPE: DNA
<213> ORGANISM: artificial sequence
<220> FEATURE:
<223> OTHER INFORMATION: synthetic primer

<400> SEQUENCE: 49
gagctgcagc tggtcgagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattgggaa atcaatcata gtggaagcac caactacaac    180
ccgtccctca agagtcgagt caccatatca gtagacacgt ccaagaacca gttctccctg   240
aagctgagct ctgtgaccgc cgcggacacg gctgtgtatt actgtgcgag aggccgaggc   300 cgattttttgg ggtggttatt aggggggctcc aactggttcg acccctgggg ccagggaacc   360
ctggtcaccg tctcctca                                                378

<210> SEQ ID NO 50
<211> LENGTH: 126
<212> TYPE: PRT
<213> ORGANISM: artificial sequence
<220> FEATURE:
<223> OTHER INFORMATION: synthetic peptide

<400> SEQUENCE: 50

Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Arg Phe Leu Gly Trp Leu Leu Gly Gly Ser Asn Trp
            100                 105                 110

Phe Asp Pro Trp Gly Gln Gly Thr Leu Val Thr Val Ser Ser
            115                 120                 125

<210> SEQ ID NO 51
<211> LENGTH: 15
<212> TYPE: DNA
<213> ORGANISM: artificial sequence
<220> FEATURE:
<223> OTHER INFORMATION: synthetic primer

<400> SEQUENCE: 51
ggttactact ggagc                                                    15

<210> SEQ ID NO 52
<211> LENGTH: 5
<212> TYPE: PRT
<213> ORGANISM: artificial sequence
<220> FEATURE:
<223> OTHER INFORMATION: synthetic peptide

<400> SEQUENCE: 52

Gly Tyr Tyr Trp Ser
1               5

<210> SEQ ID NO 53
<211> LENGTH: 48
<212> TYPE: DNA
<213> ORGANISM: artificial sequence
<220> FEATURE:
<223> OTHER INFORMATION: synthetic primer

<400> SEQUENCE: 53
gaaatcaatc atagtggaag caccaactac aacccgtccc tcaagagt                48

<210> SEQ ID NO 54
<211> LENGTH: 16
<212> TYPE: PRT
<213> ORGANISM: artificial sequence
<220> FEATURE:
<223> OTHER INFORMATION: synthetic peptide

<400> SEQUENCE: 54

Glu Ile Asn His Ser Gly Ser Thr Asn Tyr Asn Pro Ser Leu Lys Ser
1               5                   10                  15

<210> SEQ ID NO 55
<211> LENGTH: 54
<212> TYPE: DNA
<213> ORGANISM: artificial sequence
<220> FEATURE:
<223> OTHER INFORMATION: synthetic primer

<400> SEQUENCE: 55
ggccgaggcc gatttttggg gtggttatta gggggctcca actggttcga cccc         54

<210> SEQ ID NO 56
<211> LENGTH: 18
<212> TYPE: PRT
<213> ORGANISM: artificial sequence
<220> FEATURE:
<223> OTHER INFORMATION: synthetic peptide

<400> SEQUENCE: 56

Gly Arg Gly Arg Phe Leu Gly Trp Leu Leu Gly Gly Ser Asn Trp Phe
1               5                   10                  15

Asp Pro

<210> SEQ ID NO 57
<211> LENGTH: 321
<212> TYPE: DNA
<213> ORGANISM: artificial sequence
<220> FEATURE:
<223> OTHER INFORMATION: synthetic primer

<400> SEQUENCE: 57

```
gagctcgtga tgacccagtc tccatcctcc ctgtctgcat ctgtaggaga cagagtcacc    60
atcacttgcc gggcgagtca gggcattagc aattatttaa attggtatca gcagaaacca   120
gggaaagccc ctaagctcct gatctacgat gcatccaatt tggaaacagg ggtcccatca   180
aggttcagtg gcagtggatc tgggacagat ttcactctca ccatcagcag tctgcaacct   240
gaagattttg caacttacta ctgtcaacag agttacagta ccccgtacac ttttggccag   300
gggaccaaag tggatatcaa a                                             321
```

<210> SEQ ID NO 58
<211> LENGTH: 107
<212> TYPE: PRT
<213> ORGANISM: artificial sequence
<220> FEATURE:
<223> OTHER INFORMATION: synthetic peptide

<400> SEQUENCE: 58

```
Glu Leu Val Met Thr Gln Ser Pro Ser Ser Leu Ser Ala Ser Val Gly
1               5                  10                  15

Asp Arg Val Thr Ile Thr Cys Arg Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Asp Ile Lys
            100                 105
```

<210> SEQ ID NO 59
<211> LENGTH: 33
<212> TYPE: DNA
<213> ORGANISM: artificial sequence
<220> FEATURE:
<223> OTHER INFORMATION: synthetic primer

<400> SEQUENCE: 59

```
cgggcgagtc agggcattag caattattta aat                                33
```

<210> SEQ ID NO 60
<211> LENGTH: 11
<212> TYPE: PRT
<213> ORGANISM: artificial sequence
<220> FEATURE:
<223> OTHER INFORMATION: synthetic peptide

<400> SEQUENCE: 60

```
Arg Ala Ser Gln Gly Ile Ser Asn Tyr Leu Asn
1               5                  10
```

<210> SEQ ID NO 61
<211> LENGTH: 21
<212> TYPE: DNA
<213> ORGANISM: artificial sequence
<220> FEATURE:
<223> OTHER INFORMATION: synthetic primer

<400> SEQUENCE: 61
gatgcatcca atttggaaac a                                         21

<210> SEQ ID NO 62
<211> LENGTH: 7
<212> TYPE: PRT
<213> ORGANISM: artificial sequence
<220> FEATURE:
<223> OTHER INFORMATION: synthetic peptide

<400> SEQUENCE: 62

Asp Ala Ser Asn Leu Glu Thr
1               5

<210> SEQ ID NO 63
<211> LENGTH: 27
<212> TYPE: DNA
<213> ORGANISM: artificial sequence
<220> FEATURE:
<223> OTHER INFORMATION: synthetic primer

<400> SEQUENCE: 63
caacagagtt acagtacccc gtacact                                   27

<210> SEQ ID NO 64
<211> LENGTH: 9
<212> TYPE: PRT
<213> ORGANISM: artificial sequence
<220> FEATURE:
<223> OTHER INFORMATION: synthetic peptide

<400> SEQUENCE: 64

Gln Gln Ser Tyr Ser Thr Pro Tyr Thr
1               5

<210> SEQ ID NO 65
<211> LENGTH: 357
<212> TYPE: DNA
<213> ORGANISM: artificial sequence
<220> FEATURE:
<223> OTHER INFORMATION: synthetic primer

<400> SEQUENCE: 65
gagctgcagc tggtcgagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtgcgag aggccctgac   300
cgaatggggc atggttttga tatctggggc caagggacaa tggtcaccgt ctcctca      357

<210> SEQ ID NO 66
<211> LENGTH: 119
<212> TYPE: PRT
<213> ORGANISM: artificial sequence
<220> FEATURE:
<223> OTHER INFORMATION: synthetic peptide

<400> SEQUENCE: 66

Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Gly Pro Asp Arg Met Gly His Gly Phe Asp Ile Trp Gly Gln Gly
            100                 105                 110

Thr Met Val Thr Val Ser Ser
        115

<210> SEQ ID NO 67
<211> LENGTH: 15
<212> TYPE: DNA
<213> ORGANISM: artificial sequence
<220> FEATURE:
<223> OTHER INFORMATION: synthetic primer

<400> SEQUENCE: 67
ggttactact ggagc                                                         15

<210> SEQ ID NO 68
<211> LENGTH: 5
<212> TYPE: PRT
<213> ORGANISM: artificial sequence
<220> FEATURE:
<223> OTHER INFORMATION: synthetic peptide

<400> SEQUENCE: 68

Gly Tyr Tyr Trp Ser
1               5

<210> SEQ ID NO 69
<211> LENGTH: 48
<212> TYPE: DNA
<213> ORGANISM: artificial sequence
<220> FEATURE:
<223> OTHER INFORMATION: synthetic primer

<400> SEQUENCE: 69
gaaatcaatc atagtggaag caccaactac aacccgtccc tcaagagt                     48

<210> SEQ ID NO 70
<211> LENGTH: 16
<212> TYPE: PRT
<213> ORGANISM: artificial sequence
<220> FEATURE:
<223> OTHER INFORMATION: synthetic peptide

<400> SEQUENCE: 70

Glu Ile Asn His Ser Gly Ser Thr Asn Tyr Asn Pro Ser Leu Lys Ser
1               5                   10                  15

<210> SEQ ID NO 71

```
<211> LENGTH: 33
<212> TYPE: DNA
<213> ORGANISM: artificial sequence
<220> FEATURE:
<223> OTHER INFORMATION: synthetic primer

<400> SEQUENCE: 71
ggccctgacc gaatggggca tggttttgat atc                                   33

<210> SEQ ID NO 72
<211> LENGTH: 11
<212> TYPE: PRT
<213> ORGANISM: artificial sequence
<220> FEATURE:
<223> OTHER INFORMATION: synthetic peptide

<400> SEQUENCE: 72

Gly Pro Asp Arg Met Gly His Gly Phe Asp Ile
1               5                   10

<210> SEQ ID NO 73
<211> LENGTH: 321
<212> TYPE: DNA
<213> ORGANISM: artificial sequence
<220> FEATURE:
<223> OTHER INFORMATION: synthetic primer

<400> SEQUENCE: 73
gagctccaga tgacccagtc tccatcctcc ctgtctgcat ctgtaggaga cagagtcacc      60
atcacttgcc gggcaagtca gagcattagc agctatttaa attggtatca gcagaaatca    120
gggaaagccc ctaagctcct gatctatgct gcatccagtt tgcaaagtgg ggtcccatca    180
aggttcagtg gcagtggatc tgggacagat ttcactctca ccatcagtag tctgcaacct    240
gaagattttg caacttatta ctgtcaacag agttacagta gcccgtggac attcggccaa    300
gggaccaagg tggagatcaa a                                              321

<210> SEQ ID NO 74
<211> LENGTH: 107
<212> TYPE: PRT
<213> ORGANISM: artificial sequence
<220> FEATURE:
<223> OTHER INFORMATION: synthetic peptide

<400> SEQUENCE: 74

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Ser Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Trp
                85                  90                  95

Thr Phe Gly Gln Gly Thr Lys Val Glu Ile Lys
            100                 105

<210> SEQ ID NO 75
<211> LENGTH: 33
```

<212> TYPE: DNA
<213> ORGANISM: artificial sequence
<220> FEATURE:
<223> OTHER INFORMATION: synthetic primer

<400> SEQUENCE: 75
cgggcaagtc agagcattag cagctattta aat        33

<210> SEQ ID NO 76
<211> LENGTH: 11
<212> TYPE: PRT
<213> ORGANISM: artificial sequence
<220> FEATURE:
<223> OTHER INFORMATION: synthetic peptide

<400> SEQUENCE: 76

Arg Ala Ser Gln Ser Ile Ser Ser Tyr Leu Asn
1               5                   10

<210> SEQ ID NO 77
<211> LENGTH: 21
<212> TYPE: DNA
<213> ORGANISM: artificial sequence
<220> FEATURE:
<223> OTHER INFORMATION: synthetic primer

<400> SEQUENCE: 77
gctgcatcca gtttgcaaag t        21

<210> SEQ ID NO 78
<211> LENGTH: 7
<212> TYPE: PRT
<213> ORGANISM: artificial sequence
<220> FEATURE:
<223> OTHER INFORMATION: synthetic peptide

<400> SEQUENCE: 78

Ala Ala Ser Ser Leu Gln Ser
1               5

<210> SEQ ID NO 79
<211> LENGTH: 21
<212> TYPE: DNA
<213> ORGANISM: artificial sequence
<220> FEATURE:
<223> OTHER INFORMATION: synthetic primer

<400> SEQUENCE: 79
caacagagtt acagtagccc g        21

<210> SEQ ID NO 80
<211> LENGTH: 7
<212> TYPE: PRT
<213> ORGANISM: artificial sequence
<220> FEATURE:
<223> OTHER INFORMATION: synthetic peptide

<400> SEQUENCE: 80

Gln Gln Ser Tyr Ser Ser Pro
1               5

<210> SEQ ID NO 81
<211> LENGTH: 381
<212> TYPE: DNA
<213> ORGANISM: artificial sequence
<220> FEATURE:
<223> OTHER INFORMATION: synthetic primer

<400> SEQUENCE: 81

```
gagctgcagc tggtcgagtc tggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc caagtggtat   180
aatgattatg cagtatctgt gaaaagtcga ataaccatca acccagacac atccaagaac   240
cagttctccc tgcagctgaa ctctgtgact cccgaggaca cggctgtgta ttactgtgca   300
agagatcgtc gacgtatagc agctcgtcaa tactacggta tggacgtctg gggccaaggg   360
accacggtca ccgtctcctc a                                              381
```

<210> SEQ ID NO 82
<211> LENGTH: 127
<212> TYPE: PRT
<213> ORGANISM: artificial sequence
<220> FEATURE:
<223> OTHER INFORMATION: synthetic peptide

<400> SEQUENCE: 82

```
Glu Leu Gln Leu Val Glu Ser Gly Pro Gly Leu Val Lys Pro Ser Gln
1               5                   10                  15
Thr Leu Ser Leu Thr Cys Ala Ile Ser Gly Asp Ser Val Ser Ser Asn
            20                  25                  30
Ser Ala Ala Trp Asn Trp Ile Arg Gln Ser Pro Ser Arg Gly Leu Glu
        35                  40                  45
Trp Leu Gly Arg Thr Tyr Tyr Arg Ser Lys Trp Tyr Asn Asp Tyr Ala
    50                  55                  60
Val Ser Val Lys Ser Arg Ile Thr Ile Asn Pro Asp Thr Ser Lys Asn
65                  70                  75                  80
Gln Phe Ser Leu Gln Leu Asn Ser Val Thr Pro Glu Asp Thr Ala Val
                85                  90                  95
Tyr Tyr Cys Ala Arg Asp Arg Arg Ile Ala Ala Arg Gln Tyr Tyr
            100                 105                 110
Gly Met Asp Val Trp Gly Gln Gly Thr Thr Val Thr Val Ser Ser
        115                 120                 125
```

<210> SEQ ID NO 83
<211> LENGTH: 21
<212> TYPE: DNA
<213> ORGANISM: artificial sequence
<220> FEATURE:
<223> OTHER INFORMATION: synthetic primer

<400> SEQUENCE: 83

```
agcaacagtg ctgcttggaa c                                              21
```

<210> SEQ ID NO 84
<211> LENGTH: 7
<212> TYPE: PRT
<213> ORGANISM: artificial sequence
<220> FEATURE:
<223> OTHER INFORMATION: synthetic peptide

<400> SEQUENCE: 84

```
Ser Asn Ser Ala Ala Trp Asn
1               5
```

<210> SEQ ID NO 85
<211> LENGTH: 54

```
<212> TYPE: DNA
<213> ORGANISM: artificial sequence
<220> FEATURE:
<223> OTHER INFORMATION: synthetic primer

<400> SEQUENCE: 85
aggacatact acaggtccaa gtggtataat gattatgcag tatctgtgaa aagt         54

<210> SEQ ID NO 86
<211> LENGTH: 18
<212> TYPE: PRT
<213> ORGANISM: artificial sequence
<220> FEATURE:
<223> OTHER INFORMATION: synthetic peptide

<400> SEQUENCE: 86

Arg Thr Tyr Tyr Arg Ser Lys Trp Tyr Asn Asp Tyr Ala Val Ser Val
1               5                   10                  15

Lys Ser

<210> SEQ ID NO 87
<211> LENGTH: 45
<212> TYPE: DNA
<213> ORGANISM: artificial sequence
<220> FEATURE:
<223> OTHER INFORMATION: synthetic primer

<400> SEQUENCE: 87
gatcgtcgac gtatagcagc tcgtcaatac tacggtatgg acgtc                   45

<210> SEQ ID NO 88
<211> LENGTH: 15
<212> TYPE: PRT
<213> ORGANISM: artificial sequence
<220> FEATURE:
<223> OTHER INFORMATION: synthetic peptide

<400> SEQUENCE: 88

Asp Arg Arg Arg Ile Ala Ala Arg Gln Tyr Tyr Gly Met Asp Val
1               5                   10                  15

<210> SEQ ID NO 89
<211> LENGTH: 324
<212> TYPE: DNA
<213> ORGANISM: artificial sequence
<220> FEATURE:
<223> OTHER INFORMATION: synthetic primer

<400> SEQUENCE: 89
gagctcgtgt tgacacagtc tccaggcacc ctgtctttgt ctccagggga aagagccacc    60
ctctcctgca gggcaagtca gagtgttagc agcaactact tagcctggta ccagcagaaa   120
cctggccagg ctcccaggct cctcatctat ggtgcatcca gcagggccac tggcatccca   180
gacaggttca gtggcagcgg gtctgggaca gatttcactc tcaccatcag cagcctgcag   240
cctgaagatg ttgcaactta ttactgtcaa aagtataaca gtgcccctct cactttcggc   300
ggagggacca aggtggaaat caaa                                          324

<210> SEQ ID NO 90
<211> LENGTH: 108
<212> TYPE: PRT
<213> ORGANISM: artificial sequence
<220> FEATURE:
<223> OTHER INFORMATION: synthetic peptide
```

<400> SEQUENCE: 90

Glu Leu Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Lys Tyr Asn Ser Ala Pro
                85                  90                  95

Leu Thr Phe Gly Gly Gly Thr Lys Val Glu Ile Lys
            100                 105

<210> SEQ ID NO 91
<211> LENGTH: 36
<212> TYPE: DNA
<213> ORGANISM: artificial sequence
<220> FEATURE:
<223> OTHER INFORMATION: synthetic primer

<400> SEQUENCE: 91
agggcaagtc agagtgttag cagcaactac ttagcc                     36

<210> SEQ ID NO 92
<211> LENGTH: 12
<212> TYPE: PRT
<213> ORGANISM: artificial sequence
<220> FEATURE:
<223> OTHER INFORMATION: synthetic peptide

<400> SEQUENCE: 92

Arg Ala Ser Gln Ser Val Ser Ser Asn Tyr Leu Ala
1               5                   10

<210> SEQ ID NO 93
<211> LENGTH: 21
<212> TYPE: DNA
<213> ORGANISM: artificial sequence
<220> FEATURE:
<223> OTHER INFORMATION: synthetic primer

<400> SEQUENCE: 93
ggtgcatcca gcagggccac t                                     21

<210> SEQ ID NO 94
<211> LENGTH: 7
<212> TYPE: PRT
<213> ORGANISM: artificial sequence
<220> FEATURE:
<223> OTHER INFORMATION: synthetic peptide

<400> SEQUENCE: 94

Gly Ala Ser Ser Arg Ala Thr
1               5

<210> SEQ ID NO 95
<211> LENGTH: 21
<212> TYPE: DNA
<213> ORGANISM: artificial sequence
<220> FEATURE:

<223> OTHER INFORMATION: synthetic primer

<400> SEQUENCE: 95
caaaagtata acagtgcccc t                                                    21

<210> SEQ ID NO 96
<211> LENGTH: 7
<212> TYPE: PRT
<213> ORGANISM: artificial sequence
<220> FEATURE:
<223> OTHER INFORMATION: synthetic peptide

<400> SEQUENCE: 96

Gln Lys Tyr Asn Ser Ala Pro
1               5

<210> SEQ ID NO 97
<211> LENGTH: 363
<212> TYPE: DNA
<213> ORGANISM: artificial sequence
<220> FEATURE:
<223> OTHER INFORMATION: synthetic primer

<400> SEQUENCE: 97
gagctgcagc tggtcgagtc tgggggaggc ttggtacagc ctgggggtc cctgagactc            60 tcctgtgcag cctctggatt cacctttagc agctatgcca tgggctgggt ccgccaggct          120
ccagggaagg ggctggagtg ggtctcagct gttagtggta gtggtggtag cacatactac          180
gcagactccg tgaagggccg gttcaccatc tccagagaca attccaagaa cacgctgtat          240
ctgcaaatga acagcctgag agccgaggac acggccgtat attactgtgc gaaagccaaa          300
ttcctgggcc actactacgg tatggacgtc tggggccaag ggaccacggt caccgtctcc          360
tca                                                                       363

<210> SEQ ID NO 98
<211> LENGTH: 121
<212> TYPE: PRT
<213> ORGANISM: artificial sequence
<220> FEATURE:
<223> OTHER INFORMATION: synthetic peptide

<400> SEQUENCE: 98

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Lys Phe Leu Gly His Tyr Tyr Gly Met Asp Val Trp Gly
            100                 105                 110

Gln Gly Thr Thr Val Thr Val Ser Ser
        115                 120

<210> SEQ ID NO 99

```
<211> LENGTH: 15
<212> TYPE: DNA
<213> ORGANISM: artificial sequence
<220> FEATURE:
<223> OTHER INFORMATION: synthetic primer

<400> SEQUENCE: 99
agctatgcca tgggc                                                           15

<210> SEQ ID NO 100
<211> LENGTH: 5
<212> TYPE: PRT
<213> ORGANISM: artificial sequence
<220> FEATURE:
<223> OTHER INFORMATION: synthetic peptide

<400> SEQUENCE: 100

Ser Tyr Ala Met Gly
1               5

<210> SEQ ID NO 101
<211> LENGTH: 51
<212> TYPE: DNA
<213> ORGANISM: artificial sequence
<220> FEATURE:
<223> OTHER INFORMATION: synthetic primer

<400> SEQUENCE: 101
gctgttagtg gtagtggtgg tagcacatac tacgcagact ccgtgaaggg c                   51

<210> SEQ ID NO 102
<211> LENGTH: 17
<212> TYPE: PRT
<213> ORGANISM: artificial sequence
<220> FEATURE:
<223> OTHER INFORMATION: synthetic peptide

<400> SEQUENCE: 102

Ala Val Ser Gly Ser Gly Gly Ser Thr Tyr Tyr Ala Asp Ser Val Lys
1               5                   10                  15

Gly

<210> SEQ ID NO 103
<211> LENGTH: 36
<212> TYPE: DNA
<213> ORGANISM: artificial sequence
<220> FEATURE:
<223> OTHER INFORMATION: synthetic primer

<400> SEQUENCE: 103
gccaaattcc tgggccacta ctacggtatg gacgtc                                    36

<210> SEQ ID NO 104
<211> LENGTH: 12
<212> TYPE: PRT
<213> ORGANISM: artificial sequence
<220> FEATURE:
<223> OTHER INFORMATION: synthetic peptide

<400> SEQUENCE: 104

Ala Lys Phe Leu Gly His Tyr Tyr Gly Met Asp Val
1               5                   10

<210> SEQ ID NO 105
<211> LENGTH: 321
<212> TYPE: DNA
```

-continued

```
<213> ORGANISM: artificial sequence
<220> FEATURE:
<223> OTHER INFORMATION: synthetic primer

<400> SEQUENCE: 105
gagctccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg agtcccatca   180
aggttcagcg gcagtggatc tgggacagag ttcactctca caatcagcag cctgcagcct   240
gaagattttg caacttatta ctgtcttcag cataatgctt acccgtacac tttcggccag   300
gggaccaagg tggaaatcaa a                                             321

<210> SEQ ID NO 106
<211> LENGTH: 107
<212> TYPE: PRT
<213> ORGANISM: artificial sequence
<220> FEATURE:
<223> OTHER INFORMATION: synthetic peptide

<400> SEQUENCE: 106

Glu Leu Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ala Tyr Pro Tyr
                85                  90                  95

Thr Phe Gly Gln Gly Thr Lys Val Glu Ile Lys
            100                 105

<210> SEQ ID NO 107
<211> LENGTH: 33
<212> TYPE: DNA
<213> ORGANISM: artificial sequence
<220> FEATURE:
<223> OTHER INFORMATION: synthetic primer

<400> SEQUENCE: 107
cgggcaagtc agagcattag cagctattta aat                                 33

<210> SEQ ID NO 108
<211> LENGTH: 11
<212> TYPE: PRT
<213> ORGANISM: artificial sequence
<220> FEATURE:
<223> OTHER INFORMATION: synthetic peptide

<400> SEQUENCE: 108

Arg Ala Ser Gln Ser Ile Ser Ser Tyr Leu Asn
1               5                  10

<210> SEQ ID NO 109
<211> LENGTH: 21
<212> TYPE: DNA
<213> ORGANISM: artificial sequence
```

```
<220> FEATURE:
<223> OTHER INFORMATION: synthetic primer

<400> SEQUENCE: 109
gctgcatcca gtttgcaaag t                                             21

<210> SEQ ID NO 110
<211> LENGTH: 7
<212> TYPE: PRT
<213> ORGANISM: artificial sequence
<220> FEATURE:
<223> OTHER INFORMATION: synthetic peptide

<400> SEQUENCE: 110

Ala Ala Ser Ser Leu Gln Ser
1               5

<210> SEQ ID NO 111
<211> LENGTH: 27
<212> TYPE: DNA
<213> ORGANISM: artificial sequence
<220> FEATURE:
<223> OTHER INFORMATION: synthetic primer

<400> SEQUENCE: 111
cttcagcata atgcttaccc gtacact                                       27

<210> SEQ ID NO 112
<211> LENGTH: 9
<212> TYPE: PRT
<213> ORGANISM: artificial sequence
<220> FEATURE:
<223> OTHER INFORMATION: synthetic peptide

<400> SEQUENCE: 112

Leu Gln His Asn Ala Tyr Pro Tyr Thr
1               5

<210> SEQ ID NO 113
<211> LENGTH: 369
<212> TYPE: DNA
<213> ORGANISM: artificial sequence
<220> FEATURE:
<223> OTHER INFORMATION: synthetic primer

<400> SEQUENCE: 113
gagctgcagc tggtcgagtc tggtcctgtg ctggtgaaac ccacagatac cctcacgctg    60
acttgcaccg tctctgggtt ctcactcaat aatcctagaa tgggtgtgag ctggatccgt   120
cagcccccag ggaagaccct ggagtggctt gcacacattt ttccgagtga cgcaaaagcc   180
cacagtgcat ctctgaagag caggctcacc atctccaagg acacctccaa aagccaggtg   240
gtccctacca tgaccaacat ggaccctgtg acacagcca catattactg tgcacggata    300
ttgggggaat actatccccc agcctggttc gaccctggg gccagggaac cctggtcacc   360
gtctcctca                                                           369

<210> SEQ ID NO 114
<211> LENGTH: 123
<212> TYPE: PRT
<213> ORGANISM: artificial sequence
<220> FEATURE:
<223> OTHER INFORMATION: synthetic peptide

<400> SEQUENCE: 114
```

```
Glu Leu Gln Leu Val Glu Ser Gly Pro Val Leu Val Lys Pro Thr Asp
1               5                   10                  15

Thr Leu Thr Leu Thr Cys Thr Val Ser Gly Phe Ser Leu Asn Asn Pro
            20                  25                  30

Arg Met Gly Val Ser Trp Ile Arg Gln Pro Pro Gly Lys Thr Leu Glu
        35                  40                  45

Trp Leu Ala His Ile Phe Pro Ser Asp Ala Lys Ala His Ser Ala Ser
    50                  55                  60

Leu Lys Ser Arg Leu Thr Ile Ser Lys Asp Thr Ser Lys Ser Gln Val
65                  70                  75                  80

Val Pro Thr Met Thr Asn Met Asp Pro Val Thr Ala Thr Tyr Tyr
                85                  90                  95

Cys Ala Arg Ile Leu Gly Glu Tyr Tyr Pro Pro Ala Trp Phe Asp Pro
            100                 105                 110

Trp Gly Gln Gly Thr Leu Val Thr Val Ser Ser
            115                 120
```

<210> SEQ ID NO 115
<211> LENGTH: 21
<212> TYPE: DNA
<213> ORGANISM: artificial sequence
<220> FEATURE:
<223> OTHER INFORMATION: synthetic primer

<400> SEQUENCE: 115
aatcctagaa tgggtgtgag c                                              21

<210> SEQ ID NO 116
<211> LENGTH: 7
<212> TYPE: PRT
<213> ORGANISM: artificial sequence
<220> FEATURE:
<223> OTHER INFORMATION: synthetic peptide

<400> SEQUENCE: 116

```
Asn Pro Arg Met Gly Val Ser
1               5
```

<210> SEQ ID NO 117
<211> LENGTH: 48
<212> TYPE: DNA
<213> ORGANISM: artificial sequence
<220> FEATURE:
<223> OTHER INFORMATION: synthetic primer

<400> SEQUENCE: 117 cacattttc cgagtgacgc aaaagcccac agtgcatctc tgaagagc                  48

<210> SEQ ID NO 118
<211> LENGTH: 16
<212> TYPE: PRT
<213> ORGANISM: artificial sequence
<220> FEATURE:
<223> OTHER INFORMATION: synthetic peptide

<400> SEQUENCE: 118

```
His Ile Phe Pro Ser Asp Ala Lys Ala His Ser Ala Ser Leu Lys Ser
1               5                   10                  15
```

<210> SEQ ID NO 119
<211> LENGTH: 39
<212> TYPE: DNA
<213> ORGANISM: artificial sequence
<220> FEATURE:
<223> OTHER INFORMATION: synthetic primer

<400> SEQUENCE: 119
atattggggg aatactatcc cccagcctgg ttcgacccc                                39

<210> SEQ ID NO 120
<211> LENGTH: 13
<212> TYPE: PRT
<213> ORGANISM: artificial sequence
<220> FEATURE:
<223> OTHER INFORMATION: synthetic peptide

<400> SEQUENCE: 120

Ile Leu Gly Glu Tyr Tyr Pro Pro Ala Trp Phe Asp Pro
1               5                   10

<210> SEQ ID NO 121
<211> LENGTH: 339
<212> TYPE: DNA
<213> ORGANISM: artificial sequence
<220> FEATURE:
<223> OTHER INFORMATION: synthetic primer

<400> SEQUENCE: 121
gagctcgtga tgacacagtc tccagactcc ctggctgtgt ctctgggcga gagggccacc       60
atcaactgca gtccagcca gagtgtttta tacagctcca acaataagaa ctacttagct      120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agacgtggca gtttattact gtcagcaata tttgaaaatc     300
ccttatactt ttggccaggg gaccaaggtg gagatcaaa                            339

<210> SEQ ID NO 122
<211> LENGTH: 113
<212> TYPE: PRT
<213> ORGANISM: artificial sequence
<220> FEATURE:
<223> OTHER INFORMATION: synthetic peptide

<400> SEQUENCE: 122

Glu Leu Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Leu Lys Ile Pro Tyr Thr Phe Gly Gln Gly Thr Lys Val Glu Ile
            100                 105                 110

Lys

<210> SEQ ID NO 123
<211> LENGTH: 51
<212> TYPE: DNA

```
<213> ORGANISM: artificial sequence
<220> FEATURE:
<223> OTHER INFORMATION: synthetic primer

<400> SEQUENCE: 123
aagtccagcc agagtgtttt atacagctcc aacaataaga actacttagc t         51

<210> SEQ ID NO 124
<211> LENGTH: 17
<212> TYPE: PRT
<213> ORGANISM: artificial sequence
<220> FEATURE:
<223> OTHER INFORMATION: synthetic peptide

<400> SEQUENCE: 124

Lys Ser Ser Gln Ser Val Leu Tyr Ser Ser Asn Asn Lys Asn Tyr Leu
1               5                   10                  15

Ala

<210> SEQ ID NO 125
<211> LENGTH: 21
<212> TYPE: DNA
<213> ORGANISM: artificial sequence
<220> FEATURE:
<223> OTHER INFORMATION: synthetic primer

<400> SEQUENCE: 125
tgggcatcta cccgggaatc c                                           21

<210> SEQ ID NO 126
<211> LENGTH: 7
<212> TYPE: PRT
<213> ORGANISM: artificial sequence
<220> FEATURE:
<223> OTHER INFORMATION: synthetic peptide

<400> SEQUENCE: 126

Trp Ala Ser Thr Arg Glu Ser
1               5

<210> SEQ ID NO 127
<211> LENGTH: 27
<212> TYPE: DNA
<213> ORGANISM: artificial sequence
<220> FEATURE:
<223> OTHER INFORMATION: synthetic primer

<400> SEQUENCE: 127
cagcaatatt tgaaaatccc ttatact                                     27

<210> SEQ ID NO 128
<211> LENGTH: 9
<212> TYPE: PRT
<213> ORGANISM: artificial sequence
<220> FEATURE:
<223> OTHER INFORMATION: synthetic peptide

<400> SEQUENCE: 128

Gln Gln Tyr Leu Lys Ile Pro Tyr Thr
1               5

<210> SEQ ID NO 129
<211> LENGTH: 372
<212> TYPE: DNA
<213> ORGANISM: artificial sequence
<220> FEATURE:
```

<223> OTHER INFORMATION: synthetic primer

<400> SEQUENCE: 129

```
caggtgcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg gtcttgagtg gattggacag atttggcctg agatggtga tactaactac      180
aatgaaagt tcaagggtaa agccactctg actgcagacg aatcctccag cacagcctac      240
atgcaactca gcagcctagc atctgaggac tctgcggtct atttctgtgc aagacgggag     300
actacgacgg taggccgtta ttactatgct atggactact ggggccaagg gaccacggtc     360
accgtctcct cc                                                         372
```

<210> SEQ ID NO 130
<211> LENGTH: 124
<212> TYPE: PRT
<213> ORGANISM: artificial sequence
<220> FEATURE:
<223> OTHER INFORMATION: synthetic peptide

<400> SEQUENCE: 130

```
Gln Val Gln Leu Gln Gln Ser Gly Ala Glu Leu Val Arg Pro Gly Ser
1               5                   10                  15
Ser Val Lys Ile Ser Cys Lys Ala Ser Gly Tyr Ala Phe Ser Ser Tyr
            20                  25                  30
Trp Met Asn Trp Val Lys Gln Arg Pro Gly Gln Gly Leu Glu Trp Ile
        35                  40                  45
Gly Gln Ile Trp Pro Gly Asp Gly Asp Thr Asn Tyr Asn Gly Lys Phe
    50                  55                  60
Lys Gly Lys Ala Thr Leu Thr Ala Asp Glu Ser Ser Ser Thr Ala Tyr
65                  70                  75                  80
Met Gln Leu Ser Ser Leu Ala Ser Glu Asp Ser Ala Val Tyr Phe Cys
                85                  90                  95
Ala Arg Arg Glu Thr Thr Thr Val Gly Arg Tyr Tyr Tyr Ala Met Asp
            100                 105                 110
Tyr Trp Gly Gln Gly Thr Thr Val Thr Val Ser Ser
        115                 120
```

<210> SEQ ID NO 131
<211> LENGTH: 333
<212> TYPE: DNA
<213> ORGANISM: artificial sequence
<220> FEATURE:
<223> OTHER INFORMATION: synthetic primer

<400> SEQUENCE: 131

```
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaa                                   333
```

<210> SEQ ID NO 132
<211> LENGTH: 111
<212> TYPE: PRT
<213> ORGANISM: artificial sequence
<220> FEATURE:
<223> OTHER INFORMATION: synthetic peptide

<400> SEQUENCE: 132

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 133
<211> LENGTH: 360
<212> TYPE: DNA
<213> ORGANISM: artificial sequence
<220> FEATURE:
<223> OTHER INFORMATION: synthetic primer

<400> SEQUENCE: 133
gaggtgcagc tgctcgagca gtctggagct gagctggtaa ggcctgggac ttcagtgaag    60
atatcctgca aggcttctgg atacgccttc actaactact ggctaggttg ggtaaagcag    120
aggcctggac atggacttga gtggattgga gatattttcc ctggaagtgg taatatccac    180
tacaatgaga agttcaaggg caaagccaca ctgactgcag acaaatcttc gagcacagcc    240
tatatgcagc tcagtagcct gacatttgag gactctgctg tctatttctg tgcaagactg    300
aggaactggg acgagcctat ggactactgg ggccaaggga ccacggtcac cgtctcctca    360

<210> SEQ ID NO 134
<211> LENGTH: 120
<212> TYPE: PRT
<213> ORGANISM: artificial sequence
<220> FEATURE:
<223> OTHER INFORMATION: synthetic peptide

<400> SEQUENCE: 134

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

```
Gly Thr Thr Val Thr Val Ser Ser
        115                 120
```

<210> SEQ ID NO 135
<211> LENGTH: 339
<212> TYPE: DNA
<213> ORGANISM: artificial sequence
<220> FEATURE:
<223> OTHER INFORMATION: synthetic primer

<400> SEQUENCE: 135

```
gagctcgtga tgacacagtc tccatcctcc ctgactgtga cagcaggaga gaaggtcact    60
atgagctgca gtccagtca gagtctgtta acagtggaa atcaaaagaa ctacttgacc    120
tggtaccagc agaaaccagg gcagcctcct aaactgttga tctactgggc atccactagg    180
gaatctgggg tccctgatcg cttcacaggc agtggatctg gaacagattt cactctcacc    240
atcagcagtg tgcaggctga agacctggca gtttattact gtcagaatga ttatagttat    300
ccgctcacgt tcggtgctgg gaccaagctt gagatcaaa                           339
```

<210> SEQ ID NO 136
<211> LENGTH: 113
<212> TYPE: PRT
<213> ORGANISM: artificial sequence
<220> FEATURE:
<223> OTHER INFORMATION: synthetic peptide

<400> SEQUENCE: 136

```
Glu Leu Val Met Thr Gln Ser Pro Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys
```

<210> SEQ ID NO 137
<211> LENGTH: 36
<212> TYPE: DNA
<213> ORGANISM: artificial sequence
<220> FEATURE:
<223> OTHER INFORMATION: synthetic primer

<400> SEQUENCE: 137

```
aggtgtacac tccgatggta atgaagaaat gggtgg                              36
```

<210> SEQ ID NO 138
<211> LENGTH: 42
<212> TYPE: DNA
<213> ORGANISM: artificial sequence
<220> FEATURE:
<223> OTHER INFORMATION: synthetic primer

<400> SEQUENCE: 138

```
cgatccggaa tccatctcca tgcagttctc acacactctt gc                        42
```

<210> SEQ ID NO 139
<211> LENGTH: 146
<212> TYPE: DNA
<213> ORGANISM: artificial sequence
<220> FEATURE:
<223> OTHER INFORMATION: synthetic primer

<400> SEQUENCE: 139

```
gaattcacca tgggatggag ctgtatcatc ctcttcttgg tagcaacagc tacaggtgta    60
cactccgata tcaagcttcc ggacgctccc gactcaagcg cccgtgccac acagccgcaa   120
gatctggcgc cgtgtggtca gtcgac                                        146
```

<210> SEQ ID NO 140
<211> LENGTH: 393
<212> TYPE: DNA
<213> ORGANISM: artificial sequence
<220> FEATURE:
<223> OTHER INFORMATION: synthetic primer

<400> SEQUENCE: 140

```
atgggatgga gctgtatcat cctcttcttg gtagcaacag ctacaggtgt acactccgat    60
ggtaatgaag aaatgggtgg tattacacag acaccatata agtctccat ctctggaacc   120
acagtaatat tgacatgccc tcagtatcct ggatctgaaa tactatggca acacaatgat   180
aaaaacatag gcggtgatga ggatgataaa acataggca gtgatgagga tcacctgtca   240
ctgaaggaat tttcagaatt ggagcaaagt ggttattatg tctgctaccc cagaggaagc   300
aaaccagaag atgcgaactt ttatctctac ctgagggcaa gagtgtgtga gaactgcatg   360
gagatggatt ccgggcatca tcaccatcat cat                               393
```

<210> SEQ ID NO 141
<211> LENGTH: 131
<212> TYPE: PRT
<213> ORGANISM: artificial sequence
<220> FEATURE:
<223> OTHER INFORMATION: synthetic peptide

<400> SEQUENCE: 141

```
Met Gly Trp Ser Cys Ile Ile Leu Phe Leu Val Ala Thr Ala Thr Gly
1               5                   10                  15

Val His Ser Asp Gly Asn Glu Glu Met Gly Gly Ile Thr Gln Thr Pro
            20                  25                  30

Tyr Lys Val Ser Ile Ser Gly Thr Thr Val Ile Leu Thr Cys Pro Gln
        35                  40                  45

Tyr Pro Gly Ser Glu Ile Leu Trp Gln His Asn Asp Lys Asn Ile Gly
    50                  55                  60

Gly Asp Glu Asp Asp Lys Asn Ile Gly Ser Asp Glu Asp His Leu Ser
65                  70                  75                  80

Leu Lys Glu Phe Ser Glu Leu Glu Gln Ser Gly Tyr Tyr Val Cys Tyr
                85                  90                  95

Pro Arg Gly Ser Lys Pro Glu Asp Ala Asn Phe Tyr Leu Tyr Leu Arg
            100                 105                 110

Ala Arg Val Cys Glu Asn Cys Met Glu Met Asp Ser Gly His His His
        115                 120                 125

His His His
    130
```

<210> SEQ ID NO 142
<211> LENGTH: 22
<212> TYPE: DNA
<213> ORGANISM: artificial sequence
<220> FEATURE:
<223> OTHER INFORMATION: synthetic primer

<400> SEQUENCE: 142
aggtgcagct gctcgagtct gg                                    22

<210> SEQ ID NO 143
<211> LENGTH: 23
<212> TYPE: DNA
<213> ORGANISM: artificial sequence
<220> FEATURE:
<223> OTHER INFORMATION: synthetic primer

<400> SEQUENCE: 143
cagrtcacct tgctcgagtc tgg                                   23

<210> SEQ ID NO 144
<211> LENGTH: 23
<212> TYPE: DNA
<213> ORGANISM: artificial sequence
<220> FEATURE:
<223> OTHER INFORMATION: synthetic primer

<400> SEQUENCE: 144
caggtgcagc tgctcgagtc ggg                                   23

<210> SEQ ID NO 145
<211> LENGTH: 23
<212> TYPE: DNA
<213> ORGANISM: artificial sequence
<220> FEATURE:
<223> OTHER INFORMATION: synthetic primer

<400> SEQUENCE: 145
caggtgcagc tactcgagtg ggg                                   23

<210> SEQ ID NO 146
<211> LENGTH: 23
<212> TYPE: DNA
<213> ORGANISM: artificial sequence
<220> FEATURE:
<223> OTHER INFORMATION: synthetic primer

<400> SEQUENCE: 146
caggtacagc tgctcgagtc agg                                   23

<210> SEQ ID NO 147
<211> LENGTH: 30
<212> TYPE: DNA
<213> ORGANISM: artificial sequence
<220> FEATURE:
<223> OTHER INFORMATION: synthetic primer

<400> SEQUENCE: 147
tgccttacta gtctctggcc agcggaagat                            30

<210> SEQ ID NO 148
<211> LENGTH: 17
<212> TYPE: DNA
<213> ORGANISM: artificial sequence
<220> FEATURE:

<223> OTHER INFORMATION: synthetic primer

<400> SEQUENCE: 148
ctgaggagac ggtgacc                                                    17

<210> SEQ ID NO 149
<211> LENGTH: 17
<212> TYPE: DNA
<213> ORGANISM: artificial sequence
<220> FEATURE:
<223> OTHER INFORMATION: synthetic primer

<400> SEQUENCE: 149
ctgaagagac ggtgacc                                                    17

<210> SEQ ID NO 150
<211> LENGTH: 38
<212> TYPE: DNA
<213> ORGANISM: artificial sequence
<220> FEATURE:
<223> OTHER INFORMATION: synthetic primer

<400> SEQUENCE: 150
gagccgcacg agcccgagct ccagatgacc cagtctcc                              38

<210> SEQ ID NO 151
<211> LENGTH: 38
<212> TYPE: DNA
<213> ORGANISM: artificial sequence
<220> FEATURE:
<223> OTHER INFORMATION: synthetic primer

<400> SEQUENCE: 151
gagccgcacg agcccgagct cgtgwtgacr cagtctcc                              38

<210> SEQ ID NO 152
<211> LENGTH: 38
<212> TYPE: DNA
<213> ORGANISM: artificial sequence
<220> FEATURE:
<223> OTHER INFORMATION: synthetic primer

<400> SEQUENCE: 152
gagccgcacg agcccgagct cgtgatgacy cagtctcc                              38

<210> SEQ ID NO 153
<211> LENGTH: 38
<212> TYPE: DNA
<213> ORGANISM: artificial sequence
<220> FEATURE:
<223> OTHER INFORMATION: synthetic primer

<400> SEQUENCE: 153
gagccgcacg agcccgagct cacactcacg cagtctcc                              38

<210> SEQ ID NO 154
<211> LENGTH: 38
<212> TYPE: DNA
<213> ORGANISM: artificial sequence
<220> FEATURE:
<223> OTHER INFORMATION: synthetic primer

<400> SEQUENCE: 154
gagccgcacg agcccgagct cgtgctgact cagtctcc                              38

```
<210> SEQ ID NO 155
<211> LENGTH: 47
<212> TYPE: DNA
<213> ORGANISM: artificial sequence
<220> FEATURE:
<223> OTHER INFORMATION: synthetic primer

<400> SEQUENCE: 155
gacgacacta gttgcagcca ccgtacgttt gatttccacc ttggtcc                47

<210> SEQ ID NO 156
<211> LENGTH: 47
<212> TYPE: DNA
<213> ORGANISM: artificial sequence
<220> FEATURE:
<223> OTHER INFORMATION: synthetic primer

<400> SEQUENCE: 156
gacgacacta gttgcagcca ccgtacgttt gatctccasc ttggtcc                47

<210> SEQ ID NO 157
<211> LENGTH: 47
<212> TYPE: DNA
<213> ORGANISM: artificial sequence
<220> FEATURE:
<223> OTHER INFORMATION: synthetic primer

<400> SEQUENCE: 157
gacgacacta gttgcagcca ccgtacgttt gatatccacg ttggtcc                47

<210> SEQ ID NO 158
<211> LENGTH: 47
<212> TYPE: DNA
<213> ORGANISM: artificial sequence
<220> FEATURE:
<223> OTHER INFORMATION: synthetic primer

<400> SEQUENCE: 158
gacgacacta gttgcagcca ccgtacgttt aatctccagt cgtgtcc                47

<210> SEQ ID NO 159
<211> LENGTH: 41
<212> TYPE: DNA
<213> ORGANISM: artificial sequence
<220> FEATURE:
<223> OTHER INFORMATION: synthetic primer

<400> SEQUENCE: 159
gagccgcacg agcccgagct cgtgttgacg cagccgccct c                      41

<210> SEQ ID NO 160
<211> LENGTH: 41
<212> TYPE: DNA
<213> ORGANISM: artificial sequence
<220> FEATURE:
<223> OTHER INFORMATION: synthetic primer

<400> SEQUENCE: 160
gagccgcacg agcccgagct cgtgctgact cagccaccct c                      41

<210> SEQ ID NO 161
<211> LENGTH: 44
<212> TYPE: DNA
<213> ORGANISM: artificial sequence
<220> FEATURE:
<223> OTHER INFORMATION: synthetic primer
```

<400> SEQUENCE: 161
gagccgcagg agcccgagct cgccctgact cagcctscct ccgt        44

<210> SEQ ID NO 162
<211> LENGTH: 35
<212> TYPE: DNA
<213> ORGANISM: artificial sequence
<220> FEATURE:
<223> OTHER INFORMATION: synthetic primer

<400> SEQUENCE: 162
acctgcgagc tcgtgctgac tcarycmycc tctgc        35

<210> SEQ ID NO 163
<211> LENGTH: 33
<212> TYPE: DNA
<213> ORGANISM: artificial sequence
<220> FEATURE:
<223> OTHER INFORMATION: synthetic primer

<400> SEQUENCE: 163
acctgcgagc tcgtgctgac tcagccrsct tcc        33

<210> SEQ ID NO 164
<211> LENGTH: 32
<212> TYPE: DNA
<213> ORGANISM: artificial sequence
<220> FEATURE:
<223> OTHER INFORMATION: synthetic primer

<400> SEQUENCE: 164
acctgcgagc tcatgctgac tcagccccac tc        32

<210> SEQ ID NO 165
<211> LENGTH: 41
<212> TYPE: DNA
<213> ORGANISM: artificial sequence
<220> FEATURE:
<223> OTHER INFORMATION: synthetic primer

<400> SEQUENCE: 165
gagccgcacg agcccgagct cgwgctgact cagccaccyt c        41

<210> SEQ ID NO 166
<211> LENGTH: 41
<212> TYPE: DNA
<213> ORGANISM: artificial sequence
<220> FEATURE:
<223> OTHER INFORMATION: synthetic primer

<400> SEQUENCE: 166
gagccgcacg agcccgagct cgtggtgacy caggagccmt c        41

<210> SEQ ID NO 167
<211> LENGTH: 33
<212> TYPE: DNA
<213> ORGANISM: artificial sequence
<220> FEATURE:
<223> OTHER INFORMATION: synthetic primer

<400> SEQUENCE: 167
cgtgggacta gtcttgggct gacctaggac ggt        33

<210> SEQ ID NO 168
<211> LENGTH: 33

-continued

<210> SEQ ID NO 168
<211> LENGTH: 33
<212> TYPE: DNA
<213> ORGANISM: artificial sequence
<220> FEATURE:
<223> OTHER INFORMATION: synthetic primer

<400> SEQUENCE: 168
cgtgggacta gtcttgggct gaccgaggac ggt        33

<210> SEQ ID NO 169
<211> LENGTH: 36
<212> TYPE: DNA
<213> ORGANISM: artificial sequence
<220> FEATURE:
<223> OTHER INFORMATION: synthetic primer

<400> SEQUENCE: 169
actcgacgta cggatgctgc accaactgta tccatc        36

<210> SEQ ID NO 170
<211> LENGTH: 58
<212> TYPE: DNA
<213> ORGANISM: artificial sequence
<220> FEATURE:
<223> OTHER INFORMATION: synthetic primer

<400> SEQUENCE: 170
cagatcttcc tctgagatca gcttctgttc ctcacactca ttcctgttga agctcttg        58

<210> SEQ ID NO 171
<211> LENGTH: 68
<212> TYPE: DNA
<213> ORGANISM: artificial sequence
<220> FEATURE:
<223> OTHER INFORMATION: synthetic primer

<400> SEQUENCE: 171
tcagtagcgg ccgcttaatg gtgatggtgg tgatgcagat cttcctctga gatcagcttc        60
tgttcctc        68

<210> SEQ ID NO 172
<211> LENGTH: 34
<212> TYPE: DNA
<213> ORGANISM: artificial sequence
<220> FEATURE:
<223> OTHER INFORMATION: synthetic primer

<400> SEQUENCE: 172
acgtcatgta cactccgagg tgcagctgct cgag        34

<210> SEQ ID NO 173
<211> LENGTH: 35
<212> TYPE: DNA
<213> ORGANISM: artificial sequence
<220> FEATURE:
<223> OTHER INFORMATION: synthetic primer

<400> SEQUENCE: 173
tgcatgtccg gacgtacgtt tgatctcaag cttgg        35

<210> SEQ ID NO 174
<211> LENGTH: 45
<212> TYPE: DNA
<213> ORGANISM: artificial sequence
<220> FEATURE:
<223> OTHER INFORMATION: synthetic primer -continued

<400> SEQUENCE: 174
ggtggtggtg gttctggcgg cggcggctcc ggtggtggtg gttct                     45

<210> SEQ ID NO 175
<211> LENGTH: 15
<212> TYPE: PRT
<213> ORGANISM: artificial sequence
<220> FEATURE:
<223> OTHER INFORMATION: synthetic peptide

<400> SEQUENCE: 175

Gly Gly Gly Gly Ser Gly Gly Gly Gly Ser Gly Gly Gly Gly Ser
1               5                   10                  15

<210> SEQ ID NO 176
<211> LENGTH: 15
<212> TYPE: DNA
<213> ORGANISM: artificial sequence
<220> FEATURE:
<223> OTHER INFORMATION: synthetic primer

<400> SEQUENCE: 176
ggaggtggtg gatcc                                                      15

<210> SEQ ID NO 177
<211> LENGTH: 5
<212> TYPE: PRT
<213> ORGANISM: artificial sequence
<220> FEATURE:
<223> OTHER INFORMATION: synthetic peptide

<400> SEQUENCE: 177

Gly Gly Gly Gly Ser
1               5

<210> SEQ ID NO 178
<211> LENGTH: 383
<212> TYPE: DNA
<213> ORGANISM: artificial sequence
<220> FEATURE:
<223> OTHER INFORMATION: synthetic primer

<400> SEQUENCE: 178
cgtacggatg ctgcaccaac tgtatccatc ttcccaccat ccagtgagca gttaacatct     60
ggaggtgcct cagtcgtgtg cttcttgaac aacttctacc ccaaagacat caatgtcaag    120
tggaagattg atggcagtga acgacaaaat ggcgtcctga acagttggac tgatcaggac    180
agcaaagaca gcacctacag catgagcagc accctcacgt tgaccaagga cgagtatgaa    240
cgacataaca gctatacctg tgaggccact cacaagacat caacttcacc cattgtcaag    300
agcttcaaca ggaatgagtg tgaggaacag aagctgatct cagaggaaga tctgcatcac    360
caccatcacc attaagcggc cgc                                            383

<210> SEQ ID NO 179
<211> LENGTH: 124
<212> TYPE: PRT
<213> ORGANISM: artificial sequence
<220> FEATURE:
<223> OTHER INFORMATION: synthetic peptide

<400> SEQUENCE: 179

Arg Thr Asp Ala Ala Pro Thr Val Ser Ile Phe Pro Pro Ser Ser Glu
1               5                   10                  15

```
Gln Leu Thr Ser Gly Gly Ala Ser Val Val Cys Phe Leu Asn Asn Phe
             20                  25                  30
Tyr Pro Lys Asp Ile Asn Val Lys Trp Lys Ile Asp Gly Ser Glu Arg
         35                  40                  45
Gln Asn Gly Val Leu Asn Ser Trp Thr Asp Gln Asp Ser Lys Asp Ser
     50                  55                  60
Thr Tyr Ser Met Ser Ser Thr Leu Thr Leu Thr Lys Asp Glu Tyr Glu
 65                  70                  75                  80
Arg His Asn Ser Tyr Thr Cys Glu Ala Thr His Lys Thr Ser Thr Ser
                 85                  90                  95
Pro Ile Val Lys Ser Phe Asn Arg Asn Glu Cys Glu Glu Gln Lys Leu
             100                 105                 110
Ile Ser Glu Glu Asp Leu His His His His His His
         115                 120
```

<210> SEQ ID NO 180
<211> LENGTH: 741
<212> TYPE: DNA
<213> ORGANISM: artificial sequence
<220> FEATURE:
<223> OTHER INFORMATION: synthetic primer

<400> SEQUENCE: 180

| | | | | | |
|---|---|---|---|---|---|
| gagctgcagc | tggtcgagtc | tgggggaggc | gtggtccagc | ctgggaggtc | cctgagactc | 60 |
| tcctgtgcag | cctctggatt | caccttcagt | agctatggca | tgcactgggt | ccgccaggct | 120 |
| ccaggcaagg | gctggagtg | gtggcagtt | atatcatatg | atggaagtaa | taaatactac | 180 |
| gcagactccg | tgaagggccg | attcaccatc | tccagagaca | attccaagaa | cacgctgtat | 240 |
| ctgcaaatga | acagcctgag | atctgaggac | acggccgtgt | attactgtgc | gaggctcagc | 300 |
| ccgtattgta | ctaatggtgt | atgctgggat | gcttttgata | tctggggcca | agggacaatg | 360 |
| gtcaccgtct | cctcaggtgg | tggtggttct | ggcggcggcg | gctccggtgg | tggtggttct | 420 |
| gagctccaga | tgacccagtc | tccatcctcc | ctgtctgcat | ctgtcggaga | cagagtctcc | 480 |
| atcacttgtc | gggcaagtca | gaccattagc | aattatttaa | attggtatca | actgaagcca | 540 |
| gggaaagccc | ctaagctcct | gatctatgct | gcatccactt | tgcaaagtga | ggtcccaacc | 600 |
| aggttcagtg | gcagtgggtc | tgggacagat | ttcactctca | ccatcagtgg | tctgcatcct | 660 |
| gaagattttg | caacttacta | ctgtcaacag | tttaatagtt | atcctcgaac | gttcggccaa | 720 |
| gggaccaagg | tggaaatcaa | a | | | | 741 |

<210> SEQ ID NO 181
<211> LENGTH: 247
<212> TYPE: PRT
<213> ORGANISM: artificial sequence
<220> FEATURE:
<223> OTHER INFORMATION: synthetic peptide

<400> SEQUENCE: 181

```
Glu Leu Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
             20                  25                  30
Gly Met His Trp Val Arg Gln Ala Pro Gly Lys Gly Leu Glu Trp Val
         35                  40                  45
Ala Val Ile Ser Tyr Asp Gly Ser Asn Lys Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ser Glu Asp Thr Ala Val Tyr Tyr Cys
                 85                  90                  95

Ala Arg Leu Ser Pro Tyr Cys Thr Asn Gly Val Cys Trp Asp Ala Phe
            100                 105                 110

Asp Ile Trp Gly Gln Gly Thr Met Val Thr Val Ser Ser Gly Gly Gly
        115                 120                 125

Gly Ser Gly Gly Gly Gly Ser Gly Gly Gly Gly Ser Glu Leu Gln Met
    130                 135                 140

Thr Gln Ser Pro Ser Ser Leu Ser Ala Ser Val Gly Asp Arg Val Ser
145                 150                 155                 160

Ile Thr Cys Arg Ala Ser Gln Thr Ile Ser Asn Tyr Leu Asn Trp Tyr
                165                 170                 175

Gln Leu Lys Pro Gly Lys Ala Pro Lys Leu Leu Ile Tyr Ala Ala Ser
            180                 185                 190

Thr Leu Gln Ser Glu Val Pro Thr Arg Phe Ser Gly Ser Gly Ser Gly
        195                 200                 205

Thr Asp Phe Thr Leu Thr Ile Ser Gly Leu His Pro Glu Asp Phe Ala
    210                 215                 220

Thr Tyr Tyr Cys Gln Gln Phe Asn Ser Tyr Pro Arg Thr Phe Gly Gln
225                 230                 235                 240

Gly Thr Lys Val Glu Ile Lys
                245

<210> SEQ ID NO 182
<211> LENGTH: 732
<212> TYPE: DNA
<213> ORGANISM: artificial sequence
<220> FEATURE:
<223> OTHER INFORMATION: synthetic primer

<400> SEQUENCE: 182
gagctgcagc tggtcgagtc tgggggaggc ttggtaaagc cagggcggtc cctgagactc    60
tcctgtacag cttctggatt cacctttggt gattatgcta tgagctggtt ccgccaggct   120
ccagggaagg ggctggagtg ggtaggtttc attagaagca aagcttatgg tgggacaaca   180
gaatacgccg cgtctgtgaa aggcagattc accatctcaa gagatgattc aaaagcatc   240 gcctatctgc aaatgaacag cctgaaaacc gaggacacag ccgtgtatta ctgtactcca   300
cagctatggt tactacaaga tgcttttgat atctggggcc aagggacaat ggtcaccgtc   360
tcctcaggtg gtggtggttc tggcggcggc ggctccggtg gtggtggttc tgagctccag   420
atgacccagt ctccatcctc cctgtctgca tctgtaggag atagagtcac catcacttgc   480
cgggcgagtc agggcattag caattattta gcctggtatc agcagaaacc agggaaagtt   540
cctaagctcc tgatctatgc tgcatccact ttgcaatcag ggtcccatc tcggttcagt   600 ggcagtggat ctgggacaga tttcactctc accatcagca gtctgcaacc tgaagatttt   660
gcaacttact actgtcaaca gagttacagt accectccga cgttcggcca agggaccaag   720
ctggagatca aa                                                       732

<210> SEQ ID NO 183
<211> LENGTH: 244
<212> TYPE: PRT
<213> ORGANISM: artificial sequence
<220> FEATURE:
<223> OTHER INFORMATION: synthetic peptide
```

<400> SEQUENCE: 183

```
Glu Leu Gln Leu Val Glu Ser Gly Gly Leu Val Lys Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Pro Gln Leu Trp Leu Leu Gln Asp Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Glu Leu Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Gly Ile Ser Asn Tyr Leu Ala Trp Tyr Gln Gln Lys
                165                 170                 175

Pro Gly Lys Val Pro Lys Leu Leu Ile Tyr Ala Ala Ser Thr Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Pro Thr Phe Gly Gln Gly Thr Lys
225                 230                 235                 240

Leu Glu Ile Lys
```

<210> SEQ ID NO 184
<211> LENGTH: 726
<212> TYPE: DNA
<213> ORGANISM: artificial sequence
<220> FEATURE:
<223> OTHER INFORMATION: synthetic primer

<400> SEQUENCE: 184

```
gagctgcagc tggtcgagtc tggcccagga ctggtgaagc cttcggggac cctgtccctc    60
acctgcgctg tctctggtgg ctccatcagc agtagaaact ggtggagttg ggtccgccag   120
ccccagggaa aggggctgga gtggattggt gatatctatc atagtgggag caccaactac   180
aacccgtccc tcaagagtcg agtcaccata tcagtagaca gtccaagaa ccagttctcc    240
ctgaagctga gctctgtgac cgccgcggac acggccgtgt attactgtgc gagtgggtat   300
accagctgtc gtgatgcttt tgatatctgg ggccaaggga caatggtcac cgtctcctca   360
ggtggtggtg gttctggcgg cggcggctcc ggtggtggtg gttctgagct cgtgatgact   420
cagtctccat cctccctgtc tgcatctgta ggagacagag tcaccatcac ttgccgggcg   480
agtcagggca ttggcaatta tttagcctgg tatcagcaga aaccagggca gcctcctaag   540
atgctcattt actgggcatc aatccgggaa tccggggtcc ctgaccgatt cagtggcagc   600
```

```
gggtctggga cagacttcac tctcaccatc agcagcctgc aggctgaaga tgtggcagtt    660
tactactgtc agcaatatta tagtaatcct cagacgttcg gccaagggac caaggtggaa    720
atcaaa                                                               726
```

<210> SEQ ID NO 185
<211> LENGTH: 242
<212> TYPE: PRT
<213> ORGANISM: artificial sequence
<220> FEATURE:
<223> OTHER INFORMATION: synthetic peptide

<400> SEQUENCE: 185

```
Glu Leu Gln Leu Val Glu Ser Gly Pro Gly Leu Val Lys Pro Ser Gly
1               5                   10                  15

Thr Leu Ser Leu Thr Cys Ala Val Ser Gly Ser Ile Ser Ser Arg
            20                  25                  30

Asn Trp Trp Ser Trp Val Arg Gln Pro Pro Lys Gly Leu Glu Trp
        35                  40                  45

Ile Gly Asp Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Gly Tyr Thr Ser Cys Arg Asp Ala Phe Asp Ile Trp Gly Gln
            100                 105                 110

Gly Thr Met Val Thr Val Ser Ser Gly Gly Gly Ser Gly Gly Gly
        115                 120                 125

Gly Ser Gly Gly Gly Gly Ser Glu Leu Val Met Thr Gln Ser Pro Ser
130                 135                 140

Ser Leu Ser Ala Ser Val Gly Asp Arg Val Thr Ile Thr Cys Arg Ala
145                 150                 155                 160

Ser Gln Gly Ile Gly Asn Tyr Leu Ala Trp Tyr Gln Gln Lys Pro Gly
                165                 170                 175

Gln Pro Pro Lys Met Leu Ile Tyr Trp Ala Ser Ile Arg Glu Ser Gly
            180                 185                 190

Val Pro Asp Arg Phe Ser Gly Ser Gly Ser Gly Thr Asp Phe Thr Leu
        195                 200                 205

Thr Ile Ser Ser Leu Gln Ala Glu Asp Val Ala Val Tyr Tyr Cys Gln
    210                 215                 220

Gln Tyr Tyr Ser Asn Pro Gln Thr Phe Gly Gln Gly Thr Lys Val Glu
225                 230                 235                 240

Ile Lys
```

<210> SEQ ID NO 186
<211> LENGTH: 744
<212> TYPE: DNA
<213> ORGANISM: artificial sequence
<220> FEATURE:
<223> OTHER INFORMATION: synthetic primer

<400> SEQUENCE: 186

```
gagctgcagc tggtcgagtg gggcgcagga ctgttgaagc cttcggagac cctgtccctc     60
acctgcgctg tctatggtgg gtccttcagt ggttactact ggagctggat ccgccagccc    120
ccagggaagg gctggagtg gattggggaa atcaatcata gtggaagcac caactacaac    180
```

-continued

```
ccgtccctca agagtcgagt caccatatca gtagacacgt ccaagaacca gttctccctg    240
aagctgagct ctgtgaccgc cgcggacacg gctgtgtatt actgtgcgag aggccgaggc    300
cgattttggg ggtggttatt agggggctcc aactggttcg acccctgggg ccagggaacc    360
ctggtcaccg tctcctcagg tggtggtggt tctggcggcg gcggctccgg tggtggtggt    420
tctgagctcg tgatgaccca gtctccatcc tccctgtctg catctgtagg agacagagtc    480
accatcactt gccgggcgag tcagggcatt agcaattatt taaattggta tcagcagaaa    540
ccagggaaag cccctaagct cctgatctac gatgcatcca atttggaaac aggggtccca    600
tcaaggttca gtggcagtgg atctgggaca gatttcactc tcaccatcag cagtctgcaa    660
cctgaagatt ttgcaactta ctactgtcaa cagagttaca gtaccccgta cacttttggc    720
caggggacca agtggatat caaa                                            744
```

<210> SEQ ID NO 187
<211> LENGTH: 248
<212> TYPE: PRT
<213> ORGANISM: artificial sequence
<220> FEATURE:
<223> OTHER INFORMATION: synthetic peptide

<400> SEQUENCE: 187

```
Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Arg Phe Leu Gly Trp Leu Leu Gly Ser Asn Trp
            100                 105                 110

Phe Asp Pro Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Leu Val
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Gly Ile Ser Asn Tyr Leu Asn Trp
                165                 170                 175

Tyr Gln Gln Lys Pro Gly Lys Ala Pro Lys Leu Leu Ile Tyr Asp Ala
            180                 185                 190

Ser Asn Leu Glu Thr Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Tyr Thr Phe Gly
225                 230                 235                 240

Gln Gly Thr Lys Val Asp Ile Lys
                245
```

<210> SEQ ID NO 188
<211> LENGTH: 723
<212> TYPE: DNA
<213> ORGANISM: artificial sequence
<220> FEATURE:
<223> OTHER INFORMATION: synthetic primer

<400> SEQUENCE: 188

```
gagctgcagc tggtcgagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca gagtcgagt caccatatca gtagacacgt ccaagaacca gttctccctg   240
aagctgagct ctgtgaccgc cgcggacacg gctgtgtatt actgtgcgag aggccctgac   300
cgaatggggc atggttttga tatctggggc caagggacaa tggtcaccgt ctcctcaggt   360
ggtggtggtt ctgcggcgg cggctccggt ggtggtggtt ctgagctcca gatgacccag   420
tctccatcct ccctgtctgc atctgtagga gacagagtca ccatcacttg ccgggcaagt   480
cagagcatta gcagctattt aaattggtat cagcagaaat cagggaaagc ccctaagctc   540
ctgatctatg ctgcatccag tttgcaaagt ggggtcccat caaggttcag tggcagtgga   600
tctgggacag atttcactct caccatcagt agtctgcaac tgaagatttt gcaacttat   660
tactgtcaac agagttacag tagcccgtgg acattcggcc aagggaccaa ggtggagatc   720
aaa                                                                 723
```

<210> SEQ ID NO 189
<211> LENGTH: 241
<212> TYPE: PRT
<213> ORGANISM: artificial sequence
<220> FEATURE:
<223> OTHER INFORMATION: synthetic peptide

<400> SEQUENCE: 189

```
Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Asp Arg Met Gly His Gly Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Glu Leu Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Ser Gly Lys
                165                 170                 175
```

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Tyr Ser Ser Pro Trp Thr Phe Gly Gln Gly Thr Lys Val Glu Ile
225                 230                 235                 240

Lys

<210> SEQ ID NO 190
<211> LENGTH: 750
<212> TYPE: DNA
<213> ORGANISM: artificial sequence
<220> FEATURE:
<223> OTHER INFORMATION: synthetic primer

<400> SEQUENCE: 190
gagctgcagc tggtcgagtc tggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat     180
aatgattatg cagtatctgt gaaaagtcga ataaccatca acccagacac atccaagaac    240
cagttctccc tgcagctgaa ctctgtgact cccgaggaca cggctgtgta ttactgtgca    300
agagatcgtc gacgtatagc agctcgtcaa tactacggta tggacgtctg gggccaaggg    360
accacggtca ccgtctcctc aggtggtggt ggttctggcg gcggcggctc cggtggtggt    420
ggttctgagc tcgtgttgac acagtctcca ggcaccctgt ctttgtctcc aggggaaaga    480
gccaccctct cctgcagggc aagtcagagt gttagcagca actacttagc ctggtaccag    540
cagaaacctg gccaggctcc caggctcctc atctatggtg catccagcag ggccactggc    600
atcccagaca ggttcagtgg cagcgggtct gggacagatt tcactctcac catcagcagc    660
ctgcagcctg aagatgttgc aacttattac tgtcaaaagt ataacagtgc ccctctcact    720
ttcggcggag ggaccaaggt ggaaatcaaa                                      750

<210> SEQ ID NO 191
<211> LENGTH: 250
<212> TYPE: PRT
<213> ORGANISM: artificial sequence
<220> FEATURE:
<223> OTHER INFORMATION: synthetic peptide

<400> SEQUENCE: 191

Glu Leu Gln Leu Val Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Arg Arg Ile Ala Ala Arg Gln Tyr Tyr

```
                100             105             110
Gly Met Asp Val Trp Gly Gln Gly Thr Thr Val Thr Val Ser Ser Gly
            115             120             125

Gly Gly Gly Ser Gly Gly Gly Ser Gly Gly Gly Ser Glu Leu
        130             135             140

Val Leu Thr Gln Ser Pro Gly Thr Leu Ser Leu Ser Pro Gly Glu Arg
145             150             155             160

Ala Thr Leu Ser Cys Arg Ala Ser Gln Ser Val Ser Ser Asn Tyr Leu
                165             170             175

Ala Trp Tyr Gln Gln Lys Pro Gly Gln Ala Pro Arg Leu Leu Ile Tyr
            180             185             190

Gly Ala Ser Ser Arg Ala Thr Gly Ile Pro Asp Arg Phe Ser Gly Ser
        195             200             205

Gly Ser Gly Thr Asp Phe Thr Leu Thr Ile Ser Ser Leu Gln Pro Glu
    210             215             220

Asp Val Ala Thr Tyr Tyr Cys Gln Lys Tyr Asn Ser Ala Pro Leu Thr
225             230             235             240

Phe Gly Gly Gly Thr Lys Val Glu Ile Lys
            245             250

<210> SEQ ID NO 192
<211> LENGTH: 729
<212> TYPE: DNA
<213> ORGANISM: artificial sequence
<220> FEATURE:
<223> OTHER INFORMATION: synthetic primer

<400> SEQUENCE: 192
gagctgcagc tggtcgagtc tgggggaggc ttggtacagc ctgggggtc cctgagactc      60 tcctgtgcag cctctggatt cacctttagc agctatgcca tgggctgggt ccgccaggct    120
ccagggaagg gctgagtg gtctcagct gttagtggta gtggtggtag cacatactac       180
gcagactccg tgaagggccg gttcaccatc tccagagaca attccaagaa cacgctgtat    240
ctgcaaatga acagcctgag agccgaggac acggccgtat attactgtgc gaaagccaaa    300
ttcctgggcc actactacgg tatggacgtc tggggccaag gaccacggt caccgtctcc     360 tcaggtggtg gtggttctgg cggcggcggc tccggtggtg gtggttctga gctccagatg    420
acccagtctc catcctccct gtctgcatct gtaggagaca gagtcaccat cacttgccgg    480
gcaagtcaga gcattagcag ctatttaaat tggtatcagc agaaaccagg gaaagcccct    540
aagctcctga tctatgctgc atccagtttg caaagtggag tcccatcaag gttcagcggc    600
agtggatctg ggacagagtt cactctcaca atcagcagcc tgcagcctga agattttgca    660
acttattact gtcttcagca taatgcttac ccgtacactt tcggccaggg gaccaaggtg    720
gaaatcaaa                                                            729

<210> SEQ ID NO 193
<211> LENGTH: 243
<212> TYPE: PRT
<213> ORGANISM: artificial sequence
<220> FEATURE:
<223> OTHER INFORMATION: synthetic peptide

<400> SEQUENCE: 193

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Ala Met Gly Trp Val Arg Gln Ala Pro Gly Lys Gly Leu Glu Trp Val
        35                  40                  45

Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Lys Phe Leu Gly His Tyr Tyr Gly Met Asp Val Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Glu Leu Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Glu Phe Thr
        195                 200                 205

Leu Thr Ile Ser Ser Leu Gln Pro Glu Asp Phe Ala Thr Tyr Tyr Cys
    210                 215                 220

Leu Gln His Asn Ala Tyr Pro Tyr Thr Phe Gly Gln Gly Thr Lys Val
225                 230                 235                 240

Glu Ile Lys

<210> SEQ ID NO 194
<211> LENGTH: 753
<212> TYPE: DNA
<213> ORGANISM: artificial sequence
<220> FEATURE:
<223> OTHER INFORMATION: synthetic primer

<400> SEQUENCE: 194
gagctgcagc tggtcgagtc tggtcctgtg ctggtgaaac ccacagatac cctcacgctg      60
acttgcaccg tctctgggtt ctcactcaat aatcctagaa tgggtgtgag ctggatccgt     120
cagcccccag ggaagaccct ggagtggctt gcacacattt ttccgagtga cgcaaaagcc     180
cacagtgcat ctctgaagag caggctcacc atctccaagg acacctccaa aagccaggtg     240
gtccctacca tgaccaacat ggaccctgtg acacagccca tattactgtg cacggataa     300 ttgggggaat actatccccc agcctggttc gaccccctggg gccagggaac cctggtcacc     360
gtctcctcag gtggtggtgg ttctggcggc ggcggctccg gtggtggtgg ttctgagctc     420
gtgatgacac agtctccaga ctccctggct gtgtctctgg gcgagagggc caccatcaac     480
tgcaagtcca gccagagtgt tttatacagc tccaacaata gaactactt agcttggtac     540 cagcagaaac aggacagcc tcctaagctg ctcatttact gggcatctac ccgggaatcc     600
ggggtccctg accgattcag tggcagcggg tctgggacag atttcactct caccatcagc     660
agcctgcagg ctgaagacgt ggcagtttat tactgtcagc aatatttgaa aatcccttat     720 actttttggcc agggaccaa ggtggagatc aaa                                  753
```

<210> SEQ ID NO 195
<211> LENGTH: 251
<212> TYPE: PRT
<213> ORGANISM: artificial sequence
<220> FEATURE:
<223> OTHER INFORMATION: synthetic peptide

<400> SEQUENCE: 195

```
Glu Leu Gln Leu Val Glu Ser Gly Pro Val Leu Val Lys Pro Thr Asp
1               5                   10                  15

Thr Leu Thr Leu Thr Cys Thr Val Ser Gly Phe Ser Leu Asn Asn Pro
            20                  25                  30

Arg Met Gly Val Ser Trp Ile Arg Gln Pro Pro Gly Lys Thr Leu Glu
        35                  40                  45

Trp Leu Ala His Ile Phe Pro Ser Asp Ala Lys Ala His Ser Ala Ser
    50                  55                  60

Leu Lys Ser Arg Leu Thr Ile Ser Lys Asp Thr Ser Lys Ser Gln Val
65                  70                  75                  80

Val Pro Thr Met Thr Asn Met Asp Pro Val Asp Thr Ala Thr Tyr Tyr
                85                  90                  95

Cys Ala Arg Ile Leu Gly Glu Tyr Tyr Pro Pro Ala Trp Phe Asp Pro
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Glu Leu Val Met Thr Gln
130                 135                 140

Ser Pro Asp Ser Leu Ala Val Ser Leu Gly Glu Arg Ala Thr Ile Asn
145                 150                 155                 160

Cys Lys Ser Ser Gln Ser Val Leu Tyr Ser Ser Asn Asn Lys Asn Tyr
                165                 170                 175

Leu Ala Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Leu Lys Ile Pro Tyr
225                 230                 235                 240

Thr Phe Gly Gln Gly Thr Lys Val Glu Ile Lys
                245                 250
```

<210> SEQ ID NO 196
<211> LENGTH: 354
<212> TYPE: DNA
<213> ORGANISM: artificial sequence
<220> FEATURE:
<223> OTHER INFORMATION: synthetic primer

<400> SEQUENCE: 196

```
cagctggagc agtctggacc tgaactgaag aagcctggag agacagtcac gatctcctgc    60
aaggcttctg ggtataccct cacgaagttc ggaatgaact gggtgaagca ggctccagga   120
aagggtttaa agtggatggg ctggatacac acctccactg gagagccaac atattctgat   180
gacttcaagg gacggtttgc cttctctttg gaaacgtctg ccagcactgc ctatttgcgg   240
atcaacaacc tcaaaaatga ggacatggct aaatacttct gtgccagagg tggtccttac   300 gtaagggggtg ctttggacta ctgggggtcaa ggaacctcag tcaccgtctc ctcc        354
```

-continued

<210> SEQ ID NO 197
<211> LENGTH: 118
<212> TYPE: PRT
<213> ORGANISM: artificial sequence
<220> FEATURE:
<223> OTHER INFORMATION: synthetic peptide

<400> SEQUENCE: 197

Gln Leu Glu Gln Ser Gly Pro Glu Leu Lys Lys Pro Gly Glu Thr Val
1               5                   10                  15

Thr Ile Ser Cys Lys Ala Ser Gly Tyr Thr Phe Thr Lys Phe Gly Met
            20                  25                  30

Asn Trp Val Lys Gln Ala Pro Gly Lys Gly Leu Lys Trp Met Gly Trp
        35                  40                  45

Ile His Thr Ser Thr Gly Glu Pro Thr Tyr Ser Asp Asp Phe Lys Gly
    50                  55                  60

Arg Phe Ala Phe Ser Leu Glu Thr Ser Ala Ser Thr Ala Tyr Leu Arg
65                  70                  75                  80

Ile Asn Asn Leu Lys Asn Glu Asp Met Ala Lys Tyr Phe Cys Ala Arg
                85                  90                  95

Gly Gly Pro Tyr Val Arg Gly Ala Leu Asp Tyr Trp Gly Gln Gly Thr
            100                 105                 110

Ser Val Thr Val Ser Ser
        115

<210> SEQ ID NO 198
<211> LENGTH: 333
<212> TYPE: DNA
<213> ORGANISM: artificial sequence
<220> FEATURE:
<223> OTHER INFORMATION: synthetic primer

<400> SEQUENCE: 198
gacattatcc tgatccaatc tccaccttct ttggctgtgt ctctagggca gagggccacc      60
atctcctgca gaaccagcga aaatgttgac ggatacggca ttagttttat aaactggtac     120
caacagaagc caggacagcc acccaaactc ctcatctatg ctgcatccca ccaaggatcc     180
ggggtccctg ccagatttag tggcagtggg tctgggacag acttcagcct caacatccat     240
cctttggagg aggatgatac tgcaatgtat ttctgtcacc aaagtaagaa ggttccgtgg     300
acgttcggtg gaggcaccaa gctggaaatc aaa                                  333

<210> SEQ ID NO 199
<211> LENGTH: 111
<212> TYPE: PRT
<213> ORGANISM: artificial sequence
<220> FEATURE:
<223> OTHER INFORMATION: synthetic peptide

<400> SEQUENCE: 199

Asp Ile Ile Leu Ile Gln Ser Pro Pro Ser Leu Ala Val Ser Leu Gly
1               5                   10                  15

Gln Arg Ala Thr Ile Ser Cys Arg Thr Ser Glu Asn Val Asp Gly Tyr
            20                  25                  30

Gly Ile Ser Phe Ile Asn Trp Tyr Gln Gln Lys Pro Gly Gln Pro Pro
        35                  40                  45

Lys Leu Leu Ile Tyr Ala Ala Ser His Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Leu Glu Glu Asp Asp Thr Ala Met Tyr Phe Cys His Gln Ser Lys
                85                  90                  95

Lys Val Pro Trp Thr Phe Gly Gly Gly Thr Lys Leu Glu Ile Lys
            100                 105                 110

<210> SEQ ID NO 200
<211> LENGTH: 366
<212> TYPE: DNA
<213> ORGANISM: artificial sequence
<220> FEATURE:
<223> OTHER INFORMATION: synthetic primer

<400> SEQUENCE: 200
caggtgcaac tgcggcagcc tggggctgag ctggtgaagc ctggggcctc agtgaagatg      60
tcctgcaagg cttctggcta cacatttacc agttacaata tgcactgggt aaagcagaca     120
cctggacagg gcctggaatg gattggagct atttatccag aaatggtga tacttcctac      180 aatcagaagt tcaaaggcaa ggccacattg actgcagaca atcctccag cacagcctac      240 atgcagctca gcagtctgac atctgaggac tctgcggtct attactgtgc aagatcgcac     300
tacggtagta actacgtaga ctactttgac tactggggcc aaggcacact agtcacagtc     360
tcgaca                                                                 366

<210> SEQ ID NO 201
<211> LENGTH: 122
<212> TYPE: PRT
<213> ORGANISM: artificial sequence
<220> FEATURE:
<223> OTHER INFORMATION: synthetic peptide

<400> SEQUENCE: 201

Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Thr
        115                 120

<210> SEQ ID NO 202
<211> LENGTH: 318
<212> TYPE: DNA
<213> ORGANISM: artificial sequence
<220> FEATURE:
<223> OTHER INFORMATION: synthetic primer

<400> SEQUENCE: 202
caaattgttc tctcccagtc tccagcaatc ctttctgcat ctccagggga gaaggtcaca      60

-continued

```
atgacttgca gggccagctc aagtttaagt tcatgcact ggtaccagca gaagccagga      120
tcctccccca aaccctggat ttatgccaca tccaacctgg cttctggagt ccctgctcgc      180
ttcagtggca gtgggtctgg gacctcttac tctctcacaa tcagcagagt ggaggctgaa      240
gatgctgcca cttatttctg ccatcagtgg agtagtaacc cgctcacgtt cggtgctggg      300
acaaaggtgg aaataaaa                                                    318
```

<210> SEQ ID NO 203
<211> LENGTH: 106
<212> TYPE: PRT
<213> ORGANISM: artificial sequence
<220> FEATURE:
<223> OTHER INFORMATION: synthetic peptide

<400> SEQUENCE: 203

```
Gln Ile Val Leu Ser Gln Ser Pro Ala Ile Leu Ser Ala Ser Pro Gly
 1               5                  10                  15

Glu Lys Val Thr Met Thr Cys Arg Ala Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Val Glu Ile Lys
            100                 105
```

<210> SEQ ID NO 204
<211> LENGTH: 21
<212> TYPE: DNA
<213> ORGANISM: artificial sequence
<220> FEATURE:
<223> OTHER INFORMATION: synthetic primer

<400> SEQUENCE: 204

```
cctcttcttg gtagcaacag c                                                 21
```

<210> SEQ ID NO 205
<211> LENGTH: 1491
<212> TYPE: DNA
<213> ORGANISM: artificial sequence
<220> FEATURE:
<223> OTHER INFORMATION: Human anti-CD3 3-148 VH-VL x anti-CD19 VL-VH

<400> SEQUENCE: 205

```
gagctgcagc tggtcgagtc tggcccagga ctggtgaagc cttcgggac cctgtccctc       60 acctgcgctg tctctggtgg ctccatcagc agtagaaact ggtggagttg gtccgccag      120 cccccaggga aggggctgga gtggattggt gatatctatc atagtgggag caccaactac     180
aacccgtccc tcaagagtcg agtcaccata tcagtagaca gtccaagaa ccagttctcc      240 ctgaagctga gctctgtgac cgccgcggac acggccgtgt attactgtgc gagtgggtat     300
accagctgtc gtgatgcttt tgatatctgg ggccaaggga caatggtcac cgtctcctca     360
ggtggtggtg gttctggcgg cggcggctcc ggtggtggtg gttctgagct cgtgatgact     420
cagtctccat cctccctgtc tgcatctgta ggagacagag tcaccatcac ttgccgggcg     480
```

```
agtcaggca ttggcaatta tttagcctgg tatcagcaga aaccagggca gcctcctaag    540
atgctcattt actgggcatc aatccgggaa tccggggtcc ctgaccgatt cagtggcagc    600
gggtctggga cagacttcac tctcaccatc agcagcctgc aggctgaaga tgtggcagtt    660
tactactgtc agcaatatta tagtaatcct cagacgttcg gccaagggac caaggtggaa    720
atcaaaggag gtggtggatc cgatatccag ctgacccagt ctccagcttc tttggctgtg    780
tctctagggc agagggccac catctcctgc aaggccagcc aaagtgttga ttatgatggt    840
gatagttatt tgaactggta ccaacagatt ccaggacagc cacccaaact cctcatctat    900
gatgcatcca atctagtttc tgggatccca cccaggttta gtggcagtgg gtctgggaca    960
gacttcaccc tcaacatcca tcctgtggag aaggtggatg ctgcaaccta tcactgtcag   1020
caaagtactg aggatccgtg gacgttcggt ggagggacca agctcgagat caaaggtggt   1080
ggtggttctg gcggcggcgg ctccggtggt ggtggttctc aggtgcagct gcagcagtct   1140
ggggctgagc tggtgaggcc tgggtcctca gtgaagattt cctgcaaggc ttctggctat   1200
gcattcagta gctactggat gaactgggtg aagcagaggc ctggacaggg tcttgagtgg   1260
attggacaga tttggcctgg agatggtgat actaactaca atggaaagtt caagggtaaa   1320
gccactctga ctgcagacga atcctccagc acagcctaca tgcaactcag cagcctagca   1380
tctgaggact ctgcggtcta tttctgtgca agacgggaga ctacgacggt aggccgttat   1440
tactatgcta tggactactg gggccaaggg accacggtca ccgtctcctc c            1491
```

<210> SEQ ID NO 206
<211> LENGTH: 497
<212> TYPE: PRT
<213> ORGANISM: artificial sequence
<220> FEATURE:
<223> OTHER INFORMATION: Human anti-CD3 3-148 VH-VL x anti-CD19 VL-VH

<400> SEQUENCE: 206

```
Glu Leu Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Arg
            20                  25                  30

Asn Trp Trp Ser Trp Val Arg Gln Pro Pro Gly Lys Gly Leu Glu Trp
        35                  40                  45

Ile Gly Asp Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Gly Tyr Thr Ser Cys Arg Asp Ala Phe Asp Ile Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Glu Leu Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Gly Ile Gly Asn Tyr Leu Ala Trp Tyr Gln Gln Lys Pro Gly
                165                 170                 175

Gln Pro Pro Lys Met Leu Ile Tyr Trp Ala Ser Ile Arg Glu Ser Gly
            180                 185                 190
```

Val Pro Asp Arg Phe Ser Gly Ser Gly Ser Gly Thr Asp Phe Thr Leu
            195                 200                 205

Thr Ile Ser Ser Leu Gln Ala Glu Asp Val Ala Val Tyr Tyr Cys Gln
        210                 215                 220

Gln Tyr Tyr Ser Asn Pro Gln Thr Phe Gly Gln Gly Thr Lys Val Glu
225                 230                 235                 240

Ile Lys Gly Gly Gly Gly Ser Asp Ile Gln Leu Thr Gln Ser Pro Ala
                245                 250                 255

Ser Leu Ala Val Ser Leu Gly Gln Arg Ala Thr Ile Ser Cys Lys Ala
            260                 265                 270

Ser Gln Ser Val Asp Tyr Asp Gly Asp Ser Tyr Leu Asn Trp Tyr Gln
        275                 280                 285

Gln Ile Pro Gly Gln Pro Pro Lys Leu Leu Ile Tyr Asp Ala Ser Asn
        290                 295                 300

Leu Val Ser Gly Ile Pro Pro Arg Phe Ser Gly Ser Gly Ser Gly Thr
305                 310                 315                 320

Asp Phe Thr Leu Asn Ile His Pro Val Glu Lys Val Asp Ala Ala Thr
                325                 330                 335

Tyr His Cys Gln Gln Ser Thr Glu Asp Pro Trp Thr Phe Gly Gly Gly
            340                 345                 350

Thr Lys Leu Glu Ile Lys Gly Gly Gly Gly Ser Gly Gly Gly Gly Ser
        355                 360                 365

Gly Gly Gly Gly Ser Gln Val Gln Leu Gln Gln Ser Gly Ala Glu Leu
        370                 375                 380

Val Arg Pro Gly Ser Ser Val Lys Ile Ser Cys Lys Ala Ser Gly Tyr
385                 390                 395                 400

Ala Phe Ser Ser Tyr Trp Met Asn Trp Val Lys Gln Arg Pro Gly Gln
                405                 410                 415

Gly Leu Glu Trp Ile Gly Gln Ile Trp Pro Gly Asp Gly Asp Thr Asn
            420                 425                 430

Tyr Asn Gly Lys Phe Lys Gly Lys Ala Thr Leu Thr Ala Asp Glu Ser
        435                 440                 445

Ser Ser Thr Ala Tyr Met Gln Leu Ser Ser Leu Ala Ser Glu Asp Ser
        450                 455                 460

Ala Val Tyr Phe Cys Ala Arg Arg Glu Thr Thr Thr Val Gly Arg Tyr
465                 470                 475                 480

Tyr Tyr Ala Met Asp Tyr Trp Gly Gln Gly Thr Thr Val Thr Val Ser
                485                 490                 495

Ser

<210> SEQ ID NO 207
<211> LENGTH: 1509
<212> TYPE: DNA
<213> ORGANISM: artificial sequence
<220> FEATURE:
<223> OTHER INFORMATION: Human anti-CD3 3-190 VH-VL x anti-CD19 VL-VH

<400> SEQUENCE: 207
gagctgcagc tggtcgagtg gggcgcagga ctgttgaagc cttcggagac cctgtccctc     60
acctgcgctg tctatggtgg gtccttcagt ggttactact ggagctggat ccgccagccc    120
ccagggaagg gcctggagtg gattggggaa atcaatcata gtggaagcac caactacaac    180
ccgtccctca gagtcgagt caccatatca gtagacacgt ccaagaacca gttctccctg    240
aagctgagct ctgtgaccgc cgcggacacg gctgtgtatt actgtgcgag aggccgaggc    300

```
cgattttgg ggtggttatt aggggctcc aactggttcg acccctgggg ccagggaacc      360
ctggtcaccg tctcctcagg tggtggtggt tctggcggcg gcggctccgg tggtggtggt      420
tctgagctcg tgatgaccca gtctccatcc tccctgtctg catctgtagg agacagagtc      480
accatcactt gccgggcgag tcagggcatt agcaattatt taaattggta tcagcagaaa      540
ccagggaaag cccctaagct cctgatctac gatgcatcca atttggaaac aggggtccca      600
tcaaggttca gtggcagtgg atctgggaca gatttcactc tcaccatcag cagtctgcaa      660
cctgaagatt ttgcaactta ctactgtcaa cagagttaca gtaccccgta cacttttggc      720
caggggacca aagtggatat caaaggaggt ggtggatccg atatccagct gacccagtct      780
ccagcttctt tggctgtgtc tctagggcag agggccacca tctcctgcaa ggccagccaa      840
agtgttgatt atgatggtga tagttatttg aactggtacc aacagattcc aggacagcca      900
cccaaactcc tcatctatga tgcatccaat ctagtttctg gatcccacc caggtttagt      960
ggcagtgggt ctgggacaga cttcacccte aacatccatc ctgtggagaa ggtggatgct     1020
gcaacctatc actgtcagca aagtactgag gatccgtgga cgttcggtgg agggaccaag     1080
ctcgagatca aggtggtgg tggttctggc ggcggcggct ccggtggtgg tggttctcag     1140
gtgcagctgc agcagtctgg ggctgagctg gtgaggcctg gtcctcagt gaagatttcc     1200
tgcaaggctt ctggctatgc attcagtagc tactggatga actgggtgaa gcagaggcct     1260
ggacagggtc ttgagtggat tggacagatt tggcctggag atggtgatac taactacaat     1320
ggaaagttca aggtaaagc cactctgact gcagacgaat cctccagcac agcctacatg     1380
caactcagca gcctagcatc tgaggactct gcggtctatt tctgtgcaag acgggagact     1440
acgacggtag ccgttatta ctatgctatg gactactggg gccaagggac cacggtcacc     1500
gtctcctcc                                                             1509
```

<210> SEQ ID NO 208
<211> LENGTH: 503
<212> TYPE: PRT
<213> ORGANISM: artificial sequence
<220> FEATURE:
<223> OTHER INFORMATION: Human anti-CD3 3-190 VH-VL x anti-CD19 VL-VH

<400> SEQUENCE: 208

```
Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Arg Phe Leu Gly Trp Leu Leu Gly Ser Asn Trp
            100                 105                 110

Phe Asp Pro Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Leu Val
    130                 135                 140
```

```
Met Thr Gln Ser Pro Ser Ser Leu Ser Ala Ser Val Gly Asp Arg Val
145                 150                 155                 160

Thr Ile Thr Cys Arg Ala Ser Gln Gly Ile Ser Asn Tyr Leu Asn Trp
            165                 170                 175

Tyr Gln Gln Lys Pro Gly Lys Ala Pro Lys Leu Leu Ile Tyr Asp Ala
        180                 185                 190

Ser Asn Leu Glu Thr Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Ser Tyr Ser Thr Pro Tyr Thr Phe Gly
225                 230                 235                 240

Gln Gly Thr Lys Val Asp Ile Lys Gly Gly Gly Ser Asp Ile Gln
            245                 250                 255

Leu Thr Gln Ser Pro Ala Ser Leu Ala Val Ser Leu Gly Gln Arg Ala
            260                 265                 270

Thr Ile Ser Cys Lys Ala Ser Gln Ser Val Asp Tyr Asp Gly Asp Ser
            275                 280                 285

Tyr Leu Asn Trp Tyr Gln Gln Ile Pro Gly Gln Pro Pro Lys Leu Leu
290                 295                 300

Ile Tyr Asp Ala Ser Asn Leu Val Ser Gly Ile Pro Pro Arg Phe Ser
305                 310                 315                 320

Gly Ser Gly Ser Gly Thr Asp Phe Thr Leu Asn Ile His Pro Val Glu
                325                 330                 335

Lys Val Asp Ala Ala Thr Tyr His Cys Gln Gln Ser Thr Glu Asp Pro
                340                 345                 350

Trp Thr Phe Gly Gly Gly Thr Lys Leu Glu Ile Lys Gly Gly Gly Gly
                355                 360                 365

Ser Gly Gly Gly Gly Ser Gly Gly Gly Ser Gln Val Gln Leu Gln
370                 375                 380

Gln Ser Gly Ala Glu Leu Val Arg Pro Gly Ser Ser Val Lys Ile Ser
385                 390                 395                 400

Cys Lys Ala Ser Gly Tyr Ala Phe Ser Ser Tyr Trp Met Asn Trp Val
                405                 410                 415

Lys Gln Arg Pro Gly Gln Gly Leu Glu Trp Ile Gly Gln Ile Trp Pro
        420                 425                 430

Gly Asp Gly Asp Thr Asn Tyr Asn Gly Lys Phe Lys Gly Lys Ala Thr
            435                 440                 445

Leu Thr Ala Asp Glu Ser Ser Thr Ala Tyr Met Gln Leu Ser Ser
        450                 455                 460

Leu Ala Ser Glu Asp Ser Ala Val Tyr Phe Cys Ala Arg Arg Glu Thr
465                 470                 475                 480

Thr Thr Val Gly Arg Tyr Tyr Tyr Ala Met Asp Tyr Trp Gly Gln Gly
                485                 490                 495

Thr Thr Val Thr Val Ser Ser
            500
```

<210> SEQ ID NO 209
<211> LENGTH: 1488
<212> TYPE: DNA
<213> ORGANISM: artificial sequence
<220> FEATURE:
<223> OTHER INFORMATION: Human anti-CD3 3-271 VH-VL x anti-CD19 VL-VH

<400> SEQUENCE: 209

```
gagctgcagc tggtcgagtg gggcgcagga ctgttgaagc cttcggagac cctgtccctc    60
acctgcgctg tctatggtgg gtccttcagt ggttactact ggagctggat ccgccagccc   120
ccagggaagg gctggagtg gattggggaa atcaatcata gtggaagcac caactacaac    180
ccgtccctca agagtcgagt caccatatca gtagacacgt ccaagaacca gttctccctg   240
aagctgagct ctgtgaccgc cgcggacacg gctgtgtatt actgtgcgag aggccctgac   300 cgaatgggc atggttttga tatctggggc caagggacaa tggtcaccgt ctcctcaggt    360
ggtggtggtt ctggcggcgg cggctccggt ggtggtggtt ctgagctcca gatgacccag   420
tctccatcct ccctgtctgc atctgtagga gacagagtca ccatcacttg ccgggcaagt   480
cagagcatta gcagctattt aaattggtat cagcagaaat cagggaaagc ccctaagctc   540
ctgatctatg ctgcatccag tttgcaaagt ggggtcccat caaggttcag tggcagtgga   600
tctgggacag atttcactct caccatcagt agtctgcaac tgaagatttt gcaacttat    660 tactgtcaac agagttacag tagcccgtgg acattcggcc aagggaccaa ggtggagatc   720
aaaggaggtg gtggatccga tatccagctg acccagtctc cagcttcttt ggctgtgtct   780
ctagggcaga gggccaccat ctcctgcaag gccagccaaa gtgttgatta tgatggtgat   840
agttatttga actggtacca acagattcca ggacagccac ccaaactcct catctatgat   900
gcatccaatc tagtttctgg gatcccaccc aggtttagtg gcagtgggtc tgggacagac   960
ttcaccctca acatccatcc tgtggagaag gtggatgctg caacctatca ctgtcagcaa  1020
agtactgagg atccgtggac gttcggtgga gggaccaagc tcgagatcaa aggtggtggt  1080
ggttctggcg gcggcggctc cggtggtggt ggttctcagg tgcagctgca gcagtctggg  1140
gctgagctgg tgaggcctgg gtcctcagtg aagatttcct gcaaggcttc tggctatgca  1200
ttcagtagct actggatgaa ctgggtgaag cagaggcctg acagggtct tgagtggatt   1260 ggacagattt ggcctggaga tggtgatact aactacaatg aaagttcaa gggtaaagcc   1320 actctgactg cagacgaatc ctccagcaca gcctacatgc aactcagcag cctagcatct  1380
gaggactctg cggtctattt ctgtgcaaga cgggagacta cgacggtagg ccgttattac  1440
tatgctatgg actactgggg ccaagggacc acggtcaccg tctcctcc               1488

<210> SEQ ID NO 210
<211> LENGTH: 496
<212> TYPE: PRT
<213> ORGANISM: artificial sequence
<220> FEATURE:
<223> OTHER INFORMATION: Human anti-CD3 3-271 VH-VL x anti-CD19 VL-VH

<400> SEQUENCE: 210

Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Arg Gly Pro Asp Arg Met Gly His Gly Phe Asp Ile Trp Gly Gln Gly
                100                 105                 110

Thr Met Val Thr Val Ser Ser Gly Gly Gly Ser Gly Gly Gly Gly
        115                 120                 125

Ser Gly Gly Gly Ser Glu Leu Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Ser Gly Lys
                165                 170                 175

Ala Pro Lys Leu Leu Ile Tyr Ala Ala Ser Ser Leu Gln Ser Gly Val
        180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
210                 215                 220

Ser Tyr Ser Ser Pro Trp Thr Phe Gly Gln Gly Thr Lys Val Glu Ile
225                 230                 235                 240

Lys Gly Gly Gly Gly Ser Asp Ile Gln Leu Thr Gln Ser Pro Ala Ser
                245                 250                 255

Leu Ala Val Ser Leu Gly Gln Arg Ala Thr Ile Ser Cys Lys Ala Ser
            260                 265                 270

Gln Ser Val Asp Tyr Asp Gly Asp Ser Tyr Leu Asn Trp Tyr Gln Gln
        275                 280                 285

Ile Pro Gly Gln Pro Pro Lys Leu Leu Ile Tyr Asp Ala Ser Asn Leu
        290                 295                 300

Val Ser Gly Ile Pro Pro Arg Phe Ser Gly Ser Gly Ser Gly Thr Asp
305                 310                 315                 320

Phe Thr Leu Asn Ile His Pro Val Glu Lys Val Asp Ala Ala Thr Tyr
                325                 330                 335

His Cys Gln Gln Ser Thr Glu Asp Pro Trp Thr Phe Gly Gly Gly Thr
            340                 345                 350

Lys Leu Glu Ile Lys Gly Gly Gly Ser Gly Gly Gly Gly Ser Gly
        355                 360                 365

Gly Gly Gly Ser Gln Val Gln Leu Gln Gln Ser Gly Ala Glu Leu Val
    370                 375                 380

Arg Pro Gly Ser Ser Val Lys Ile Ser Cys Lys Ala Ser Gly Tyr Ala
385                 390                 395                 400

Phe Ser Ser Tyr Trp Met Asn Trp Val Lys Gln Arg Pro Gly Gln Gly
                405                 410                 415

Leu Glu Trp Ile Gly Gln Ile Trp Pro Gly Asp Gly Asp Thr Asn Tyr
            420                 425                 430

Asn Gly Lys Phe Lys Gly Lys Ala Thr Leu Thr Ala Asp Glu Ser Ser
        435                 440                 445

Ser Thr Ala Tyr Met Gln Leu Ser Ser Leu Ala Ser Glu Asp Ser Ala
    450                 455                 460

Val Tyr Phe Cys Ala Arg Arg Glu Thr Thr Thr Val Gly Arg Tyr Tyr
465                 470                 475                 480

Tyr Ala Met Asp Tyr Trp Gly Gln Gly Thr Thr Val Thr Val Ser Ser
                485                 490                 495

<210> SEQ ID NO 211
<211> LENGTH: 1494
<212> TYPE: DNA

<213> ORGANISM: artificial sequence
<220> FEATURE:
<223> OTHER INFORMATION: Human anti-CD3 4-10 VH-VL x anti-CD19 VL-VH

<400> SEQUENCE: 211

```
gagctgcagc tggtcgagtc tgggggaggc ttggtacagc ctgggggtc cctgagactc      60
tcctgtgcag cctctggatt cacctttagc agctatgcca tgggctgggt ccgccaggct    120
ccagggaagg gctggagtg gtctcagct gttagtggta gtggtggtag cacatactac      180
gcagactccg tgaagggccg gttcaccatc tccagagaca attccaagaa cacgctgtat    240
ctgcaaatga acagcctgag agccgaggac acggccgtat attactgtgc gaaagccaaa    300
ttcctgggcc actactacgg tatggacgtc tggggccaag ggaccacggt caccgtctcc    360
tcaggtggtg gtggttctgg cggcggcggc tccgtggtgg gtggttctga gctccagatg    420
acccagtctc catcctccct gtctgcatct gtaggagaca gagtcaccat cacttgccgg    480
gcaagtcaga gcattagcag ctatttaaat tggtatcagc agaaaccagg gaaagcccct    540
aagctcctga tctatgctgc atccagtttg caaagtggag tcccatcaag gttcagcggc    600
agtggatctg ggacagagtt cactctcaca atcagcagcc tgcagcctga gattttgca    660
acttattact gtcttcagca taatgcttac ccgtacactt tcggccaggg gaccaaggtg    720
gaaatcaaag gaggtggtgg atccgatatc cagctgaccc agtctccagc ttctttggct    780
gtgtctctag gcagagggc caccatctcc tgcaaggcca gccaaagtgt tgattatgat    840
ggtgatagtt atttgaactg gtaccaacag attccaggac agccacccaa actcctcatc    900
tatgatgcat ccaatctagt ttctgggatc ccacccaggt ttagtggcag tgggtctggg    960
acagacttca ccctcaacat ccatcctgtg gagaaggtgg atgctgcaac ctatcactgt   1020
cagcaaagta ctgaggatcc gtggacgttc ggtggaggga ccaagctcga gatcaaaggt   1080
ggtggtggtt ctggcggcgg cggctccggt ggtggtggtt ctcaggtgca gctgcagcag   1140
tctggggctg agctggtgag gcctgggtcc tcagtgaaga tttcctgcaa ggcttctggc   1200
tatgcattca gtagctactg gatgaactgg gtgaagcaga ggcctggaca gggtcttgag   1260
tggattggac agatttggcc tggagatggt gatactaact acaatggaaa gttcaagggt   1320
aaagccactc tgactgcaga cgaatcctcc agcacagcct acatgcaact cagcagccta   1380
gcatctgagg actctgcggt ctatttctgt gcaagacggg agactacgac ggtaggccgt   1440
tattactatg ctatggacta ctggggccaa gggaccacgg tcaccgtctc ctcc          1494
```

<210> SEQ ID NO 212
<211> LENGTH: 498
<212> TYPE: PRT
<213> ORGANISM: artificial sequence
<220> FEATURE:
<223> OTHER INFORMATION: Human anti-CD3 4-10 VH-VL x anti-CD19 VL-VH

<400> SEQUENCE: 212

```
Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Val Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Ala Lys Phe Leu Gly His Tyr Tyr Gly Met Asp Val Trp Gly
                100                 105                 110

Gln Gly Thr Thr Val Thr Val Ser Gly Gly Gly Ser Gly Gly
                115                 120                 125

Gly Gly Ser Gly Gly Gly Ser Glu Leu Gln Met Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
                180                 185                 190

Gly Val Pro Ser Arg Phe Ser Gly Ser Gly Ser Gly Thr Glu Phe Thr
                195                 200                 205

Leu Thr Ile Ser Ser Leu Gln Pro Glu Asp Phe Ala Thr Tyr Tyr Cys
            210                 215                 220

Leu Gln His Asn Ala Tyr Pro Tyr Thr Phe Gly Gln Gly Thr Lys Val
225                 230                 235                 240

Glu Ile Lys Gly Gly Gly Gly Ser Asp Ile Gln Leu Thr Gln Ser Pro
                245                 250                 255

Ala Ser Leu Ala Val Ser Leu Gly Gln Arg Ala Thr Ile Ser Cys Lys
                260                 265                 270

Ala Ser Gln Ser Val Asp Tyr Asp Gly Asp Ser Tyr Leu Asn Trp Tyr
            275                 280                 285

Gln Gln Ile Pro Gly Gln Pro Pro Lys Leu Leu Ile Tyr Asp Ala Ser
            290                 295                 300

Asn Leu Val Ser Gly Ile Pro Pro Arg Phe Ser Gly Ser Gly Ser Gly
305                 310                 315                 320

Thr Asp Phe Thr Leu Asn Ile His Pro Val Glu Lys Val Asp Ala Ala
                325                 330                 335

Thr Tyr His Cys Gln Gln Ser Thr Glu Asp Pro Trp Thr Phe Gly Gly
                340                 345                 350

Gly Thr Lys Leu Glu Ile Lys Gly Gly Gly Gly Ser Gly Gly Gly Gly
                355                 360                 365

Ser Gly Gly Gly Gly Ser Gln Val Gln Leu Gln Gln Ser Gly Ala Glu
        370                 375                 380

Leu Val Arg Pro Gly Ser Ser Val Lys Ile Ser Cys Lys Ala Ser Gly
385                 390                 395                 400

Tyr Ala Phe Ser Ser Tyr Trp Met Asn Trp Val Lys Gln Arg Pro Gly
                405                 410                 415

Gln Gly Leu Glu Trp Ile Gly Gln Ile Trp Pro Gly Asp Gly Asp Thr
                420                 425                 430

Asn Tyr Asn Gly Lys Phe Lys Gly Lys Ala Thr Leu Thr Ala Asp Glu
                435                 440                 445

Ser Ser Ser Thr Ala Tyr Met Gln Leu Ser Ser Leu Ala Ser Glu Asp
            450                 455                 460

Ser Ala Val Tyr Phe Cys Ala Arg Arg Glu Thr Thr Thr Val Gly Arg
465                 470                 475                 480

Tyr Tyr Tyr Ala Met Asp Tyr Trp Gly Gln Gly Thr Thr Val Thr Val
                485                 490                 495
```

Ser Ser

<210> SEQ ID NO 213
<211> LENGTH: 1518
<212> TYPE: DNA
<213> ORGANISM: artificial sequence
<220> FEATURE:
<223> OTHER INFORMATION: Human anti-CD3 4-48 VH-VL x anti-CD19 VL-VH

<400> SEQUENCE: 213

```
gagctgcagc tggtcgagtc tggtcctgtg ctggtgaaac ccacagatac cctcacgctg      60
acttgcaccg tctctgggtt ctcactcaat aatcctagaa tgggtgtgag ctggatccgt     120
cagcccccag ggaagaccct ggagtggctt gcacacattt tccgagtga cgcaaaagcc     180
cacagtgcat ctctgaagag caggctcacc atctccaagg acacctccaa agccaggtg     240
gtccctacca tgaccaacat ggaccctgtg acacagcca catattactg cacggata      300
ttgggggaat actatccccc agcctggttc gaccccctggg gccagggaac cctggtcacc     360
gtctcctcag gtggtggtgg ttctggcggc ggcggctccg gtggtggtgg ttctgagctc     420
gtgatgcaca gtctccaga ctccctggct gtgtctctgg gcgagagggc caccatcaac      480
tgcaagtcca gccagagtgt tttatacagc tccaacaata gaactactt agcttggtac      540
cagcagaaac aggacagcc tcctaagctg ctcatttact gggcatctac ccggaatcc      600
ggggtccctg accgattcag tggcagcggg tctgggacag atttcactct caccatcagc      660
agcctgcagg ctgaagacgt ggcagtttat tactgtcagc aatatttgaa aatcccttat      720
acttttggcc aggggaccaa ggtggagatc aaaggaggtg gtggatccga tatccagctg      780
acccagtctc cagcttcttt ggctgtgtct ctagggcaga gggccaccat ctcctgcaag      840
gccagccaaa gtgttgatta tgatggtgat agttatttga actggtacca acagattcca      900
ggacagccac ccaaactcct catctatgat gcatccaatc tagtttctgg gatcccaccc      960
aggtttagtg gcagtgggtc tgggacagac ttcaccctca catccatcc tgtggagaag     1020
gtggatgctg caacctatca ctgtcagcaa agtactgagg atccgtggac gttcggtgga     1080
gggaccaagc tcgagatcaa aggtggtggt ggttctggcg gcggcggctc cggtggtggt     1140
ggttctcagg tgcagctgca gcagtctggg gctgagctgg tgaggcctgg gtcctcagtg     1200
aagatttcct gcaaggcttc tggctatgca ttcagtagct actggatgaa ctgggtgaag     1260
cagaggcctg gacagggtct tgagtggatt ggacagattt ggcctggaga tggtgatact     1320
aactacaatg gaaagttcaa gggtaaagcc actctgactg cagacgaatc ctccagcaca     1380
gcctacatgc aactcagcag cctagcatct gaggactctg cggtctattt ctgtgcaaga     1440
cgggagacta cgacggtagg ccgttattac tatgctatgg actactgggg ccaagggacc     1500
acggtcaccg tctcctcc                                                  1518
```

<210> SEQ ID NO 214
<211> LENGTH: 506
<212> TYPE: PRT
<213> ORGANISM: artificial sequence
<220> FEATURE:
<223> OTHER INFORMATION: Human anti-CD3 4-48 VH-VL x anti-CD19 VL-VH

<400> SEQUENCE: 214

Glu Leu Gln Leu Val Glu Ser Gly Pro Val Leu Val Lys Pro Thr Asp
 1               5                  10                  15

Thr Leu Thr Leu Thr Cys Thr Val Ser Gly Phe Ser Leu Asn Asn Pro

-continued

```
            20                  25                  30
Arg Met Gly Val Ser Trp Ile Arg Gln Pro Gly Lys Thr Leu Glu
            35                  40                  45
Trp Leu Ala His Ile Phe Pro Ser Asp Ala Lys Ala His Ser Ala Ser
        50                  55                  60
Leu Lys Ser Arg Leu Thr Ile Ser Lys Asp Thr Ser Lys Ser Gln Val
 65                  70                  75                  80
Val Pro Thr Met Thr Asn Met Asp Pro Val Asp Thr Ala Thr Tyr Tyr
                85                  90                  95
Cys Ala Arg Ile Leu Gly Glu Tyr Tyr Pro Ala Trp Phe Asp Pro
                100                 105                 110
Trp Gly Gln Gly Thr Leu Val Thr Val Ser Ser Gly Gly Gly Ser
                115                 120                 125
Gly Gly Gly Gly Ser Gly Gly Gly Ser Glu Leu Val Met Thr Gln
                130                 135                 140
Ser Pro Asp Ser Leu Ala Val Ser Leu Gly Glu Arg Ala Thr Ile Asn
145                 150                 155                 160
Cys Lys Ser Ser Gln Ser Val Leu Tyr Ser Ser Asn Asn Lys Asn Tyr
                165                 170                 175
Leu Ala Trp Tyr Gln Gln Lys Pro Gly Gln Pro Lys Leu Leu Ile
                180                 185                 190
Tyr Trp Ala Ser Thr Arg Glu Ser Gly Val Pro Asp Arg Phe Ser Gly
                195                 200                 205
Ser Gly Ser Gly Thr Asp Phe Thr Leu Thr Ile Ser Ser Leu Gln Ala
                210                 215                 220
Glu Asp Val Ala Val Tyr Tyr Cys Gln Gln Tyr Leu Lys Ile Pro Tyr
225                 230                 235                 240
Thr Phe Gly Gln Gly Thr Lys Val Glu Ile Lys Gly Gly Gly Gly Ser
                245                 250                 255
Asp Ile Gln Leu Thr Gln Ser Pro Ala Ser Leu Ala Val Ser Leu Gly
                260                 265                 270
Gln Arg Ala Thr Ile Ser Cys Lys Ala Ser Gln Ser Val Asp Tyr Asp
                275                 280                 285
Gly Asp Ser Tyr Leu Asn Trp Tyr Gln Gln Ile Pro Gly Gln Pro Pro
                290                 295                 300
Lys Leu Leu Ile Tyr Asp Ala Ser Asn Leu Val Ser Gly Ile Pro Pro
305                 310                 315                 320
Arg Phe Ser Gly Ser Gly Ser Gly Thr Asp Phe Thr Leu Asn Ile His
                325                 330                 335
Pro Val Glu Lys Val Asp Ala Ala Thr Tyr His Cys Gln Gln Ser Thr
                340                 345                 350
Glu Asp Pro Trp Thr Phe Gly Gly Thr Lys Leu Glu Ile Lys Gly
                355                 360                 365
Gly Gly Gly Ser Gly Gly Gly Gly Ser Gly Gly Gly Gly Ser Gln Val
                370                 375                 380
Gln Leu Gln Gln Ser Gly Ala Glu Leu Val Arg Pro Gly Ser Ser Val
385                 390                 395                 400
Lys Ile Ser Cys Lys Ala Ser Gly Tyr Ala Phe Ser Ser Tyr Trp Met
                405                 410                 415
Asn Trp Val Lys Gln Arg Pro Gly Gln Gly Leu Glu Trp Ile Gly Gln
                420                 425                 430
Ile Trp Pro Gly Asp Gly Asp Thr Asn Tyr Asn Gly Lys Phe Lys Gly
                435                 440                 445
```

Lys Ala Thr Leu Thr Ala Asp Glu Ser Ser Thr Ala Tyr Met Gln
        450                 455                 460

Leu Ser Ser Leu Ala Ser Glu Asp Ser Ala Val Tyr Phe Cys Ala Arg
465                 470                 475                 480

Arg Glu Thr Thr Thr Val Gly Arg Tyr Tyr Tyr Ala Met Asp Tyr Trp
                485                 490                 495

Gly Gln Gly Thr Thr Val Thr Val Ser Ser
            500                 505

<210> SEQ ID NO 215
<211> LENGTH: 1491
<212> TYPE: DNA
<213> ORGANISM: artificial sequence
<220> FEATURE:
<223> OTHER INFORMATION: anti-CD19 VL-VH x human anti-CD3 3-148 VH-VL

<400> SEQUENCE: 215

```
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaaggtggtg gtggttctgg cggcggcggc     360
tccggtggtg gtggttctca ggtgcagctg cagcagtctg ggctgagct ggtgaggcct      420
gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca gcctacat gcaactcagc agcctagcat ctgaggactc tgcggtctat       660
ttctgtgcaa gacgggagac tacgacggta ggccgttatt actatgctat ggactactgg     720
ggccaaggga ccacggtcac cgtctcctcc ggaggtggtg gatccgagct gcagctggtc     780
gagtctggcc caggactggt gaagccttcg ggaccctgt ccctcacctg cgctgtctct      840
ggtggctcca tcagcagtag aaactggtgg agttgggtcc gccagccccc agggaagggg    900
ctggagtgga ttggtgatat ctatcatagt gggagcacca actacaaccc gtccctcaag    960
agtcgagtca ccatatcagt agacaagtcc aagaaccagt tctccctgaa gctgagctct   1020
gtgaccgccg cggacacggc cgtgtattac tgtgcgagtg gtataccag ctgtcgtgat    1080
gctttgata tctggggcca agggacaatg gtcaccgtct cctcaggtgg tggtggttct    1140
ggcggcggcg gctccggtgg tggtggttct gagctcgtga tgactcagtc tccatcctcc   1200
ctgtctgcat ctgtaggaga cagagtcacc atcacttgcc gggcgagtca gggcattggc   1260
aattatttag cctggtatca gcagaaacca gggcagcctc taagatgct catttactgg    1320
gcatcaatcc gggaatccgg ggtccctgac cgattcagtg gcagcgggtc tgggacagac   1380
ttcactctca ccatcagcag cctgcaggct gaagatgtgg cagtttacta ctgtcagcaa   1440
tattatagta atcctcagac gttcggccaa gggaccaagg tggaaatcaa a            1491
```

<210> SEQ ID NO 216
<211> LENGTH: 497
<212> TYPE: PRT
<213> ORGANISM: artificial sequence
<220> FEATURE:

-continued

<223> OTHER INFORMATION: anti-CD19 VL-VH x human anti-CD3 3-148 VH-VL

<400> SEQUENCE: 216

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Glu
                245                 250                 255

Leu Gln Leu Val Glu Ser Gly Pro Gly Leu Val Lys Pro Ser Gly Thr
            260                 265                 270

Leu Ser Leu Thr Cys Ala Val Ser Gly Gly Ser Ile Ser Ser Arg Asn
        275                 280                 285

Trp Trp Ser Trp Val Arg Gln Pro Pro Gly Lys Gly Leu Glu Trp Ile
    290                 295                 300

Gly Asp Ile Tyr His Ser Gly Ser Thr Asn Tyr Asn Pro Ser Leu Lys
305                 310                 315                 320

Ser Arg Val Thr Ile Ser Val Asp Lys Ser Lys Asn Gln Phe Ser Leu
                325                 330                 335

Lys Leu Ser Ser Val Thr Ala Ala Asp Thr Ala Val Tyr Tyr Cys Ala
            340                 345                 350

Ser Gly Tyr Thr Ser Cys Arg Asp Ala Phe Asp Ile Trp Gly Gln Gly
        355                 360                 365

Thr Met Val Thr Val Ser Ser Gly Gly Gly Ser Gly Gly Gly Gly
    370                 375                 380

Ser Gly Gly Gly Gly Ser Glu Leu Val Met Thr Gln Ser Pro Ser Ser
385                 390                 395                 400
```

```
Leu Ser Ala Ser Val Gly Asp Arg Val Thr Ile Thr Cys Arg Ala Ser
                405                 410                 415

Gln Gly Ile Gly Asn Tyr Leu Ala Trp Tyr Gln Gln Lys Pro Gly Gln
            420                 425                 430

Pro Pro Lys Met Leu Ile Tyr Trp Ala Ser Ile Arg Glu Ser Gly Val
        435                 440                 445

Pro Asp Arg Phe Ser Gly Ser Gly Ser Gly Thr Asp Phe Thr Leu Thr
    450                 455                 460

Ile Ser Ser Leu Gln Ala Glu Asp Val Ala Val Tyr Tyr Cys Gln Gln
465                 470                 475                 480

Tyr Tyr Ser Asn Pro Gln Thr Phe Gly Gln Gly Thr Lys Val Glu Ile
                485                 490                 495

Lys

<210> SEQ ID NO 217
<211> LENGTH: 1509
<212> TYPE: DNA
<213> ORGANISM: artificial sequence
<220> FEATURE:
<223> OTHER INFORMATION: anti-CD19 VL-VH x human anti-CD3 3-190 VH-VL

<400> SEQUENCE: 217
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaag ctcgagatc aaaggtggtg gtggttctgg cggcggcggc     360
tccggtggtg gtggttctca ggtgcagctg cagcagtctg ggctgagct ggtgaggcct     420 gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca cagcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgagct gcagctggtc     780
gagtggggcg caggactgtt gaagccttcg gagaccctgt ccctcacctg cgctgtctat     840
ggtgggtcct tcagtggtta ctactggagc tggatccgcc agccccagg gaaggggctg     900 gagtggattg ggaaatcaa tcatagtgga agcaccaact acaacccgtc cctcaagagt     960
cgagtcacca tatcagtaga cacgtccaag aaccagttct ccctgaagct gagctctgtg    1020
accgccgcgg acacggctgt gtattactgt gcgagaggcc gaggccgatt tttggggtgg    1080
ttattagggg gctccaactg gttcgacccc tggggccagg gaaccctggt caccgtctcc    1140
tcaggtggtg gtggttctgg cggcggcggc tccggtggtg gtggttctga gctcgtgatg    1200
acccagtctc catcctccct gtctgcatct gtaggagaca gagtcaccat cacttgccgg    1260
gcgagtcagg gcattagcaa ttatttaaat tggtatcagc agaaaccagg gaaagcccct    1320
aagctcctga tctacgatgc atccaatttg gaaacagggg tcccatcaag gttcagtggc    1380
agtggatctg ggacagattt cactctcacc atcagcagtc tgcaacctga agattttgca    1440
acttactact gtcaacagag ttacagtacc ccgtacactt ttggccaggg gaccaaagtg    1500
``` gatatcaaa                                                       1509

<210> SEQ ID NO 218
<211> LENGTH: 503
<212> TYPE: PRT
<213> ORGANISM: artificial sequence
<220> FEATURE:
<223> OTHER INFORMATION: anti-CD19 VL-VH x human anti-CD3 3-190 VH-VL

<400> SEQUENCE: 218

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Glu
                245                 250                 255

Leu Gln Leu Val Glu Trp Gly Ala Gly Leu Leu Lys Pro Ser Glu Thr
            260                 265                 270

Leu Ser Leu Thr Cys Ala Val Tyr Gly Gly Ser Phe Ser Gly Tyr Tyr
        275                 280                 285

Trp Ser Trp Ile Arg Gln Pro Pro Gly Lys Gly Leu Glu Trp Ile Gly
    290                 295                 300

Glu Ile Asn His Ser Gly Ser Thr Asn Tyr Asn Pro Ser Leu Lys Ser
305                 310                 315                 320

Arg Val Thr Ile Ser Val Asp Thr Ser Lys Asn Gln Phe Ser Leu Lys
                325                 330                 335

Leu Ser Ser Val Thr Ala Ala Asp Thr Ala Val Tyr Tyr Cys Ala Arg
            340                 345                 350

```
Gly Arg Gly Arg Phe Leu Gly Trp Leu Leu Gly Ser Asn Trp Phe
            355                 360                 365
Asp Pro Trp Gly Gln Gly Thr Leu Val Thr Val Ser Ser Gly Gly Gly
    370                 375                 380
Gly Ser Gly Gly Gly Ser Gly Gly Gly Ser Glu Leu Val Met
385                 390                 395                 400
Thr Gln Ser Pro Ser Ser Leu Ser Ala Ser Val Gly Asp Arg Val Thr
                405                 410                 415
Ile Thr Cys Arg Ala Ser Gln Gly Ile Ser Asn Tyr Leu Asn Trp Tyr
            420                 425                 430
Gln Gln Lys Pro Gly Lys Ala Pro Lys Leu Leu Ile Tyr Asp Ala Ser
            435                 440                 445
Asn Leu Glu Thr Gly Val Pro Ser Arg Phe Ser Gly Ser Gly Ser Gly
        450                 455                 460
Thr Asp Phe Thr Leu Thr Ile Ser Ser Leu Gln Pro Glu Asp Phe Ala
465                 470                 475                 480
Thr Tyr Tyr Cys Gln Gln Ser Tyr Ser Thr Pro Tyr Thr Phe Gly Gln
                485                 490                 495
Gly Thr Lys Val Asp Ile Lys
            500

<210> SEQ ID NO 219
<211> LENGTH: 1488
<212> TYPE: DNA
<213> ORGANISM: artificial sequence
<220> FEATURE:
<223> OTHER INFORMATION: anti-CD19 VL-VH x human anti-CD3 3-271 VH-VL

<400> SEQUENCE: 219
gatatccagc tgacccagtc tccagcttct ttggctgtgt ctctagggca gagggccacc      60
atctcctgca aggccagcca agtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg agggaccaa gctcgagatc aaaggtggtg gtggttctgg cggcggcggc     360
tccggtggtg gtggttctca ggtgcagctg cagcagtctg ggctgagct ggtgaggcct     420
gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca gcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgagct gcagctggtc     780
gagtggggcg caggactgtt gaagccttcg gagaccctgt ccctcacctg cgctgtctat     840
ggtgggtcct tcagtggtta ctactggagc tggatccgcc agcccccagg aaggggctg     900
gagtggattg ggaaatcaa tcatagtgga agcaccaact acaacccgtc cctcaagagt     960
cgagtcacca tatcagtaga cacgtccaag aaccagttct ccctgaagct gagctctgtg    1020
accgccgcgg acacggctgt gtattactgt gcgagaggcc ctgaccgaat ggggcatggt    1080
tttgatatct ggggccaagg gacaatggtc accgtctcct caggtggtgg tggttctggc    1140
ggcggcggct ccggtggtgg tggttctgag ctccagatga cccagtctcc atcctccctg    1200
```

-continued

```
tctgcatctg taggagacag agtcaccatc acttgccggg caagtcagag cattagcagc  1260
tatttaaatt ggtatcagca gaaatcaggg aaagccccta agctcctgat ctatgctgca  1320
tccagtttgc aaagtggggt cccatcaagg ttcagtggca gtggatctgg gacagatttc  1380
actctcacca tcagtagtct gcaacctgaa gattttgcaa cttattactg tcaacagagt  1440
tacagtagcc cgtggacatt cggccaaggg accaaggtgg agatcaaa              1488
```

<210> SEQ ID NO 220
<211> LENGTH: 496
<212> TYPE: PRT
<213> ORGANISM: artificial sequence
<220> FEATURE:
<223> OTHER INFORMATION: anti-CD19 VL-VH x human anti-CD3 3-271 VH-VL

<400> SEQUENCE: 220

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Glu
                245                 250                 255

Leu Gln Leu Val Glu Trp Gly Ala Gly Leu Leu Lys Pro Ser Glu Thr
            260                 265                 270

Leu Ser Leu Thr Cys Ala Val Tyr Gly Gly Ser Phe Ser Gly Tyr Tyr
        275                 280                 285

Trp Ser Trp Ile Arg Gln Pro Pro Gly Lys Gly Leu Glu Trp Ile Gly
    290                 295                 300

Glu Ile Asn His Ser Gly Ser Thr Asn Tyr Asn Pro Ser Leu Lys Ser
```

```
                305                 310                 315                 320
Arg Val Thr Ile Ser Val Asp Thr Ser Lys Asn Gln Phe Ser Leu Lys
                    325                 330                 335

Leu Ser Ser Val Thr Ala Ala Asp Thr Ala Val Tyr Tyr Cys Ala Arg
                    340                 345                 350

Gly Pro Asp Arg Met Gly His Gly Phe Asp Ile Trp Gly Gln Gly Thr
                    355                 360                 365

Met Val Thr Val Ser Ser Gly Gly Gly Ser Gly Gly Gly Gly Ser
370                 375                 380

Gly Gly Gly Gly Ser Glu Leu Gln Met Thr Gln Ser Pro Ser Ser Leu
385                 390                 395                 400

Ser Ala Ser Val Gly Asp Arg Val Thr Ile Thr Cys Arg Ala Ser Gln
                    405                 410                 415

Ser Ile Ser Ser Tyr Leu Asn Trp Tyr Gln Gln Lys Ser Gly Lys Ala
                    420                 425                 430

Pro Lys Leu Leu Ile Tyr Ala Ala Ser Ser Leu Gln Ser Gly Val Pro
                    435                 440                 445

Ser Arg Phe Ser Gly Ser Gly Ser Gly Thr Asp Phe Thr Leu Thr Ile
        450                 455                 460

Ser Ser Leu Gln Pro Glu Asp Phe Ala Thr Tyr Tyr Cys Gln Gln Ser
465                 470                 475                 480

Tyr Ser Ser Pro Trp Thr Phe Gly Gln Gly Thr Lys Val Glu Ile Lys
                    485                 490                 495
```

<210> SEQ ID NO 221
<211> LENGTH: 1494
<212> TYPE: DNA
<213> ORGANISM: artificial sequence
<220> FEATURE:
<223> OTHER INFORMATION: anti-CD19 VL-VH x human anti-CD3 4-10 VH-VL

<400> SEQUENCE: 221

```
gatatccagc tgacccagtc tccagcttct ttggctgtgt ctctagggca gagggccacc      60
atctcctgca aggccagcca aagtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat actgtcagc aaagtactga ggatccgtgg     300
acgttcggtg agggaccaa gctcgagatc aaaggtggtg gtggttctgg cggcggcggc     360
tccggtggtg gtggttctca ggtgcagctg cagcagtctg ggctgagct ggtgaggcct     420
gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca gcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgagct gcagctggtc     780
gagtctgggg gaggcttggt acagcctggg gggtccctga gactcctg tgcagcctct     840
ggattcacct ttagcagcta tgccatgggc tgggtccgcc aggctccagg aaggggctg     900
gagtgggtct cagctgttag tggtagtggt ggtagcacat actacgcaga ctccgtgaag     960
ggccggttca ccatctccag agacaattcc aagaacacgc tgtatctgca aatgaacagc    1020
```

```
ctgagagccg aggacacggc cgtatattac tgtgcgaaag ccaaattcct gggccactac    1080
tacggtatgg acgtctgggg ccaagggacc acggtcaccg tctcctcagg tggtggtggt    1140
tctggcggcg gcggctccgg tggtggtggt tctgagctcc agatgaccca gtctccatcc    1200
tccctgtctg catctgtagg agacagagtc accatcactt gccgggcaag tcagagcatt    1260
agcagctatt taaattggta tcagcagaaa ccagggaaag cccctaagct cctgatctat    1320
gctgcatcca gtttgcaaag tggagtccca tcaaggttca gcggcagtgg atctgggaca    1380
gagttcactc tcacaatcag cagcctgcag cctgaagatt ttgcaactta ttactgtctt    1440
cagcataatg cttacccgta cactttcggc caggggacca aggtggaaat caaa          1494
```

<210> SEQ ID NO 222
<211> LENGTH: 498
<212> TYPE: PRT
<213> ORGANISM: artificial sequence
<220> FEATURE:
<223> OTHER INFORMATION: anti-CD19 VL-VH x human anti-CD3 4-10 VH-VL

<400> SEQUENCE: 222

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240

Gly Gln Gly Thr Thr Val Thr Val Ser Ser Gly Gly Gly Gly Ser Glu
                245                 250                 255

Leu Gln Leu Val Glu Ser Gly Gly Gly Leu Val Gln Pro Gly Gly Ser
            260                 265                 270

Leu Arg Leu Ser Cys Ala Ala Ser Gly Phe Thr Phe Ser Ser Tyr Ala
        275                 280                 285
```

Met Gly Trp Val Arg Gln Ala Pro Gly Lys Gly Leu Glu Trp Val Ser
        290                 295                 300

Ala Val Ser Gly Ser Gly Gly Ser Thr Tyr Tyr Ala Asp Ser Val Lys
305                 310                 315                 320

Gly Arg Phe Thr Ile Ser Arg Asp Asn Ser Lys Asn Thr Leu Tyr Leu
                325                 330                 335

Gln Met Asn Ser Leu Arg Ala Glu Asp Thr Ala Val Tyr Tyr Cys Ala
                340                 345                 350

Lys Ala Lys Phe Leu Gly His Tyr Tyr Gly Met Asp Val Trp Gly Gln
        355                 360                 365

Gly Thr Thr Val Thr Val Ser Ser Gly Gly Gly Ser Gly Gly Gly
        370                 375                 380

Gly Ser Gly Gly Gly Gly Ser Glu Leu Gln Met Thr Gln Ser Pro Ser
385                 390                 395                 400

Ser Leu Ser Ala Ser Val Gly Asp Arg Val Thr Ile Thr Cys Arg Ala
                405                 410                 415

Ser Gln Ser Ile Ser Ser Tyr Leu Asn Trp Tyr Gln Gln Lys Pro Gly
                420                 425                 430

Lys Ala Pro Lys Leu Leu Ile Tyr Ala Ala Ser Ser Leu Gln Ser Gly
        435                 440                 445

Val Pro Ser Arg Phe Ser Gly Ser Gly Ser Gly Thr Glu Phe Thr Leu
450                 455                 460

Thr Ile Ser Ser Leu Gln Pro Glu Asp Phe Ala Thr Tyr Tyr Cys Leu
465                 470                 475                 480

Gln His Asn Ala Tyr Pro Tyr Thr Phe Gly Gly Gly Thr Lys Val Glu
                485                 490                 495

Ile Lys

<210> SEQ ID NO 223
<211> LENGTH: 1518
<212> TYPE: DNA
<213> ORGANISM: artificial sequence
<220> FEATURE:
<223> OTHER INFORMATION: anti-CD19 VL-VH x human anti-CD3 4-48 VH-VL

<400> SEQUENCE: 223

```
gatatccagc tgacccagtc tccagcttct ttggctgtgt ctctagggca gagggccacc      60
atctcctgca aggccagcca agtgttgat tatgatggtg atagttattt gaactggtac     120
caacagattc caggacagcc acccaaactc ctcatctatg atgcatccaa tctagtttct     180
gggatcccac ccaggtttag tggcagtggg tctgggacag acttcaccct caacatccat     240
cctgtggaga aggtggatgc tgcaacctat cactgtcagc aaagtactga ggatccgtgg     300
acgttcggtg gagggaccaa gctcgagatc aaaggtggtg gtggttctgg cggcggcggc     360
tccggtggtg gtggttctca ggtgcagctg cagcagtctg ggctgagct ggtgaggcct     420 gggtcctcag tgaagatttc ctgcaaggct tctggctatg cattcagtag ctactggatg     480
aactgggtga agcagaggcc tggacagggt cttgagtgga ttggacagat ttggcctgga     540
gatggtgata ctaactacaa tggaaagttc aagggtaaag ccactctgac tgcagacgaa     600
tcctccagca cagcctacat gcaactcagc agcctagcat ctgaggactc tgcggtctat     660
ttctgtgcaa gacgggagac tacgacggta ggccgttatt actatgctat ggactactgg     720
ggccaaggga ccacggtcac cgtctcctcc ggaggtggtg gatccgagct gcagctggtc     780
gagtctggtc ctgtgctggt gaaacccaca gatacccctca cgctgacttg caccgtctct     840
```

```
gggttctcac tcaataatcc tagaatgggt gtgagctgga tccgtcagcc cccagggaag    900
accctggagt ggcttgcaca cattttccg agtgacgcaa aagcccacag tgcatctctg    960
aagagcaggc tcaccatctc caaggacacc tccaaaagcc aggtggtccc taccatgacc   1020
aacatggacc tgtggacac agccacatat tactgtgcac ggatattggg ggaatactat    1080 ccccagcct ggttcgaccc ctggggccag ggaaccctgg tcaccgtctc ctcaggtggt    1140
ggtggttctg gcggcggcgg ctccggtggt ggtggttctg agctcgtgat gacacagtct   1200
ccagactccc tggctgtgtc tctgggcgag agggccacca tcaactgcaa gtccagccag   1260
agtgttttat acagctccaa caataagaac tacttagctt ggtaccagca gaaaccagga   1320
cagcctccta agctgctcat ttactgggca tctacccggg aatccggggt ccctgaccga   1380
ttcagtggca gcgggtctgg gacagatttc actctcacca tcagcagcct gcaggctgaa   1440
gacgtggcag tttattactg tcagcaatat ttgaaaatcc cttatacttt tggccagggg   1500
accaaggtgg agatcaaa                                                 1518
```

<210> SEQ ID NO 224
<211> LENGTH: 506
<212> TYPE: PRT
<213> ORGANISM: artificial sequence
<220> FEATURE:
<223> OTHER INFORMATION: anti-CD19 VL-VH x human anti-CD3 4-48 VH-VL

<400> SEQUENCE: 224

```
Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160

Asn Trp Val Lys Gln Arg Pro Gly Gln Gly Leu Glu Trp Ile Gly Gln
                165                 170                 175

Ile Trp Pro Gly Asp Gly Asp Thr Asn Tyr Asn Gly Lys Phe Lys Gly
            180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Tyr Ala Met Asp Tyr Trp
225                 230                 235                 240
```

Gly Gln Gly Thr Thr Val Thr Val Ser Ser Gly Gly Gly Ser Glu
            245                 250                 255

Leu Gln Leu Val Glu Ser Gly Pro Val Leu Lys Pro Thr Asp Thr
            260                 265                 270

Leu Thr Leu Thr Cys Thr Val Ser Gly Phe Ser Leu Asn Asn Pro Arg
            275                 280                 285

Met Gly Val Ser Trp Ile Arg Gln Pro Pro Gly Lys Thr Leu Glu Trp
            290                 295                 300

Leu Ala His Ile Phe Pro Ser Asp Ala Lys Ala His Ser Ala Ser Leu
305                 310                 315                 320

Lys Ser Arg Leu Thr Ile Ser Lys Asp Thr Ser Lys Ser Gln Val Val
            325                 330                 335

Pro Thr Met Thr Asn Met Asp Pro Val Asp Thr Ala Thr Tyr Tyr Cys
            340                 345                 350

Ala Arg Ile Leu Gly Glu Tyr Tyr Pro Pro Ala Trp Phe Asp Pro Trp
            355                 360                 365

Gly Gln Gly Thr Leu Val Thr Val Ser Ser Gly Gly Gly Ser Gly
            370                 375                 380

Gly Gly Gly Ser Gly Gly Gly Ser Glu Leu Val Met Thr Gln Ser
385                 390                 395                 400

Pro Asp Ser Leu Ala Val Ser Leu Gly Glu Arg Ala Thr Ile Asn Cys
            405                 410                 415

Lys Ser Ser Gln Ser Val Leu Tyr Ser Ser Asn Asn Lys Asn Tyr Leu
            420                 425                 430

Ala Trp Tyr Gln Gln Lys Pro Gly Gln Pro Pro Lys Leu Leu Ile Tyr
            435                 440                 445

Trp Ala Ser Thr Arg Glu Ser Gly Val Pro Asp Arg Phe Ser Gly Ser
            450                 455                 460

Gly Ser Gly Thr Asp Phe Thr Leu Thr Ile Ser Ser Leu Gln Ala Glu
465                 470                 475                 480

Asp Val Ala Val Tyr Tyr Cys Gln Gln Tyr Leu Lys Ile Pro Tyr Thr
            485                 490                 495

Phe Gly Gln Gly Thr Lys Val Glu Ile Lys
            500                 505

<210> SEQ ID NO 225
<211> LENGTH: 1485
<212> TYPE: DNA
<213> ORGANISM: artificial sequence
<220> FEATURE:
<223> OTHER INFORMATION: Human anti-CD3 3-148 VH-VL x anti-EpCAM 5-10
      VH-VL

<400> SEQUENCE: 225
gagctgcagc tggtcgagtc tggcccagga ctggtgaagc cttcggggac cctgtccctc      60
acctgcgctg tctctggtgg ctccatcagc agtagaaact ggtggagttg gtccgccag      120 cccccaggga aggggctgga gtggattggt gatatctatc atagtgggag caccaactac     180
aacccgtccc tcaagagtcg agtcaccata tcagtagaca gtccaagaa ccagttctcc      240 ctgaagctga gctctgtgac cgccgcggac acggccgtgt attactgtgc gagtgggtat     300
accagctgtc gtgatgcttt tgatatctgg ggccaaggga caatggtcac cgtctcctca     360
ggtggtggtg gttctggcgg cggcggctcc ggtggtggtg gttctgagct cgtgatgact     420
cagtctccat cctccctgtc tgcatctgta ggagacagag tcaccatcac ttgccgggcg     480

```
agtcaggca ttggcaatta tttagcctgg tatcagcaga accagggca gcctcctaag    540
atgctcattt actgggcatc aatccgggaa tccgggtcc ctgaccgatt cagtggcagc    600
gggtctggga cagacttcac tctcaccatc agcagcctgc aggctgaaga tgtggcagtt    660
tactactgtc agcaatatta tagtaatcct cagacgttcg gccaagggac caaggtggaa    720
atcaaaggag gtggtggatc cgaggtgcag ctgctcgagc agtctggagc tgagctggta    780
aggcctggga cttcagtgaa gatatcctgc aaggcttctg gatacgcctt cactaactac    840
tggctaggtt gggtaaagca gaggcctgga catggacttg agtggattgg agatattttc    900
cctggaagtg gtaatatcca ctacaatgag aagttcaagg gcaaagccac actgactgca    960
gacaaatctt cgagcacagc ctatatgcag ctcagtagcc tgacatttga ggactctgct   1020
gtctatttct gtgcaagact gaggaactgg gacgagccta tggactactg gggccaaggg   1080
accacggtca ccgtctcctc aggtggtggt ggttctggcg gcggcggctc cggtggtggt   1140
ggttctgagc tcgtgatgac acagtctcca tcctccctga ctgtgacagc aggagagaag   1200
gtcactatga gctgcaagtc cagtcagagt ctgttaaaca gtggaaatca aagaactac   1260
ttgacctggt accagcagaa accagggcag cctcctaaac tgttgatcta ctgggcatcc   1320
actagggaat ctggggtccc tgatcgcttc acaggcagtg gatctggaac agatttcact   1380
ctcaccatca gcagtgtgca ggctgaagac ctggcagttt attactgtca gaatgattat   1440
agttatccgc tcacgttcgg tgctgggacc aagcttgaga tcaaa            1485
```

<210> SEQ ID NO 226
<211> LENGTH: 495
<212> TYPE: PRT
<213> ORGANISM: artificial sequence
<220> FEATURE:
<223> OTHER INFORMATION: Human anti-CD3 3-148 VH-VL x anti-EpCAM 5-10 VH-VL

<400> SEQUENCE: 226

```
Glu Leu Gln Leu Val Glu Ser Gly Pro Gly Leu Val Lys Pro Ser Gly
1               5                   10                  15

Thr Leu Ser Leu Thr Cys Ala Val Ser Gly Gly Ser Ile Ser Ser Arg
            20                  25                  30

Asn Trp Trp Ser Trp Val Arg Gln Pro Pro Gly Lys Gly Leu Glu Trp
        35                  40                  45

Ile Gly Asp Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Gly Tyr Thr Ser Cys Arg Asp Ala Phe Asp Ile Trp Gly Gln
            100                 105                 110

Gly Thr Met Val Thr Val Ser Ser Gly Gly Gly Ser Gly Gly Gly
        115                 120                 125

Gly Ser Gly Gly Gly Gly Ser Glu Leu Val Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Gly Ile Gly Asn Tyr Leu Ala Trp Tyr Gln Gln Lys Pro Gly
                165                 170                 175

Gln Pro Pro Lys Met Leu Ile Tyr Trp Ala Ser Ile Arg Glu Ser Gly
```

```
                180              185              190
Val Pro Asp Arg Phe Ser Gly Ser Gly Ser Gly Thr Asp Phe Thr Leu
            195              200              205
Thr Ile Ser Ser Leu Gln Ala Glu Asp Val Ala Val Tyr Tyr Cys Gln
        210              215              220
Gln Tyr Tyr Ser Asn Pro Gln Thr Phe Gly Gln Gly Thr Lys Val Glu
225              230              235              240
Ile Lys Gly Gly Gly Gly Ser Glu Val Gln Leu Leu Glu Gln Ser Gly
            245              250              255
Ala Glu Leu Val Arg Pro Gly Thr Ser Val Lys Ile Ser Cys Lys Ala
        260              265              270
Ser Gly Tyr Ala Phe Thr Asn Tyr Trp Leu Gly Trp Val Lys Gln Arg
    275              280              285
Pro Gly His Gly Leu Glu Trp Ile Gly Asp Ile Phe Pro Gly Ser Gly
        290              295              300
Asn Ile His Tyr Asn Glu Lys Phe Lys Gly Lys Ala Thr Leu Thr Ala
305              310              315              320
Asp Lys Ser Ser Ser Thr Ala Tyr Met Gln Leu Ser Ser Leu Thr Phe
            325              330              335
Glu Asp Ser Ala Val Tyr Phe Cys Ala Arg Leu Arg Asn Trp Asp Glu
        340              345              350
Pro Met Asp Tyr Trp Gly Gln Gly Thr Thr Val Thr Val Ser Ser Gly
        355              360              365
Gly Gly Ser Gly Gly Gly Gly Ser Gly Gly Gly Gly Ser Glu Leu
    370              375              380
Val Met Thr Gln Ser Pro Ser Ser Leu Thr Val Thr Ala Gly Glu Lys
385              390              395              400
Val Thr Met Ser Cys Lys Ser Ser Gln Ser Leu Leu Asn Ser Gly Asn
            405              410              415
Gln Lys Asn Tyr Leu Thr Trp Tyr Gln Gln Lys Pro Gly Gln Pro Pro
        420              425              430
Lys Leu Leu Ile Tyr Trp Ala Ser Thr Arg Glu Ser Gly Val Pro Asp
    435              440              445
Arg Phe Thr Gly Ser Gly Ser Gly Thr Asp Phe Thr Leu Thr Ile Ser
    450              455              460
Ser Val Gln Ala Glu Asp Leu Ala Val Tyr Tyr Cys Gln Asn Asp Tyr
465              470              475              480
Ser Tyr Pro Leu Thr Phe Gly Ala Gly Thr Lys Leu Glu Ile Lys
            485              490              495

<210> SEQ ID NO 227
<211> LENGTH: 1503
<212> TYPE: DNA
<213> ORGANISM: artificial sequence
<220> FEATURE:
<223> OTHER INFORMATION: Human anti-CD3 3-190 VH-VL x anti- EpCAM 5-10
      VH-VL

<400> SEQUENCE: 227
gagctgcagc tggtcgagtg gggcgcagga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca gagtcgagt caccatatca gtagacacgt ccaagaacca gttctccctg     240
aagctgagct ctgtgaccgc cgcggacacg gctgtgtatt actgtgcgag aggccgaggc     300
```

```
cgattttttgg ggtggttatt aggggggctcc aactggttcg acccctgggg ccagggaacc    360
ctggtcaccg tctcctcagg tggtggtggt tctggcggcg gcggctccgg tggtggtggt    420
tctgagctcg tgatgaccca gtctccatcc tccctgtctg catctgtagg agacagagtc    480
accatcactt gccgggcgag tcagggcatt agcaattatt taaattggta tcagcagaaa    540
ccagggaaag cccctaagct cctgatctac gatgcatcca atttggaaac aggggtccca    600
tcaaggttca gtggcagtgg atctgggaca gatttcactc tcaccatcag cagtctgcaa    660
cctgaagatt ttgcaactta ctactgtcaa cagagttaca gtaccccgta cacttttggc    720
caggggacca aagtggatat caaaggaggt ggtggatccg aggtgcagct gctcgagcag    780
tctggagctg agctggtaag gcctgggact tcagtgaaga tatcctgcaa ggcttctgga    840
tacgccttca ctaactactg gctaggttgg gtaaagcaga ggcctggaca tggacttgag    900
tggattggag atattttccc tggaagtggt aatatccact acaatgagaa gttcaagggc    960
aaagccacac tgactgcaga caaatcttcg agcacagcct atatgcagct cagtagcctg   1020
acatttgagg actctgctgt ctatttctgt gcaagactga ggaactggga cgagcctatg   1080
gactactggg gccaagggac cacggtcacc gtctcctcag gtggtggtgg ttctggcggc   1140
ggcggctccg gtggtggtgg ttctgagctc gtgatgacac agtctccatc ctccctgact   1200
gtgacagcag agagaaaggt cactatgagc tgcaagtcca gtcagagtct gttaaacagt   1260
ggaaatcaaa agaactactt gacctggtac cagcagaaac agggcagcc tcctaaactg   1320
ttgatctact gggcatccac tagggaatct ggggtccctg atcgcttcac aggcagtgga   1380
tctggaacag atttcactct caccatcagc agtgtgcagg ctgaagacct ggcagtttat   1440
tactgtcaga tgattatag ttatccgctc acgttcggtg ctgggaccaa gcttgagatc   1500
aaa                                                                  1503

<210> SEQ ID NO 228
<211> LENGTH: 501
<212> TYPE: PRT
<213> ORGANISM: artificial sequence
<220> FEATURE:
<223> OTHER INFORMATION: Human anti-CD3 3-190 VH-VL x anti- EpCAM 5-10
      VH-VL

<400> SEQUENCE: 228

Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Arg Phe Leu Gly Trp Leu Leu Gly Ser Asn Trp
            100                 105                 110

Phe Asp Pro Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Leu Val
```

```
                130             135             140
Met Thr Gln Ser Pro Ser Ser Leu Ser Ala Ser Val Gly Asp Arg Val
145                 150                 155                 160

Thr Ile Thr Cys Arg Ala Ser Gln Gly Ile Ser Asn Tyr Leu Asn Trp
                165                 170                 175

Tyr Gln Gln Lys Pro Gly Lys Ala Pro Lys Leu Leu Ile Tyr Asp Ala
            180                 185                 190

Ser Asn Leu Glu Thr Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Tyr Thr Phe Gly
225                 230                 235                 240

Gln Gly Thr Lys Val Asp Ile Lys Gly Gly Gly Ser Glu Val Gln
                245                 250                 255

Leu Leu Glu Gln Ser Gly Ala Glu Leu Val Arg Pro Gly Thr Ser Val
                260                 265                 270

Lys Ile Ser Cys Lys Ala Ser Gly Tyr Ala Phe Thr Asn Tyr Trp Leu
                275                 280                 285

Gly Trp Val Lys Gln Arg Pro Gly His Gly Leu Glu Trp Ile Gly Asp
    290                 295                 300

Ile Phe Pro Gly Ser Gly Asn Ile His Tyr Asn Glu Lys Phe Lys Gly
305                 310                 315                 320

Lys Ala Thr Leu Thr Ala Asp Lys Ser Ser Thr Ala Tyr Met Gln
                325                 330                 335

Leu Ser Ser Leu Thr Phe Glu Asp Ser Ala Val Tyr Phe Cys Ala Arg
                340                 345                 350

Leu Arg Asn Trp Asp Glu Pro Met Asp Tyr Trp Gly Gln Gly Thr Thr
            355                 360                 365

Val Thr Val Ser Ser Gly Gly Gly Ser Gly Gly Gly Gly Ser Gly
    370                 375                 380

Gly Gly Gly Ser Glu Leu Val Met Thr Gln Ser Pro Ser Ser Leu Thr
385                 390                 395                 400

Val Thr Ala Gly Glu Lys Val Thr Met Ser Cys Lys Ser Ser Gln Ser
                405                 410                 415

Leu Leu Asn Ser Gly Asn Gln Lys Asn Tyr Leu Thr Trp Tyr Gln Gln
            420                 425                 430

Lys Pro Gly Gln Pro Pro Lys Leu Leu Ile Tyr Trp Ala Ser Thr Arg
        435                 440                 445

Glu Ser Gly Val Pro Asp Arg Phe Thr Gly Ser Gly Ser Gly Thr Asp
    450                 455                 460

Phe Thr Leu Thr Ile Ser Ser Val Gln Ala Glu Asp Leu Ala Val Tyr
465                 470                 475                 480

Tyr Cys Gln Asn Asp Tyr Ser Tyr Pro Leu Thr Phe Gly Ala Gly Thr
                485                 490                 495

Lys Leu Glu Ile Lys
            500

<210> SEQ ID NO 229
<211> LENGTH: 1482
<212> TYPE: DNA
<213> ORGANISM: artificial sequence
<220> FEATURE:
<223> OTHER INFORMATION: Human anti-CD3 3-271 VH-VL x anti- EpCAM 5-10
      VH-VL
```

-continued

<400> SEQUENCE: 229

```
gagctgcagc tggtcgagtg gggcgcagga ctgttgaagc cttcggagac cctgtccctc      60
acctgcgctg tctatggtgg gtccttcagt ggttactact ggagctggat ccgccagccc     120
ccagggaagg gctggagtg gattgggaa atcaatcata gtggaagcac caactacaac       180
ccgtccctca agagtcgagt caccatatca gtagacacgt ccaagaacca gttctccctg     240
aagctgagct ctgtgaccgc cgcggacacg gctgtgtatt actgtgcgag aggccctgac     300
cgaatggggc atggttttga tatctggggc caagggacaa tggtcaccgt ctcctcaggt     360
ggtggtggtt ctggcggcgg cggctccggt ggtggtggtt ctgagctcca gatgacccag     420
tctccatcct ccctgtctgc atctgtagga gacagagtca ccatcacttg ccgggcaagt     480
cagagcatta gcagctattt aaattggtat cagcagaaat cagggaaagc ccctaagctc     540
ctgatctatg ctgcatccag tttgcaaagt ggggtcccat caaggttcag tggcagtgga     600
tctgggacag atttcactct caccatcagt agtctgcaac tgaagatttt gcaacttat     660
tactgtcaac agagttacag tagcccgtgg acattcggcc aagggaccaa ggtggagatc     720
aaaggaggtg gtggatccga ggtgcagctg ctcgagcagt ctggagctga gctggtaagg     780
cctgggactt cagtgaagat atcctgcaag gcttctggat acgccttcac taactactgg     840
ctaggttggg taaagcagag gcctggacat ggacttgagt ggattggaga tattttccct     900
ggaagtggta atatccacta caatgagaag ttcaagggca aagccacact gactgcagac     960
aaatcttcga gcacagccta tatgcagctc agtagcctga catttgagga ctctgctgtc    1020
tatttctgtg caagactgag gaactgggac gagcctatgg actactgggg ccaagggacc    1080
acggtcaccg tctcctcagg tggtggtggt tctggcggcg cggctccgg tggtggtggt     1140
tctgagctcg tgatgacaca gtctccatcc tccctgactg tgacagcagg agagaaggtc    1200
actatgagct gcaagtccag tcagagtctg ttaaacagtg gaaatcaaaa gaactacttg    1260
acctggtacc agcagaaacc agggcagcct cctaaactgt tgatctactg ggcatccact    1320
agggaatctg gggtccctga tcgcttcaca ggcagtggat ctggaacaga tttcactctc    1380
accatcagca gtgtgcaggc tgaagacctg gcagtttatt actgtcagaa tgattatagt    1440
tatccgctca cgttcggtgc tgggaccaag cttgagatca aa                       1482
```

<210> SEQ ID NO 230
<211> LENGTH: 494
<212> TYPE: PRT
<213> ORGANISM: artificial sequence
<220> FEATURE:
<223> OTHER INFORMATION: Human anti-CD3 3-271 VH-VL x anti- EpCAM 5-10 VH-VL

<400> SEQUENCE: 230

```
Glu Leu Gln Leu Val Glu Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80
```

```
Lys Leu Ser Ser Val Thr Ala Ala Asp Thr Ala Val Tyr Tyr Cys Ala
                85                  90                  95

Arg Gly Pro Asp Arg Met Gly His Gly Phe Asp Ile Trp Gly Gln Gly
            100                 105                 110

Thr Met Val Thr Val Ser Ser Gly Gly Gly Ser Gly Gly Gly Gly
            115                 120                 125

Ser Gly Gly Gly Ser Glu Leu Gln Met Thr Gln Ser Pro Ser Ser
130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Ser Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
    210                 215                 220

Ser Tyr Ser Ser Pro Trp Thr Phe Gly Gln Gly Thr Lys Val Glu Ile
225                 230                 235                 240

Lys Gly Gly Gly Gly Ser Glu Val Gln Leu Leu Glu Gln Ser Gly Ala
            245                 250                 255

Glu Leu Val Arg Pro Gly Thr Ser Val Lys Ile Ser Cys Lys Ala Ser
            260                 265                 270

Gly Tyr Ala Phe Thr Asn Tyr Trp Leu Gly Trp Val Lys Gln Arg Pro
            275                 280                 285

Gly His Gly Leu Glu Trp Ile Gly Asp Ile Phe Pro Gly Ser Gly Asn
            290                 295                 300

Ile His Tyr Asn Glu Lys Phe Lys Gly Lys Ala Thr Leu Thr Ala Asp
305                 310                 315                 320

Lys Ser Ser Ser Thr Ala Tyr Met Gln Leu Ser Ser Leu Thr Phe Glu
                325                 330                 335

Asp Ser Ala Val Tyr Phe Cys Ala Arg Leu Arg Asn Trp Asp Glu Pro
            340                 345                 350

Met Asp Tyr Trp Gly Gln Gly Thr Thr Val Thr Val Ser Ser Gly Gly
            355                 360                 365

Gly Gly Ser Gly Gly Gly Ser Gly Gly Gly Ser Glu Leu Val
            370                 375                 380

Met Thr Gln Ser Pro Ser Ser Leu Thr Val Thr Ala Gly Glu Lys Val
385                 390                 395                 400

Thr Met Ser Cys Lys Ser Ser Gln Ser Leu Leu Asn Ser Gly Asn Gln
                405                 410                 415

Lys Asn Tyr Leu Thr Trp Tyr Gln Gln Lys Pro Gly Gln Pro Pro Lys
            420                 425                 430

Leu Leu Ile Tyr Trp Ala Ser Thr Arg Glu Ser Gly Val Pro Asp Arg
            435                 440                 445

Phe Thr Gly Ser Gly Ser Gly Thr Asp Phe Thr Leu Thr Ile Ser Ser
            450                 455                 460

Val Gln Ala Glu Asp Leu Ala Val Tyr Tyr Cys Gln Asn Asp Tyr Ser
465                 470                 475                 480

Tyr Pro Leu Thr Phe Gly Ala Gly Thr Lys Leu Glu Ile Lys
            485                 490
```

<210> SEQ ID NO 231
<211> LENGTH: 1488
<212> TYPE: DNA
<213> ORGANISM: artificial sequence
<220> FEATURE:
<223> OTHER INFORMATION: Human anti-CD3 4-10 VH-VL x anti- EpCAM 5-10 VH-VL

<400> SEQUENCE: 231

```
gagctgcagc tggtcgagtc tgggggaggc ttggtacagc ctgggggtc cctgagactc      60
tcctgtgcag cctctggatt cacctttagc agctatgcca tgggctgggt ccgccaggct     120
ccagggaagg gctggagtg gtctcagct gttagtggta gtggtggtag cacatactac       180
gcagactccg tgaagggccg gttcaccatc tccagagaca attccaagaa cacgctgtat     240
ctgcaaatga acagcctgag agccgaggac acggccgtat attactgtgc gaaagccaaa     300
ttcctgggcc actactacgg tatggacgtc tggggccaag gaccacggt caccgtctcc      360
tcaggtggtg gtggttctgg cggcggcgg tccggtggtg gtggttctga gctccagatg     420
acccagtctc catcctccct gtctgcatct gtaggagaca gagtcaccat cacttgccgg     480
gcaagtcaga gcattagcag ctatttaaat tggtatcagc agaaaccagg gaaagcccct    540
aagctcctga tctatgctgc atccagtttg caaagtggag tcccatcaag gttcagcggc    600
agtggatctg gacagagtt cactctcaca atcagcagcc tgcagcctga gattttgca     660
acttattact gtcttcagca taatgcttac ccgtacactt tcggccaggg gaccaaggtg   720
gaaatcaaag gaggtggtgg atccgaggtg cagctgctcg agcagtctgg agctgagctg   780
gtaaggcctg gacttcagt gaagatatcc tgcaaggctt ctggatacgc cttcactaac   840
tactggctag gttgggtaaa gcagaggcct ggacatggac ttgagtggat tggagatatt   900
tccctggaa gtggtaatat ccactacaat gagaagttca aggcaaagc cacactgact    960
gcagacaaat cttcgagcac agcctatatg cagctcagta gcctgacatt tgaggactct  1020
gctgtctatt tctgtgcaag actgaggaac tgggacgagc ctatggacta ctggggccaa  1080
gggaccacgg tcaccgtctc ctcaggtggt ggtggttctg gcggcggcgg ctccggtggt  1140
ggtggttctg agctcgtgat gacacagtct ccatcctccc tgactgtgac agcaggagag  1200
aaggtcacta tgagctgcaa gtccagtcag agtctgttaa acagtggaaa tcaaaagaac  1260
tacttgacct ggtaccagca gaaaccaggg cagcctccta aactgttgat ctactgggca  1320
tccactaggg aatctggggt ccctgatcgc ttcacaggca gtggatctgg aacagatttc  1380
actctcacca tcagcagtgt gcaggctgaa gacctggcag tttattactg tcagaatgat  1440
tatagttatc cgctcacgtt cggtgctggg accaagcttg agatcaaa                1488
```

<210> SEQ ID NO 232
<211> LENGTH: 496
<212> TYPE: PRT
<213> ORGANISM: artificial sequence
<220> FEATURE:
<223> OTHER INFORMATION: Human anti-CD3 4-10 VH-VL x anti- EpCAM 5-10 VH-VL

<400> SEQUENCE: 232

Glu Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

-continued

Ser Ala Val Ser Gly Ser Gly Gly Ser Thr Tyr Tyr Ala Asp Ser Val
    50              55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Lys Phe Leu Gly His Tyr Tyr Gly Met Asp Val Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Glu Leu Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Glu Phe Thr
        195                 200                 205

Leu Thr Ile Ser Ser Leu Gln Pro Glu Asp Phe Ala Thr Tyr Tyr Cys
210                 215                 220

Leu Gln His Asn Ala Tyr Pro Tyr Thr Phe Gly Gln Gly Thr Lys Val
225                 230                 235                 240

Glu Ile Lys Gly Gly Gly Gly Ser Glu Val Gln Leu Leu Glu Gln Ser
                245                 250                 255

Gly Ala Glu Leu Val Arg Pro Gly Thr Ser Val Lys Ile Ser Cys Lys
            260                 265                 270

Ala Ser Gly Tyr Ala Phe Thr Asn Tyr Trp Leu Gly Trp Val Lys Gln
        275                 280                 285

Arg Pro Gly His Gly Leu Glu Trp Ile Gly Asp Ile Phe Pro Gly Ser
    290                 295                 300

Gly Asn Ile His Tyr Asn Glu Lys Phe Lys Gly Lys Ala Thr Leu Thr
305                 310                 315                 320

Ala Asp Lys Ser Ser Ser Thr Ala Tyr Met Gln Leu Ser Ser Leu Thr
                325                 330                 335

Phe Glu Asp Ser Ala Val Tyr Phe Cys Ala Arg Leu Arg Asn Trp Asp
            340                 345                 350

Glu Pro Met Asp Tyr Trp Gly Gln Gly Thr Thr Val Thr Val Ser Ser
        355                 360                 365

Gly Gly Gly Gly Ser Gly Gly Gly Gly Ser Gly Gly Gly Gly Ser Glu
    370                 375                 380

Leu Val Met Thr Gln Ser Pro Ser Ser Leu Thr Val Thr Ala Gly Glu
385                 390                 395                 400

Lys Val Thr Met Ser Cys Lys Ser Ser Gln Ser Leu Leu Asn Ser Gly
                405                 410                 415

Asn Gln Lys Asn Tyr Leu Thr Trp Tyr Gln Gln Lys Pro Gly Gln Pro
            420                 425                 430

Pro Lys Leu Leu Ile Tyr Trp Ala Ser Thr Arg Glu Ser Gly Val Pro
        435                 440                 445

Asp Arg Phe Thr Gly Ser Gly Ser Gly Thr Asp Phe Thr Leu Thr Ile
    450                 455                 460

Ser Ser Val Gln Ala Glu Asp Leu Ala Val Tyr Tyr Cys Gln Asn Asp
465                 470                 475                 480

Tyr Ser Tyr Pro Leu Thr Phe Gly Ala Gly Thr Lys Leu Glu Ile Lys
            485                 490                 495

<210> SEQ ID NO 233
<211> LENGTH: 1512
<212> TYPE: DNA
<213> ORGANISM: artificial sequence
<220> FEATURE:
<223> OTHER INFORMATION: Human anti-CD3 4-48 VH-VL x anti- EpCAM 5-10
      VH-VL

<400> SEQUENCE: 233

```
gagctgcagc tggtcgagtc tggtcctgtg ctggtgaaac ccacagatac cctcacgctg      60
acttgcaccg tctctgggtt ctcactcaat aatcctagaa tgggtgtgag ctggatccgt     120
cagcccccag ggaagaccct ggagtggctt gcacacattt ttccgagtga cgcaaaagcc     180
cacagtgcat ctctgaagag caggctcacc atctccaagg acacctccaa aagccaggtg     240
gtccctacca tgaccaacat ggaccctgtg acacagcca catattactg tgcacggata     300
ttgggggaat actatccccc agcctggttc gaccctggg gccagggaac cctggtcacc     360
gtctcctcag gtggtggtgg ttctggcggc ggcggctccg gtggtggtgg ttctgagctc     420
gtgatgacac agtctccaga ctccctggct gtgtctctgg gcgagagggc caccatcaac     480
tgcaagtcca gccagagtgt tttatacagc tccaacaata gaaactactt agcttggtac     540
cagcagaaac aggacagcc tcctaagctg ctcatttact gggcatctac ccgggaatcc     600
ggggtccctg accgattcag tggcagcggg tctgggacag atttcactct caccatcagc     660
agcctgcagg ctgaagacgt ggcagtttat tactgtcagc aatatttgaa aatcccttat     720
acttttggcc aggggaccaa ggtggagatc aaaggaggtg gtggatccga ggtgcagctg     780
ctcgagcagt ctggagctga gctggtaagg cctgggactt cagtgaagat atcctgcaag     840
gcttctggat acgccttcac taactactgg ctaggttggg taaagcagag gcctggacat     900
ggacttgagt ggattggaga tattttccct ggaagtggta atatccacta caatgagaag     960
ttcaagggca agccacact gactgcagac aaatcttcga gcacagccta tatgcagctc    1020
agtagcctga catttgagga ctctgctgtc tatttctgtg caagactgag gaactgggac    1080
gagcctatgg actactgggg ccaagggacc acggtcaccg tctcctcagg tggtggtggt    1140
tctggcggcg gcggctccgg tggtggtggt tctgagctcg tgatgacaca gtctccatcc    1200
tccctgactg tgacagcagg agagaaggtc actatgagct gcaagtccag tcagagtctg    1260
ttaaacagtg gaaatcaaaa gaactacttg acctggtacc agcagaaacc agggcagcct    1320
cctaaactgt tgatctactg ggcatccact agggaatctg ggtccctga tcgcttcaca    1380 ggcagtggat ctggaacaga tttcactctc accatcagca gtgtgcaggc tgaagacctg    1440
gcagtttatt actgtcagaa tgattatagt tatccgctca cgttcggtgc tgggaccaag    1500
cttgagatca aa                                                        1512
```

<210> SEQ ID NO 234
<211> LENGTH: 504
<212> TYPE: PRT
<213> ORGANISM: artificial sequence
<220> FEATURE:
<223> OTHER INFORMATION: Human anti-CD3 4-48 VH-VL x anti- EpCAM 5-10
      VH-VL

<400> SEQUENCE: 234

-continued

```
Glu Leu Gln Leu Val Glu Ser Gly Pro Val Leu Val Lys Pro Thr Asp
1               5                   10                  15

Thr Leu Thr Leu Thr Cys Thr Val Ser Gly Phe Ser Leu Asn Asn Pro
                20                  25                  30

Arg Met Gly Val Ser Trp Ile Arg Gln Pro Pro Gly Lys Thr Leu Glu
            35                  40                  45

Trp Leu Ala His Ile Phe Pro Ser Asp Ala Lys Ala His Ser Ala Ser
        50                  55                  60

Leu Lys Ser Arg Leu Thr Ile Ser Lys Asp Thr Ser Lys Ser Gln Val
65                  70                  75                  80

Val Pro Thr Met Thr Asn Met Asp Pro Val Asp Thr Ala Thr Tyr Tyr
                85                  90                  95

Cys Ala Arg Ile Leu Gly Glu Tyr Tyr Pro Pro Ala Trp Phe Asp Pro
                100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Glu Leu Val Met Thr Gln
130                 135                 140

Ser Pro Asp Ser Leu Ala Val Ser Leu Gly Glu Arg Ala Thr Ile Asn
145                 150                 155                 160

Cys Lys Ser Ser Gln Ser Val Leu Tyr Ser Ser Asn Asn Lys Asn Tyr
                165                 170                 175

Leu Ala Trp Tyr Gln Gln Lys Pro Gly Gln Pro Pro Lys Leu Leu Ile
                180                 185                 190

Tyr Trp Ala Ser Thr Arg Glu Ser Gly Val Pro Asp Arg Phe Ser Gly
                195                 200                 205

Ser Gly Ser Gly Thr Asp Phe Thr Leu Thr Ile Ser Ser Leu Gln Ala
210                 215                 220

Glu Asp Val Ala Val Tyr Tyr Cys Gln Gln Tyr Leu Lys Ile Pro Tyr
225                 230                 235                 240

Thr Phe Gly Gln Gly Thr Lys Val Glu Ile Lys Gly Gly Gly Gly Ser
                245                 250                 255

Glu Val Gln Leu Leu Glu Gln Ser Gly Ala Glu Leu Val Arg Pro Gly
                260                 265                 270

Thr Ser Val Lys Ile Ser Cys Lys Ala Ser Gly Tyr Ala Phe Thr Asn
                275                 280                 285

Tyr Trp Leu Gly Trp Val Lys Gln Arg Pro Gly His Gly Leu Glu Trp
                290                 295                 300

Ile Gly Asp Ile Phe Pro Gly Ser Gly Asn Ile His Tyr Asn Glu Lys
305                 310                 315                 320

Phe Lys Gly Lys Ala Thr Leu Thr Ala Asp Lys Ser Ser Ser Thr Ala
                325                 330                 335

Tyr Met Gln Leu Ser Ser Leu Thr Phe Glu Asp Ser Ala Val Tyr Phe
                340                 345                 350

Cys Ala Arg Leu Arg Asn Trp Asp Glu Pro Met Asp Tyr Trp Gly Gln
                355                 360                 365

Gly Thr Thr Val Thr Val Ser Ser Gly Gly Gly Gly Ser Gly Gly Gly
            370                 375                 380

Gly Ser Gly Gly Gly Gly Ser Glu Leu Val Met Thr Gln Ser Pro Ser
385                 390                 395                 400

Ser Leu Thr Val Thr Ala Gly Glu Lys Val Thr Met Ser Cys Lys Ser
                405                 410                 415
```

```
Ser Gln Ser Leu Leu Asn Ser Gly Asn Gln Lys Asn Tyr Leu Thr Trp
            420                 425                 430
Tyr Gln Gln Lys Pro Gly Gln Pro Pro Lys Leu Leu Ile Tyr Trp Ala
            435                 440                 445
Ser Thr Arg Glu Ser Gly Val Pro Asp Arg Phe Thr Gly Ser Gly Ser
            450                 455                 460
Gly Thr Asp Phe Thr Leu Thr Ile Ser Ser Val Gln Ala Glu Asp Leu
465                 470                 475                 480
Ala Val Tyr Tyr Cys Gln Asn Asp Tyr Ser Tyr Pro Leu Thr Phe Gly
                485                 490                 495
Ala Gly Thr Lys Leu Glu Ile Lys
            500

<210> SEQ ID NO 235
<211> LENGTH: 1485
<212> TYPE: DNA
<213> ORGANISM: artificial sequence
<220> FEATURE:
<223> OTHER INFORMATION: anti-EpCAM 5-10 VL-VH x human anti-CD3 3-148
      VH-VL

<400> SEQUENCE: 235
```

| | | | | | |
|---|---|---|---|---|---|
| gagctcgtga | tgacacagtc | tccatcctcc | ctgactgtga | cagcaggaga | gaaggtcact | 60 |
| atgagctgca | agtccagtca | gagtctgtta | aacagtggaa | atcaaaagaa | ctacttgacc | 120 |
| tggtaccagc | agaaaccagg | gcagcctcct | aaactgttga | tctactgggc | atccactagg | 180 |
| gaatctgggg | tccctgatcg | cttcacaggc | agtggatctg | gaacagattt | cactctcacc | 240 |
| atcagcagtg | tgcaggctga | agacctggca | gtttattact | gtcagaatga | ttatagttat | 300 |
| ccgctcacgt | tcggtgctgg | gaccaagctt | gagatcaaag | gtggtggtgg | ttctggcggc | 360 |
| ggcggctccg | gtggtggtgg | ttctgaggtg | cagctgctcg | agcagtctgg | agctgagctg | 420 |
| gtaaggcctg | ggacttcagt | gaagatatcc | tgcaaggctt | ctggatacgc | cttcactaac | 480 |
| tactggctag | gttgggtaaa | gcagaggcct | ggacatggac | ttgagtggat | tggagatatt | 540 |
| ttccctggaa | gtggtaatat | ccactacaat | gagaagttca | agggcaaagc | cacactgact | 600 |
| gcagacaaat | cttcgagcac | agcctatatg | cagctcagta | gcctgacatt | tgaggactct | 660 |
| gctgtctatt | tctgtgcaag | actgaggaac | tgggacgagc | ctatggacta | ctggggccaa | 720 |
| gggaccacgg | tcaccgtctc | ctcaggaggt | ggtggatccg | agctgcagct | ggtcgagtct | 780 |
| ggcccaggac | tggtgaagcc | ttcggggacc | ctgtccctca | cctgcgctgt | ctctggtggc | 840 |
| tccatcagca | gtagaaactg | gtggagttgg | gtccgccagc | ccccagggaa | ggggctggag | 900 |
| tggattggtg | atatctatca | tagtgggagc | accaactaca | acccgtccct | caagagtcga | 960 |
| gtcaccatat | cagtagacaa | gtccaagaac | cagttctccc | tgaagctgag | ctctgtgacc | 1020 |
| gccgcggaca | cggccgtgta | ttactgtgcg | agtgggtata | ccagctgtcg | tgatgctttt | 1080 |
| gatatctggg | gccaagggac | aatggtcacc | gtctcctcag | gtggtggtgg | ttctggcggc | 1140 |
| ggcggctccg | gtggtggtgg | ttctgagctc | gtgatgactc | agtctccatc | ctccctgtct | 1200 |
| gcatctgtag | gagacagagt | caccatcact | tgccgggcga | gtcagggcat | tggcaattat | 1260 |
| ttagcctggt | atcagcagaa | accagggcag | cctcctaaga | tgctcattta | ctgggcatca | 1320 |
| atccgggaat | ccggggtccc | tgaccgattc | agtggcagcg | gtctgggac | agacttcact | 1380 |
| ctcaccatca | gcagcctgca | ggctgaagat | gtggcagttt | actactgtca | gcaatattat | 1440 |
| agtaatcctc | agacgttcgg | ccaagggacc | aaggtggaaa | tcaaa | | 1485 |

<210> SEQ ID NO 236
<211> LENGTH: 495
<212> TYPE: PRT
<213> ORGANISM: artificial sequence
<220> FEATURE:
<223> OTHER INFORMATION: anti-EpCAM 5-10 VL-VH x human anti-CD3 3-148 VH-VL

<400> SEQUENCE: 236

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Glu Leu Gln
                245                 250                 255

Leu Val Glu Ser Gly Pro Gly Leu Val Lys Pro Ser Gly Thr Leu Ser
            260                 265                 270

Leu Thr Cys Ala Val Ser Gly Gly Ser Ile Ser Ser Arg Asn Trp Trp
        275                 280                 285

Ser Trp Val Arg Gln Pro Pro Gly Lys Gly Leu Glu Trp Ile Gly Asp
    290                 295                 300

Ile Tyr His Ser Gly Ser Thr Asn Tyr Asn Pro Ser Leu Lys Ser Arg
305                 310                 315                 320

Val Thr Ile Ser Val Asp Lys Ser Lys Asn Gln Phe Ser Leu Lys Leu
                325                 330                 335

Ser Ser Val Thr Ala Ala Asp Thr Ala Val Tyr Tyr Cys Ala Ser Gly
            340                 345                 350

Tyr Thr Ser Cys Arg Asp Ala Phe Asp Ile Trp Gly Gln Gly Thr Met
        355                 360                 365
```

```
Val Thr Val Ser Ser Gly Gly Gly Ser Gly Gly Gly Ser Gly
        370                 375                 380

Gly Gly Gly Ser Glu Leu Val Met Thr Gln Ser Pro Ser Ser Leu Ser
385                 390                 395                 400

Ala Ser Val Gly Asp Arg Val Thr Ile Thr Cys Arg Ala Ser Gln Gly
                405                 410                 415

Ile Gly Asn Tyr Leu Ala Trp Tyr Gln Gln Lys Pro Gly Gln Pro Pro
            420                 425                 430

Lys Met Leu Ile Tyr Trp Ala Ser Ile Arg Glu Ser Gly Val Pro Asp
        435                 440                 445

Arg Phe Ser Gly Ser Gly Ser Gly Thr Asp Phe Thr Leu Thr Ile Ser
    450                 455                 460

Ser Leu Gln Ala Glu Asp Val Ala Val Tyr Tyr Cys Gln Gln Tyr Tyr
465                 470                 475                 480

Ser Asn Pro Gln Thr Phe Gly Gln Gly Thr Lys Val Glu Ile Lys
                485                 490                 495

<210> SEQ ID NO 237
<211> LENGTH: 1503
<212> TYPE: DNA
<213> ORGANISM: artificial sequence
<220> FEATURE:
<223> OTHER INFORMATION: anti-EpCAM 5-10 VL-VH x human anti-CD3 3-190
      VH-VL

<400> SEQUENCE: 237
gagctcgtga tgacacagtc tccatcctcc ctgactgtga cagcaggaga gaaggtcact     60
atgagctgca agtccagtca gagtctgtta acagtggaa atcaaaagaa ctacttgacc    120
tggtaccagc agaaaccagg gcagcctcct aaactgttga tctactgggc atccactagg    180
gaatctgggg tccctgatcg cttcacaggc agtggatctg gaacagattt cactctcacc    240
atcagcagtg tgcaggctga agacctggca gtttattact gtcagaatga ttatagttat    300
ccgctcacgt tcggtgctgg gaccaagctt gagatcaaag gtggtggtgg ttctggcggc    360
ggcggctccg gtggtggtgg ttctgaggtg cagctgctcg agcagtctgg agctgagctg    420
gtaaggcctg ggacttcagt gaagatatcc tgcaaggctt ctggatacgc cttcactaac    480
tactggctag ttgggtaaa gcagaggcct ggacatggac ttgagtggat tgagatatt     540 ttccctggaa gtggtaatat ccactacaat gagaagttca gggcaaagc cacactgact    600 gcagacaaat cttcgagcac agcctatatg cagctcagta gcctgacatt tgaggactct    660
gctgtctatt tctgtgcaag actgaggaac tgggacgagc tatggactac tggggccaa    720 gggaccacgg tcaccgtctc ctcaggaggt ggtggatccg agctgcagct ggtcgagtgg    780
ggcgcaggac tgttgaagcc ttcggagacc ctgtccctca cctgcgctgt ctatggtggg    840
tccttcagtg gttactactg gagctggatc cgccagcccc cagggaaggg gctggagtgg    900 attgggggaaa tcaatcatag tggaagcacc aactacaacc cgtccctcaa gagtcgagtc    960
accatatcag tagacacgtc caagaaccag ttctccctga agctgagctc tgtgaccgcc   1020
gcggacacgg ctgtgtatta ctgtgcgaga ggccgaggcc gatttttggg gtggttatta   1080
gggggctcca actggttcga cccctggggc cagggaaccc tggtcaccgt ctcctcaggt   1140
ggtggtggtt ctggcggcgg cggctccggt ggtggtggtt ctgagctcgt gatgacccag   1200
tctccatcct cccctgtctgc atctgtagga gacagagtca ccatcacttg ccgggcgagt   1260
cagggcatta gcaattattt aaattggtat cagcagaaac cagggaaagc ccctaagctc   1320
```

-continued

```
ctgatctacg atgcatccaa tttggaaaca ggggtcccat caaggttcag tggcagtgga    1380
tctgggacag atttcactct caccatcagc agtctgcaac ctgaagattt tgcaacttac    1440
tactgtcaac agagttacag taccccgtac acttttggcc aggggaccaa agtggatatc    1500
aaa                                                                 1503

<210> SEQ ID NO 238
<211> LENGTH: 501
<212> TYPE: PRT
<213> ORGANISM: artificial sequence
<220> FEATURE:
<223> OTHER INFORMATION: anti-EpCAM 5-10 VL-VH x human anti-CD3 3-190
      VH-VL

<400> SEQUENCE: 238

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Ser Gly Gly Gly Ser Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Glu Leu Gln
                245                 250                 255

Leu Val Glu Trp Gly Ala Gly Leu Leu Lys Pro Ser Glu Thr Leu Ser
            260                 265                 270

Leu Thr Cys Ala Val Tyr Gly Gly Ser Phe Ser Gly Tyr Tyr Trp Ser
        275                 280                 285

Trp Ile Arg Gln Pro Pro Gly Lys Gly Leu Glu Trp Ile Gly Glu Ile
    290                 295                 300

Asn His Ser Gly Ser Thr Asn Tyr Asn Pro Ser Leu Lys Ser Arg Val
305                 310                 315                 320
```

Thr Ile Ser Val Asp Thr Ser Lys Asn Gln Phe Ser Leu Lys Leu Ser
            325                 330                 335

Ser Val Thr Ala Ala Asp Thr Ala Val Tyr Tyr Cys Ala Arg Gly Arg
            340                 345                 350

Gly Arg Phe Leu Gly Trp Leu Leu Gly Gly Ser Asn Trp Phe Asp Pro
            355                 360                 365

Trp Gly Gln Gly Thr Leu Val Thr Val Ser Ser Gly Gly Gly Gly Ser
        370                 375                 380

Gly Gly Gly Gly Ser Gly Gly Gly Ser Glu Leu Val Met Thr Gln
385                 390                 395                 400

Ser Pro Ser Ser Leu Ser Ala Ser Val Gly Asp Arg Val Thr Ile Thr
                405                 410                 415

Cys Arg Ala Ser Gln Gly Ile Ser Asn Tyr Leu Asn Trp Tyr Gln Gln
            420                 425                 430

Lys Pro Gly Lys Ala Pro Lys Leu Leu Ile Tyr Asp Ala Ser Asn Leu
        435                 440                 445

Glu Thr Gly Val Pro Ser Arg Phe Ser Gly Ser Gly Ser Gly Thr Asp
    450                 455                 460

Phe Thr Leu Thr Ile Ser Ser Leu Gln Pro Glu Asp Phe Ala Thr Tyr
465                 470                 475                 480

Tyr Cys Gln Gln Ser Tyr Ser Thr Pro Tyr Thr Phe Gly Gln Gly Thr
                485                 490                 495

Lys Val Asp Ile Lys
            500

<210> SEQ ID NO 239
<211> LENGTH: 1482
<212> TYPE: DNA
<213> ORGANISM: artificial sequence
<220> FEATURE:
<223> OTHER INFORMATION: anti-EpCAM 5-10 VL-VH x human anti-CD3 3-271
      VH-VL

<400> SEQUENCE: 239
gagctcgtga tgacacagtc tccatcctcc ctgactgtga cagcaggaga gaaggtcact      60
atgagctgca agtccagtca gagtctgtta aacagtggaa atcaaaagaa ctacttgacc     120
tggtaccagc agaaaccagg gcagcctcct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
ccgctcacgt tcggtgctgg gaccaagctt gagatcaaag gtggtggtgg ttctggcggc     360
ggcggctccg gtggtggtgg ttctgaggtg cagctgctcg agcagtctgg agctgagctg     420
gtaaggcctg ggacttcagt gaagatatcc tgcaaggctt ctggatacgc cttcactaac     480
tactggctag ttgggtaaa gcagaggcct ggacatggac ttgagtggat tggagatatt     540
ttccctggaa gtggtaatat ccactacaat gagaagttca gggcaaagc cacactgact     600 gcagacaaat cttcgagcac agcctatatg cagctcagta gcctgacatt tgaggactct     660
gctgtctatt tctgtgcaag actgaggaac tgggacgagc ctatggacta ctggggccaa     720
gggaccacgg tcaccgtctc ctcaggaggt ggtggatccg agctgcagct ggtcgagtgg     780
ggcgcaggac tgttgaagcc ttcggagacc ctgtccctca cctgcgctgt ctatggtggg     840
tccttcagtg gttactactg gagctggatc cgccagcccc cagggaaggg gctgagtgg     900 attggggaaa tcaatcatag tggaagcacc aactacaacc cgtccctcaa gagtcgagtc     960

-continued

```
accatatcag tagacacgtc caagaaccag ttctccctga agctgagctc tgtgaccgcc    1020
gcggacacgg ctgtgtatta ctgtgcgaga ggccctgacc gaatgggca tggttttgat    1080 atctggggcc aagggacaat ggtcaccgtc tcctcaggtg gtggtggttc tggcggcggc    1140
ggctccggtg gtggtggttc tgagctccag atgacccagt ctccatcctc cctgtctgca    1200
tctgtaggag acagagtcac catcacttgc cgggcaagtc agagcattag cagctattta    1260
aattggtatc agcagaaatc agggaaagcc cctaagctcc tgatctatgc tgcatccagt    1320
ttgcaaagtg ggtcccatc aaggttcagt ggcagtggat ctgggacaga tttcactctc    1380
accatcagta gtctgcaacc tgaagatttt gcaacttatt actgtcaaca gagttacagt    1440
agcccgtgga cattcggcca agggaccaag gtggagatca aa                      1482
```

<210> SEQ ID NO 240
<211> LENGTH: 494
<212> TYPE: PRT
<213> ORGANISM: artificial sequence
<220> FEATURE:
<223> OTHER INFORMATION: anti-EpCAM 5-10 VL-VH x human anti-CD3 3-271
      VH-VL

<400> SEQUENCE: 240

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Thr Ala
        195                 200                 205

Tyr Met Gln Leu Ser Ser Leu Thr Phe Glu Asp Ser Ala Val Tyr Phe
    210                 215                 220

Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Gly Ser Glu Leu Gln
                245                 250                 255

Leu Val Glu Trp Gly Ala Gly Leu Leu Lys Pro Ser Glu Thr Leu Ser
```

```
                260               265                270
Leu Thr Cys Ala Val Tyr Gly Gly Ser Phe Ser Gly Tyr Tyr Trp Ser
            275               280                285
Trp Ile Arg Gln Pro Pro Gly Lys Gly Leu Glu Trp Ile Gly Glu Ile
            290               295                300
Asn His Ser Gly Ser Thr Asn Tyr Asn Pro Ser Leu Lys Ser Arg Val
305               310               315                320
Thr Ile Ser Val Asp Thr Ser Lys Asn Gln Phe Ser Leu Lys Leu Ser
                325               330                335
Ser Val Thr Ala Ala Asp Thr Ala Val Tyr Tyr Cys Ala Arg Gly Pro
                340               345                350
Asp Arg Met Gly His Gly Phe Asp Ile Trp Gly Gln Gly Thr Met Val
            355               360                365
Thr Val Ser Ser Gly Gly Gly Gly Ser Gly Gly Gly Gly Ser Gly Gly
            370               375                380
Gly Gly Ser Glu Leu Gln Met Thr Gln Ser Pro Ser Ser Leu Ser Ala
385               390               395                400
Ser Val Gly Asp Arg Val Thr Ile Thr Cys Arg Ala Ser Gln Ser Ile
                405               410                415
Ser Ser Tyr Leu Asn Trp Tyr Gln Gln Lys Ser Gly Lys Ala Pro Lys
                420               425                430
Leu Leu Ile Tyr Ala Ala Ser Ser Leu Gln Ser Gly Val Pro Ser Arg
            435               440                445
Phe Ser Gly Ser Gly Ser Gly Thr Asp Phe Thr Leu Thr Ile Ser Ser
            450               455                460
Leu Gln Pro Glu Asp Phe Ala Thr Tyr Tyr Cys Gln Gln Ser Tyr Ser
465               470               475                480
Ser Pro Trp Thr Phe Gly Gln Gly Thr Lys Val Glu Ile Lys
                485               490

<210> SEQ ID NO 241
<211> LENGTH: 1488
<212> TYPE: DNA
<213> ORGANISM: artificial sequence
<220> FEATURE:
<223> OTHER INFORMATION: anti-EpCAM 5-10 VL-VH x human anti-CD3 4-10
      VH-VL

<400> SEQUENCE: 241
gagctcgtga tgacacagtc tccatcctcc ctgactgtga cagcaggaga gaaggtcact      60
atgagctgca gtccagtca gagtctgtta acagtggaa atcaaaagaa ctacttgacc      120
tggtaccagc agaaaccagg gcagcctcct aaactgttga tctactgggc atccactagg      180
gaatctgggg tccctgatcg cttcacaggc agtggatctg gaacagattt cactctcacc      240
atcagcagtg tgcaggctga agacctggca gtttattact gtcagaatga ttatagttat      300
ccgctcacgt cggtgctgg gaccaagctt gagatcaaag gtggtggtgg ttctggcggc      360
ggcggctccg gtggtggtgg ttctgaggtg cagctgctcg agcagtctgg agctgagctg      420
gtaaggcctg gacttcagt gaagatatcc tgcaaggctt ctggatacgc cttcactaac      480
tactggctag gttgggtaaa gcagaggcct ggacatggac ttgagtggat tgagatatt      540 ttccctggaa gtggtaatat ccactacaat gagaagttca aggcaaagc cacactgact      600 gcagacaaat cttcgagcac agcctatatg cagctcagta gcctgacatt tgaggactct      660
gctgtctatt tctgtgcaag actgaggaac tgggacgagc ctatggacta ctggggccaa      720
```

```
gggaccacgg tcaccgtctc ctcaggaggt ggtggatccg agctgcagct ggtcgagtct   780
gggggaggct tggtacagcc tgggggtcc  ctgagactct cctgtgcagc ctctggattc   840
acctttagca gctatgccat gggctgggtc cgccaggctc cagggaaggg gctggagtgg   900
gtctcagctg ttagtggtag tggtggtagc acatactacg cagactccgt gaagggccgg   960
ttcaccatct ccagagacaa ttccaagaac acgctgtatc tgcaaatgaa cagcctgaga  1020
gccgaggaca cggccgtata ttactgtgcg aaagccaaat tcctgggcca ctactacggt  1080
atggacgtct ggggccaagg gaccacggtc accgtctcct caggtggtgg tggttctggc  1140
ggcggcggct ccggtggtgg tggttctgag ctccagatga cccagtctcc atcctccctg  1200
tctgcatctg taggagacag agtcaccatc acttgccggg caagtcagag cattagcagc  1260
tatttaaatt ggtatcagca gaaaccaggg aaagccccta agctcctgat ctatgctgca  1320
tccagtttgc aaagtggagt cccatcaagg ttcagcggca gtggatctgg gacagagttc  1380
actctcacaa tcagcagcct gcagcctgaa gattttgcaa cttattactg tcttcagcat  1440
aatgcttacc cgtacacttt cggccagggg accaaggtgg aaatcaaa             1488
```

```
<210> SEQ ID NO 242
<211> LENGTH: 496
<212> TYPE: PRT
<213> ORGANISM: artificial sequence
<220> FEATURE:
<223> OTHER INFORMATION: anti-EpCAM 5-10 VL-VH x human anti-CD3 4-10
      VH-VL

<400> SEQUENCE: 242
```

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
        195                 200                 205

Tyr Met Gln Leu Ser Ser Leu Thr Phe Glu Asp Ser Ala Val Tyr Phe
    210                 215                 220
```

```
Cys Ala Arg Leu Arg Asn Trp Asp Glu Pro Met Asp Tyr Trp Gly Gln
225                 230                 235                 240

Gly Thr Thr Val Thr Val Ser Ser Gly Gly Gly Ser Glu Leu Gln
            245                 250                 255

Leu Val Glu Ser Gly Gly Gly Leu Val Gln Pro Gly Gly Ser Leu Arg
        260                 265                 270

Leu Ser Cys Ala Ala Ser Gly Phe Thr Phe Ser Ser Tyr Ala Met Gly
    275                 280                 285

Trp Val Arg Gln Ala Pro Gly Lys Gly Leu Glu Trp Val Ser Ala Val
290                 295                 300

Ser Gly Ser Gly Gly Ser Thr Tyr Tyr Ala Asp Ser Val Lys Gly Arg
305                 310                 315                 320

Phe Thr Ile Ser Arg Asp Asn Ser Lys Asn Thr Leu Tyr Leu Gln Met
            325                 330                 335

Asn Ser Leu Arg Ala Glu Asp Thr Ala Val Tyr Tyr Cys Ala Lys Ala
        340                 345                 350

Lys Phe Leu Gly His Tyr Tyr Gly Met Asp Val Trp Gly Gln Gly Thr
    355                 360                 365

Thr Val Thr Val Ser Ser Gly Gly Gly Gly Ser Gly Gly Gly Gly Ser
370                 375                 380

Gly Gly Gly Gly Ser Glu Leu Gln Met Thr Gln Ser Pro Ser Ser Leu
385                 390                 395                 400

Ser Ala Ser Val Gly Asp Arg Val Thr Ile Thr Cys Arg Ala Ser Gln
            405                 410                 415

Ser Ile Ser Ser Tyr Leu Asn Trp Tyr Gln Gln Lys Pro Gly Lys Ala
        420                 425                 430

Pro Lys Leu Leu Ile Tyr Ala Ala Ser Ser Leu Gln Ser Gly Val Pro
    435                 440                 445

Ser Arg Phe Ser Gly Ser Gly Ser Gly Thr Glu Phe Thr Leu Thr Ile
450                 455                 460

Ser Ser Leu Gln Pro Glu Asp Phe Ala Thr Tyr Tyr Cys Leu Gln His
465                 470                 475                 480

Asn Ala Tyr Pro Tyr Thr Phe Gly Gln Gly Thr Lys Val Glu Ile Lys
            485                 490                 495

<210> SEQ ID NO 243
<211> LENGTH: 1512
<212> TYPE: DNA
<213> ORGANISM: artificial sequence
<220> FEATURE:
<223> OTHER INFORMATION: anti-EpCAM 5-10 VL-VH x human anti-CD3 4-48
      VH-VL

<400> SEQUENCE: 243
gagctcgtga tgacacagtc tccatcctcc ctgactgtga cagcaggaga gaaggtcact      60
atgagctgca gtccagtca gagtctgtta aacagtggaa atcaaaagaa ctacttgacc     120
tggtaccagc agaaaccagg gcagcctcct aaactgttga tctactgggc atccactagg    180
gaatctgggg tccctgatcg cttcacaggc agtggatctg aacagattt cactctcacc     240 atcagcagtg tgcaggctga agacctggca gtttattact gtcagaatga ttatagttat    300
ccgctcacgt tcggtgctgg gaccaagctt gagatcaaag gtggtggtgg ttctggcggc    360
ggcggctccg gtggtggtgg ttctgaggtg cagctgctcg agcagtctgg agctgagctg    420
gtaaggcctg gacttcagt gaagatatcc tgcaaggctt ctggatacgc cttcactaac    480
tactggctag gttgggtaaa gcagaggcct ggacatggac ttgagtggat tggagatatt    540
```

```
ttccctggaa gtggtaatat ccactacaat gagaagttca agggcaaagc cacactgact    600
gcagacaaat cttcgagcac agcctatatg cagctcagta gcctgacatt tgaggactct    660
gctgtctatt tctgtgcaag actgaggaac tgggacgagc ctatggacta ctggggccaa    720
gggaccacgg tcaccgtctc ctcaggaggt ggtggatccg agctgcagct ggtcgagtct    780
ggtcctgtgc tggtgaaacc cacagatacc ctcacgctga cttgcaccgt ctctgggttc    840
tcactcaata atcctagaat gggtgtgagc tggatccgtc agccccagg gaagaccctg    900 gagtggcttg cacacatttt tccgagtgac gcaaaagccc acagtgcatc tctgaagagc    960
aggctcacca tctccaagga cacctccaaa agccaggtgg tccctaccat gaccaacatg   1020
gaccctgtgg acacagccac atattactgt gcacggatat gggggaata ctatccccca   1080 gcctggttcg acccctgggg ccagggaacc ctggtcaccg tctcctcagg tggtggtggt   1140
tctggcggcg gcggctccgg tggtggtggt tctgagctcg tgatgacaca gtctccagac   1200
tccctggctg tgtctctggg cgagagggcc accatcaact gcaagtccag ccagagtgtt   1260
ttatacagct ccaacaataa gaactactta gcttggtacc agcagaaacc aggacagcct   1320
cctaagctgc tcatttactg ggcatctacc cgggaatccg gggtccctga ccgattcagt   1380
ggcagcgggt ctgggacaga tttcactctc accatcagca gcctgcaggc tgaagacgtg   1440
gcagtttatt actgtcagca atatttgaaa atcccttata cttttggcca ggggaccaag   1500
gtggagatca aa                                                       1512

<210> SEQ ID NO 244
<211> LENGTH: 504
<212> TYPE: PRT
<213> ORGANISM: artificial sequence
<220> FEATURE:
<223> OTHER INFORMATION: anti-EpCAM 5-10 VL-VH x human anti-CD3 4-48
      VH-VL

<400> SEQUENCE: 244
```

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Gly Gly Gly Gly Ser Gly Gly Gly Ser Gly Gly Gly Gly Ser
        115                 120                 125

Glu Val Gln Leu Leu Glu Gln Ser Gly Ala Glu Leu Val Arg Pro Gly
    130                 135                 140

Thr Ser Val Lys Ile Ser Cys Lys Ala Ser Gly Tyr Ala Phe Thr Asn
145                 150                 155                 160

Tyr Trp Leu Gly Trp Val Lys Gln Arg Pro Gly His Gly Leu Glu Trp
                165                 170                 175

Ile Gly Asp Ile Phe Pro Gly Ser Gly Asn Ile His Tyr Asn Glu Lys
            180                 185                 190

Phe Lys Gly Lys Ala Thr Leu Thr Ala Asp Lys Ser Ser Ser Thr Ala
            195                 200                 205

Tyr Met Gln Leu Ser Ser Leu Thr Phe Glu Asp Ser Ala Val Tyr Phe
            210                 215                 220

Cys Ala Arg Leu Arg Asn Trp Asp Glu Pro Met Asp Tyr Trp Gly Gln
225                 230                 235                 240

Gly Thr Thr Val Thr Val Ser Gly Gly Gly Gly Ser Glu Leu Gln
            245                 250                 255

Leu Val Glu Ser Gly Pro Val Leu Val Lys Pro Thr Asp Thr Leu Thr
            260                 265                 270

Leu Thr Cys Thr Val Ser Gly Phe Ser Leu Asn Asn Pro Arg Met Gly
            275                 280                 285

Val Ser Trp Ile Arg Gln Pro Pro Gly Lys Thr Leu Glu Trp Leu Ala
            290                 295                 300

His Ile Phe Pro Ser Asp Ala Lys Ala His Ser Ala Ser Leu Lys Ser
305                 310                 315                 320

Arg Leu Thr Ile Ser Lys Asp Thr Ser Lys Ser Gln Val Val Pro Thr
            325                 330                 335

Met Thr Asn Met Asp Pro Val Asp Thr Ala Thr Tyr Tyr Cys Ala Arg
            340                 345                 350

Ile Leu Gly Glu Tyr Tyr Pro Pro Ala Trp Phe Asp Pro Trp Gly Gln
            355                 360                 365

Gly Thr Leu Val Thr Val Ser Ser Gly Gly Gly Ser Gly Gly Gly
            370                 375                 380

Gly Ser Gly Gly Gly Ser Glu Leu Val Met Thr Gln Ser Pro Asp
385                 390                 395                 400

Ser Leu Ala Val Ser Leu Gly Glu Arg Ala Thr Ile Asn Cys Lys Ser
            405                 410                 415

Ser Gln Ser Val Leu Tyr Ser Ser Asn Asn Lys Asn Tyr Leu Ala Trp
            420                 425                 430

Tyr Gln Gln Lys Pro Gly Gln Pro Pro Lys Leu Leu Ile Tyr Trp Ala
            435                 440                 445

Ser Thr Arg Glu Ser Gly Val Pro Asp Arg Phe Ser Gly Ser Gly Ser
450                 455                 460

Gly Thr Asp Phe Thr Leu Thr Ile Ser Ser Leu Gln Ala Glu Asp Val
465                 470                 475                 480

Ala Val Tyr Tyr Cys Gln Gln Tyr Leu Lys Ile Pro Tyr Thr Phe Gly
            485                 490                 495

Gln Gly Thr Lys Val Glu Ile Lys
            500

<210> SEQ ID NO 245
<211> LENGTH: 1488
<212> TYPE: DNA
<213> ORGANISM: artificial sequence
<220> FEATURE:
<223> OTHER INFORMATION: anti-CD20 VL-VH x human anti-CD3 3-190 VH-VL

<400> SEQUENCE: 245
caaattgttc tctcccagtc tccagcaatc ctttctgcat ctccagggga gaaggtcaca      60
atgacttgca gggccagctc aagtttaagt tcatgcact ggtaccagca gaagccagga     120
tcctccccca aaccctggat ttatgccaca tccaacctgg cttctggagt ccctgctcgc     180

```
ttcagtggca gtgggtctgg gacctcttac tctctcacaa tcagcagagt ggaggctgaa      240
gatgctgcca cttatttctg ccatcagtgg agtagtaacc cgctcacgtt cggtgctggg      300
acaaaggtgg aaataaaagg tggtggtggt tctggcggcg gcggctccgg tggtggtggt      360
tctcaggtgc aactgcggca gcctgggggc tgagctggtga agcctggggc tcagtgaag      420
atgtcctgca aggcttctgg ctacacattt accagttaca atatgcactg ggtaaagcag      480
acacctggac agggcctgga atggattgga gctatttatc caggaaatgg tgatacttcc      540
tacaatcaga agttcaaagg caaggccaca ttgactgcag acaaatcctc cagcacagcc      600
tacatgcagc tcagcagtct gacatctgag gactctgcgg tctattactg tgcaagatcg      660
cactacggta gtaactacgt agactacttt gactactggg gccaaggcac actagtcaca      720
gtctcgacag gaggtggtgg atccgagctg cagctggtcg agtggggcgc aggactgttg      780
aagccttcgg agaccctgtc cctcacctgc gctgtctatg gtgggtcctt cagtggttac      840
tactggagct ggatccgcca gccccccaggg aaggggctgg agtggattgg ggaaatcaat      900
catagtggaa gcaccaacta caacccgtcc ctcaagagtc gagtcaccat atcagtagac      960
acgtccaaga accagttctc cctgaagctg agctctgtga ccgccgcgga cacggctgtg     1020
tattactgtg cgagaggccg aggccgattt ttggggtggt tattaggggg ctccaactgg     1080
ttcgaccct ggggccaggg aaccctggtc accgtctcct caggtggtgg tggttctggc     1140
ggcggcggct ccggtggtgg tggttctgag ctcgtgatga cccagtctcc atcctccctg     1200
tctgcatctg taggagacag agtcaccatc acttgccggg cgagtcaggg cattagcaat     1260
tatttaaatt ggtatcagca gaaaccaggg aaagccccta agctcctgat ctacgatgca     1320
tccaatttgg aaacaggggt cccatcaagg ttcagtggca gtggatctgg gacagatttc     1380
actctcacca tcagcagtct gcaacctgaa gattttgcaa cttactactg tcaacagagt     1440
tacagtaccc cgtacacttt tggccagggg accaaagtgg atatcaaa               1488
```

<210> SEQ ID NO 246
<211> LENGTH: 496
<212> TYPE: PRT
<213> ORGANISM: artificial sequence
<220> FEATURE:
<223> OTHER INFORMATION: anti-CD20 VL-VH x human anti-CD3 3-190 VH-VL

<400> SEQUENCE: 246

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Val Glu Ile Lys Gly Gly Gly Ser Gly
                100                 105                 110

Gly Gly Gly Ser Gly Gly Gly Ser Gln Val Gln Leu Arg Gln Pro
        115                 120                 125

Gly Ala Glu Leu Val Lys Pro Gly Ala Ser Val Lys Met Ser Cys Lys
```

130                 135                 140
Ala Ser Gly Tyr Thr Phe Thr Ser Tyr Asn Met His Trp Val Lys Gln
145                 150                 155                 160

Thr Pro Gly Gln Gly Leu Glu Trp Ile Gly Ala Ile Tyr Pro Gly Asn
                165                 170                 175

Gly Asp Thr Ser Tyr Asn Gln Lys Phe Lys Gly Lys Ala Thr Leu Thr
            180                 185                 190

Ala Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Ser His Tyr Gly Ser
    210                 215                 220

Asn Tyr Val Asp Tyr Phe Asp Tyr Trp Gly Gln Gly Thr Leu Val Thr
225                 230                 235                 240

Val Ser Thr Gly Gly Gly Gly Ser Glu Leu Gln Leu Val Glu Trp Gly
                245                 250                 255

Ala Gly Leu Leu Lys Pro Ser Glu Thr Leu Ser Leu Thr Cys Ala Val
            260                 265                 270

Tyr Gly Gly Ser Phe Ser Gly Tyr Tyr Trp Ser Trp Ile Arg Gln Pro
        275                 280                 285

Pro Gly Lys Gly Leu Glu Trp Ile Gly Glu Ile Asn His Ser Gly Ser
    290                 295                 300

Thr Asn Tyr Asn Pro Ser Leu Lys Ser Arg Val Thr Ile Ser Val Asp
305                 310                 315                 320

Thr Ser Lys Asn Gln Phe Ser Leu Lys Leu Ser Ser Val Thr Ala Ala
                325                 330                 335

Asp Thr Ala Val Tyr Tyr Cys Ala Arg Gly Arg Gly Arg Phe Leu Gly
            340                 345                 350

Trp Leu Leu Gly Ser Asn Trp Phe Asp Pro Trp Gly Gln Gly Thr
        355                 360                 365

Leu Val Thr Val Ser Ser Gly Gly Gly Ser Gly Gly Gly Gly Ser
        370                 375                 380

Gly Gly Gly Gly Ser Glu Leu Val Met Thr Gln Ser Pro Ser Ser Leu
385                 390                 395                 400

Ser Ala Ser Val Gly Asp Arg Val Thr Ile Thr Cys Arg Ala Ser Gln
                405                 410                 415

Gly Ile Ser Asn Tyr Leu Asn Trp Tyr Gln Gln Lys Pro Gly Lys Ala
            420                 425                 430

Pro Lys Leu Leu Ile Tyr Asp Ala Ser Asn Leu Glu Thr Gly Val Pro
        435                 440                 445

Ser Arg Phe Ser Gly Ser Gly Ser Gly Thr Asp Phe Thr Leu Thr Ile
    450                 455                 460

Ser Ser Leu Gln Pro Glu Asp Phe Ala Thr Tyr Tyr Cys Gln Gln Ser
465                 470                 475                 480

Tyr Ser Thr Pro Tyr Thr Phe Gly Gln Gly Thr Lys Val Asp Ile Lys
                485                 490                 495

<210> SEQ ID NO 247
<211> LENGTH: 1470
<212> TYPE: DNA
<213> ORGANISM: artificial sequence
<220> FEATURE:
<223> OTHER INFORMATION: anti-CD20 VL-VH x human anti-CD3 3-148 VH-VL

<400> SEQUENCE: 247
caaattgttc tctcccagtc tccagcaatc ctttctgcat ctccagggga gaaggtcaca      60

-continued

```
atgacttgca gggccagctc aagtttaagt tcatgcact ggtaccagca gaagccagga      120
tcctccccca aaccctggat ttatgccaca tccaacctgg cttctggagt ccctgctcgc      180
ttcagtggca gtgggtctgg gacctcttac tctctcacaa tcagcagagt ggaggctgaa      240
gatgctgcca cttatttctg ccatcagtgg agtagtaacc cgctcacgtt cggtgctggg      300
acaaaggtgg aaataaaagg tggtggtggt tctggcggcg cgggctccgg tggtggtggt      360
tctcaggtgc aactgcggca gcctggggct gagctggtga agcctggggc ctcagtgaag      420
atgtcctgca aggcttctgg ctacacattt accagttaca atatgcactg gtaaagcag       480 acacctggac agggcctgga atggattgga gctatttatc caggaaatgg tgatacttcc      540
tacaatcaga agttcaaagg caaggccaca ttgactgcag acaaatcctc cagcacagcc      600
tacatgcagc tcagcagtct gacatctgag actctgcgg tctattactg tgcaagatcg       660
cactacggta gtaactacgt agactacttt gactactggg gccaaggcac actagtcaca      720
gtctcgacag gaggtggtgg atccgagctg cagctggtcg agtctggccc aggactggtg      780
aagccttcgg ggaccctgtc cctcacctgc gctgtctctg gtggctccat cagcagtaga      840
aactggtgga gttgggtccg ccagccccca gggaaggggc tggagtggat tggtgatatc      900
tatcatagtg ggagcaccaa ctacaacccg tccctcaaga gtcgagtcac catatcagta      960
gacaagtcca agaaccagtt ctccctgaag ctgagtctg tgaccgccgc ggacacggcc     1020
gtgtattact gtgcgagtgg gtataccagc tgtcgtgatg cttttgatat ctggggccaa     1080
gggacaatgg tcaccgtctc ctcaggtggt ggtggttctg gcggcggcgg ctccggtggt     1140
ggtggttctg agctcgtgat gactcagtct ccatcctccc tgtctgcatc tgtaggagac     1200
agagtcacca tcacttgccg ggcgagtcag ggcattggca attatttagc ctggtatcag     1260
cagaaaccag gcagcctcc taagatgctc atttactggg catcaatccg ggaatccggg     1320
gtccctgacc gattcagtgg cagcgggtct gggacagact tcactctcac catcagcagc     1380
ctgcaggctg aagatgtggc agtttactac tgtcagcaat attatagtaa tcctcagacg     1440
ttcggccaag ggaccaaggt ggaaatcaaa                                       1470
```

<210> SEQ ID NO 248
<211> LENGTH: 490
<212> TYPE: PRT
<213> ORGANISM: artificial sequence
<220> FEATURE:
<223> OTHER INFORMATION: anti-CD20 VL-VH x human anti-CD3 3-148 VH-VL

<400> SEQUENCE: 248

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
                20                  25                  30

His Trp Tyr Gln Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Phe Cys His Gln Trp Ser Ser Asn Pro Leu Thr
                85                  90                  95

Phe Gly Ala Gly Thr Lys Val Glu Ile Lys Gly Gly Gly Ser Gly
                100                 105                 110
```

Gly Gly Gly Ser Gly Gly Gly Ser Gln Val Gln Leu Arg Gln Pro
            115                 120                 125

Gly Ala Glu Leu Val Lys Pro Gly Ala Ser Val Lys Met Ser Cys Lys
    130                 135                 140

Ala Ser Gly Tyr Thr Phe Thr Ser Tyr Asn Met His Trp Val Lys Gln
145                 150                 155                 160

Thr Pro Gly Gln Gly Leu Glu Trp Ile Gly Ala Ile Tyr Pro Gly Asn
            165                 170                 175

Gly Asp Thr Ser Tyr Asn Gln Lys Phe Lys Gly Lys Ala Thr Leu Thr
        180                 185                 190

Ala Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Ser His Tyr Gly Ser
    210                 215                 220

Asn Tyr Val Asp Tyr Phe Asp Tyr Trp Gly Gln Gly Thr Leu Val Thr
225                 230                 235                 240

Val Ser Thr Gly Gly Gly Gly Ser Glu Leu Gln Leu Val Glu Ser Gly
            245                 250                 255

Pro Gly Leu Val Lys Pro Ser Gly Thr Leu Ser Leu Thr Cys Ala Val
        260                 265                 270

Ser Gly Gly Ser Ile Ser Ser Arg Asn Trp Trp Ser Trp Val Arg Gln
        275                 280                 285

Pro Pro Gly Lys Gly Leu Glu Trp Ile Gly Asp Ile Tyr His Ser Gly
    290                 295                 300

Ser Thr Asn Tyr Asn Pro Ser Leu Lys Ser Arg Val Thr Ile Ser Val
305                 310                 315                 320

Asp Lys Ser Lys Asn Gln Phe Ser Leu Lys Leu Ser Ser Val Thr Ala
            325                 330                 335

Ala Asp Thr Ala Val Tyr Tyr Cys Ala Ser Gly Tyr Thr Ser Cys Arg
        340                 345                 350

Asp Ala Phe Asp Ile Trp Gly Gln Gly Thr Met Val Thr Val Ser Ser
        355                 360                 365

Gly Gly Gly Gly Ser Gly Gly Gly Ser Gly Gly Gly Gly Ser Glu
    370                 375                 380

Leu Val Met Thr Gln Ser Pro Ser Ser Leu Ser Ala Ser Val Gly Asp
385                 390                 395                 400

Arg Val Thr Ile Thr Cys Arg Ala Ser Gln Gly Ile Gly Asn Tyr Leu
            405                 410                 415

Ala Trp Tyr Gln Gln Lys Pro Gly Gln Pro Pro Lys Met Leu Ile Tyr
        420                 425                 430

Trp Ala Ser Ile Arg Glu Ser Gly Val Pro Asp Arg Phe Ser Gly Ser
        435                 440                 445

Gly Ser Gly Thr Asp Phe Thr Leu Thr Ile Ser Ser Leu Gln Ala Glu
    450                 455                 460

Asp Val Ala Val Tyr Tyr Cys Gln Gln Tyr Tyr Ser Asn Pro Gln Thr
465                 470                 475                 480

Phe Gly Gln Gly Thr Lys Val Glu Ile Lys
            485                 490

<210> SEQ ID NO 249
<211> LENGTH: 1491
<212> TYPE: DNA
<213> ORGANISM: artificial sequence
<220> FEATURE:

<223> OTHER INFORMATION: anti-CCR5 VL-VH x human anti-CD3 3-190 VH-VL

<400> SEQUENCE: 249

```
gacattatcc tgatccaatc tccaccttct ttggctgtgt ctctagggca gagggccacc        60
atctcctgca gaaccagcga aaatgttgac ggatacggca ttagttttat aaactggtac       120
caacagaagc caggacagcc acccaaactc ctcatctatg ctgcatccca ccaaggatcc       180
ggggtccctg ccagatttag tggcagtggg tctgggacag acttcagcct caacatccat       240
cctttggagg aggatgatac tgcaatgtat ttctgtcacc aaagtaagaa ggttccgtgg       300
acgttcggtg gaggcaccaa gctggaaatc aaaggtggtg gtggttctgg cggcggcggc       360
tccggtggtg gtggttctca gctggagcag tctggacctg aactgaagaa gcctggagag       420
acagtcacga tctcctgcaa ggcttctggg tataccttca cgaagttcgg aatgaactgg       480
gtgaagcagg ctccaggaaa gggtttaaag tggatgggct ggatacacac ctccactgga       540
gagccaacat attctgatga cttcaaggga cggtttgcct tctctttgga aacgtctgcc       600
agcactgcct atttgcggat caacaacctc aaaaatgagg acatggctaa atacttctgt       660
gccagaggtg gtccttacgt aagggggtgct ttggactact ggggtcaagg aacctcagtc       720
accgtctcct ccggaggtgg tggatccgag ctgcagctgg tcgagtgggg cgcaggactg       780
ttgaagcctt cggagaccct gtccctcacc tgcgctgtct atggtgggtc cttcagtggt       840
tactactgga gctggatccg ccagccccca gggaaggggc tggagtggat tggggaaatc       900
aatcatagtg gaagcaccaa ctacaacccg tccctcaaga gtcgagtcac catatcagta       960
gacacgtcca agaaccagtt ctccctgaag ctgagctctg tgaccgccgc ggacacggct      1020
gtgtattact gtgcgagagg ccgaggccga ttttgggggt ggttattagg gggctccaac      1080
tggttcgacc cctggggcca gggaaccctg gtcaccgtct cctcaggtgg tggtggttct      1140
ggcggcggcg gctccggtgg tggtggttct gagctcgtga tgacccagtc tccatcctcc      1200
ctgtctgcat ctgtaggaga cagagtcacc atcacttgcc gggcgagtca gggcattagc      1260
aattatttaa attggtatca gcagaaacca gggaaagccc ctaagctcct gatctacgat      1320
gcatccaatt tggaaacagg ggtcccatca aggttcagtg gcagtggatc tgggacagat      1380
ttcactctca ccatcagcag tctgcaacct gaagattttg caacttacta ctgtcaacag      1440
agttacagta ccccgtacac ttttggccag gggaccaaag tggatatcaa a              1491
```

<210> SEQ ID NO 250
<211> LENGTH: 497
<212> TYPE: PRT
<213> ORGANISM: artificial sequence
<220> FEATURE:
<223> OTHER INFORMATION: anti-CCR5 VL-VH x human anti-CD3 3-190 VH-VL

<400> SEQUENCE: 250

```
Asp Ile Ile Leu Ile Gln Ser Pro Pro Ser Leu Ala Val Ser Leu Gly
1               5                   10                  15

Gln Arg Ala Thr Ile Ser Cys Arg Thr Ser Glu Asn Val Asp Gly Tyr
            20                  25                  30

Gly Ile Ser Phe Ile Asn Trp Tyr Gln Gln Lys Pro Gly Gln Pro Pro
        35                  40                  45

Lys Leu Leu Ile Tyr Ala Ala Ser His Gln Gly Ser Gly Val Pro Ala
    50                  55                  60

Arg Phe Ser Gly Ser Gly Ser Gly Thr Asp Phe Ser Leu Asn Ile His
65                  70                  75                  80
```

```
Pro Leu Glu Glu Asp Thr Ala Met Tyr Phe Cys His Gln Ser Lys
             85                  90                  95
Lys Val Pro Trp Thr Phe Gly Gly Gly Thr Lys Leu Glu Ile Lys Gly
            100                 105                 110
Gly Gly Gly Ser Gly Gly Gly Ser Gly Gly Gly Ser Gln Leu
            115                 120                 125
Glu Gln Ser Gly Pro Glu Leu Lys Lys Pro Gly Glu Thr Val Thr Ile
130                 135                 140
Ser Cys Lys Ala Ser Gly Tyr Thr Phe Thr Lys Phe Gly Met Asn Trp
145                 150                 155                 160
Val Lys Gln Ala Pro Gly Lys Gly Leu Lys Trp Met Gly Trp Ile His
            165                 170                 175
Thr Ser Thr Gly Glu Pro Thr Tyr Ser Asp Asp Phe Lys Gly Arg Phe
            180                 185                 190
Ala Phe Ser Leu Glu Thr Ser Ala Ser Thr Ala Tyr Leu Arg Ile Asn
            195                 200                 205
Asn Leu Lys Asn Glu Asp Met Ala Lys Tyr Phe Cys Ala Arg Gly Gly
            210                 215                 220
Pro Tyr Val Arg Gly Ala Leu Asp Tyr Trp Gly Gln Gly Thr Ser Val
225                 230                 235                 240
Thr Val Ser Ser Gly Gly Gly Ser Glu Leu Gln Leu Val Glu Trp
            245                 250                 255
Gly Ala Gly Leu Leu Lys Pro Ser Glu Thr Leu Ser Leu Thr Cys Ala
            260                 265                 270
Val Tyr Gly Gly Ser Phe Ser Gly Tyr Tyr Trp Ser Trp Ile Arg Gln
            275                 280                 285
Pro Pro Gly Lys Gly Leu Glu Trp Ile Gly Glu Ile Asn His Ser Gly
            290                 295                 300
Ser Thr Asn Tyr Asn Pro Ser Leu Lys Ser Arg Val Thr Ile Ser Val
305                 310                 315                 320
Asp Thr Ser Lys Asn Gln Phe Ser Leu Lys Leu Ser Ser Val Thr Ala
            325                 330                 335
Ala Asp Thr Ala Val Tyr Tyr Cys Ala Arg Gly Arg Gly Arg Phe Leu
            340                 345                 350
Gly Trp Leu Leu Gly Gly Ser Asn Trp Phe Asp Pro Trp Gly Gln Gly
            355                 360                 365
Thr Leu Val Thr Val Ser Ser Gly Gly Gly Ser Gly Gly Gly Gly
            370                 375                 380
Ser Gly Gly Gly Ser Glu Leu Val Met Thr Gln Ser Pro Ser Ser
385                 390                 395                 400
Leu Ser Ala Ser Val Gly Asp Arg Val Thr Ile Thr Cys Arg Ala Ser
            405                 410                 415
Gln Gly Ile Ser Asn Tyr Leu Asn Trp Tyr Gln Gln Lys Pro Gly Lys
            420                 425                 430
Ala Pro Lys Leu Leu Ile Tyr Asp Ala Ser Asn Leu Glu Thr Gly Val
            435                 440                 445
Pro Ser Arg Phe Ser Gly Ser Gly Ser Gly Thr Asp Phe Thr Leu Thr
            450                 455                 460
Ile Ser Ser Leu Gln Pro Glu Asp Phe Ala Thr Tyr Tyr Cys Gln Gln
465                 470                 475                 480
Ser Tyr Ser Thr Pro Tyr Thr Phe Gly Gln Gly Thr Lys Val Asp Ile
            485                 490                 495
Lys
```

<210> SEQ ID NO 251
<211> LENGTH: 1473
<212> TYPE: DNA
<213> ORGANISM: artificial sequence
<220> FEATURE:
<223> OTHER INFORMATION: anti-CCR5 VL-VH x human anti-CD3 3-148 VH-VL

<400> SEQUENCE: 251

```
gacattatcc tgatccaatc tccaccttct ttggctgtgt ctctagggca gagggccacc      60
atctcctgca gaaccagcga aaatgttgac ggatacggca ttagtttttat aaactggtac    120
caacagaagc caggacagcc acccaaactc ctcatctatg ctgcatccca ccaaggatcc    180
ggggtccctg ccagatttag tggcagtggg tctgggacag acttcagcct caacatccat    240
cctttggagg aggatgatac tgcaatgtat ttctgtcacc aaagtaagaa ggttccgtgg    300
acgttcggtg gaggcaccaa gctggaaatc aaaggtggtg gtggttctgg cggcggcggc    360
tccggtggtg gtggttctca gctggagcag tctggacctg aactgaagaa gcctggagag    420
acagtcacga tctcctgcaa ggcttctggg tataccttca cgaagttcgg aatgaactgg    480
gtgaagcagg ctccaggaaa gggtttaaag tggatgggct ggataacacac ctccactgga    540
gagccaacat attctgatga cttcaaggga cggtttgcct tctctttgga aacgtctgcc    600
agcactgcct atttgcggat caacaacctc aaaaatgagg acatggctaa atacttctgt    660
gccagaggtg gtccttacgt aagggggtgct ttggactact ggggtcaagg aacctcagtc    720
accgtctcct ccggaggtgg tggatccgag ctgcagctgg tcgagtctgg cccaggactg    780
gtgaagcctt cggggaccct gtccctcacc tgcgctgtct ctggtggctc catcagcagt    840
agaaactggt ggagttgggt ccgccagccc cagggaagg gctgagtg gattggtgat    900
atctatcata gtgggagcac caactacaac ccgtccctca gagtcgagt caccatatca    960
gtagacaagt ccaagaacca gttctccctg aagctgagct ctgtgaccgc cgcggacacg   1020
gccgtgtatt actgtgcgag tgggtatacc agctgtcgtg atgctttttga tatctggggc   1080
caagggacaa tggtcaccgt ctcctcaggt ggtggtggtt ctggcggcgg cggctccggt   1140
ggtggtggtt ctgagctcgt gatgactcag tctccatcct ccctgtctgc atctgtagga   1200
gacagagtca ccatcacttg ccgggcgagt cagggcattg gcaattattt agcctggtat   1260
cagcagaaac caggggcagcc tcctaagatg ctcatttact gggcatcaat ccgggaatcc   1320
ggggtccctg accgattcag tggcagcggg tctgggacag acttcactct caccatcagc   1380
agcctgcagg ctgaagatgt ggcagtttac tactgtcagc aatattatag taatcctcag   1440
acgttcggcc aagggaccaa ggtggaaatc aaa                                1473
```

<210> SEQ ID NO 252
<211> LENGTH: 491
<212> TYPE: PRT
<213> ORGANISM: artificial sequence
<220> FEATURE:
<223> OTHER INFORMATION: anti-CCR5 VL-VH x human anti-CD3 3-148 VH-VL

<400> SEQUENCE: 252

Asp Ile Ile Leu Ile Gln Ser Pro Ser Leu Ala Val Ser Leu Gly
1               5                  10                  15

Gln Arg Ala Thr Ile Ser Cys Arg Thr Ser Glu Asn Val Asp Gly Tyr
            20                  25                  30

Gly Ile Ser Phe Ile Asn Trp Tyr Gln Gln Lys Pro Gly Gln Pro Pro
        35                  40                  45

```
Lys Leu Leu Ile Tyr Ala Ala Ser His Gln Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Leu Glu Glu Asp Asp Thr Ala Met Tyr Phe Cys His Gln Ser Lys
                 85                  90                  95

Lys Val Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Leu
        115                 120                 125

Glu Gln Ser Gly Pro Glu Leu Lys Lys Pro Gly Glu Thr Val Thr Ile
130                 135                 140

Ser Cys Lys Ala Ser Gly Tyr Thr Phe Thr Lys Phe Gly Met Asn Trp
145                 150                 155                 160

Val Lys Gln Ala Pro Gly Lys Gly Leu Lys Trp Met Gly Trp Ile His
                165                 170                 175

Thr Ser Thr Gly Glu Pro Thr Tyr Ser Asp Asp Phe Lys Gly Arg Phe
            180                 185                 190

Ala Phe Ser Leu Glu Thr Ser Ala Ser Thr Ala Tyr Leu Arg Ile Asn
        195                 200                 205

Asn Leu Lys Asn Glu Asp Met Ala Lys Tyr Phe Cys Ala Arg Gly Gly
210                 215                 220

Pro Tyr Val Arg Gly Ala Leu Asp Tyr Trp Gly Gln Gly Thr Ser Val
225                 230                 235                 240

Thr Val Ser Ser Gly Gly Gly Gly Ser Glu Leu Gln Leu Val Glu Ser
                245                 250                 255

Gly Pro Gly Leu Val Lys Pro Ser Gly Thr Leu Ser Leu Thr Cys Ala
            260                 265                 270

Val Ser Gly Gly Ser Ile Ser Ser Arg Asn Trp Trp Ser Trp Val Arg
        275                 280                 285

Gln Pro Pro Gly Lys Gly Leu Glu Trp Ile Gly Asp Ile Tyr His Ser
290                 295                 300

Gly Ser Thr Asn Tyr Asn Pro Ser Leu Lys Ser Arg Val Thr Ile Ser
305                 310                 315                 320

Val Asp Lys Ser Lys Asn Gln Phe Ser Leu Lys Leu Ser Ser Val Thr
                325                 330                 335

Ala Ala Asp Thr Ala Val Tyr Tyr Cys Ala Ser Gly Tyr Thr Ser Cys
            340                 345                 350

Arg Asp Ala Phe Asp Ile Trp Gly Gln Gly Thr Met Val Thr Val Ser
        355                 360                 365

Ser Gly Gly Gly Gly Ser Gly Gly Gly Gly Ser Gly Gly Gly Gly Ser
370                 375                 380

Glu Leu Val Met Thr Gln Ser Pro Ser Ser Leu Ser Ala Ser Val Gly
385                 390                 395                 400

Asp Arg Val Thr Ile Thr Cys Arg Ala Ser Gln Gly Ile Gly Asn Tyr
                405                 410                 415

Leu Ala Trp Tyr Gln Gln Lys Pro Gly Gln Pro Pro Lys Met Leu Ile
            420                 425                 430

Tyr Trp Ala Ser Ile Arg Glu Ser Gly Val Pro Asp Arg Phe Ser Gly
        435                 440                 445

Ser Gly Ser Gly Thr Asp Phe Thr Leu Thr Ile Ser Ser Leu Gln Ala
450                 455                 460
```

-continued

```
Glu Asp Val Ala Val Tyr Tyr Cys Gln Gln Tyr Tyr Ser Asn Pro Gln
465                 470                 475                 480

Thr Phe Gly Gln Gly Thr Lys Val Glu Ile Lys
                485                 490
```